United States Patent
Martinez et al.

(10) Patent No.: US 10,669,296 B2
(45) Date of Patent: Jun. 2, 2020

(54) LXR AGONISTS AND USES THEREOF

(71) Applicant: Rgenix, Inc., New York, NY (US)

(72) Inventors: Eduardo J. Martinez, Bryn Mawr, PA (US); Bernd Kaiser, Wallingford, CT (US); Sohail F. Tavazoie, New York, NY (US); Isabel Kurth, New York, NY (US); Foster Casimir Gonsalves, Long Island City, NY (US); David M. Darst, Jr., New York, NY (US); Masoud Fakhr Tavazoie, New York, NY (US)

(73) Assignee: Rgenix, Inc., New York, NY (US)

( * ) Notice: Subject to any disclaimer, the term of this patent is extended or adjusted under 35 U.S.C. 154(b) by 0 days.

(21) Appl. No.: 15/110,343

(22) PCT Filed: Jan. 9, 2015

(86) PCT No.: PCT/US2015/010909
§ 371 (c)(1),
(2) Date: Jul. 7, 2016

(87) PCT Pub. No.: WO2015/106164
PCT Pub. Date: Jul. 16, 2015

(65) Prior Publication Data
US 2017/0066791 A1    Mar. 9, 2017

Related U.S. Application Data

(60) Provisional application No. 61/926,150, filed on Jan. 10, 2014.

(51) Int. Cl.
| | |
|---|---|
| *A61K 45/06* | (2006.01) |
| *A61K 31/165* | (2006.01) |
| *A61K 31/445* | (2006.01) |
| *A61K 31/138* | (2006.01) |
| *A61K 31/195* | (2006.01) |
| *A61K 31/145* | (2006.01) |
| *A61K 31/24* | (2006.01) |
| *A61K 31/357* | (2006.01) |
| *A61K 31/675* | (2006.01) |
| *A61K 31/661* | (2006.01) |
| *A61K 31/40* | (2006.01) |

(Continued)

(52) U.S. Cl.
CPC ...... *C07F 9/657172* (2013.01); *A61K 31/138* (2013.01); *A61K 31/145* (2013.01); *A61K 31/165* (2013.01); *A61K 31/195* (2013.01); *A61K 31/24* (2013.01); *A61K 31/357* (2013.01); *A61K 31/366* (2013.01); *A61K 31/397* (2013.01); *A61K 31/40* (2013.01); *A61K 31/445* (2013.01); *A61K 31/661* (2013.01); *A61K 31/675* (2013.01); *A61K 45/06* (2013.01); *C07B 59/004* (2013.01); *C07C 217/18* (2013.01); *C07C 217/20* (2013.01); *C07C 217/22* (2013.01); *C07C 217/58* (2013.01); *C07C 259/06* (2013.01); *C07C 311/51* (2013.01); *C07C 317/04* (2013.01); *C07C 317/14* (2013.01); *C07C 317/22* (2013.01); *C07C 317/46* (2013.01); *C07C 323/09* (2013.01); *C07C 323/32* (2013.01); *C07D 205/04* (2013.01); *C07D 207/48* (2013.01); *C07D 209/48* (2013.01); *C07D 211/42* (2013.01); *C07D 211/96* (2013.01); *C07D 311/76* (2013.01); *C07D 317/46* (2013.01); *C07F 9/09* (2013.01); *C07F 9/094* (2013.01); *C07F 9/12* (2013.01); *C07F 9/304* (2013.01); *C07F 9/65744* (2013.01); *C07B 2200/05* (2013.01); *C07C 2601/14* (2017.05)

(58) Field of Classification Search
CPC .... A61K 45/06; A61K 31/165; A61K 31/445; A61K 31/138; A61K 31/195; A61K 31/145; A61K 31/24; A61K 31/357; A61K 31/675; A61K 31/661; A61K 31/40; A61K 31/397; A61K 31/366; C07C 259/06; C07C 311/51; C07C 317/22; C07C 317/46; C07C 317/14; C07C 317/04; C07C 217/18; C07C 217/20; C07C 217/22; C07C 217/58; C07C 323/32; C07C 323/09; C07D 311/76; C07D 317/46; C07D 205/04; C07D 207/48; C07D 209/48; C07D 211/42; C07D 211/96; C07F 9/12; C07F 9/09; C07B 59/00

See application file for complete search history.

(56) References Cited

U.S. PATENT DOCUMENTS

| | | | |
|---|---|---|---|
| 5,324,731 | A | 6/1994 | Kaddurah-Daouk et al. |
| 5,676,978 | A | 10/1997 | Teicher et al. |

(Continued)

FOREIGN PATENT DOCUMENTS

| | | | |
|---|---|---|---|
| DE | 2951400 A1 | | 7/1981 |
| JP | 2006232703 | * | 9/2006 |

(Continued)

OTHER PUBLICATIONS

Collins et al., caplus an 2002:240713.*

(Continued)

*Primary Examiner* — Sun Jae Yoo
(74) *Attorney, Agent, or Firm* — Clark & Elbing LLP

(57) ABSTRACT

This invention features compounds that modulate the activity of liver X receptors, pharmaceutical compositions including the compounds of the invention, and methods of utilizing those compositions for modulating the activity of liver X receptors in the treatment of cancer.

19 Claims, No Drawings

Specification includes a Sequence Listing.

(51) Int. Cl.

| | |
|---|---|
| *A61K 31/397* | (2006.01) |
| *A61K 31/366* | (2006.01) |
| *C07C 259/06* | (2006.01) |
| *C07C 311/51* | (2006.01) |
| *C07C 317/22* | (2006.01) |
| *C07C 317/46* | (2006.01) |
| *C07C 317/14* | (2006.01) |
| *C07C 317/04* | (2006.01) |
| *C07C 217/18* | (2006.01) |
| *C07C 217/20* | (2006.01) |
| *C07C 217/22* | (2006.01) |
| *C07C 217/58* | (2006.01) |
| *C07C 323/32* | (2006.01) |
| *C07C 323/09* | (2006.01) |
| *C07D 311/76* | (2006.01) |
| *C07D 317/46* | (2006.01) |
| *C07D 205/04* | (2006.01) |
| *C07D 207/48* | (2006.01) |
| *C07D 209/48* | (2006.01) |
| *C07D 211/42* | (2006.01) |
| *C07D 211/96* | (2006.01) |
| *C07F 9/12* | (2006.01) |
| *C07F 9/09* | (2006.01) |
| *C07B 59/00* | (2006.01) |
| *C07F 9/6571* | (2006.01) |
| *C07F 9/6574* | (2006.01) |
| *C07F 9/30* | (2006.01) |

(56) References Cited

U.S. PATENT DOCUMENTS

| | | | |
|---|---|---|---|
| 6,316,503 B1 | 11/2001 | Li et al. | |
| 6,906,069 B1 | 6/2005 | Li et al. | |
| 7,183,295 B2 * | 2/2007 | Yamazaki | C07D 413/12 514/339 |
| 7,247,748 B2 | 7/2007 | Thompson et al. | |
| 7,365,085 B2 | 4/2008 | Bhat et al. | |
| 7,560,586 B2 | 7/2009 | Thompson et al. | |
| 7,576,215 B2 | 8/2009 | Collini et al. | |
| 7,790,745 B2 | 9/2010 | Yang et al. | |
| 7,799,782 B2 | 9/2010 | Munson et al. | |
| 7,998,995 B2 | 8/2011 | Boren et al. | |
| 9,399,028 B2 | 7/2016 | Tavazoie et al. | |
| 9,526,710 B2 | 12/2016 | Tavazoie et al. | |
| 9,707,195 B2 | 7/2017 | Tavazoie et al. | |
| 9,962,348 B2 | 5/2018 | Tavazoie et al. | |
| 2002/0107233 A1 | 8/2002 | Liao et al. | |
| 2003/0125357 A1 | 7/2003 | Adams et al. | |
| 2003/0153541 A1 | 8/2003 | Dudley et al. | |
| 2004/0072868 A1 | 4/2004 | Collins et al. | |
| 2005/0080111 A1 | 4/2005 | Bayne et al. | |
| 2005/0107444 A1 | 5/2005 | Thompsom et al. | |
| 2005/0113419 A1 | 5/2005 | Huang et al. | |
| 2005/0113580 A1 | 5/2005 | Thompson et al. | |
| 2005/0131014 A1 | 6/2005 | Collini et al. | |
| 2005/0215577 A1 | 9/2005 | Dehmlow et al. | |
| 2005/0245515 A1 | 11/2005 | Dehmlow et al. | |
| 2005/0261319 A1 | 11/2005 | Deuschle et al. | |
| 2005/0282908 A1 | 12/2005 | Collins et al. | |
| 2006/0030612 A1 | 2/2006 | Steffan et al. | |
| 2006/0074115 A1 | 4/2006 | Dehmlow et al. | |
| 2006/0135601 A1 | 6/2006 | Dehmlow et al. | |
| 2006/0178398 A1 | 8/2006 | Adams et al. | |
| 2007/0093524 A1 | 4/2007 | Nambi et al. | |
| 2007/0161553 A1 | 7/2007 | Mathieu et al. | |
| 2009/0004297 A1 | 1/2009 | Ranganathan | |
| 2009/0030082 A1 | 1/2009 | Forman | |
| 2009/0175791 A1 | 7/2009 | Kavile et al. | |
| 2009/0247587 A1 | 10/2009 | Okuda et al. | |
| 2009/0286780 A1 | 11/2009 | Okuda et al. | |
| 2010/0048944 A1 | 2/2010 | Parhami | |
| 2010/0069367 A1 | 3/2010 | Boren et al. |
| 2010/0298410 A1 | 11/2010 | Obad et al. |
| 2011/0028384 A1 | 2/2011 | Blacklow et al. |
| 2011/0166079 A1 | 7/2011 | Vitek et al. |
| 2011/0237791 A1 | 9/2011 | Kawaguchi et al. |
| 2012/0156216 A1 | 6/2012 | Oh |
| 2013/0071403 A1 | 3/2013 | Rolland et al. |
| 2015/0023955 A1 | 1/2015 | Tavazoie et al. |
| 2015/0033693 A1 | 2/2015 | Ito et al. |
| 2015/0045399 A1 | 2/2015 | Mohan |
| 2015/0051214 A1 | 2/2015 | Dong et al. |
| 2015/0065515 A1 | 3/2015 | Dong et al. |
| 2015/0073053 A1 | 3/2015 | Tavazoie et al. |
| 2015/0080406 A1 | 3/2015 | Leftheris et al. |
| 2015/0152094 A1 | 6/2015 | Mohan |
| 2015/0225366 A1 | 8/2015 | Li |
| 2015/0246924 A1 | 9/2015 | Dong et al. |
| 2015/0299136 A1 | 10/2015 | Busch et al. |
| 2017/0066791 A1 | 3/2017 | Martinez et al. |
| 2017/0119807 A1 | 5/2017 | Lee et al. |

FOREIGN PATENT DOCUMENTS

| | | |
|---|---|---|
| WO | WO-96/39135 A1 | 12/1996 |
| WO | WO-00/66611 A1 | 11/2000 |
| WO | WO-01/66534 A2 | 9/2001 |
| WO | WO-02/13594 A1 | 2/2002 |
| WO | WO-2002/090375 A2 | 11/2002 |
| WO | WO-03/031408 A2 | 4/2003 |
| WO | WO-2003/043998 A1 | 5/2003 |
| WO | WO-2003/045382 A1 | 6/2003 |
| WO | WO-2003/059874 A1 | 7/2003 |
| WO | WO-2003/059884 A1 | 7/2003 |
| WO | WO-2003/060078 A2 | 7/2003 |
| WO | WO-03082205 A2 | 10/2003 |
| WO | WO-03082802 A1 | 10/2003 |
| WO | WO-2003/090732 A1 | 11/2003 |
| WO | WO-2003/090746 A1 | 11/2003 |
| WO | WO-2003/090869 A1 | 11/2003 |
| WO | WO-2003/099769 A1 | 12/2003 |
| WO | WO-2003/099775 A1 | 12/2003 |
| WO | WO-2003/106435 A1 | 12/2003 |
| WO | WO-2004/009091 A1 | 1/2004 |
| WO | WO-2004/011448 A1 | 2/2004 |
| WO | WO-2004/026816 A1 | 4/2004 |
| WO | WO-2004043939 A1 | 5/2004 |
| WO | WO-2004/058717 A1 | 7/2004 |
| WO | WO-2004/072041 A1 | 8/2004 |
| WO | WO-2004/072042 A2 | 8/2004 |
| WO | WO-2004/072046 A2 | 8/2004 |
| WO | WO-2005/005416 A1 | 1/2005 |
| WO | WO-2005/005417 A1 | 1/2005 |
| WO | WO-2005/016277 A2 | 2/2005 |
| WO | WO-2005/023782 A1 | 3/2005 |
| WO | WO-2005/077122 A2 | 8/2005 |
| WO | WO-2005/077124 A2 | 8/2005 |
| WO | WO-2005/113499 A1 | 12/2005 |
| WO | WO-2006/000323 A1 | 1/2006 |
| WO | WO-2006/003923 A1 | 1/2006 |
| WO | WO-2006/046593 A1 | 5/2006 |
| WO | WO-2006/073363 A1 | 7/2006 |
| WO | WO-2006/073364 A1 | 7/2006 |
| WO | WO-2006/073365 A1 | 7/2006 |
| WO | WO-2006/073366 A1 | 7/2006 |
| WO | WO-2006/073367 A1 | 7/2006 |
| WO | WO-2006/109633 A1 | 10/2006 |
| WO | WO-2007002563 A1 | 1/2007 |
| WO | WO-2007/022563 A1 | 3/2007 |
| WO | WO-2008/011071 A2 | 1/2008 |
| WO | WO-2008/027988 A2 | 3/2008 |
| WO | WO-2009/021868 A2 | 2/2009 |
| WO | WO-2009/086129 A1 | 7/2009 |
| WO | WO-2009/086130 A1 | 7/2009 |
| WO | WO-2009/133692 A1 | 11/2009 |
| WO | WO-2009/138438 A1 | 11/2009 |
| WO | WO-2009/144961 A1 | 12/2009 |
| WO | WO-2009/150109 A1 | 12/2009 |
| WO | WO-2009148915 A2 | 12/2009 |

(56) References Cited

FOREIGN PATENT DOCUMENTS

| WO | WO-2010/023317 A1 | 3/2010 |
|---|---|---|
| WO | WO-2010/025169 A2 | 3/2010 |
| WO | WO-2010/025179 A1 | 3/2010 |
| WO | WO-2010/036613 A1 | 4/2010 |
| WO | WO-2010/059627 A1 | 5/2010 |
| WO | WO-2010/125811 A1 | 11/2010 |
| WO | WO-2010/138598 A2 | 12/2010 |
| WO | WO-2011/014661 A2 | 2/2011 |
| WO | WO-2011/051282 A1 | 5/2011 |
| WO | WO-2011/055391 A1 | 5/2011 |
| WO | WO-2011/103175 A2 | 8/2011 |
| WO | WO-2011/115892 A1 | 9/2011 |
| WO | WO-2011/130426 A2 | 10/2011 |
| WO | WO-2011/158667 A1 | 12/2011 |
| WO | WO-2012/004748 A1 | 1/2012 |
| WO | WO-2012/095505 A1 | 7/2012 |
| WO | WO-2012/096573 A1 | 7/2012 |
| WO | WO-2012/135082 A1 | 10/2012 |
| WO | WO-2013/057148 A1 | 4/2013 |
| WO | WO-2013/076257 A1 | 5/2013 |
| WO | WO-2013/130892 A1 | 9/2013 |
| WO | WO-2013/138565 A1 | 9/2013 |
| WO | WO-2013/138568 A1 | 9/2013 |
| WO | WO-2014/028461 A2 | 2/2014 |
| WO | WO-2014/144037 A1 | 9/2014 |

OTHER PUBLICATIONS

Cairns et al., 2003, caplus an 2003:796421.*
Ostermayer et al., 1981, caplus an 1981:121135.*
Thompson et al., 2003, caplus an 2003:796645.*
Mohr, 1981, caplus an 1981:586827.*
Fujikura-et-al., 1983, caplus an 1983:178855.*
Yamasaki-et-al., 2005, caplus an 2005:238962.*
Yamaguchi et. al., 2006, caplus an 2006:910678.*
Invitation to Pay Additional Fees for International Application No. PCT/US2015/010909, dated Mar. 11, 2015 (3 pages).
PUBCHEM, Compund Summary for CID 51369, created Mar. 27, 2005, <https://pubchem.ncbi.nlm.nih.gov/compound/51369?from=summary>, retrieved on Feb. 23, 2015 (18 pages).
PUBCHEM, Compound Summary for CID 52723103, created May 20, 2011 <https://pubchem.ncbi.nlm.nih.gov/compound/52723103>, retrieved on Nov. 7, 2016 (3 pages).
International Search Report and Written Opinion for International Patent Application No. PCT/US2015/010909, dated Jun. 11, 2015 (14 pages).
International Preliminary Report on Patentability for International Patent Application No. PCT/US2015/010909, dated Jul. 12, 2016 (7 pages).
Riddell et al., "The LXR agonist TO901317 selectively lowers hippocampal Abeta42 and improves memory in the Tg2576 mouse model of Alzheimer's disease," Mol Cell Neurosci. 34(4):621-8 (2007).
Berge et al., "Pharmaceutical salts," J Pharm Sci. 66(1):1-19 (1977).
Fowler et al., "Liver X receptor activators display anti-inflammatory activity in irritant and allergic contact dermatitis models: liver-X-receptor-specific inhibition of inflammation and primary cytokine production," J Invest Dermatol. 120(2):246-55 (2003).
Schmuth et al., "Thematic review series: skin lipids. Peroxisome proliferator-activated receptors and liver X receptors in epidermal biology," J Lipid Res. 49(3):499-509 (2008).
Garbe et al., "Systematic review of medical treatment in melanoma: current status and future prospects," Oncologist. 16(1):5-24 (2011).
"Convergent multi-miRNA targeting of ApoE drives LRP1/LRP8-dependent melanoma metastasis and angiogenesis," available in PMC Nov. 21, 2013, published in final edited form as: Cell. 151(5):1068-82 (2012) (27 pages).
Li et al., "Liver X receptor modulators: a review of recently patented compounds (2007-2009)," Expert Opin Ther Pat. 20(4):535-62 (2010).

Marino et al., "The discovery of tertiary-amine LXR agonists with potent cholesterol efflux activity in macrophages," Bioorg Med Chem Lett. 19(19):5617-21 (2009).
Extended European Search Report for European Patent Application No. 15734952.3, dated Jun. 7, 2017 (8 pages).
Viennois et al., "Selective liver X receptor modulators (SLiMs): What use in human health?" Mol Cell Endocrinol. 351(2):129-41 (2011).
Roz et al., "Macrophage Apolipoprotein E and Proliferation of MCF-7 Breast Cancer Cells: Role of LXR" Anticancer Res. 33:3383-90 (2013).
Pancheva et al., "Broad-Spectrum Therapeutic Suppression of Metastatic Melanoma through Nuclear Hormone Receptor Activation" Cell 156(5):986-1001 (2014).
Bergenfelz et al., "Systemic Monocytic-MDSCs Are Generated from Monocytes and Correlate with Disease Progression in Breast Cancer Patients," PLoS One 10(5):1-23 (2015).
Chuu et al., "Modulation of liver X receptor signaling as novel therapy for prostate cancer," J Biomed Sci. 14(5):543-553 (2007).
Gielen et al., "Increase in Both CD14-Positive and CD15-Positive Myeloid-Derived Suppresor Cell Subpopulations in the Blood of Patients With Glioma But Predominance of CD15-Positive Myeloid-Derived Suppresor Cells in Glioma Tissue," J Neuropathol Exp Neur., 74(5):390-400 (2015).
Gros et al., "Myeloid Cells Obtained from the Blood but Not from the Tumor can Suppress T-cell Proliferation in Patients with Melanoma," Clin Cancer Res 18(19):5212-5223 (2012).
Haas, Michael J., "Melanoma: three ways around BRAF inhibition," SciBX. 3(47):(2010) (3 pages).
Li et al., "miR-495 and miR-551a inhibit the migration and invasion of human gastric cancer cells by directly interacting with PRL-3," Cancer Lett 323(1):41-47 (2012).
Obermajer et al., "$PGE_2$-Induced CXCL12 Production and CXCR4 Expression Controls the Accumulation of Human MDSCs in Ovarian Cancer Environment," Cancer Res 71(24): 7463-7470 (2011) (9 pages).
Ostrand-Rosenberg et al., "Myeloid-derived suppressor cells: linking inflammation and cancer," J Immunol.182(8):4499-4506 (2009).
Pencheva et al., "Control of Metastatic Progression by microRNA Regulatory Networks," Available in PMC Dec. 15, 2015, published in final edited form as: Nat Cell Biol. 15(6):546-554 (2013) (21 pages).
Rudolph et al., "Increased frequencies of CD11b+CD33+CD14+HLA-DRlow myeloid-derived suppressor cells are an early eent in melanoma patients," Exp Dermatology 23(3):202-204 (2014).
Scoles et al., "Liver X receptor agonist inhibits proliferation of ovarian carcinoma cells stimulated by oxidized low density lipoprotein," Gynecol Oncol. 116(1):109-116 (2010).
Talmadge et al., "History of myeloid derived suppressor cells (MDSCs) in the macro- and micro-environment of tumour-bearing hosts," Available in PMC Mar. 13, 2015, published in final edited for as: Nat Rev Cancer. 13(10):739-752 (2013) (34 pages).
Weber et al., "Phase I/II Study of Metastatic Melanoma Patients Treated with Nivolumab Who Had Progressed after Ipilimumab," Cancer Immunol Res 4(4):345-353 (2016) (10 pages).
Zhang et al., "A novel subset of B7-H3+CD14+HLA-DR$^{-/low}$ myeloid-derived suppressor cells are associated with progression of human NSCLC," OncoImmunology 4(2): e977164-1-12 (2015).
Zhang et al., "Liver X receptor activation induces apoptosis of melanoma cell through caspase pathway," Cancer Cell. Int. 14(1):1-6 (2014).
Zigler et al., "Tumor Immunotherapy in Melanoma: Strategies for Overcoming Mechanisms of Resistance and Escape," Am J Clin Dermatol 9(5):307-313 (2008).
Communication pursuant to Article 94(3) EPC for European Application No. 15734952.3, dated Jul. 18, 2019 (6 pages).
First Examination Report for Australian Application No. 2015204572, dated Jul. 15, 2019 (7 pages).
PubChem Compound Summary for CID 10301050, Created Oct. 25, 2006, Modified Jan. 19, 2019 (9 pages).
PubChem Compound Summary for CID 422253, Created Mar. 26, 2005, Modified Jan. 19, 2019 (11 pages).

(56) References Cited

OTHER PUBLICATIONS

PubChem Substance Record for SID 168474198, available Dec. 2, 2013 (6 pages).
Communication pursuant to Article 94(3) EPC for European Patent Application No. 15734952.3, dated Aug. 29, 2018 (6 pages).

\* cited by examiner

LXR AGONISTS AND USES THEREOF

REFERENCE TO A SEQUENCE LISTING

This application contains a Sequence Listing in computer readable form. The computer readable form is incorporated herein by reference.

BACKGROUND OF THE INVENTION

This invention relates to the field of compounds that modulate the activity of liver X receptors and their use in therapy, including the treatment of cancer.

Liver X receptors (LXRs) belong to a family of nuclear hormone receptors that are endogenously activated by cholesterol and its oxidized derivatives to mediate transcription of genes involved in maintaining glucose, cholesterol, and fatty acid metabolism. LXRα is found predominantly in the liver, with low levels found in kidney, intestine, spleen, and adrenal tissue. LXRβ is ubiquitous in mammals and was found in nearly all tissues examined. Given the intricate link between lipid metabolism and cancer cell growth, the ubiquitous expression of LXRβ in some types of cancer is unlikely to be coincidental, allowing cancer cells to synthesize lipids and lipoprotein particles to sustain their growth. At the same time, however, such stable basal expression levels make LXRβ an ideal therapeutic target

SUMMARY OF THE INVENTION

This invention features compounds that modulate the activity of liver X receptors, pharmaceutical compositions including the compounds of the invention, and methods of utilizing those compositions for modulating the activity of liver X receptors (e.g., for the treatment of cancer).

Accordingly, in a first aspect the invention features a compound of Formula I:

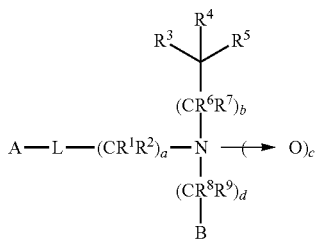

Formula I wherein A is:

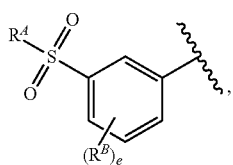

Formula Ia

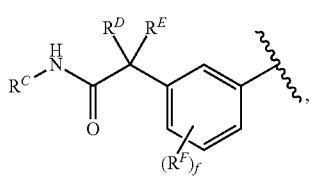

Formula Ib

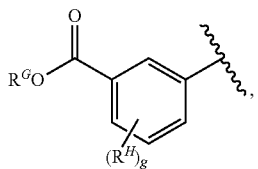

Formula Ic

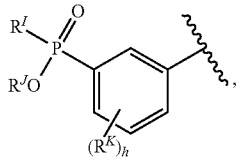

Formula Id

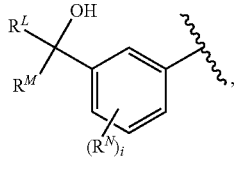

Formula Ie

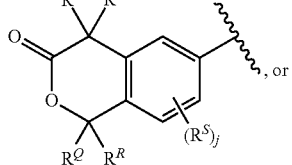

Formula If

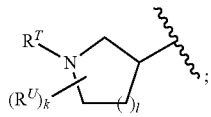

Formula Ig wherein e, f, g, h, and i are independently 0, 1, 2, 3, or 4;
j is 0, 1, 2, or 3;
k is 0, 1, 2, 3, 4, 5, 6, 7, or 8;
l is 0 1, or 2;
$R^A$, $R^C$, $R^I$, $R^L$, $R^M$, and $R^T$ are independently hydrogen, hydroxyl, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_8$-$C_{12}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl;

$R^D$, $R^E$, $R^G$, $R^O$, $R^P$, $R^Q$, and $R^R$ are independently hydrogen, hydroxy, optionally substituted amino, azido, halo, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_8$-$C_{12}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl;

each $R^B$, $R^F$, $R^H$, $R^K$, $R^N$, and $R^S$ are independently hydroxyl, optionally substituted amino, halo, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_8$-$C_{12}$ cycloalkenyl, optionally substituted $C_4$-$C_{10}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl;

$R^J$ is hydrogen, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_8$-$C_{12}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl; or $R^I$ and $R^J$ combine to form an optionally substituted $C_2$-$C_9$ heterocyclyl or $R^J$ and $R^K$ combine to form an optionally substituted $C_2$-$C_9$ heterocyclyl;

$R^U$ is hydroxyl, oxo, optionally substituted amino, halo, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_8$-$C_{12}$ cycloalkenyl, optionally substituted $C_4$-$C_{10}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl; and L is absent, —O—, —S—, —N($R^{12}$)—, or —C($R^4$)($R^5$)—;

a is 2, 3, 4, 5, 6, 7, or 8;

b, c, and d are independently 0 or 1;

each $R^1$, $R^2$, $R^6$, $R^7$, $R^8$, and $R^9$ are independently hydrogen, hydroxyl, halo, optionally substituted amino, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_4$-$C_{10}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl; or $R^1$ and $R^2$ combine to form an optionally substituted $C_3$-$C_{10}$ cycloalkyl, optionally substituted $C_2$-$C_9$ heteroaryl, or optionally substituted $C_2$-$C_9$ heterocyclyl; or $R^6$ and $R^7$ combine to form an optionally substituted $C_3$-$C_{10}$ cycloalkyl, optionally substituted $C_2$-$C_9$ heteroaryl, or optionally substituted $C_2$-$C_9$ heterocyclyl; or $R^8$ and $R^9$ combine to form an optionally substituted $C_3$-$C_{10}$ cycloalkyl, optionally substituted $C_2$-$C_9$ heteroaryl, or optionally substituted $C_2$-$C_9$ heterocyclyl;

$R^3$ is hydrogen, hydroxyl, optionally substituted amino, optionally substituted $C_1$-$C_6$ alkyl, optionally substituted $C_3$-$C_{10}$ cycloalkyl, optionally substituted $C_6$-$C_{10}$ aryl, optionally substituted $C_2$-$C_9$ heteroaryl, or optionally substituted $C_2$-$C_9$ heterocyclyl;

$R^4$ and $R^5$ are independently hydrogen, hydroxyl, halo, optionally substituted amino, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_4$-$C_{10}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl; and B is optionally substituted $C_3$-$C_{10}$ cycloalkyl, optionally substituted $C_6$-$C_{10}$ aryl, optionally substituted $C_2$-$C_9$ heteroaryl, or optionally substituted $C_2$-$C_9$ heterocyclyl;

or a pharmaceutically acceptable salt thereof and/or a prodrug thereof. In some embodiments, c is 0. In other embodiments, $R^4$ is hydrogen. In certain embodiments, $R^4$ is fluorine. In some embodiments, $R^5$ is hydrogen. In some embodiments, $R^5$ is fluorine. In certain embodiments, b is 1. In some embodiments, b is 0. In some embodiments, each $R^6$ is hydrogen. In other embodiments, each $R^7$ is hydrogen. In certain embodiments, d is 1. In some embodiments, each $R^8$ is hydrogen. In other embodiments, each $R^9$ is hydrogen. In certain embodiments, $R^3$ is optionally substituted $C_6$-$C_{10}$ aryl (e.g., phenyl or 4-fluoro-phenyl). In some embodiments, $R^5$ is optionally substituted $C_6$-$C_{10}$ aryl (e.g., phenyl). In some embodiments, $R^5$ is optionally substituted $C_3$-$C_{10}$ cycloalkyl (e.g., cyclohexyl). In some embodiments, $R^4$ is optionally substituted $C_1$-$C_6$ alkyl (e.g., methyl). In certain embodiments, $R^5$ is optionally substituted $C_1$-$C_6$ alkyl (e.g., methyl). In some embodiments, $R^4$ and $R^5$ are both optionally substituted $C_1$-$C_6$ alkyl (e.g., methyl). In some embodiments, $R^5$ is hydrogen, methyl, or phenyl. In other embodiments, a is 3. In certain embodiments, each $R^1$ is hydrogen. In some embodiments, each $R^2$ is hydrogen. In other embodiments, at least one $R^2$ is optionally substituted $C_1$-$C_6$ alkyl (e.g., methyl). In certain embodiments, —($CR^1R^2$)$_3$— has the structure:

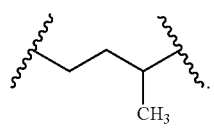

In some embodiments, —($CR^1R^2$)$_3$— has the structure:

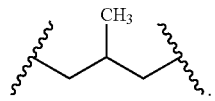

In some embodiments, —(CR¹R²)₃— has the structure:

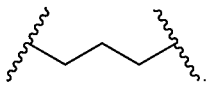

In some embodiments, —(CR¹R²)₃— has the structure:

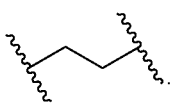 [SMILES: *CC*]

In certain embodiments, L is —O—. In certain embodiments, L is absent. In some embodiments, B is optionally substituted $C_6$-$C_{10}$ aryl (e.g., 2-chloro-3-trifluoromethyl-phenyl, 2-fluoro-3-trifluoromethyl-phenyl, 3-(1,1,2,2-tetra-fluoroethoxy)-phenyl, 3-trifluoromethyl-phenyl, 3-trifluoromethyl-4-fluoro-phenyl, 3-trifluoromethoxy-phenyl, or 2,2-difluoro-1,3-benzodioxole).

In some embodiments, A is:

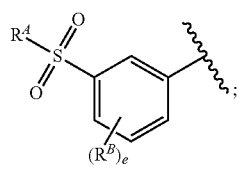

Formula Ia wherein e is 0, 1, 2, 3, or 4;

$R^A$ is hydrogen, hydroxyl, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_8$-$C_{12}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl; and each $R^B$ is independently hydroxyl, optionally substituted amino, halo, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_8$-$C_{12}$ cycloalkenyl, optionally substituted $C_4$-$C_{10}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl; or a prodrug thereof.

In other embodiments, $R^A$ is optionally substituted $C_1$-$C_6$ alkyl (e.g., methyl). In certain embodiments, e is 0. In some embodiments, e is 1 or 2. In other embodiments, each $R^B$ is halo (e.g., fluoro), optionally substituted $C_1$-$C_6$ alkyl (e.g., —CH₂OH, —CD₂OH, —CH₂CH₂OH, —C(CH₃)₂OH, —CH(CH₃)OH, —C(CF₃)₂OH, —CH(CF₃)OH, —CH₂OP(O)(OH)₂, —CH₂NH₂, or —CH₂NHC(O)CH₃), or optionally substituted $C_1$-$C_6$ acyl (e.g., —C(O)OH, —C(O)OCH₃, —C(O)CH₃, —C(O)NHCH₃, —C(O)NH₂, —C(O)N(CH₃)₂, —C(O)CF₃, or —C(O)H).

In some embodiments, A is:

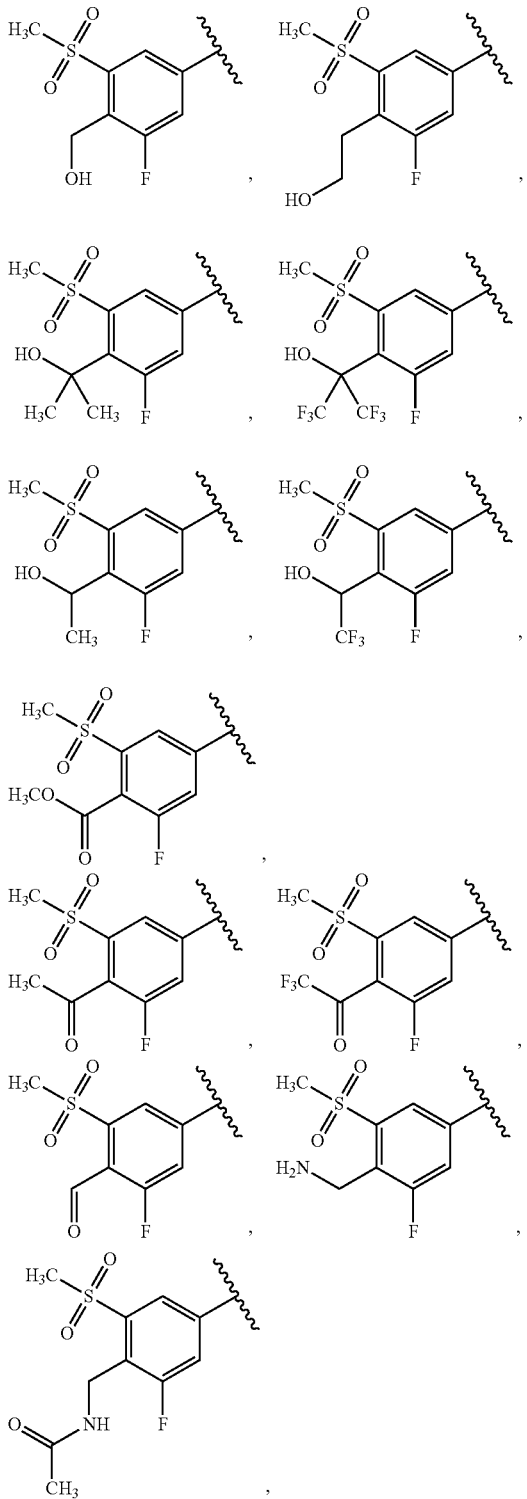

-continued

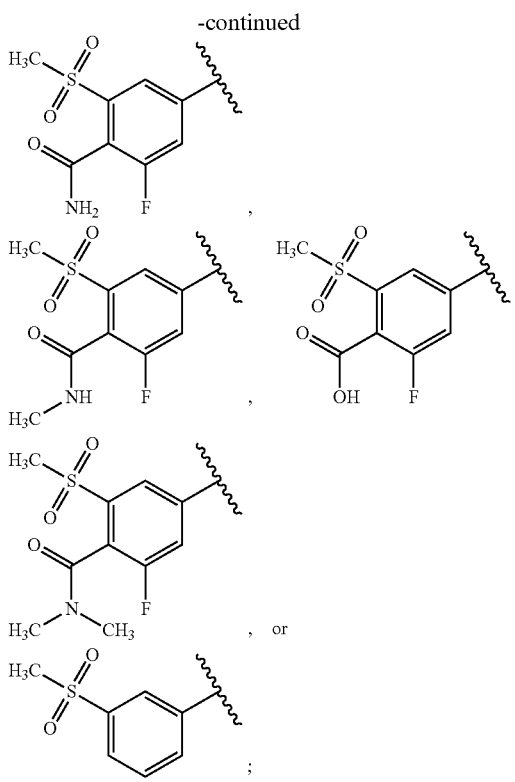

or a prodrug thereof.

In some embodiments, A is:

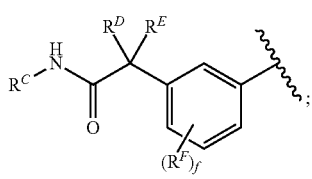

Formula Ib wherein f is 0, 1, 2, 3, or 4;

$R^C$ is hydrogen, hydroxyl, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_8$-$C_{12}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl;

$R^D$ and $R^E$ are independently hydrogen, hydroxy, optionally substituted amino, azido, halo, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_8$-$C_{12}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl; and each $R^F$ is independently hydroxyl, optionally substituted amino, halo, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_8$-$C_{12}$ cycloalkenyl, optionally substituted $C_4$-$C_{10}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl;

or a prodrug thereof.

In other embodiments, f is 0. In certain embodiments, $R^D$ is hydroxyl or optionally substituted $C_1$-$C_6$ heteroalkyl (e.g., —$SO_2$—$CH_3$). In some embodiments, $R^E$ is hydrogen, halo, or optionally substituted $C_1$-$C_6$ alkyl (e.g., methyl). In other embodiments, $R^F$ is hydrogen, halo, or optionally substituted $C_1$-$C_6$ alkyl (e.g., methyl).

In some embodiments, A is:

In some embodiments, A is:

Formula Ic wherein g is 0, 1, 2, 3, or 4;

$R^G$ is hydrogen, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_8$-$C_{12}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl; and each $R^H$ is independently hydroxyl, optionally substituted amino, halo, thiol, optionally substituted amino acid, optionally substituted C₁-C₆ acyl, optionally substituted C₁-C₆ alkyl, optionally substituted C₂-C₆ alkenyl, optionally substituted C₂-C₆ alkynyl, optionally substituted C₁-C₆ heteroalkyl, optionally substituted C₂-C₆ heteroalkenyl, optionally substituted C₂-C₆ heteroalkynyl, optionally substituted C₃-C₁₀ cycloalkyl, optionally substituted C₈-C₁₂ cycloalkenyl, optionally substituted C₄-C₁₀ cycloalkynyl, optionally substituted C₆-C₁₀ aryl, optionally substituted C₆-C₁₀ aryl C₁-C₆ alkyl, optionally substituted C₂-C₉ heteroaryl, optionally substituted C₂-C₉ heteroaryl C₁-C₆ alkyl, optionally substituted C₂-C₉ heterocyclyl, or optionally substituted C₂-C₉ heterocyclyl C₁-C₆ alkyl;

or a prodrug thereof.

In other embodiments, g is 0. In certain embodiments, R^H is hydrogen.

In some embodiments, A is:

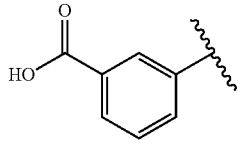

In some embodiments, A is:

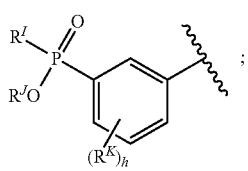

Formula Id wherein h is 0, 1, 2, 3, or 4;

R^I is hydrogen, hydroxyl, optionally substituted C₁-C₆ acyl, optionally substituted C₁-C₆ alkyl, optionally substituted C₂-C₆ alkenyl, optionally substituted C₂-C₆ alkynyl, optionally substituted C₁-C₆ heteroalkyl, optionally substituted C₂-C₆ heteroalkenyl, optionally substituted C₂-C₆ heteroalkynyl, optionally substituted C₃-C₁₀ cycloalkyl, optionally substituted C₄-C₁₀ cycloalkenyl, optionally substituted C₈-C₁₂ cycloalkynyl, optionally substituted C₆-C₁₀ aryl, optionally substituted C₆-C₁₀ aryl C₁-C₆ alkyl, optionally substituted C₂-C₉ heteroaryl, optionally substituted C₂-C₉ heteroaryl C₁-C₆ alkyl, optionally substituted C₂-C₉ heterocyclyl, or optionally substituted C₂-C₉ heterocyclyl C₁-C₆ alkyl;

R^J is independently hydrogen, optionally substituted C₁-C₆ acyl, optionally substituted C₁-C₆ alkyl, optionally substituted C₂-C₆ alkenyl, optionally substituted C₂-C₆ alkynyl, optionally substituted C₁-C₆ heteroalkyl, optionally substituted C₂-C₆ heteroalkenyl, optionally substituted C₂-C₆ heteroalkynyl, optionally substituted C₃-C₁₀ cycloalkyl, optionally substituted C₄-C₁₀ cycloalkenyl, optionally substituted C₈-C₁₂ cycloalkynyl, optionally substituted C₆-C₁₀ aryl, optionally substituted C₆-C₁₀ aryl C₁-C₆ alkyl, optionally substituted C₂-C₉ heteroaryl, optionally substituted C₂-C₉ heteroaryl C₁-C₆ alkyl, optionally substituted C₂-C₉ heterocyclyl, or optionally substituted C₂-C₉ heterocyclyl C₁-C₆ alkyl; or R^I and R^J combine to form an optionally substituted C₂-C₉ heterocyclyl; or R^J and R^K combine to form an optionally substituted C₂-C₉ heterocyclyl; and each R^K is independently hydroxyl, optionally substituted amino, halo, thiol, optionally substituted amino acid, optionally substituted C₁-C₆ acyl, optionally substituted C₁-C₆ alkyl, optionally substituted C₂-C₆ alkenyl, optionally substituted C₂-C₆ alkynyl, optionally substituted C₁-C₆ heteroalkyl, optionally substituted C₂-C₆ heteroalkenyl, optionally substituted C₂-C₆ heteroalkynyl, optionally substituted C₃-C₁₀ cycloalkyl, optionally substituted C₈-C₁₂ cycloalkenyl, optionally substituted C₄-C₁₀ cycloalkynyl, optionally substituted C₆-C₁₀ aryl, optionally substituted C₆-C₁₀ aryl C₁-C₆ alkyl, optionally substituted C₂-C₉ heteroaryl, optionally substituted C₂-C₉ heteroaryl C₁-C₆ alkyl, optionally substituted C₂-C₉ heterocyclyl, or optionally substituted C₂-C₉ heterocyclyl C₁-C₆ alkyl;

or a prodrug thereof.

In other embodiments, R^J is hydrogen or R^J and R^K combine to form an optionally substituted C₂-C₉ heterocyclyl. In certain embodiments, R^I is optionally substituted C₁-C₆ alkyl (e.g., methyl). In some embodiments, h is 0. In other embodiments, h is 1. In certain embodiments, R^K is optionally substituted C₁-C₆ alkyl (e.g., 13 CH₂OH) or R^J and R^K combine to form an optionally substituted C₂-C₉ heterocyclyl (e.g., A is

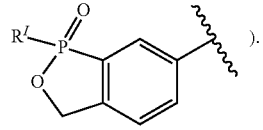

).

In some embodiments, A is:

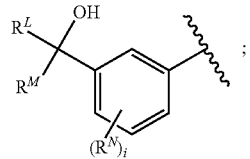

Formula Ie wherein i is 0, 1, 2, 3, or 4;

R^L and R^M are independently hydrogen, hydroxyl, optionally substituted C₁-C₆ acyl, optionally substituted C₁-C₆ alkyl, optionally substituted C₂-C₆ alkenyl, optionally substituted C₂-C₆ alkynyl, optionally substituted C₁-C₆ heteroalkyl, optionally substituted C₂-C₆ heteroalkenyl, optionally substituted C₂-C₆ heteroalkynyl, optionally substituted C₃-C₁₀ cycloalkyl, optionally substituted C₄-C₁₀ cycloalkenyl, optionally substituted C₈-C₁₂ cycloalkynyl, optionally substituted C₆-C₁₀ aryl, optionally substituted C₆-C₁₀ aryl C₁-C₆ alkyl, optionally substituted C₂-C₉ heteroaryl, optionally substituted C₂-C₉ heteroaryl C₁-C₆ alkyl, optionally substituted C₂-C₉ heterocyclyl, or optionally substituted C₂-C₉ heterocyclyl C₁-C₆ alkyl; and each R^N is independently hydroxyl, optionally substituted amino, halo, thiol, optionally substituted amino acid, optionally substituted C₁-C₆ acyl, optionally substituted C₁-C₆ alkyl, optionally substituted C₂-C₆ alkenyl, optionally substituted C₂-C₆ alkynyl, optionally substituted C₁-C₆ heteroalkyl, optionally substituted C₂-C₆ heteroalkenyl, optionally substituted C₂-C₆ heteroalkynyl, optionally substituted C₃-C₁₀ cycloalkyl, optionally substituted C₈-C₁₂ cycloalkenyl, optionally substituted C₄-C₁₀ cycloalkynyl, optionally substituted C₆-C₁₀ aryl, optionally substituted C₆-C₁₀ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl; or a prodrug thereof.

In other embodiments, i is 0. In certain embodiments, $R^L$ is hydrogen or optionally substituted $C_1$-$C_6$ alkyl (e.g., methyl or trifluoromethyl). In some embodiments, $R^M$ is hydrogen or optionally substituted $C_1$-$C_6$ alkyl (e.g., methyl or trifluoromethyl).

In some embodiments, A is:

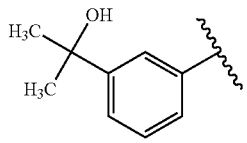

In some embodiments, A is:

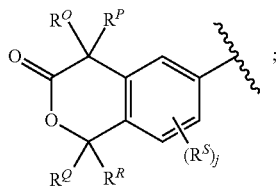

Formula If wherein j is 0, 1, 2, or 3;

$R^O$, $R^P$, $R^Q$, and $R^R$ are independently hydrogen, hydroxyl, optionally substituted amino, azido, halo, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_9$-$C_{12}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl; and each $R^S$ is independently hydroxyl, optionally substituted amino, halo, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_8$-$C_{12}$ cycloalkenyl, optionally substituted $C_4$-$C_{10}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl;

or a prodrug thereof.

In other embodiments, j is 0. In certain embodiments, $R^O$ is hydrogen, halo, or optionally substituted $C_1$-$C_6$ alkyl. In some embodiments, $R^P$ is hydrogen, halo, or optionally substituted $C_1$-$C_6$ alkyl. In other embodiments, $R^Q$ is hydrogen. In certain embodiments, $R^R$ is hydrogen.

In certain embodiments, A is:

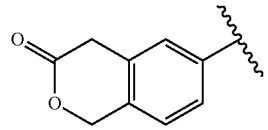

In some embodiments, A is:

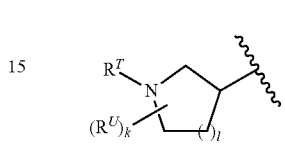

Formula Ig wherein k is 0, 1, 2, 3, 4, 5, 6, 7, or 8;

l is 0, 1, or 2;

$R^T$ is hydrogen, hydroxyl, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_9$-$C_{12}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl;

each $R^u$ is independently hydroxyl, oxo, optionally substituted amino, halo, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_9$-$C_{12}$ cycloalkenyl, optionally substituted $C_4$-$C_{10}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl; and or a prodrug thereof.

In certain embodiments, k is 0. In certain embodiments, l is 0. In some embodiments, l is 1. In certain embodiments, l is 2. In other embodiments, $R^T$ is optionally substituted $C_1$-$C_6$ alkyl (e.g., —$CH_2CO_2H$ or

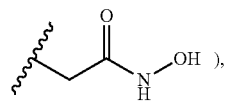

), or, optionally substituted $C_1$-$C_6$ heteroalkyl (e.g., —$SO_2$—$CH_3$).

In other embodiments, k is 0. In certain embodiments, k is 1. In some embodiments, $R^U$ is optionally substituted $C_1$-$C_6$ acyl (e.g., —$CO_2H$) or optionally substituted $C_1$-$C_6$ alkyl (e.g., —$CH_2OH$). In some embodiments, l is 0. In other embodiments, l is 1. In certain embodiments, l is 2.

In some embodiments, A is:

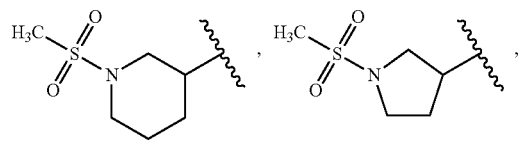

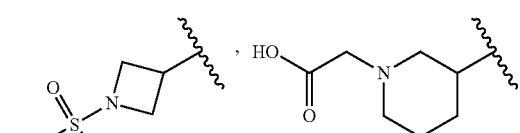

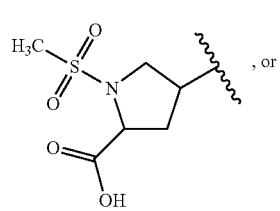

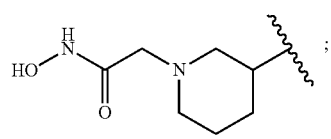

or a prodrug thereof.

In some embodiments, the compound is a prodrug, or a pharmaceutically acceptable salt of a prodrug (e.g., A includes an —OR$^V$ group, wherein R$^V$ is:

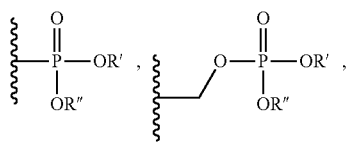

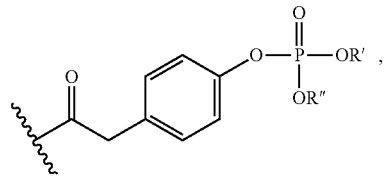

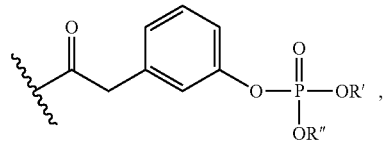

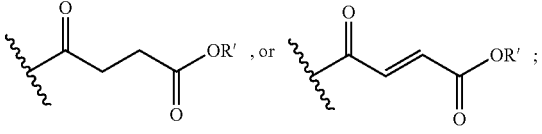

wherein each R' and R" is independently hydrogen, optionally substituted $C_1$-$C_6$ alkyl, such as methyl or t-butyl, or optionally substituted $C_6$-$C_{10}$ aryl $C_1$-$C_6$ alkyl, such as benzyl).

In some embodiments A is:

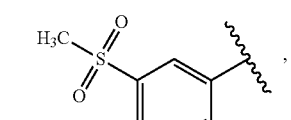

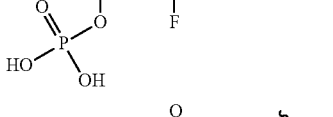

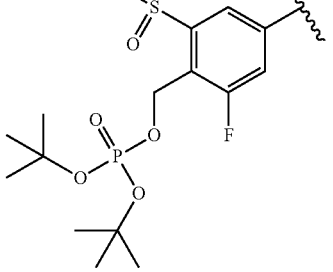

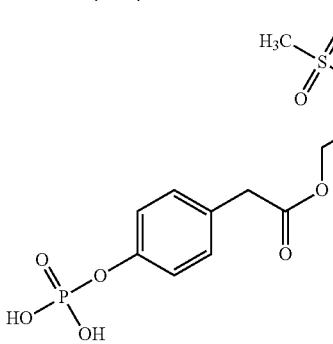

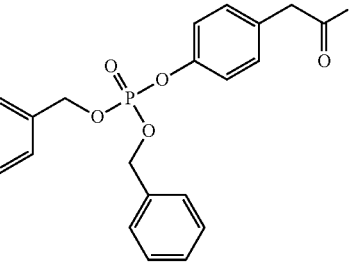

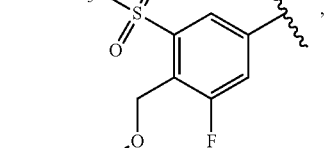

-continued
In some embodiments, the compound has the structure:
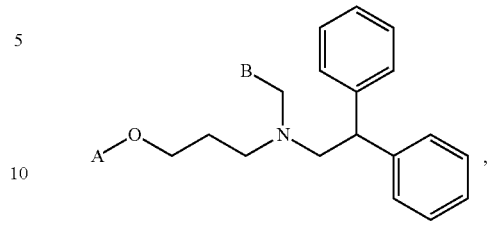
,
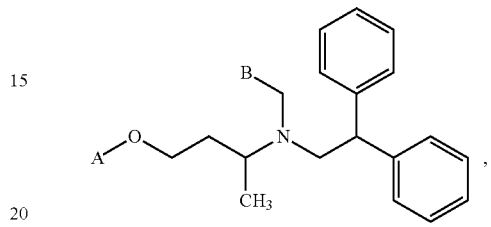
,
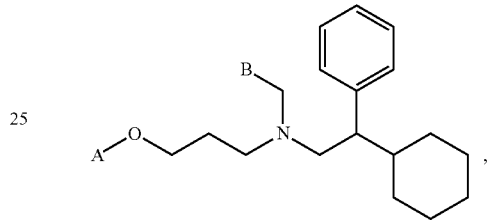
,
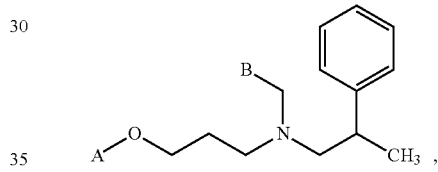
,
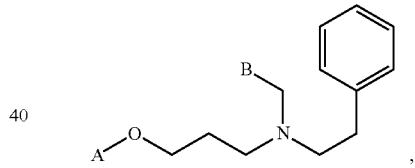
,
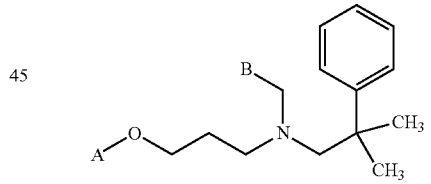
,
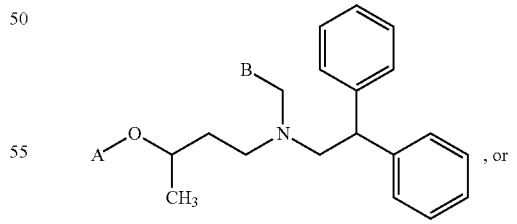
, or
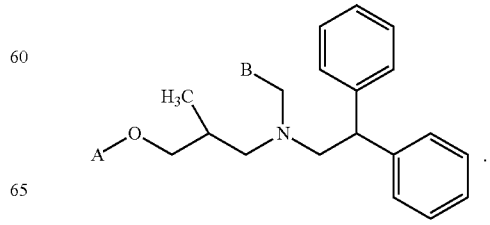
.

In some embodiments, the compound has the structure:

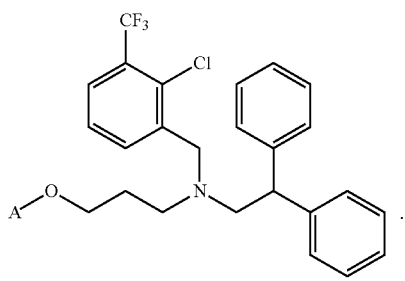

In certain embodiments, the compound has the structure:

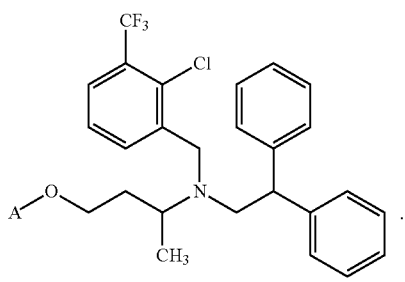

In certain embodiments, the compound has the structure:

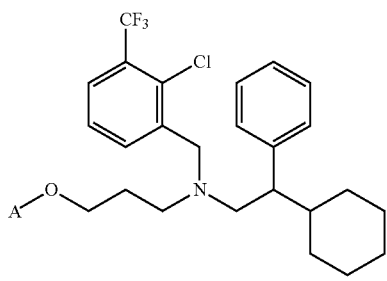

In some embodiments, the compound has the structure:

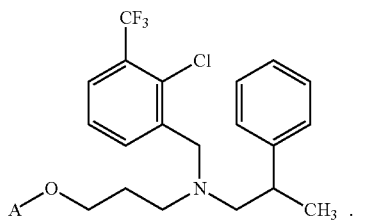

In certain embodiments, the compound has the structure:

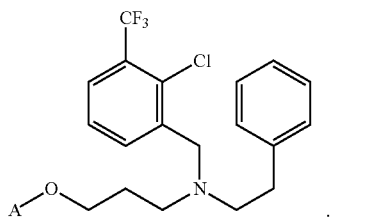

In some embodiments, the compound has the structure:

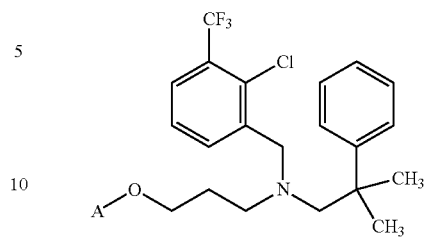

In some embodiments, the compound has the structure:

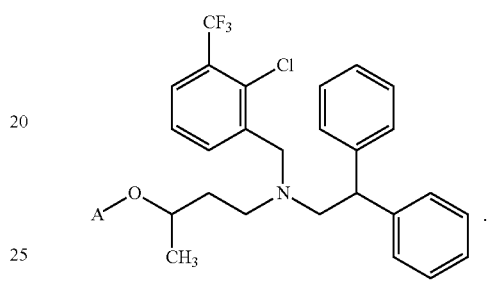

In certain embodiments, the compound has the structure:

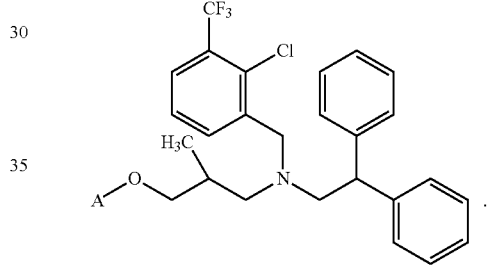

In another aspect, the invention features a compound selected from any one of compounds 1 to 97 of Table 1:

TABLE 1

Exemplary Compounds of the Invention

| # | Structure |
|---|---|
| 1 | 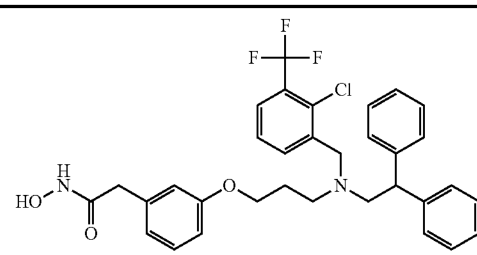 |
| 2 | 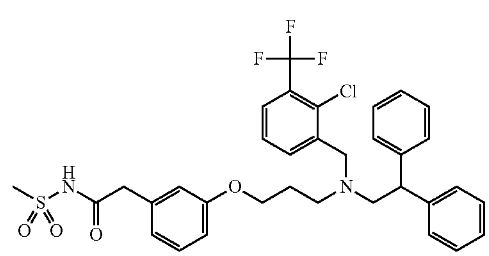 [SMILES: CS(=O)(=O)NC(=O)Cc1cccc(OCCCN(Cc2cccc(C(F)(F)F)c2Cl)CC(c2ccccc2)c2ccccc2)c1] |

TABLE 1-continued

Exemplary Compounds of the Invention

| # | Structure |
|---|---|
| 3 | (structure) |
| 4 | (structure) |
| 5 | (structure) |
| 6 | (structure) |
| 7 | (structure) |
| 8 | (structure) |
| 9 | (structure) |
| 10 | (structure) |
| 11 | (structure) |
| 12 | (structure) |
| 13 | (structure) |

TABLE 1-continued

Exemplary Compounds of the Invention

| # | Structure |
|---|---|
| 14 | 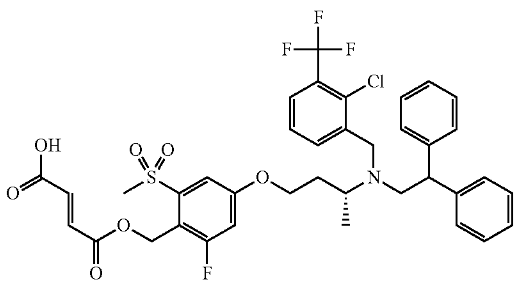 [SMILES: C[C@H](CCOc1cc(F)c(COC(=O)/C=C/C(=O)O)c(S(C)(=O)=O)c1)N(Cc1cccc(C(F)(F)F)c1Cl)CC(c1ccccc1)c1ccccc1] |
| 15 | 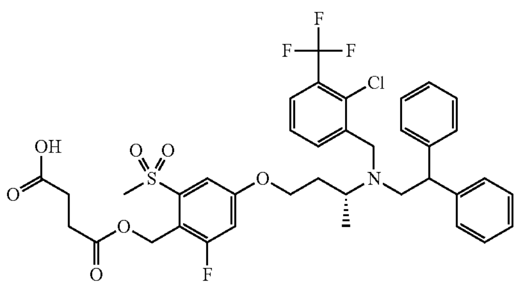 |
| 16 | 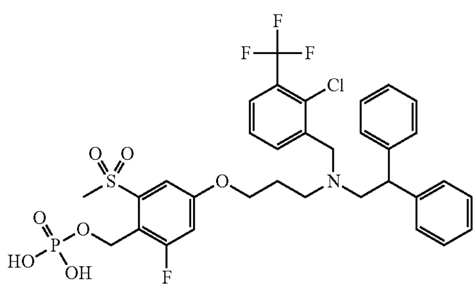 [SMILES: CS(=O)(=O)c1cc(OCCCN(Cc2cccc(C(F)(F)F)c2Cl)CC(c2ccccc2)c2ccccc2)cc(F)c1COP(=O)(O)O] |
| 17 | 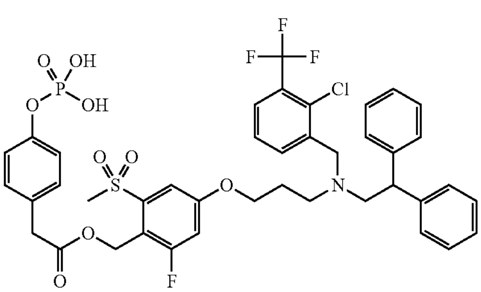 [SMILES: CS(=O)(=O)c1cc(OCCCN(Cc2cccc(C(F)(F)F)c2Cl)CC(c2ccccc2)c2ccccc2)cc(F)c1COC(=O)Cc1ccc(OP(=O)(O)O)cc1] |
| 18 | 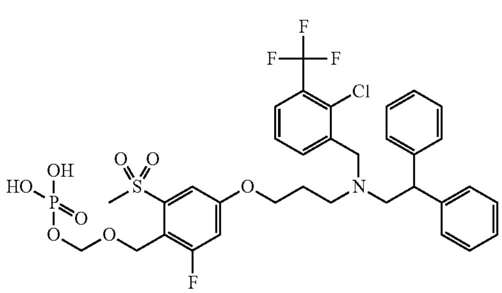 [SMILES: CS(=O)(=O)c1cc(OCCCN(Cc2cccc(C(F)(F)F)c2Cl)CC(c2ccccc2)c2ccccc2)cc(F)c1COCOP(=O)(O)O] |
| 19 | |
| 20 | |
| 21 | |
| 22 | |
| 23 | |

TABLE 1-continued

Exemplary Compounds of the Invention

| # | Structure |
|---|---|
| 24 | 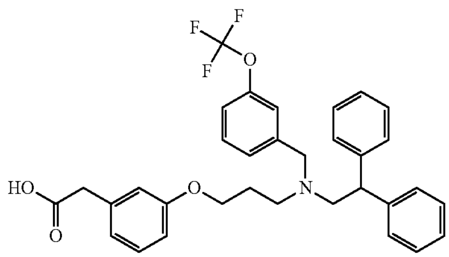 [SMILES: O=C(O)Cc1cccc(OCCCN(Cc2cccc(OC(F)(F)F)c2)CC(c2ccccc2)c2ccccc2)c1] |
| 25 | 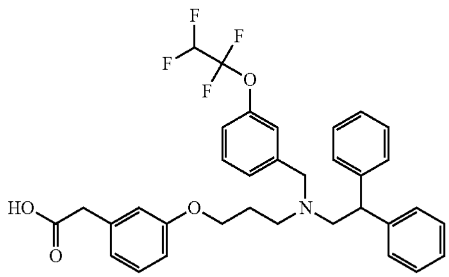 [SMILES: O=C(O)Cc1cccc(OCCCN(Cc2cccc(OC(F)(F)C(F)F)c2)CC(c2ccccc2)c2ccccc2)c1] |
| 26 | 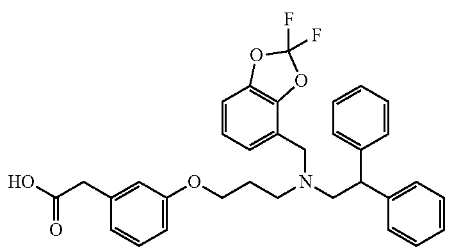 [SMILES: O=C(O)Cc1cccc(OCCCN(Cc2cccc3c2OC(F)(F)O3)CC(c2ccccc2)c2ccccc2)c1] |
| 27 | 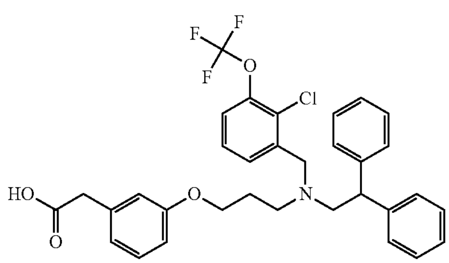 [SMILES: O=C(O)Cc1cccc(OCCCN(Cc2cccc(OC(F)(F)F)c2Cl)CC(c2ccccc2)c2ccccc2)c1] |
| 28 | 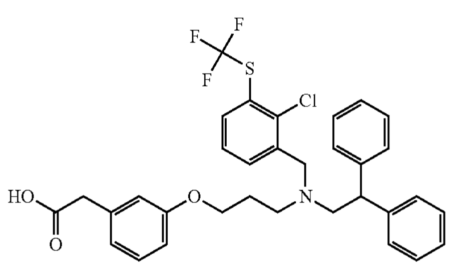 [SMILES: O=C(O)Cc1cccc(OCCCN(Cc2cccc(SC(F)(F)F)c2Cl)CC(c2ccccc2)c2ccccc2)c1] |
| 29 | 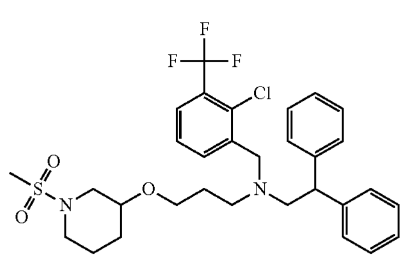 [SMILES: CS(=O)(=O)N1CCCC(OCCCN(Cc2cccc(C(F)(F)F)c2Cl)CC(c2ccccc2)c2ccccc2)C1] |
| 30 | |
| 31 | |
| 32 | |
| 33 | |
| 34 | |

TABLE 1-continued

Exemplary Compounds of the Invention

| # | Structure |
|---|---|
| 35 | (structure) |
| 36 | (structure) |
| 37 | (structure) |
| 38 | (structure) |
| 39 | (structure) |
| 40 | (structure) |
| 42 | (structure) |
| 43 | (structure) |
| 44 | (structure) |
| 45 | (structure) |

TABLE 1-continued

Exemplary Compounds of the Invention

| # | Structure |
|---|---|
| 59 | (chemical structure) |
| 60 | (chemical structure) |
| 61 | (chemical structure) |
| 62 | (chemical structure) |
| 63 | (chemical structure) |
| 64 | (chemical structure) |
| 65 | (chemical structure) |
| 66 | (chemical structure) |
| 67 | (chemical structure) |
| 68 | (chemical structure) |
| 69 | (chemical structure) |

TABLE 1-continued

Exemplary Compounds of the Invention

| # | Structure |
|---|---|
| 70 | (structure) |
| 71 | (structure) |
| 72 | (structure) |
| 73 | (structure) |
| 74 | (structure) |
| 75 | (structure) |
| 77 | (structure) |
| 78 | (structure) |
| 79 | (structure) |
| 80 | (structure) |

TABLE 1-continued

Exemplary Compounds of the Invention

| # | Structure |
|---|---|
| 81 | (structure) |
| 82 | (structure) |
| 83 | (structure) |
| 84 | (structure) |
| 85 | (structure) |
| 87 | (structure) |
| 88 | (structure) |
| 89 | (structure) |
| 90 | (structure) |
| 91 | (structure) |
| 92 | (structure) |

TABLE 1-continued

Exemplary Compounds of the Invention

| # | Structure |
|---|---|
| 93 | (structure) |
| 94 | (structure) |
| 95 | (structure) |
| 96 | (structure) |
| 97 | (structure) |

In another aspect, the invention features a compound have the structure of any compound described herein, (e.g., any one of compounds 1 to 680.

In another aspect, the invention features a method of treating cancer. This method includes: administering an effective amount (e.g., an amount sufficient to increase the expression level or activity level of ApoE to a level sufficient to slow the spread of metastasis of the cancer) a compound described herein or a pharmaceutically acceptable salt thereof to a subject in need thereof.

In another aspect, the invention features another method of treating cancer in a subject in need thereof. This method includes contacting cells (e.g., cancer cells and/or healthy cells) in the subject with a compound described herein or a pharmaceutically acceptable salt thereof, In another aspect, the invention features a method of slowing the spread of a migrating cancer. This method includes administering an effective amount of a compound described herein or a pharmaceutically acceptable salt thereof to a subject in need thereof.

In another aspect, the invention features a method for inhibiting proliferation or growth of cancer stem cells or cancer initiating cells. This method includes contacting a cell with an effective amount of a compound described herein or a pharmaceutically acceptable salt thereof.

In another aspect, the invention features a method for reducing the rate of tumor seeding of a cancer. This method includes administering an effective amount of a compound described herein or a pharmaceutically acceptable salt thereof to a subject in need thereof.

In another aspect, the invention features a method of reducing or treating metastatic nodule-forming of cancer. This method includes administering an effective amount of a compound described herein or a pharmaceutically acceptable salt thereof to a subject in need thereof.

In some embodiments of any of the foregoing methods, the cancer is a drug resistant cancer or has failed to respond to a prior therapy (e.g., a cancer resistant to, or a cancer that has failed to respond to prior treatment with, vemurafenib, dacarbazine, a CTLA4 inhibitor, a PD1 inhibitor, interferon therapy, a BRAF inhibitor, a MEK inhibitor, radiotherapy, temozolimide, irinotecan, a CAR-T therapy, herceptin, perjeta, tamoxifen, xeloda, docetaxol, platinum agents such as carboplatin, taxanes such as paclitaxel and docetaxel, ALK inhibitors, MET inihibitors, alimta, abraxane, adriamycin, gemcitabine, avastin, halaven, neratinib, a PARP inhibitor, ARN810, an mTOR inhibitor, topotecan, gemzar, a VEGFR2 inhibitor, a folate receptor antagonist, demcizumab, fosbretabulin, or a PDL1 inhibitor).

In other embodiments of any of the foregoing methods, the cancer is metastatic. The cancer can include cells exhibiting migration and/or invasion of migrating cells and/or include cells exhibiting endothelial recruitment and/or angiogenesis. In other embodiments, the cancer is a cell migration cancer. In still other embodiments, the cell migration cancer is a non-metastatic cell migration cancer.

The cancer can be a cancer spread via seeding the surface of the peritoneal, pleural, pericardial, or subarachnoid spaces. Alternatively, the cancer can be a cancer spread via the lymphatic system, or a cancer spread hematogenously.

In particular embodiments, the cancer is a cell migration cancer that is a non-metastatic cell migration cancer, such as ovarian cancer, mesothelioma, or primary lung cancer.

In certain embodiments, the compound increases the expression level of ApoE at least 2.5-fold in vitro. In certain embodiments, the compound is selective for LXRβ over LXRα. In other embodiments, the compound has activity for LXRβ that is at least 2.5-fold greater than the activity of said compound for LXRα. In some embodiments, the compound has activity for LXRβ that is at least 10-fold greater than the activity of said compound for LXRα. In further embodiments, the compound has activity for LXRβ that is at least 100-fold greater than the activity of said compound for LXRα. In certain embodiments, the compound has activity for LXRβ that is at least within 2.5-fold of the activity of said compound for LXRα.

In certain embodiments, of any of the foregoing methods, the cancer includes cells which express LRP1.

In other embodiments of any of the foregoing methods, the cancer is breast cancer, colon cancer, renal cell cancer, non-small cell lung cancer, hepatocellular carcinoma, gastric cancer, ovarian cancer, pancreatic cancer, esophageal cancer, prostate cancer, sarcoma, glioblastoma, diffuse large B-cell lymphoma, leukemia (e.g., acute myeloid leukemia), multiple myeloma, or melanoma. In some embodiments of any of the foregoing methods, the cancer is melanoma. In other embodiments of any of the foregoing methods, the cancer is breast cancer. In certain embodiments of any of the foregoing methods, the cancer is renal cell cancer. In further embodiments of any of the foregoing methods, the cancer is pancreatic cancer. In other embodiments of any of the foregoing methods, the cancer is non-small cell lung cancer. In some embodiments of any of the foregoing methods, the cancer is colon cancer. In further embodiments of any of the foregoing methods, the cancer is ovarian cancer. In other embodiments of any of the foregoing methods, the cancer is glioblastoma. In some embodiments, the cancer is breast cancer. In other embodiments, the cancer is prostate cancer. In certain embodiments, the cancer is diffuse large B-cell lymphoma. In some embodiments, the cancer is leukemia (e.g., acute myeloid leukemia). In some embodiments, the cancer is multiple myeloma.

In some embodiments, the cancer is melanoma that is resistant to, or has failed to respond to prior treatment with, vemurafenib, dacarbazine, interferon therapy, a CTLA-4 inhibitor, a BRAF inhibitor, a MEK inhibitor, a PD1 inhibitor, a PDL-1 inhibitor, or a CAR-T therapy. In other embodiments, the cancer is glioblastoma that is resistant to, or has failed to respond to prior treatment with, temozolimide, radiotherapy, avastin, irinotecan, a VEGFR2 inhibitor, a CAR-T therapy, or an mTOR inhibitor. In certain embodiments, the cancer is non-small cell lung cancer that is resistant to, or has failed to respond to prior treatment with, an EGFR inhibitor, platinum agents (e.g., carboplatin), avastin, an ALK inhibitor, a MET inhibitor, a taxane (e.g., paclitaxel or doceltaxel), gemzar, alimta, radiotherapy, a PD1 inhibitor, a PDL1 inhibitor, or a CAR-T therapy. In some embodiments, the cancer is a breast cancer that is resistant to, or has failed to respond to prior treatment with, herceptin, perjeta, tamoxifen, xeloda, docetaxel, carboplatin, paclitaxel, abraxane, adriamycin, gemcitabine, avastin, halaven, neratinib, a PARP inhibitor, a PD1 inhibitor, a PDL1 inhibitor, a CAR-T therapy, ARN810, or an mTOR inhibitor. In other embodiments, the cancer is ovarian cancer that is resistant to, or has failed to respond to prior treatment with, a PARP inhibitor, avastin, carboplatin, paclitaxel, docetaxel, topotecan, gemzar, a VEGR2 inhibitor, a folate receptor antagonist, a PD1 inhibitor, a PDL1 inhibitor, a CAR-T therapy, demcizumab, or fosbretabulin.

In another aspect, the invention features a method of treating inflammation, cardiovascular disease, diabetes, or atherosclerosis (e.g., by increasing reverse cholesterol transport, inhibiting cholesterol absorption, or decreasing inflammation), including administering to a subject in need thereof, any of the foregoing compounds.

In another aspect, the invention features a method of treating an angiogenic disorder, including administering to a subject in need thereof, any of the foregoing compounds.

In some embodiments, the angiogenic disorder is cancer (e.g., vascularized tumors) or metastasis of cancer, chronic inflammatory illnesses (e.g., rheumatoid arthritis), inflammatory bowel disease (e.g., Crohn's disease or ulcerative colitis)), diabetic retinopathy, chronic radiation-induced proctitis, peripheral vascular disease (e.g., atherosclerosis, thromboembolic disease, Buerger's disease (thromboangiitis obliterans)), cardiovascular disease (e.g., atherosclerosis, heart disease, myocardial infarction, or coronary artery disease), tissue organ engraftment rejection, macular degeneration, or sequelae of ischemic reperfusion injury.

In another aspect, the invention features a method of treating dementia (e.g., Alzheimer's disease), including administering to a subject in need thereof, any of the foregoing compounds.

A number of other disorders or conditions can be treated with the above-described compounds. Examples include arthritis, psoriasis, Grave's disease, vascular restenosis (including restenosis following angioplasty), arteriovenous malformations (AVM), meningioma, hemangioma, neovascular glaucoma, chronic kidney disease, diabetic nephropathy, polycystic kidney disease, interstitial lung disease, pulmonary hypertension, chronic obstructive pulmonary disease (COPD), emphysema, autoimmune hepatitis, chronic inflammatory liver disease, hepatic cirrhosis, rosacea, angiofibroma, atherosclerotic plaques, corneal graft neovascularization, hemophilic joints, hypertrophic scars, Osler-Weber syndrome, pyogenic granuloma retrolental fibroplasia, scleroderma, trachoma, vascular adhesions, synovitis, dermatitis, and endometriosis.

In some embodiments of any of the foregoing methods, the method further includes administration of an additional anticancer therapy (e.g., an antiproliferative). In other embodiments, the additional anticancer therapy is any one of the antiproliferatives listed in Table 3.

In some embodiments, the antiproliferative and compound of the invention are administered within 28 days of each (e.g., within 21, 14, 10, 7, 5, 4, 3, 2, or 1 days) or within 24 hours (e.g., 12, 6, 3, 2, or 1 hours; or concomitantly) other in amounts that together are effective to treat the subject. In certain embodiments, the antiproliferative is: a chemotherapeutic or cytotoxic agent, a differentiation-inducing agent (e.g. retinoic acid, vitamin D, cytokines), a hormonal agent, an immunological agent, or an anti-angiogenic agent. Chemotherapeutic and cytotoxic agents include, but are not limited to, alkylating agents, cytotoxic antibiotics, antimetabolites, vinca alkaloids, etoposides, and others (e.g., paclitaxel, taxol, docetaxel, taxotere, cis-platinum). A list of additional compounds having antiproliferative activity can be found in L. Brunton, B. Chabner and B. Knollman (eds). Goodman and Gilman's The Pharmacological Basis of Therapeutics, Twelfth Edition, 2011, McGraw Hill Companies, New York, N.Y.

In other embodiments, the antiproliferative is a PD1 inhibitor, a VEGF inhibitor, a VEGFR2 inhibitor, a PDL1 inhibitor, a BRAF inhibitor, a CTLA-4 inhibitor, a MEK inhibitor, an ERK inhibitor, vemurafenib, dacarbazine, trametinib, dabrafenib, MEDI-4736, an mTOR inhibitor, a CAR-T therapy, abiraterone, enzalutamine, ARN-509, 5-FU, FOLFOX, FOLFIRI, herceptin, xeloda, a PD1 antibody (e.g., pembrolizumab or nivolumab), a PDL-1 antibody, a CTLA-4 antibody (e.g, ipilimumab), ramucirumab, rindopepimut, glembatumumab, vedotin, ANG1005, and/or ANG4043.

In some embodiments, the cancer is a renal cell carcinoma and the antiproliferative is a PD1 inhibitor, a PDL-1 inhibitor, or an mTOR inhibitor. In other embodiments, the cancer is diffuse large B-cell lymphoma and the antiproliferative is a CAR-T therapy. In certain embodiments, the cancer is prostate cancer and the antiproliferative is abiraterone, enzalutamide, or ARN-509. In some embodiments, the cancer is hepatocellular carcinoma, gastric cancer, or esophageal cancer and the antiproliferative is 5-FU, FOLFOX, FOLFIRI, herceptin, or xeloda. In some embodiments, the cancer is sarcoma and the antiproliferative is gemcitabine. In other embodiments, the cancer is pancreatic cancer and the antiproliferative is irinotecan, cisplatin, abraxane, a taxane (e.g., paclitaxel or docetaxel), or capecitabine.

The method may further include administering an antiproliferative selected from the group consisting of alkylating agents, platinum agents, antimetabolites, topoisomerase inhibitors, antitumor antibiotics, antimitotic agents, aromatase inhibitors, thymidylate synthase inhibitors, DNA antagonists, farnesyltransferase inhibitors, pump inhibitors, histone acetyltransferase inhibitors, metalloproteinase inhibitors, ribonucleoside reductase inhibitors, TNF alpha agonists/antagonists, endothelin A receptor antagonist, retinoic acid receptor agonists, immuno-modulators, hormonal and antihormonal agents, photodynamic agents, tyrosine kinase inhibitors, antisense compounds, corticosteroids, HSP90 inhibitors, proteosome inhibitors (for example, NPI-0052), CD40 inhibitors, anti-CSI antibodies, FGFR3 inhibitors, VEGF inhibitors, MEK inhibitors, cyclin D1 inhibitors, NF-kB inhibitors, anthracyclines, histone deacetylases, kinesin inhibitors, phosphatase inhibitors, COX2 inhibitors, mTOR inhibitors, calcineurin antagonists, IMiDs, or other agents used to treat proliferative diseases. Examples of such compounds are provided in Tables 3.

In another aspect, the invention features a method of treating a dermal disease, disorder, or condition (e.g., skin aging, scarring, psoriasis, atopic dermatitis, eczema, urticaria, rosacea, burns, or acne) including administering an effective amount of a compound of the invention, or pharmaceutically acceptable salts thereof to a subject in need thereof.

In another aspect, the invention features a method of treating a neurological disorder (e.g., Alzheimers disease) including administering an effective amount of a compound of the invention, or pharmaceutically acceptable salts thereof to a subject in need thereof.

In some embodiments of any of the foregoing methods, administering comprises contacting a cell with an effective amount of a compound described herein.

Chemical Terms

As used herein, the term "compound," is meant to include all stereoisomers, geometric isomers, tautomers, and isotopes of the structures depicted.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins and C=N double bonds can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds of the present disclosure also include tautomeric forms. Tautomeric forms result from the swapping of a single bond with an adjacent double bond and the concomitant migration of a proton. Tautomeric forms include prototropic tautomers which are isomeric protonation states having the same empirical formula and total charge. Examples prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the present disclosure also include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

The compounds and salts of the present disclosure can be prepared in combination with solvent or water molecules to form solvates and hydrates by routine methods.

At various places in the present specification, substituents of compounds of the present disclosure are disclosed in groups or in ranges. It is specifically intended that the present disclosure include each and every individual sub-combination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl. Herein a phrase of the form "optionally substituted X" (e.g., optionally substituted alkyl) is intended to be equivalent to "X, wherein X is optionally substituted" (e.g., "alkyl, wherein the alkyl is optionally substituted"). It is not intended to mean that the feature "X" (e.g., alkyl) per se is optional.

The term "acyl," as used herein, represents a hydrogen or an alkyl group (e.g., a haloalkyl group), as defined herein, that is attached to the parent molecular group through a carbonyl group, as defined herein, and is exemplified by formyl (i.e., a carboxyaldehyde group), acetyl, trifluoroacetyl, propionyl, and butanoyl. Exemplary unsubstituted acyl groups include from 1 to 7, from 1 to 11, or from 1 to 21 carbons. In some embodiments, the alkyl group is further substituted with 1, 2, 3, or 4 substituents as described herein.

Non-limiting examples of optionally substituted acyl groups include, alkoxycarbonyl, alkoxycarbonylacyl, arylalkoxycarbonyl, aryloyl, carbamoyl, carboxyaldehyde, (heterocyclyl) imino, and (heterocyclyl)oyl:

The "alkoxycarbonyl" group, which as used herein, represents an alkoxy, as defined herein, attached to the parent molecular group through a carbonyl atom (e.g., —C(O)—OR, where R is H or an optionally substituted $C_{1-6}$, $C_{1-10}$, or $C_{1-20}$ alkyl group). Exemplary unsubstituted alkoxycarbonyl include from 1 to 21 carbons (e.g., from 1 to 11 or from 1 to 7 carbons). In some embodiments, the alkoxy group is further substituted with 1, 2, 3, or 4 substituents as described herein.

The "alkoxycarbonylacyl" group, which as used herein, represents an acyl group, as defined herein, that is substituted with an alkoxycarbonyl group, as defined herein (e.g., —C(O)-alkyl-C(O)—OR, where R is an optionally substituted $C_{1-6}$, $C_{1-10}$, or $C_{1-20}$ alkyl group). Exemplary unsubstituted alkoxycarbonylacyl include from 3 to 41 carbons (e.g., from 3 to 10, from 3 to 13, from 3 to 17, from 3 to 21, or from 3 to 31 carbons, such as $C_{1-6}$ alkoxycarbonyl-$C_{1-6}$ acyl, $C_{1-10}$ alkoxycarbonyl-$C_{1-10}$ acyl, or $C_{1-20}$ alkoxycarbonyl-$C_{1-20}$ acyl). In some embodiments, each alkoxy and alkyl group is further independently substituted with 1, 2, 3, or 4 substituents, as described herein (e.g., a hydroxy group) for each group.

The "arylalkoxycarbonyl" group, which as used herein, represents an arylalkoxy group, as defined herein, attached to the parent molecular group through a carbonyl (e.g., —C(O)—O-alkyl-aryl). Exemplary unsubstituted arylalkoxy groups include from 8 to 31 carbons (e.g., from 8 to 17 or from 8 to 21 carbons, such as $C_{6-10}$ aryl-$C_{1-6}$ alkoxycarbonyl, $C_{6-10}$ aryl-$C_{1-10}$ alkoxy-carbonyl, or $C_{6-10}$ aryl-$C_{1-20}$ alkoxy-carbonyl). In some embodiments, the arylalkoxycarbonyl group can be substituted with 1, 2, 3, or 4 substituents as defined herein.

The "aryloyl" group, which as used herein, represents an aryl group, as defined herein, that is attached to the parent molecular group through a carbonyl group. Exemplary unsubstituted aryloyl groups are of 7 to 11 carbons. In some embodiments, the aryl group can be substituted with 1, 2, 3, or 4 substituents as defined herein.

The "carbamoyl" group, which as used herein, represents —C(O)—N($R^{N1}$)$_2$, where the meaning of each $R^{N1}$ is found in the definition of "amino" provided herein.

The "carboxyaldehyde" group, which as used herein, represents an acyl group having the structure —CHO.

The "(heterocyclyl) imino" group, which as used herein, represents a heterocyclyl group, as defined herein, attached to the parent molecular group through an imino group. In some embodiments, the heterocyclyl group can be substituted with 1, 2, 3, or 4 substituent groups as defined herein.

The "(heterocyclyl)oyl" group, which as used herein, represents a heterocyclyl group, as defined herein, attached to the parent molecular group through a carbonyl group. In some embodiments, the heterocyclyl group can be substituted with 1, 2, 3, or 4 substituent groups as defined herein.

The term "alkyl," as used herein, is inclusive of both straight chain and branched chain saturated groups from 1 to 20 carbons (e.g., from 1 to 10 or from 1 to 6), unless otherwise specified. Alkyl groups are exemplified by methyl, ethyl, n- and iso-propyl, n-, sec-, iso- and tert-butyl, and neopentyl, and may be optionally substituted with one, two, three, or, in the case of alkyl groups of two carbons or more, four substituents independently selected from the group consisting of: (1) $C_{1-6}$ alkoxy; (2) $C_{1-6}$ alkylsulfinyl; (3) amino, as defined herein (e.g., unsubstituted amino (i.e., —NH$_2$) or a substituted amino (i.e., —N($R^{N1}$)$_2$, where $R^{N1}$ is as defined for amino); (4) $C_{6-10}$ aryl-$C_{1-6}$ alkoxy; (5) azido; (6) halo; (7) ($C_{2-9}$ heterocyclyl)oxy; (8) hydroxy, optionally substituted with an O-protecting group; (9) nitro; (10) oxo (e.g., carboxyaldehyde or acyl); (11) $C_{1-7}$ spirocyclyl; (12) thioalkoxy; (13) thiol; (14) —CO$_2$$R^{A'}$, optionally substituted with an O-protecting group and where $R^{A'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (15) —C(O)NR$^{B'}$R$^{C'}$, where each of R$^{B'}$ and R$^{D'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (16) —SO$_2$R$^{D'}$, where R$^{D'}$ is selected from the group consisting of (a) $C_{1-6}$ alkyl, (b) $C_{6-10}$ aryl, (c) $C_{1-6}$ alk-$C_{6-10}$ aryl, and (d) hydroxy; (17)-SO$_2$NR$^{E'}$R$^{F'}$, where each of R$^{E'}$, and R$^{F'}$, is, independently, selected from the group consisting of (a) hydrogen, (b) $C_{1-6}$ alkyl, (c) $C_{6-10}$ aryl and (d) $C_{1-6}$ alk-$C_{6-10}$ aryl; (18) —C(O)R$^{G'}$, where R$^{G'}$, is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (19) —NR$^{H'}$C(O)R$^{I'}$, wherein R$^{H'}$ is selected from the group consisting of (a1) hydrogen and (b1) $C_{1-6}$ alkyl, and R$^{I'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (20) —NR$^{J'}$C(O)OR$^{K'}$, wherein R$^{J'}$ is selected from the group consisting of (a1) hydrogen and (b1) $C_{1-6}$ alkyl, and R$^{K'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; and (21) amidine. In some embodiments, each of these groups can be further substituted as described herein. For example, the alkylene group of a $C_1$-alkaryl can be further substituted with an oxo group to afford the respective aryloyl substituent.

The term "alkylene" and the prefix "alk-," as used herein, represent a saturated divalent hydrocarbon group derived from a straight or branched chain saturated hydrocarbon by the removal of two hydrogen atoms, and is exemplified by methylene, ethylene, and isopropylene. The term "$C_{x-y}$ alkylene" and the prefix "$C_{x-y}$ alk-" represent alkylene groups having between x and y carbons. Exemplary values for x are 1, 2, 3, 4, 5, and 6, and exemplary values for y are 2, 3, 4, 5, 6, 7, 8, 9, 10, 12, 14, 16, 18, or 20 (e.g., $C_{1-6}$, $C_{1-10}$, $C_{2-20}$, $C_{2-6}$, $C_{2-10}$, or $C_{2-20}$ alkylene). In some embodiments, the alkylene can be further substituted with 1, 2, 3, or 4 substituent groups as defined herein for an alkyl group.

Non-limiting examples of optionally substituted alkyl and alkylene groups include acylaminoalkyl, acyloxyalkyl, alkoxyalkyl, alkoxycarbonylalkyl, alkylsulfinyl, alkylsulfinylalkyl, aminoalkyl, carbamoylalkyl, carboxyalkyl, carboxyaminoalkyl, haloalkyl, hydroxyalkyl, perfluoroalkyl, and sulfoalkyl:

The "acylaminoalkyl" group, which as used herein, represents an acyl group, as defined herein, attached to an amino group that is in turn attached to the parent molecular group through an alkylene group, as defined herein (i.e., -alkyl-N($R^{N1}$)—C(O)—R, where R is H or an optionally substituted $C_{1-6}$, $C_{1-10}$, or $C_{1-20}$ alkyl group (e.g., haloalkyl) and $R^{N1}$ is as defined herein). Exemplary unsubstituted acylaminoalkyl groups include from 1 to 41 carbons (e.g., from 1 to 7, from 1 to 13, from 1 to 21, from 2 to 7, from 2 to 13, from 2 to 21, or from 2 to 41 carbons). In some embodiments, the alkylene group is further substituted with 1, 2, 3, or 4 substituents as described herein, and/or the amino group is —$NH_2$ or —$NHR^{N1}$, wherein $R^{N1}$ is, independently, OH, $NO_2$, $NH_2$, $NR^{N2}{}_2$, $SO_2OR^{N2}$, $SO_2R^{N2}$, $SOR^{N2}$, alkyl, aryl, acyl (e.g., acetyl, trifluoroacetyl, or others described herein), or alkoxycarbonylalkyl, and each $R^{N2}$ can be H, alkyl, or aryl.

The "acyloxyalkyl" group, which as used herein, represents an acyl group, as defined herein, attached to an oxygen atom that in turn is attached to the parent molecular group though an alkylene group (i.e., -alkyl-O—C(O)—R, where R is H or an optionally substituted $C_{1-6}$, $C_{1-10}$, or $C_{1-20}$ alkyl group). Exemplary unsubstituted acyloxyalkyl groups include from 1 to 21 carbons (e.g., from 1 to 7 or from 1 to 11 carbons). In some embodiments, the alkylene group is, independently, further substituted with 1, 2, 3, or 4 substituents as described herein.

The "alkoxyalkyl" group, which as used herein, represents an alkyl group that is substituted with an alkoxy group. Exemplary unsubstituted alkoxyalkyl groups include between 2 to 40 carbons (e.g., from 2 to 12 or from 2 to 20 carbons, such as $C_{1-6}$ alkoxy-$C_{1-6}$ alkyl, $C_{1-10}$ alkoxy-$C_{1-10}$ alkyl, or $C_{1-20}$ alkoxy-$C_{1-20}$ alkyl). In some embodiments, the alkyl and the alkoxy each can be further substituted with 1, 2, 3, or 4 substituent groups as defined herein for the respective group.

The "alkoxycarbonylalkyl" group, which as used herein, represents an alkyl group, as defined herein, that is substituted with an alkoxycarbonyl group, as defined herein (e.g., -alkyl-C(O)—OR, where R is an optionally substituted $C_{1-20}$, $C_{1-10}$, or $C_{1-6}$ alkyl group). Exemplary unsubstituted alkoxycarbonylalkyl include from 3 to 41 carbons (e.g., from 3 to 10, from 3 to 13, from 3 to 17, from 3 to 21, or from 3 to 31 carbons, such as $C_{1-6}$ alkoxycarbonyl-$C_{1-6}$ alkyl, $C_{1-10}$ alkoxycarbonyl-$C_{1-10}$ alkyl, or $C_{1-20}$ alkoxycarbonyl-$C_{1-20}$ alkyl). In some embodiments, each alkyl and alkoxy group is further independently substituted with 1, 2, 3, or 4 substituents as described herein (e.g., a hydroxy group).

The "alkylsulfinylalkyl" group, which as used herein, represents an alkyl group, as defined herein, substituted with an alkylsulfinyl group. Exemplary unsubstituted alkylsulfinylalkyl groups are from 2 to 12, from 2 to 20, or from 2 to 40 carbons. In some embodiments, each alkyl group can be further substituted with 1, 2, 3, or 4 substituent groups as defined herein.

The "aminoalkyl" group, which as used herein, represents an alkyl group, as defined herein, substituted with an amino group, as defined herein. The alkyl and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl, e.g., carboxy, and/or an N-protecting group).

The "carbamoylalkyl" group, which as used herein, represents an alkyl group, as defined herein, substituted with a carbamoyl group, as defined herein. The alkyl group can be further substituted with 1, 2, 3, or 4 substituent groups as described herein.

The "carboxyalkyl" group, which as used herein, represents an alkyl group, as defined herein, substituted with a carboxy group, as defined herein. The alkyl group can be further substituted with 1, 2, 3, or 4 substituent groups as described herein, and the carboxy group can be optionally substituted with one or more O-protecting groups.

The "carboxyaminoalkyl" group, which as used herein, represents an aminoalkyl group, as defined herein, substituted with a carboxy, as defined herein. The carboxy, alkyl, and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl, e.g., carboxy, and/or an N-protecting group, and/or an O-protecting group).

The "haloalkyl" group, which as used herein, represents an alkyl group, as defined herein, substituted with a halogen group (i.e., F, Cl, Br, or I). A haloalkyl may be substituted with one, two, three, or, in the case of alkyl groups of two carbons or more, four halogens. Haloalkyl groups include perfluoroalkyls (e.g., —$CF_3$), —$CHF_2$, —$CH_2F$, —$CCl_3$, —$CH_2CH_2Br$, —$CH_2CH(CH_2CH_2Br)CH_3$, and —$CHICH_3$. In some embodiments, the haloalkyl group can be further substituted with 1, 2, 3, or 4 substituent groups as described herein for alkyl groups.

The "hydroxyalkyl" group, which as used herein, represents an alkyl group, as defined herein, substituted with one to three hydroxy groups, with the proviso that no more than one hydroxy group may be attached to a single carbon atom of the alkyl group, and is exemplified by hydroxymethyl and dihydroxypropyl. In some embodiments, the hydroxyalkyl group can be substituted with 1, 2, 3, or 4 substituent groups (e.g., O-protecting groups) as defined herein for an alkyl.

The "perfluoroalkyl" group, which as used herein, represents an alkyl group, as defined herein, where each hydrogen radical bound to the alkyl group has been replaced by a fluoride radical. Perfluoroalkyl groups are exemplified by trifluoromethyl.

The "sulfoalkyl" group, which as used herein, represents an alkyl group, as defined herein, substituted with a sulfo group of —$SO_3H$. In some embodiments, the alkyl group can be further substituted with 1, 2, 3, or 4 substituent groups as described herein, and the sulfo group can be further substituted with one or more O-protecting groups (e.g., as described herein).

The term "alkenyl," as used herein, represents monovalent straight or branched chain groups of, unless otherwise specified, from 2 to 20 carbons (e.g., from 2 to 6 or from 2 to 10 carbons) containing one or more carbon-carbon double bonds and is exemplified by ethenyl, 1-propenyl, 2-propenyl, 2-methyl-1-propenyl, 1-butenyl, and 2-butenyl. Alkenyls include both cis and trans isomers. Alkenyl groups may be optionally substituted with 1, 2, 3, or 4 substituent groups that are selected, independently, from amino, aryl, cycloalkyl, or heterocyclyl (e.g., heteroaryl), as defined herein, or any of the exemplary alkyl substituent groups described herein.

Non-limiting examples of optionally substituted alkenyl groups include, alkoxycarbonylalkenyl, aminoalkenyl, and hydroxyalkenyl:

The "alkoxycarbonylalkenyl" group, which as used herein, represents an alkenyl group, as defined herein, that is substituted with an alkoxycarbonyl group, as defined herein (e.g., -alkenyl-C(O)—OR, where R is an optionally substituted $C_{1-20}$, $C_{1-10}$, or $C_{1-6}$ alkyl group). Exemplary unsubstituted alkoxycarbonylalkenyl include from 4 to 41 carbons (e.g., from 4 to 10, from 4 to 13, from 4 to 17, from 4 to 21, or from 4 to 31 carbons, such as $C_{1-6}$ alkoxycarbonyl-$C_{2-6}$ alkenyl, $C_{1-10}$ alkoxycarbonyl-$C_{2-10}$ alkenyl, or $C_{1-20}$ alkoxycarbonyl-$C_{2-20}$ alkenyl). In some embodiments, each alkyl, alkenyl, and alkoxy group is further independently substituted with 1, 2, 3, or 4 substituents as described herein (e.g., a hydroxy group).

The "aminoalkenyl" group, which as used herein, represents an alkenyl group, as defined herein, substituted with an amino group, as defined herein. The alkenyl and amino each can be further substituted with 1, 2, 3, or 4 substituent groups as described herein for the respective group (e.g., $CO_2R^{A'}$, where $R^{A'}$, is selected from the group consisting of (a) $C_{1-6}$ alkyl, (b) $C_{6-10}$ aryl, (c) hydrogen, and (d) $C_{1-6}$ alk-$C_{6-10}$ aryl, e.g., carboxy, and/or an N-protecting group).

The "hydroxyalkenyl" group, which as used herein, represents an alkenyl group, as defined herein, substituted with one to three hydroxy groups, with the proviso that no more than one hydroxy group may be attached to a single carbon atom of the alkyl group, and is exemplified by dihydroxypropenyl, and hydroxyisopentenyl. In some embodiments, the hydroxyalkenyl group can be substituted with 1, 2, 3, or 4 substituent groups (e.g., O-protecting groups) as defined herein for an alkyl.

The term "alkynyl," as used herein, represents monovalent straight or branched chain groups from 2 to 20 carbon atoms (e.g., from 2 to 4, from 2 to 6, or from 2 to 10 carbons) containing a carbon-carbon triple bond and is exemplified by ethynyl, and 1-propynyl. Alkynyl groups may be optionally substituted with 1, 2, 3, or 4 substituent groups that are selected, independently, from aryl, cycloalkyl, or heterocyclyl (e.g., heteroaryl), as defined herein, or any of the exemplary alkyl substituent groups described herein.

Non-limiting examples of optionally substituted alkynyl groups include alkoxycarbonylalkynyl, aminoalkynyl, and hydroxyalkynyl:

The "alkoxycarbonylalkynyl" group, which as used herein, represents an alkynyl group, as defined herein, that is substituted with an alkoxycarbonyl group, as defined herein (e.g., -alkynyl-C(O)—OR, where R is an optionally substituted $C_{1-20}$, $C_{1-10}$, or $C_{1-6}$ alkyl group). Exemplary unsubstituted alkoxycarbonylalkynyl include from 4 to 41 carbons (e.g., from 4 to 10, from 4 to 13, from 4 to 17, from 4 to 21, or from 4 to 31 carbons, such as $C_{1-6}$ alkoxycarbonyl-$C_{2-6}$ alkynyl, $C_{1-10}$ alkoxycarbonyl-$C_{2-10}$ alkynyl, or $C_{1-20}$ alkoxycarbonyl-$C_{2-20}$ alkynyl). In some embodiments, each alkyl, alkynyl, and alkoxy group is further independently substituted with 1, 2, 3, or 4 substituents as described herein (e.g., a hydroxy group).

The "aminoalkynyl" group, which as used herein, represents an alkynyl group, as defined herein, substituted with an amino group, as defined herein. The alkynyl and amino each can be further substituted with 1, 2, 3, or 4 substituent groups as described herein for the respective group (e.g., $CO_2R^{A'}$, where $R^{A'}$, is selected from the group consisting of (a) $C_{1-6}$ alkyl, (b) $C_{6-10}$ aryl, (c) hydrogen, and (d) $C_{1-6}$ alk-$C_{6-10}$ aryl, e.g., carboxy, and/or an N-protecting group).

The "hydroxyalkynyl" group, which as used herein, represents an alkynyl group, as defined herein, substituted with one to three hydroxy groups, with the proviso that no more than one hydroxy group may be attached to a single carbon atom of the alkyl group. In some embodiments, the hydroxyalkynyl group can be substituted with 1, 2, 3, or 4 substituent groups (e.g., O-protecting groups) as defined herein for an alkyl.

The term "amidine," as used herein, represents a —C(=NH)NH$_2$ group.

The term "amino," as used herein, represents —N($R^{N1}$)$_2$, wherein each $R^{N1}$ is, independently, H, OH, NO$_2$, N($R^{N2}$)$_2$, SO$_2$O$R^{N2}$, SO$_2$$R^{N2}$, SO$R^{N2}$, an N-protecting group, alkyl, alkenyl, alkynyl, alkoxy, aryl, alkaryl, cycloalkyl, alkcycloalkyl, carboxyalkyl (e.g., optionally substituted with an O-protecting group, such as optionally substituted arylalkoxycarbonyl groups or any described herein), sulfoalkyl, acyl (e.g., acetyl, trifluoroacetyl, or others described herein), alkoxycarbonylalkyl (e.g., optionally substituted with an O-protecting group, such as optionally substituted arylalkoxycarbonyl groups or any described herein), heterocyclyl (e.g., heteroaryl), or alkheterocyclyl (e.g., alkheteroaryl), wherein each of these recited $R^{N1}$ groups can be optionally substituted, as defined herein for each group; or two $R^{N1}$ combine to form a heterocyclyl or an N-protecting group, and wherein each $R^{N2}$ is, independently, H, alkyl, or aryl. The amino groups of the invention can be an unsubstituted amino (i.e., —NH$_2$) or a substituted amino (i.e., —N($R^{N1}$)$_2$). In a preferred embodiment, amino is —NH$_2$ or —NHR$^{N1}$, wherein $R^{N1}$ is, independently, OH, NO$_2$, NH$_2$, N$R^{N2}{}_2$, SO$_2$O$R^{N2}$, SO$_2$$R^{N2}$, SO$R^{N2}$, alkyl, carboxyalkyl, sulfoalkyl, acyl (e.g., acetyl, trifluoroacetyl, or others described herein), alkoxycarbonylalkyl (e.g., t-butoxycarbonylalkyl) or aryl, and each $R^{N2}$ can be H, $C_{1-20}$ alkyl (e.g., $C_{1-6}$ alkyl), or $C_{6-10}$ aryl.

Non-limiting examples of optionally substituted amino groups include acylamino and carbamyl:

The "acylamino" group, which as used herein, represents an acyl group, as defined herein, attached to the parent molecular group though an amino group, as defined herein (i.e., —N($R^{N1}$)—C(O)—R, where R is H or an optionally substituted $C_{1-6}$, $C_{1-10}$, or $C_{1-20}$ alkyl group (e.g., haloalkyl) and $R^{N1}$ is as defined herein). Exemplary unsubstituted acylamino groups include from 1 to 41 carbons (e.g., from 1 to 7, from 1 to 13, from 1 to 21, from 2 to 7, from 2 to 13, from 2 to 21, or from 2 to 41 carbons). In some embodiments, the alkyl group is further substituted with 1, 2, 3, or 4 substituents as described herein, and/or the amino group is —NH$_2$ or —NHR$^{N1}$, wherein $R^{N1}$ is, independently, OH, NO$_2$, NH$_2$, N$R^{N2}{}_2$, SO$_2$O$R^{N2}$, SO$_2$$R^{N2}$, SO$R^{N2}$, alkyl, aryl, acyl (e.g., acetyl, trifluoroacetyl, or others described herein), or alkoxycarbonylalkyl, and each $R^{N2}$ can be H, alkyl, or aryl.

The "carbamyl" group, which as used herein, refers to a carbamate group having the structure —N$R^{N1}$C(=O)OR or —OC(=O)N($R^{N1}$)$_2$, where the meaning of each $R^{N1}$ is found in the definition of "amino" provided herein, and R is alkyl, cycloalkyl, alkcycloalkyl, aryl, alkaryl, heterocyclyl (e.g., heteroaryl), or alkheterocyclyl (e.g., alkheteroaryl), as defined herein.

The term "amino acid," as described herein, refers to a molecule having a side chain, an amino group, and an acid group (e.g., a carboxy group of —CO$_2$H or a sulfo group of —SO$_3$H), wherein the amino acid is attached to the parent molecular group by the side chain, amino group, or acid group (e.g., the side chain). In some embodiments, the amino acid is attached to the parent molecular group by a carbonyl group, where the side chain or amino group is attached to the carbonyl group. Exemplary side chains include an optionally substituted alkyl, aryl, heterocyclyl, alkaryl, alkheterocyclyl, aminoalkyl, carbamoylalkyl, and carboxyalkyl. Exemplary amino acids include alanine, arginine, asparagine, aspartic acid, cysteine, glutamic acid, glutamine, glycine, histidine, hydroxynorvaline, isoleucine, leucine, lysine, methionine, norvaline, ornithine, phenylalanine, proline, pyrrolysine, selenocysteine, serine, taurine, threonine, tryptophan, tyrosine, and valine. Amino acid groups may be optionally substituted with one, two, three, or, in the case of amino acid groups of two carbons or more, four substituents independently selected from the group consisting of: (1) $C_{1-6}$ alkoxy; (2) $C_{1-6}$ alkylsulfinyl; (3) amino, as defined herein (e.g., unsubstituted amino (i.e., —NH$_2$) or a substituted amino (i.e., —N(R$^{N1}$)$_2$, where R$^{N1}$ is as defined for amino); (4) $C_{6-10}$ aryl-$C_{1-6}$ alkoxy; (5) azido; (6) halo; (7) ($C_{2-9}$ heterocyclyl)oxy; (8) hydroxy; (9) nitro; (10) oxo (e.g., carboxyaldehyde or acyl); (11) $C_{1-7}$ spirocyclyl; (12) thioalkoxy; (13) thiol; (14) —CO$_2$R$^{A'}$, where R$^{A'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted $C_{1-6}$ alkyl; (15) —C(O)NR$^{B'}$R$^{C'}$, where each of R$^{B'}$ and R$^{C'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (16) —SO$_2$R$^{D'}$, where R$^{D'}$ is selected from the group consisting of (a) $C_{1-6}$ alkyl, (b) $C_{6-10}$ aryl, (c) $C_{1-6}$ alk-$C_{6-10}$ aryl, and (d) hydroxy; (17) —SO$_2$NR$^{E'}$R$^{F'}$, where each of R$^{E'}$, and R$^{F'}$ is, independently, selected from the group consisting of (a) hydrogen, (b) $C_{1-6}$ alkyl, (c) $C_{6-10}$ aryl and (d) $C_{1-6}$ alk-$C_{6-10}$ aryl; (18) —C(O)R$^{G'}$, where R$^{G'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted $C_{1-6}$ alkyl; (19) —NR$^{H'}$C(O)R$^{I'}$, wherein R$^{H'}$ is selected from the group consisting of (a1) hydrogen and (b1) $C_{1-6}$ alkyl, and R$^{I'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted $C_{1-6}$ alkyl; (20) —NR$^{J'}$C(O)OR$^{K'}$, wherein R$^{J'}$ is selected from the group consisting of (a1) hydrogen and (b1) $C_{1-6}$ alkyl, and R$^{K'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted $C_{1-6}$ alkyl; and (21) amidine. In some embodiments, each of these groups can be further substituted as described herein.

The term "aryl," as used herein, represents a mono-, bicyclic, or multicyclic carbocyclic ring system having one or two aromatic rings and is exemplified by phenyl, naphthyl, 1,2-dihydronaphthyl, 1,2,3,4-tetrahydronaphthyl, anthracenyl, phenanthrenyl, fluorenyl, indanyl, and indenyl, and may be optionally substituted with 1, 2, 3, 4, or 5 substituents independently selected from the group consisting of: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —(CH$_2$)$_q$CO$_2$R$^{A'}$, where q is an integer from zero to four, and R$^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —(CH$_2$)$_q$CONR$^{B'}$R$^{C'}$, where q is an integer from zero to four and where R$^{B'}$ and R$^{C'}$ are independently selected from the group consisting of (a) hydrogen, (b) $C_{1-6}$ alkyl, (c) $C_{6-10}$ aryl, and (d) $C_{1-6}$ alk-$C_{6-10}$ aryl; (19) —(CH$_2$)$_q$SO$_2$R$^{D'}$, where q is an integer from zero to four and where R$^{D'}$ is selected from the group consisting of (a) alkyl, (b) $C_{6-10}$ aryl, and (c) alk-$C_{6-10}$ aryl; (20) —(CH$_2$)$_q$SO$_2$NR$^{E'}$R$^{F'}$, where q is an integer from zero to four and where each of R$^{E'}$ and R$^{F'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) $C_{6-10}$ aryl-$C_{1-6}$ alkoxy; (25) $C_{1-6}$ alk-$C_{1-12}$ heterocyclyl (e.g., $C_{1-6}$ alk-$C_{1-12}$ heteroaryl); (26) $C_{2-20}$ alkenyl; and (27) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The "arylalkyl" group, which as used herein, represents an aryl group, as defined herein, attached to the parent molecular group through an alkylene group, as defined herein. Exemplary unsubstituted arylalkyl groups are from 7 to 30 carbons (e.g., from 7 to 16 or from 7 to 20 carbons, such as $C_{1-6}$ alk-$C_{6-10}$ aryl, $C_{1-10}$ alk-$C_{6-10}$ aryl, or $C_{1-20}$ alk-$C_{6-10}$ aryl). In some embodiments, the alkylene and the aryl each can be further substituted with 1, 2, 3, or 4 substituent groups as defined herein for the respective groups. Other groups preceded by the prefix "alk-" are defined in the same manner, where "alk" refers to a $C_{1-6}$ alkylene, unless otherwise noted, and the attached chemical structure is as defined herein.

The term "azido" represents an —$N_3$ group, which can also be represented as —N=N=N.

The term "bicyclic," as used herein, refer to a structure having two rings, which may be aromatic or non-aromatic. Bicyclic structures include spirocyclyl groups, as defined herein, and two rings that share one or more bridges, where such bridges can include one atom or a chain including two, three, or more atoms. Exemplary bicyclic groups include a bicyclic carbocyclyl group, where the first and second rings are carbocyclyl groups, as defined herein; a bicyclic aryl groups, where the first and second rings are aryl groups, as defined herein; bicyclic heterocyclyl groups, where the first ring is a heterocyclyl group and the second ring is a carbocyclyl (e.g., aryl) or heterocyclyl (e.g., heteroaryl) group; and bicyclic heteroaryl groups, where the first ring is a heteroaryl group and the second ring is a carbocyclyl (e.g., aryl) or heterocyclyl (e.g., heteroaryl) group. In some embodiments, the bicyclic group can be substituted with 1, 2, 3, or 4 substituents as defined herein for cycloalkyl, heterocyclyl, and aryl groups.

The term "boranyl," as used herein, represents —$B(R^{B1})_3$, where each $R^{B1}$ is, independently, selected from the group consisting of H and optionally substituted alkyl. In some embodiments, the boranyl group can be substituted with 1, 2, 3, or 4 substituents as defined herein for alkyl.

The terms "carbocyclic" and "carbocyclyl," as used herein, refer to an optionally substituted $C_{3-12}$ monocyclic, bicyclic, or tricyclic structure in which the rings, which may be aromatic or non-aromatic, are formed by carbon atoms. Carbocyclic structures include cycloalkyl, cycloalkenyl, and aryl groups.

The term "carbonyl," as used herein, represents a C(O) group, which can also be represented as C=O.

The term "carboxy," as used herein, means —$CO_2H$.

The term "cyano," as used herein, represents an —CN group.

The term "cycloalkyl," as used herein represents a monovalent saturated or unsaturated non-aromatic cyclic hydrocarbon group from three to eight carbons, unless otherwise specified, and is exemplified by cyclopropyl, cyclobutyl, cyclopentyl, cyclohexyl, cycloheptyl, and bicycle heptyl. When the cycloalkyl group includes one carbon-carbon double bond, the cycloalkyl group can be referred to as a "cycloalkenyl" group. Exemplary cycloalkenyl groups include cyclopentenyl, and cyclohexenyl. The cycloalkyl groups of this invention can be optionally substituted with: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —$(CH_2)_qCO_2R^{A'}$, where q is an integer from zero to four, and $R^{A'}$ is selected from the group consisting of (a) $C_{1-6}$ alkyl, (b) $C_{6-10}$ aryl, (c) hydrogen, and (d) alk-$C_{6-10}$ aryl; (18) —$(CH_2)_qCONR^{B'}R^{C'}$, where q is an integer from zero to four and where $R^{B'}$ and $R^{C'}$ are independently selected from the group consisting of (a) hydrogen, (b) $C_{6-10}$ alkyl, (c) $C_{6-10}$ aryl, and (d) alk-$C_{6-10}$ aryl; (19) —$(CH_2)_qSO_2R^{D'}$, where q is an integer from zero to four and where $R^D$ is selected from the group consisting of (a) $C_{6-10}$ alkyl, (b) $C_{6-10}$ aryl, and (c) $C_{1-6}$ alk-$C_{6-10}$ aryl; (20) —$(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_{6-10}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) $C_{6-10}$ aryl-$C_{1-6}$ alkoxy; (25) $C_{1-6}$ alk-$C_{1-12}$ heterocyclyl (e.g., $C_{1-6}$ alk-$C_{1-12}$ heteroaryl); (26) oxo; (27) $C_{2-20}$ alkenyl; and (28) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The "cycloalkylalkyl" group, which as used herein, represents a cycloalkyl group, as defined herein, attached to the parent molecular group through an alkylene group, as defined herein (e.g., an alkylene group of from 1 to 4, from 1 to 6, from 1 to 10, or form 1 to 20 carbons). In some embodiments, the alkylene and the cycloalkyl each can be further substituted with 1, 2, 3, or 4 substituent groups as defined herein for the respective group.

The term "diastereomer," as used herein means stereoisomers that are not mirror images of one another and are non-superimposable on one another.

The term "enantiomer," as used herein, means each individual optically active form of a compound of the invention, having an optical purity or enantiomeric excess (as determined by methods standard in the art) of at least 80% (i.e., at least 90% of one enantiomer and at most 10% of the other enantiomer), preferably at least 90% and more preferably at least 98%.

The term "halo," as used herein, represents a halogen selected from bromine, chlorine, iodine, or fluorine.

The term "heteroalkyl," as used herein, refers to an alkyl group, as defined herein, in which one or two of the constituent carbon atoms have each been replaced by nitrogen, oxygen, or sulfur. In some embodiments, the heteroalkyl group can be further substituted with 1, 2, 3, or 4 substituent groups as described herein for alkyl groups. The terms "heteroalkenyl" and heteroalkynyl," as used herein refer to alkenyl and alkynyl groups, as defined herein, respectively, in which one or two of the constituent carbon atoms have each been replaced by nitrogen, oxygen, or sulfur. In some embodiments, the heteroalkenyl and heteroalkynyl groups can be further substituted with 1, 2, 3, or 4 substituent groups as described herein for alkyl groups.

Non-limiting examples of optionally substituted heteroalkyl, heteroalkenyl, and heteroalkynyl groups include acyloxy, alkenyloxy, alkoxy, alkoxyalkoxy, alkoxycarbonylalkoxy, alkynyloxy, aminoalkoxy, arylalkoxy, carboxyalkoxy, cycloalkoxy, haloalkoxy, (heterocyclyl)oxy, perfluoroalkoxy, thioalkoxy, and thioheterocyclylalkyl:

The "acyloxy" group, which as used herein, represents an acyl group, as defined herein, attached to the parent molecular group though an oxygen atom (i.e., —O—C(O)—R, where R is H or an optionally substituted $C_{1-6}$, $C_{1-10}$, or $C_{1-20}$ alkyl group). Exemplary unsubstituted acyloxy groups include from 1 to 21 carbons (e.g., from 1 to 7 or from 1 to 11 carbons). In some embodiments, the alkyl group is further substituted with 1, 2, 3, or 4 substituents as described herein.

The "alkenyloxy" group, which as used here, represents a chemical substituent of formula —OR, where R is a $C_{2-20}$ alkenyl group (e.g., $C_{2-6}$ or $C_{2-10}$ alkenyl), unless otherwise specified. Exemplary alkenyloxy groups include ethenyloxy, and propenyloxy. In some embodiments, the alkenyl group can be further substituted with 1, 2, 3, or 4 substituent groups as defined herein (e.g., a hydroxy group).

The "alkoxy" group, which as used herein, represents a chemical substituent of formula —OR, where R is a $C_{1-20}$ alkyl group (e.g., $C_{1-6}$ or $C_{1-10}$ alkyl), unless otherwise specified. Exemplary alkoxy groups include methoxy, ethoxy, propoxy (e.g., n-propoxy and isopropoxy), and t-butoxy. In some embodiments, the alkyl group can be further substituted with 1, 2, 3, or 4 substituent groups as defined herein (e.g., hydroxy or alkoxy).

The "alkoxyalkoxy" group, which as used herein, represents an alkoxy group that is substituted with an alkoxy group. Exemplary unsubstituted alkoxyalkoxy groups include between 2 to 40 carbons (e.g., from 2 to 12 or from 2 to 20 carbons, such as $C_{1-6}$ alkoxy-$C_{1-6}$ alkoxy, $C_{1-10}$ alkoxy-$C_{1-10}$ alkoxy, or $C_{1-20}$ alkoxy-$C_{1-20}$ alkoxy). In some embodiments, the each alkoxy group can be further substituted with 1, 2, 3, or 4 substituent groups as defined herein.

The "alkoxycarbonylalkoxy" group, which as used herein, represents an alkoxy group, as defined herein, that is substituted with an alkoxycarbonyl group, as defined herein (e.g., —O-alkyl-C(O)—OR, where R is an optionally substituted $C_{1-6}$, $C_{1-10}$, or $C_{1-20}$ alkyl group). Exemplary unsubstituted alkoxycarbonylalkoxy include from 3 to 41 carbons (e.g., from 3 to 10, from 3 to 13, from 3 to 17, from 3 to 21, or from 3 to 31 carbons, such as $C_{1-6}$ alkoxycarbonyl-$C_{1-6}$ alkoxy, $C_{1-10}$ alkoxycarbonyl-$C_{1-10}$ alkoxy, or $C_{1-20}$ alkoxycarbonyl-$C_{1-20}$ alkoxy). In some embodiments, each alkoxy group is further independently substituted with 1, 2, 3, or 4 substituents, as described herein (e.g., a hydroxy group).

The "alkynyloxy" group, which as used herein, represents a chemical substituent of formula —OR, where R is a $C_{2-20}$ alkynyl group (e.g., $C_{2-6}$ or $C_{2-10}$ alkynyl), unless otherwise specified. Exemplary alkynyloxy groups include ethynyloxy, and propynyloxy. In some embodiments, the alkynyl group can be further substituted with 1, 2, 3, or 4 substituent groups as defined herein (e.g., a hydroxy group).

The "aminoalkoxy" group, which as used herein, represents an alkoxy group, as defined herein, substituted with an amino group, as defined herein. The alkyl and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl, e.g., carboxy).

The "arylalkoxy" group, which as used herein, represents an alkaryl group, as defined herein, attached to the parent molecular group through an oxygen atom. Exemplary unsubstituted arylalkoxy groups include from 7 to 30 carbons (e.g., from 7 to 16 or from 7 to 20 carbons, such as $C_{6-10}$ aryl-$C_{1-6}$ alkoxy, $C_{6-10}$ aryl-$C_{1-10}$ alkoxy, or $C_{6-10}$ aryl-$C_{1-20}$ alkoxy). In some embodiments, the arylalkoxy group can be substituted with 1, 2, 3, or 4 substituents as defined herein.

The "aryloxy" group, which as used herein, represents a chemical substituent of formula —OR', where R' is an aryl group of 6 to 18 carbons, unless otherwise specified. In some embodiments, the aryl group can be substituted with 1, 2, 3, or 4 substituents as defined herein.

The "carboxyalkoxy" group, which as used herein, represents an alkoxy group, as defined herein, substituted with a carboxy group, as defined herein. The alkoxy group can be further substituted with 1, 2, 3, or 4 substituent groups as described herein for the alkyl group, and the carboxy group can be optionally substituted with one or more O-protecting groups.

The "cycloalkoxy" group, which as used herein, represents a chemical substituent of formula —OR, where R is a $C_{3-8}$ cycloalkyl group, as defined herein, unless otherwise specified. The cycloalkyl group can be further substituted with 1, 2, 3, or 4 substituent groups as described herein. Exemplary unsubstituted cycloalkoxy groups are from 3 to 8 carbons. In some embodiment, the cycloalkyl group can be further substituted with 1, 2, 3, or 4 substituent groups as described herein.

The "haloalkoxy" group, which as used herein, represents an alkoxy group, as defined herein, substituted with a halogen group (i.e., F, Cl, Br, or I). A haloalkoxy may be substituted with one, two, three, or, in the case of alkyl groups of two carbons or more, four halogens. Haloalkoxy groups include perfluoroalkoxys (e.g., —OCF$_3$), —OCHF$_2$, —OCH$_2$F, —OCCl$_3$, —OCH$_2$CH$_2$Br, —OCH$_2$CH(CH$_2$CH$_2$Br)CH$_3$, and —OCHICH$_3$. In some embodiments, the haloalkoxy group can be further substituted with 1, 2, 3, or 4 substituent groups as described herein for alkyl groups.

The "(heterocyclyl)oxy" group, which as used herein, represents a heterocyclyl group, as defined herein, attached to the parent molecular group through an oxygen atom. In some embodiments, the heterocyclyl group can be substituted with 1, 2, 3, or 4 substituent groups as defined herein.

The "perfluoroalkoxy" group, which as used herein, represents an alkoxy group, as defined herein, where each hydrogen radical bound to the alkoxy group has been replaced by a fluoride radical. Perfluoroalkoxy groups are exemplified by trifluoromethoxy.

The "alkylsulfinyl" group, which as used herein, represents an alkyl group attached to the parent molecular group through an —S(O)— group. Exemplary unsubstituted alkylsulfinyl groups are from 1 to 6, from 1 to 10, or from 1 to 20 carbons. In some embodiments, the alkyl group can be further substituted with 1, 2, 3, or 4 substituent groups as defined herein.

The "thioarylalkyl" group, which as used herein, represents a chemical substituent of formula —SR, where R is an arylalkyl group. In some embodiments, the arylalkyl group can be further substituted with 1, 2, 3, or 4 substituent groups as described herein.

The "thioalkoxy" group as used herein, represents a chemical substituent of formula —SR, where R is an alkyl group, as defined herein. In some embodiments, the alkyl group can be further substituted with 1, 2, 3, or 4 substituent groups as described herein.

The "thioheterocyclylalkyl" group, which as used herein, represents a chemical substituent of formula —SR, where R is an heterocyclylalkyl group. In some embodiments, the heterocyclylalkyl group can be further substituted with 1, 2, 3, or 4 substituent groups as described herein.

The term "heteroaryl," as used herein, represents that subset of heterocyclyls, as defined herein, which are aromatic: i.e., they contain 4n+2 pi electrons within the mono- or multicyclic ring system.

Exemplary unsubstituted heteroaryl groups are of 1 to 12 (e.g., 1 to 11, 1 to 10, 1 to 9, 2 to 12, 2 to 11, 2 to 10, or 2 to 9) carbons. In some embodiment, the heteroaryl is substituted with 1, 2, 3, or 4 substituents groups as defined for a heterocyclyl group.

The term "heteroarylalkyl" refers to a heteroaryl group, as defined herein, attached to the parent molecular group through an alkylene group, as defined herein. Exemplary unsubstituted heteroarylalkyl groups are from 2 to 32 carbons (e.g., from 2 to 22, from 2 to 18, from 2 to 17, from 2 to 16, from 3 to 15, from 2 to 14, from 2 to 13, or from 2 to 12 carbons, such as $C_{1-6}$ alk-$C_{1-12}$ heteroaryl, $C_{1-10}$ alk-$C_{1-12}$ heteroaryl, or $C_{1-20}$ alk-$C_{1-12}$ heteroaryl). In some embodiments, the alkylene and the heteroaryl each can be further substituted with 1, 2, 3, or 4 substituent groups as defined herein for the respective group. Heteroarylalkyl groups are a subset of heterocyclylalkyl groups.

The term "heterocyclyl," as used herein represents a 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. Exemplary unsubstituted heterocyclyl groups are of 1 to 12 (e.g., 1 to 11, 1 to 10, 1 to 9, 2 to 12, 2 to 11, 2 to 10, or 2 to 9) carbons. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, and benzothienyl. Examples of fused heterocyclyls include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, indazolyl, quinolyl, isoquinolyl, quinoxalinyl, dihydroquinoxalinyl, quinazolinyl, cinnolinyl, phthalazinyl, benzimidazolyl, benzothiazolyl, benzoxazolyl, benzothiadiazolyl, furyl, thienyl, thiazolidinyl, isothiazolyl, triazolyl, tetrazolyl, oxadiazolyl (e.g., 1,2,3-oxadiazolyl), purinyl, thiadiazolyl (e.g., 1,2,3-thiadiazolyl), tetrahydrofuranyl, dihydrofuranyl, tetrahydrothienyl, dihydrothienyl, dihydroindolyl, dihydroquinolyl, tetrahydroquinolyl, tetrahydroisoquinolyl, dihydroisoquinolyl, pyranyl, dihydropyranyl, dithiazolyl, benzofuranyl, isobenzofuranyl, and benzothienyl, including dihydro and tetrahydro forms thereof, where one or more double bonds are reduced and replaced with hydrogens. Still other exemplary heterocyclyls include: 2,3,4,5-tetrahydro-2-oxo-oxazolyl; 2,3-dihydro-2-oxo-1H-imidazolyl; 2,3,4,5-tetrahydro-5-oxo-1H-pyrazolyl (e.g., 2,3,4,5-tetrahydro-2-phenyl-5-oxo-1H-pyrazolyl); 2,3,4,5-tetrahydro-2,4-dioxo-1H-imidazolyl (e.g., 2,3,4,5-tetrahydro-2,4-dioxo-5-methyl-5-phenyl-1H-imidazolyl); 2,3-dihydro-2-thioxo-1,3,4-oxadiazolyl (e.g., 2,3-dihydro-2-thioxo-5-phenyl-1,3,4-oxadiazolyl); 4,5-dihydro-5-oxo-1H-triazolyl (e.g., 4,5-dihydro-3-methyl-4-amino 5-oxo-1H-triazolyl); 1,2,3,4-tetrahydro-2,4-dioxopyridinyl (e.g., 1,2,3,4-tetrahydro-2,4-dioxo-3,3-diethylpyridinyl); 2,6-dioxo-piperidinyl (e.g., 2,6-dioxo-3-ethyl-3-phenylpiperidinyl); 1,6-dihydro-6-oxopyridiminyl; 1,6-dihydro-4-oxopyrimidinyl (e.g., 2-(methylthio)-1,6-dihydro-4-oxo-5-methylpyrimidin-1-yl); 1,2,3,4-tetrahydro-2,4-dioxopyrimidinyl (e.g., 1,2,3,4-tetrahydro-2,4-dioxo-3-ethylpyrimidinyl); 1,6-dihydro-6-oxo-pyridazinyl (e.g., 1,6-dihydro-6-oxo-3-ethylpyridazinyl); 1,6-dihydro-6-oxo-1,2,4-triazinyl (e.g., 1,6-dihydro-5-isopropyl-6-oxo-1,2,4-triazinyl); 2,3-dihydro-2-oxo-1H-indolyl (e.g., 3,3-dimethyl-2,3-dihydro-2-oxo-1H-indolyl and 2,3-dihydro-2-oxo-3,3'-spiropropane-1H-indol-1-yl); 1,3-dihydro-1-oxo-2H-iso-indolyl; 1,3-dihydro-1,3-dioxo-2H-iso-indolyl; 1H-benzopyrazolyl (e.g., 1-(ethoxycarbonyl)-1H-benzopyrazolyl); 2,3-dihydro-2-oxo-1H-benzimidazolyl (e.g., 3-ethyl-2,3-dihydro-2-oxo-1H-benzimidazolyl); 2,3-dihydro-2-oxo-benzoxazolyl (e.g., 5-chloro-2,3-dihydro-2-oxo-benzoxazolyl); 2,3-dihydro-2-oxo-benzoxazolyl; 2-oxo-2H-benzopyranyl; 1,4-benzodioxanyl; 1,3-benzodioxanyl; 2,3-dihydro-3-oxo,4H-1,3-benzothiazinyl; 3,4-dihydro-4-oxo-3H-quinazolinyl (e.g., 2-methyl-3,4-dihydro-4-oxo-3H-quinazolinyl); 1,2,3,4-tetrahydro-2,4-dioxo-3H-quinazolyl (e.g., 1-ethyl-1,2,3,4-tetrahydro-2,4-dioxo-3H-quinazolyl); 1,2,3,6-tetrahydro-2,6-dioxo-7H-purinyl (e.g., 1,2,3,6-tetrahydro-1,3-dimethyl-2,6-dioxo-7H-purinyl); 1,2,3,6-tetrahydro-2,6-dioxo-1H-purinyl (e.g., 1,2,3,6-tetrahydro-3,7-dimethyl-2,6-dioxo-1H-purinyl); 2-oxobenz[c,d]indolyl; 1,1-dioxo-2H-naphth[1,8-c,d]isothiazolyl; and 1,8-naphthylenedicarboxamido. Additional heterocyclics include 3,3a,4,5,6,6a-hexahydro-pyrrolo[3,4-b]pyrrol-(2H)-yl, and 2,5-diazabicyclo[2.2.1]heptan-2-yl, homopiperazinyl (or diazepanyl), tetrahydropyranyl, dithiazolyl, benzofuranyl, benzothienyl, oxepanyl, thiepanyl, azocanyl, oxecanyl, and thiocanyl. Heterocyclic groups also include groups of the formula

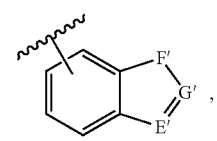

where
E' is selected from the group consisting of —N— and —CH—; F' is selected from the group consisting of —N=CH—, —NH—CH$_2$—, —NH—C(O)—, —NH—, —CH=N—, —CH$_2$—NH—, —C(O)—NH—, —CH=CH—, —CH$_2$—, —CH$_2$CH$_2$—, —CH$_2$O—, —OCH$_2$—, —O—, and —S—; and G' is selected from the group consisting of —CH— and —N—. Any of the heterocyclyl groups mentioned herein may be optionally substituted with one, two, three, four or five substituents independently selected from the group consisting of: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{2-12}$ heteroaryl); (13)

($C_{1-12}$ heterocyclyl)oxy; (14) hydroxy; (15) nitro; (16) $C_{1-20}$ thioalkoxy (e.g., $C_{1-6}$ thioalkoxy); (17) —$(CH_2)_qCO_2R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —$(CH_2)_qCONR^{E}R^{D'}$, where q is an integer from zero to four and where $R^{B'}$ and $R^{C'}$ are independently selected from the group consisting of (a) hydrogen, (b) $C_{1-6}$ alkyl, (c) $C_{6-10}$ aryl, and (d) $C_{1-6}$ alk-$C_{6-10}$ aryl; (19) —$(CH_2)_qSO_2R^{D'}$, where q is an integer from zero to four and where $R^{D'}$ is selected from the group consisting of (a) $C_{1-6}$ alkyl, (b) $C_{6-10}$ aryl, and (c) $C_{1-6}$ alk-$C_{6-10}$ aryl; (20) —$(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) arylalkoxy; (25) $C_{1-6}$ alk-$C_{1-12}$ heterocyclyl (e.g., $C_{1-6}$ alk-$C_{1-12}$ heteroaryl); (26) oxo; (27) ($C_{1-12}$ heterocyclyl) imino; (28) $C_{2-20}$ alkenyl; and (29) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The "heterocyclylalkyl" group, which as used herein, represents a heterocyclyl group, as defined herein, attached to the parent molecular group through an alkylene group, as defined herein. Exemplary unsubstituted heterocyclylalkyl groups are from 2 to 32 carbons (e.g., from 2 to 22, from 2 to 18, from 2 to 17, from 2 to 16, from 3 to 15, from 2 to 14, from 2 to 13, or from 2 to 12 carbons, such as $C_{1-6}$ alk-$C_{1-12}$ heterocyclyl, $C_{1-10}$ alk-$C_{1-12}$ heterocyclyl, or $C_{1-20}$ alk-$C_{1-12}$ heterocyclyl). In some embodiments, the alkylene and the heterocyclyl each can be further substituted with 1, 2, 3, or 4 substituent groups as defined herein for the respective group.

The term "hydrocarbon," as used herein, represents a group consisting only of carbon and hydrogen atoms.

The term "hydroxy," as used herein, represents an —OH group. In some embodiments, the hydroxy group can be substituted with 1, 2, 3, or 4 substituent groups (e.g., O-protecting groups) as defined herein for an alkyl.

The term "isomer," as used herein, means any tautomer, stereoisomer, enantiomer, or diastereomer of any compound of the invention. It is recognized that the compounds of the invention can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

The term "N-protected amino," as used herein, refers to an amino group, as defined herein, to which is attached one or two N-protecting groups, as defined herein.

The term "N-protecting group," as used herein, represents those groups intended to protect an amino group against undesirable reactions during synthetic procedures. Commonly used N-protecting groups are disclosed in Greene, "Protective Groups in Organic Synthesis," 3$^{rd}$ Edition (John Wiley & Sons, New York, 1999), which is incorporated herein by reference. N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, and phenylalanine; sulfonyl-containing groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, alkaryl groups such as benzyl, triphenylmethyl, and benzyloxymethyl, and silyl groups, such as trimethylsilyl. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —$NO_2$ group.

The term "O-protecting group," as used herein, represents those groups intended to protect an oxygen containing (e.g., phenol, hydroxyl, or carbonyl) group against undesirable reactions during synthetic procedures. Commonly used O-protecting groups are disclosed in Greene, "Protective Groups in Organic Synthesis," 3$^{rd}$ Edition (John Wiley & Sons, New York, 1999), which is incorporated herein by reference. Exemplary O-protecting groups include acyl, aryloyl, or carbamyl groups, such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, a-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl; alkylcarbonyl groups, such as acyl, acetyl, propionyl, and pivaloyl; optionally substituted arylcarbonyl groups, such as benzoyl; silyl groups, such as trimethylsilyl (TMS), tert-butyldimethylsilyl (TBDMS), tri-iso-propylsilyloxymethyl (TOM), and triisopropylsilyl (TIPS); ether-forming groups with the hydroxyl, such methyl, methoxymethyl, tetrahydropyranyl, benzyl, p-methoxybenzyl, and trityl; alkoxycarbonyls, such as methoxycarbonyl, ethoxycarbonyl, isopropoxycarbonyl, n-isopropoxycarbonyl, n-butyloxycarbonyl, isobutyloxycarbonyl, sec-butyloxycarbonyl, t-butyloxycarbonyl, 2-ethylhexyloxycarbonyl, cyclohexyloxycarbonyl, and methyloxycarbonyl; alkoxyalkoxycarbonyl groups, such as methoxymethoxycarbonyl, ethoxymethoxycarbonyl, 2-methoxyethoxycarbonyl, 2-ethoxyethoxycarbonyl, 2-butoxyethoxycarbonyl, 2-methoxyethoxymethoxycarbonyl, allyloxycarbonyl, propargyloxycarbonyl, 2-butenoxycarbonyl, and 3-methyl-2-butenoxycarbonyl; haloalkoxycarbonyls, such as 2-chloroethoxycarbonyl, 2-chloroethoxycarbonyl, and 2,2,2-trichloroethoxycarbonyl; optionally substituted arylalkoxycarbonyl groups, such as benzyloxycarbonyl, p-methylbenzyloxycarbonyl, p-methoxybenzyloxycarbonyl, p-nitrobenzyloxycarbonyl, 2,4-dinitrobenzyloxycarbonyl, 3,5-dimethylbenzyloxycarbonyl, p-chlorobenzyloxycarbonyl, p-bromobenzyloxy-carbonyl, and fluorenylmethyloxycarbonyl; and optionally substituted aryloxycarbonyl groups, such as phenoxycarbonyl, p-nitrophenoxycarbonyl, o-nitrophenoxycarbonyl, 2,4-dinitrophenoxycarbonyl, p-methyl-phenoxycarbonyl, m-methylphenoxycarbonyl, o-bromophenoxycarbonyl, 3,5-dimethylphenoxycarbonyl, p-chlorophenoxycarbonyl, and 2-chloro-4-nitrophenoxycarbonyl); substituted alkyl, aryl, and alkaryl ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1[2-(trimethylsilypethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenymethylsilyl); carbonates (e.g., methyl, methoxymethyl, 9-fluorenylmethyl; ethyl; 2,2, 2-trichloroethyl; 2-(trimethylsilyl)ethyl; vinyl, allyl, nitrophenyl; benzyl; methoxybenzyl; 3,4-dimethoxybenzyl; and nitrobenzyl); carbonyl-protecting groups (e.g., acetal and ketal groups, such as dimethyl acetal, and 1,3-dioxolane; acylal groups; and dithiane groups, such as 1,3-dithianes, and 1,3-dithiolane); carboxylic acid-protecting groups (e.g., ester groups, such as methyl ester, benzyl ester, t-butyl ester, and orthoesters; and oxazoline groups.

The term "oxo" as used herein, represents =O.

The prefix "perfluoro," as used herein, represents anyl group, as defined herein, where each hydrogen radical bound to the alkyl group has been replaced by a fluoride radical. For example, perfluoroalkyl groups are exemplified by trifluoromethyl.

The term "protected hydroxyl," as used herein, refers to an oxygen atom bound to an O-protecting group.

The term "spirocyclyl," as used herein, represents a $C_{2-7}$ alkylene diradical, both ends of which are bonded to the same carbon atom of the parent group to form a spirocyclic group, and also a $C_{1-6}$ heteroalkylene diradical, both ends of which are bonded to the same atom. The heteroalkylene radical forming the spirocyclyl group can containing one, two, three, or four heteroatoms independently selected from the group consisting of nitrogen, oxygen, and sulfur. In some embodiments, the spirocyclyl group includes one to seven carbons, excluding the carbon atom to which the diradical is attached. The spirocyclyl groups of the invention may be optionally substituted with 1, 2, 3, or 4 substituents provided herein as optional substituents for cycloalkyl and/or heterocyclyl groups.

The term "stereoisomer," as used herein, refers to all possible different isomeric as well as conformational forms which a compound may possess (e.g., a compound of any formula described herein), in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

The term "sulfonyl," as used herein, represents an —S(O)$_2$— group.

The term "thiol," as used herein represents an —SH group.

Definitions

The term "angiogenic disorder," used herein, refers to a disorder characterized by pathological angiogenesis. A disorder characterized by pathological angiogenesis refers to a disorder where abnormal or aberrant angiogenesis, alone or in combination with others, contributes to causation, origination, or symptom of the disorder. Examples of this disorder include various cancers (e.g., vascularized tumors), eye disorders, inflammatory disorders, and others.

Typical vascularized tumors that can be treated with the methods of the invention include solid tumors, particularly carcinomas, which require a vascular component for the provision of oxygen and nutrients. Exemplary solid tumors include, but are not limited to, carcinomas of the lung, breast, bone, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, glioblastomas, neuroblastomas, Kaposi's sarcoma, and sarcomas.

The term "cancer" refers to any cancer caused by the proliferation of malignant neoplastic cells, such as tumors, neoplasms, carcinomas, sarcomas, leukemias, and lymphomas.

"Cell migration" as used in this application involves the invasion by the cancer cells into the surrounding tissue and the crossing of the vessel wall to exit the vasculature in distal organs of the cancer cell.

By "cell migration cancers" is meant cancers that migrate by invasion by the cancer cells into the surrounding tissue and the crossing of the vessel wall to exit the vasculature in distal organs of the cancer cell.

As used herein, "drug resistant cancer" refers to any cancer that is resistant to an antiproliferative in Table 3.

As used herein, "metastatic nodule" refers to an aggregation of tumor cells in the body at a site other than the site of the original tumor.

As used herein, "metastatic tumor" refers to a tumor or cancer in which the cancer cells forming the tumor have a high potential to or have begun to, metastasize, or spread from one location to another location or locations within a subject, via the lymphatic system or via haematogenous spread, for example, creating secondary tumors within the subject. Such metastatic behavior may be indicative of malignant tumors. In some cases, metastatic behavior may be associated with an increase in cell migration and/or invasion behavior of the tumor cells.

Examples of cancers that can be defined as metastatic include but are not limited to non-small cell lung cancer, breast cancer, ovarian cancer, colorectal cancer, biliary tract cancer, bladder cancer, brain cancer including glioblastomas and medullablastomas, cervical cancer, choriocarcinoma, endometrial cancer, esophageal cancer, gastric cancer, hematological neoplasms, multiple myeloma, leukemia, intraepithelial neoplasms, livercancer, lymphomas, neuroblastomas, oral cancer, pancreatic cancer, prostate cancer, sarcoma, skin cancer including melanoma, basocellular cancer, squamous cell cancer, testicular cancer, stromal tumors, germ cell tumors, thyroid cancer, and renal cancer.

As used herein, "migrating cancer" refers to a cancer in which the cancer cells forming the tumor migrate and subsequently grow as malignant implants at a site other than the site of the original tumor. The cancer cells migrate via seeding the surface of the peritoneal, pleural, pericardial, or subarachnoid spaces to spread into the body cavities; via invasion of the lymphatic system through invasion of lymphatic cells and transport to regional and distant lymph nodes and then to other parts of the body; via haematogenous spread through invasion of blood cells; or via invasion of the surrounding tissue. Migrating cancers include metastatic tumors and cell migration cancers, such as ovarian cancer, mesothelioma, and primary lung cancer, each of which is characterized by cellular migration.

"Non-metastatic cell migration cancer" as used herein refers to cancers that do not migrate via the lymphatic system or via haematogenous spread.

"Progression-free survival" as used herein, refers to the length of time during and after medication or treatment during which the disease being treated (e.g., cancer) does not get worse. "Proliferation" as used in this application involves reproduction or multiplication of similar forms (cells) due to constituting (cellular) elements.

As used herein, "slowing the spread of metastasis" refers to reducing or stopping the formation of new loci; or reducing, stopping, or reversing the tumor load.

As used herein, "slowing the spread of migrating cancer" refers to reducing or stopping the formation of new loci; or reducing, stopping, or reversing the tumor load.

As used herein, and as well understood in the art, "to treat" a condition or "treatment" of the condition (e.g., the conditions described herein such as cancer) is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

As used herein, "tumor seeding" refers to the spillage of tumor cell clusters and their subsequent growth as malignant implants at a site other than the site of the original tumor.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the description below. Other features, objects, and advantages of the invention will be apparent from the description and from the claims.

DETAILED DESCRIPTION OF THE INVENTION

The present invention features methods for preventing or reducing aberrant proliferation, differentiation, or survival of cells. For example, compounds of the invention may be useful in reducing the risk of, or preventing, tumors from increasing in size or from reaching a metastatic state. The subject compounds may be administered to halt the progression or advancement of cancer. In addition, the instant invention includes use of the subject compounds to reduce the risk of, or prevent, a recurrence of cancer.

Compounds

The invention features compounds useful in the treatment of cancer. Exemplary compounds described herein include compounds having a structure according to Formula I as described herein:

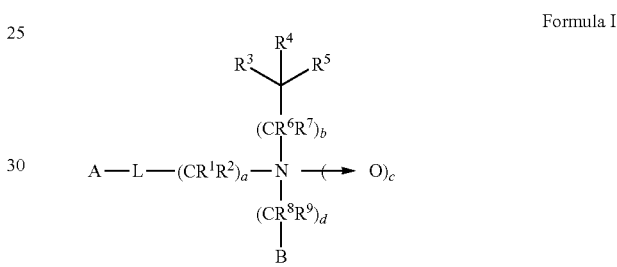

Formula I wherein A is:

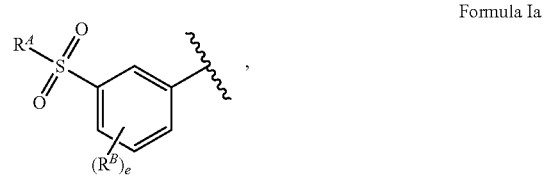

Formula Ia

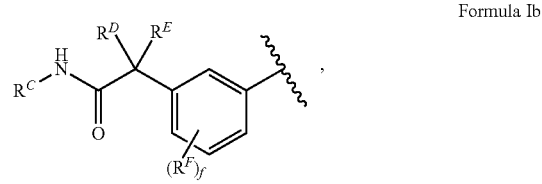

Formula Ib

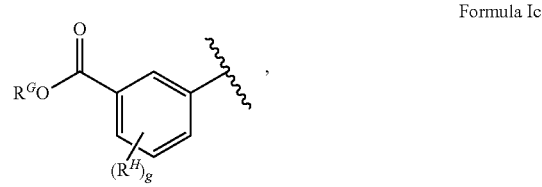

Formula Ic

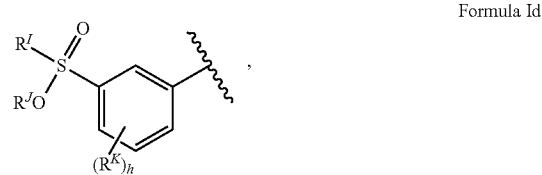

Formula Id

-continued

Formula Ie

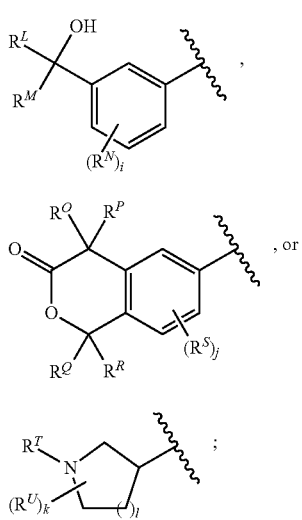

, or

Formula If

Formula Ig wherein e, f, g, h, and i are independently 0, 1, 2, 3, or 4;
j is 0, 1, 2, or 3;
k is 0, 1, 2, 3, 4, 5, 6, 7, or 8;
l is 0, 1, or 2;
$R^A$, $R^C$, $R^I$, $R^L$, $R^M$, and $R^T$ are independently hydrogen, hydroxyl, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_8$-$C_{12}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl;

$R^D$, $R^E$, $R^G$, $R^O$, $R^P$, $R^Q$, and $R^R$ are independently hydrogen, hydroxy, optionally substituted amino, azido, halo, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_8$-$C_{12}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl;

each $R^B$, $R^F$, $R^H$, $R^K$, $R^N$, and $R^S$ are independently hydroxyl, optionally substituted amino, halo, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_8$-$C_{12}$ cycloalkenyl, optionally substituted $C_4$-$C_{10}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl;

$R^J$ is hydrogen, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_9$-$C_{12}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl; or $R^I$ and $R^J$ combine to form an optionally substituted $C_2$-$C_9$ heterocyclyl or $R^J$ and $R^K$ combine to form an optionally substituted $C_2$-$C_9$ heterocyclyl;

$R^U$ is hydroxyl, oxo, optionally substituted amino, halo, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_8$-$C_{12}$ cycloalkenyl, optionally substituted $C_4$-$C_{10}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl; and L is absent, —O—, —S—, —N($R^{12}$)—, or —C($R^4$)($R^5$)—;

a is 2, 3, 4, 5, 6, 7, or 8;

b, c, and d are independently 0 or 1;

each $R^1$, $R^2$, $R^6$, $R^7$, $R^8$, and $R^9$ are independently hydrogen, hydroxyl, halo, optionally substituted amino, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_4$-$C_{10}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl; or $R^1$ and $R^2$ combine to form an optionally substituted $C_3$-$C_{10}$ cycloalkyl, optionally substituted $C_2$-$C_9$ heteroaryl, or optionally substituted $C_2$-$C_9$ heterocyclyl; or $R^6$ and $R^7$ combine to form an optionally substituted $C_3$-$C_{10}$ cycloalkyl, optionally substituted $C_2$-$C_9$ heteroaryl, or optionally substituted $C_2$-$C_9$ heterocyclyl; or $R^8$ and $R^9$ combine to form an optionally substituted $C_3$-$C_{10}$ cycloalkyl, optionally substituted $C_2$-$C_9$ heteroaryl, or optionally substituted $C_2$-$C_9$ heterocyclyl;

$R^3$ is hydrogen, hydroxyl, optionally substituted amino, optionally substituted $C_1$-$C_6$ alkyl, optionally substituted $C_3$-$C_{10}$ cycloalkyl, optionally substituted $C_6$-$C_{10}$ aryl, optionally substituted $C_2$-$C_9$ heteroaryl, or optionally substituted $C_2$-$C_9$ heterocyclyl;

$R^4$ and $R^5$ are independently hydrogen, hydroxyl, halo, optionally substituted amino, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_4$-$C_{10}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl; and B is optionally substituted $C_3$-$C_{10}$ cycloalkyl, optionally substituted $C_6$-$C_{10}$ aryl, optionally substituted $C_2$-$C_9$ heteroaryl, or optionally substituted $C_2$-$C_9$ heterocyclyl;

or a pharmaceutically acceptable salt thereof and/or a prodrug thereof.

In some embodiments, the compound is a prodrug or a pharmaceutically acceptable salt of a prodrug (e.g., A includes a moiety —$OR^V$, wherein $R^V$ is:

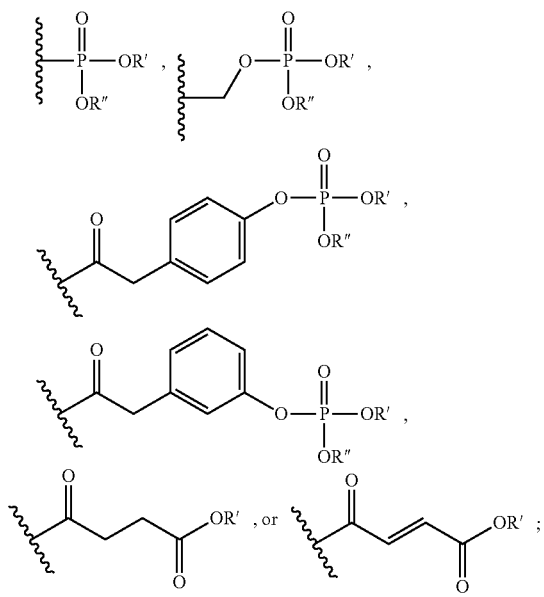

wherein each R' and R" is independently hydrogen, optionally substituted $C_1$-$C_6$ alkyl, such as methyl or t-butyl, or optionally substituted $C_6$-$C_{10}$ aryl $C_1$-$C_6$ alkyl, such as benzyl).

For example, in some embodiments A is:

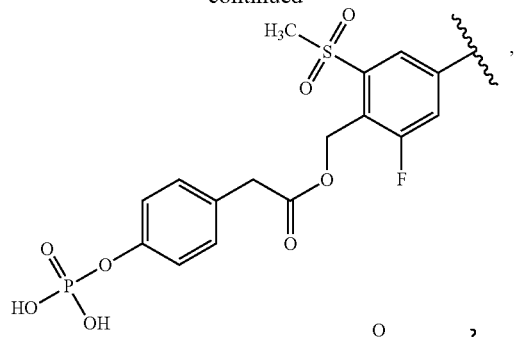

-continued

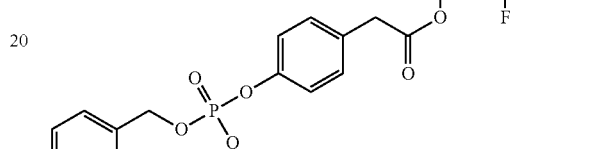

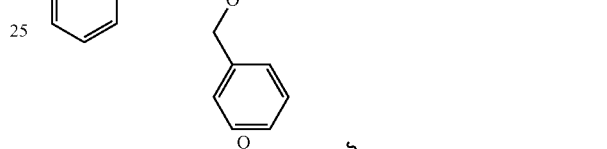

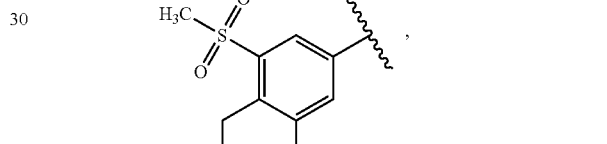

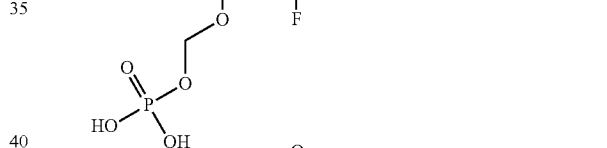

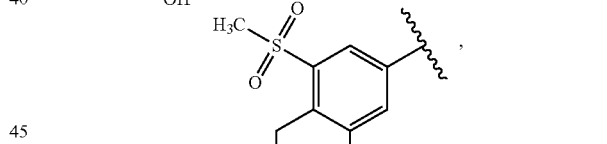

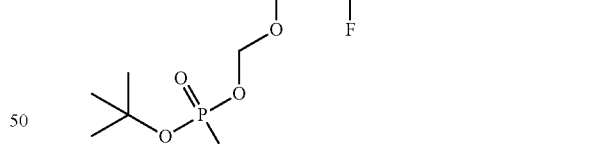

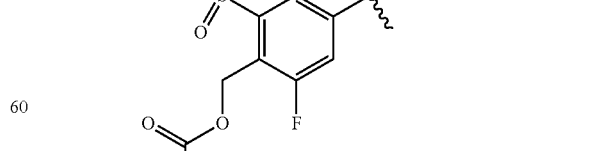

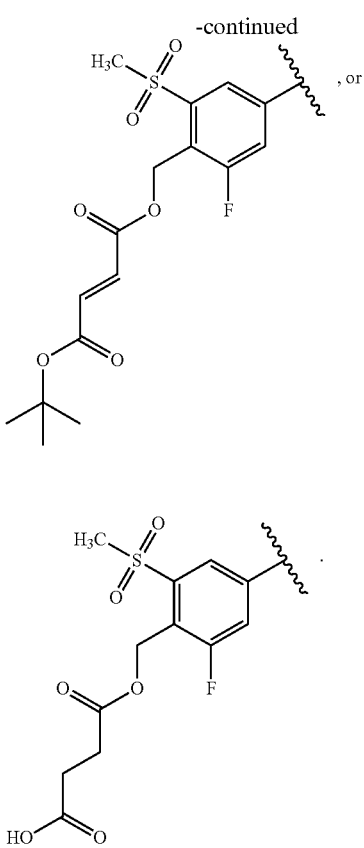

, or

Other embodiments (e.g., any compound described herein), as well as exemplary methods for the synthesis of these compounds, are described herein.

Utility and Administration

The compounds described herein (e.g., a compound according to Formula I or any of compound of Table 1 or Table 4) are useful in the methods of the invention and, while not bound by theory, are believed to exert their desirable effects through their ability to act as LXR agonists. The compounds described herein (e.g., a compound according to Formula I or any of Table 1 or Table 4) can also be used for the treatment of certain conditions such as cancer.

While nuclear hormone receptors have emerged as key therapeutic targets in hormonally driven cancers, their potential for therapeutic benefit in non-hormonally induced epithelial cancers has not been explored. Melanoma, a non-hormonally driven carcinoma with steeply increasing incidence, represents the most aggressive type of skin cancer that incurs ~48,000 deaths annually worldwide (Lucas et al., 2006). Presently, there are no effective therapies for the prevention of melanoma metastasis, with interferon alpha (IFN-α), the only FDA-approved adjuvant therapy in melanoma, conferring a 5-year overall survival benefit of an inappreciable 1-3% (Garbe et al., Oncologist, 2011, 16(1): 5-24). The poor clinical prognosis and the lack of curative and preventative therapies for patients with advanced (stages IV) melanoma necessitate the development and implementation of novel approaches that prevent metastatic relapse rates in this cancer. LXRβ is the major LXR isoform expressed by melanoma cells and pharmacologic modulation of LXRβ strongly inhibits melanoma progression phenotypes—cell invasion, endothelial recruitment, tumor progression, and metastasis. LXRβ targeting mediates melanoma suppression through the transcriptional induction of cancer-derived and systemic ApoE—a potent metastasis suppressor in melanoma.

LXRα and LXRβ, initially discovered by multiple groups at roughly the same time, belong to a family of nuclear hormone receptors that are endogenously activated by cholesterol and its oxidized derivatives to mediate transcription of genes involved in maintaining glucose, cholesterol, and fatty acid metabolism. Given the intricate link between lipid metabolism and cancer cell growth (Cairns et al., Nat Rev Cancer, 2011 February; 11(2):85-95), the ubiquitous expression of LXRβ in melanoma is unlikely to be coincidental, allowing melanoma cells to synthesize lipids and lipoprotein particles to sustain their growth. At the same time, however, such stable basal expression levels make LXRβ an ideal therapeutic target, as exemplified by the broad-ranging responsiveness of melanoma cells to LXRβ activation therapy.

Compounds have been shown to have selectivity for LXRβ or LXRα. This selectivity may allow for increased activity and/or decreased off target effects. Examples of compounds with selectivity towards LXRβ or LXRα are shown in Table 2.

TABLE 2

EC$_{50}$ values for selected compounds against LXRα and LXRβ

| Compound | EC$_{50}$ – LXRα (nM) | EC$_{50}$ – LXRβ (nM) |
|---|---|---|
| 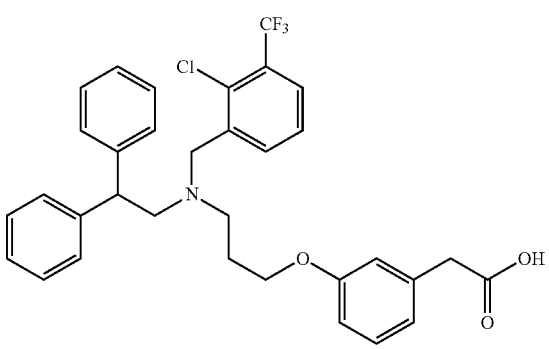 GW3965 | 200 | 40 |

TABLE 2-continued

EC$_{50}$ values for selected compounds against LXRα and LXRβ

| Compound | EC$_{50}$ – LXRα (nM) | EC$_{50}$ – LXRβ (nM) |
|---|---|---|
| 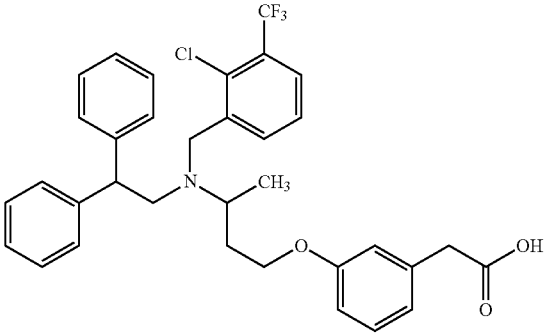 SB742881 | 74 | 25 |
| 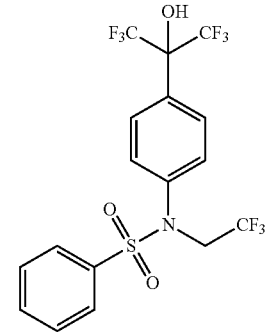 TO901317 | 20 | 50 |
| 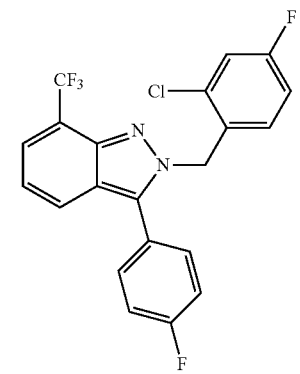 LXR-623 | 179 | 24 |

As used herein, reference to the activity of an LXR agonist at LXRα and LXRβ refer to the activity as measured using the ligand sensing assay (LiSA) described in Spencer et al. J. Med. Chem. 2001, 44, 886-897, incorporated herein by reference. In some embodiments, the LXR agonist has an EC$_{50}$ of less than 1 μM in the ligand sensing assay (e.g., 0.5 nm to 500 nM, 10 nM to 100 nM). For example, the methods of the invention can be performed using an LXRβ agonist having activity for LXRβ that is at least 3-fold greater than the activity of the agonist for LXRα, or having activity for LXRβ that is at least 10-fold greater than the activity of the agonist for LXRα, or having activity for LXRβ that is at least 100-fold greater than the activity of the agonist for LXRα, or having activity for LXRβ that is at least within 3-fold of the activity of the agonist for LXRα. The term "greater activity" in the LiSA assay assay refers to a lower EC$_{50}$. For example, GW3965 has approximately 6-fold greater activity for LXRβ (EC$_{50}$=40) compared to LXRα (EC$_{50}$=200).

As used herein, the term "increases the level of ApoE expression in vitro" refers to certain LXR agonists capable of increasing the level of ApoE expression 2.5-fold in the qPCR assay of Example 1 at a concentration of less than 5 μM (e.g., at a concentration of 100 nM to 2 μM, at a concentration of less than or equal to 1 µM). The LXR agonists exhibiting this in vitro effect can be highly efficacious for use in the methods of the invention.

As used herein, the term "increases the level of ApoE expression in vivo" refers to certain LXR agonists capable of increasing the level of ApoE expression 2.5-fold in the whole blood gene expression analysis assay of Example 4 at a concentration of less than 5 µM (e.g., at a concentration of 100 nM to 2 µM, at a concentration of less than or equal to 1 µM). The LXR agonists exhibiting this in vivo effect can be highly efficacious for use in the methods of the invention.

Treatment Methods

As disclosed herein, and known in the art (e.g., as disclosed in Pencheva et al. Cell 151(5): 1068-1082, 2012 incorporated herein by reference) ApoE and LXR function as metastasis suppressors or inhibitors of the same process. Cancer-secreted ApoE suppresses invasion and endothelial recruitment by activating melanoma cell LRP1 and endothelial LRP8 receptors, respectively. Accordingly, this invention provides methods for treating cancer via increasing in the subject the expression level or activity level of ApoE.

Compounds that increase expression of ApoE or are LXR agonists have been shown to be effective in the treatment of murine models of atherosclerosis, diabetes, anti-inflammation, and Alzheimer's disease as disclosed in Li et al. Expert Opin. Ther. Pat. 20(4):535-562, 2010, herein incorporated by reference.

The invention also provides methods for treating in a subject an angiogenic disorder or a disorder of angiogenesis. The terms "angiogenic disorder," "disorder of angiogenesis," and "angiogenesis disorder" are used interchangeably herein, and refer to a disorder characterized by pathological angiogenesis. A disorder characterized by pathological angiogenesis refers to a disorder where abnormal or aberrant angiogenesis, alone or in combination with others, contributes to causation, origination, or symptom of the disorder. Examples of this disorder include various cancers (e.g., vascularized tumors), eye disorders, inflammatory disorders, and others.

Typical vascularized tumors that can be treated with the method include solid tumors, particularly carcinomas, which require a vascular component for the provision of oxygen and nutrients. Exemplary solid tumors include, but are not limited to, carcinomas of the lung, breast, bone, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, glioblastomas, neuroblastomas, Kaposi's sarcoma, and sarcomas.

A number of disorders or conditions, other than cancer, also can be treated with the above-described method. Examples include arthritis, rheumatoid arthritis, psoriasis, atherosclerosis, diabetic retinopathy, age-related macular degeneration, Grave's disease, vascular restenosis (including restenosis following angioplasty), arteriovenous malformations (AVM), meningioma, hemangioma, neovascular glaucoma, chronic kidney disease, diabetic nephropathy, polycystic kidney disease, interstitial lung disease, pulmonary hypertension, chronic obstructive pulmonary disease (COPD), emphysema, autoimmune hepatitis, chronic inflammatory liver disease, hepatic cirrhosis, cutaneous T-cell lymphoma, rosacea, and basal cell carcinoma.

Other treatment targets include those described in, e.g., US Applications 2009004297, 20090175791, and 20070161553, such as angiofibroma, atherosclerotic plaques, corneal graft neovascularization, hemophilic joints, hypertrophic scars, Osler-Weber syndrome, pyogenic granuloma retrolental fibroplasia, scleroderma, trachoma, vascular adhesions, synovitis, dermatitis, various other inflammatory diseases and disorders, and endometriosis.

Treating cancer can result in a reduction in size or volume of a tumor. For example, after treatment, tumor size is reduced by 5% or greater (e.g., 10%, 20%, 30%, 40%, 50%, 60%, 70%, 80%, 90% or greater) relative to its size prior to treatment. Size of a tumor may be measured by any reproducible means of measurement. The size of a tumor may be measured as a diameter of the tumor or by any reproducible means of measurement.

Treating cancer may further result in a decrease in number of tumors. For example, after treatment, tumor number is reduced by 5% or greater (e.g., 10%, 20%, 30%, 40%, 50%, 60%, 70%, 80%, 90% or greater) relative to number prior to treatment. Number of tumors may be measured by any reproducible means of measurement. The number of tumors may be measured by counting tumors visible to the naked eye or at a specified magnification (e.g., 2×, 3×, 4×, 5×, 10×, or 50×).

Treating cancer can result in a decrease in number of metastatic nodules in other tissues or organs distant from the primary tumor site. For example, after treatment, the number of metastatic nodules is reduced by 5% or greater (e.g., 10%, 20%, 30%, 40%, 50%, 60%, 70%, 80%, 90% or greater) relative to number prior to treatment. The number of metastatic noduless may be measured by any reproducible means of measurement. The number of metastatic nodules may be measured by counting metastatic nodules visible to the naked eye or at a specified magnification (e.g., 2×, 10×, or 50×).

Treating cancer can result in an increase in average survival time of a population of subjects treated according to the present invention in comparison to a population of untreated subjects. For example, the average survival time is increased by more than 30 days (more than 60 days, 90 days, or 120 days). An increase in average survival time of a population may be measured by any reproducible means. An increase in average survival time of a population may be measured, for example, by calculating for a population the average length of survival following initiation of treatment with the compound of the invention. An increase in average survival time of a population may also be measured, for example, by calculating for a population the average length of survival following completion of a first round of treatment with the compound of the invention.

Treating cancer can also result in a decrease in the mortality rate of a population of treated subjects in comparison to an untreated population. For example, the mortality rate is decreased by more than 2% (e.g., more than 5%, 10%, or 25%). A decrease in the mortality rate of a population of treated subjects may be measured by any reproducible means, for example, by calculating for a population the average number of disease-related deaths per unit time following initiation of treatment with the compound of the invention. A decrease in the mortality rate of a population may also be measured, for example, by calculating for a population the average number of disease-related deaths per unit time following completion of a first round of treatment with the compound of the invention.

Treating cancer can also result in an increased average progression-free survival time of a population of treated subjects in comparison to an untreated population. For example the average progression-free survival time is increased by more than 30 days (more than 60 days, 90 days, or 120 days). An increase in average progression-free survival time of a population may be measured by any reproducible means. An increase in average progression-free survival time of a population may be measured, for example, by calculating for a population the average length of progression-free survival following initiation of treatment with the compound of the invention. An increase in average progression-free survival time of a population may also be measured, for example, by calculating for a population the average length of progression-free survival following completion of a first round of treatment with the compound of the invention.

An increase in ApoE levels has also been shown to be effective for the treatment of neurological disorders. For example, Jiang et al., Neuron, 2008, 58(5):681-693, herein incorporated by reference, have shown brain ApoE induction by GW3965 leads to therapeutic reduction of amyloid-beta plaques in a mouse model of Alzheimer's disease resulting in improved memory deficits. Other references which establish a link between increased ApoE expression by LXR agonists and the treatment of Alzheimers disease include Donkin et al., J Biol Chem, 2010, 285:34144-34154; Fitz et al., J Neurosci. 2010, 30:6862-6872; Koldamova et al., J Biol Chem 2008, 280:4079-4088; and Riddell et al. Mol Cell Neurosci, 2007, 34:621-628, each of which is incorporated herein by reference. Accordingly, this invention provides methods for treating neurological disorders such as Alzheimers disease via increasing in the subject the expression level or activity level of ApoE.

As is known in the art, LXR activation is associated with inflammation, hyperproliferation, and/or disordered skin barrier differentiation, e.g., see International Patent Publication Nos.: WO2013/130892 and WO2013/138565, each of which is herein incorporated by reference. Further LXR activation also modulates several pathways underlying etiology and pathology of skin aging. Accordingly, this invention provides methods for treating dermal diseases, disorders, or conditions (e.g., skin aging, scarring, psoriasis, atopic dermatitis, eczema, urticaria, rosacea, burns, or acne) including administering an effective amount of a compound of the invention.

The liver X receptors (LXR alpha and LXR beta) are highly expressed in the epidermis and LXR activators stimulate keratinocyte proliferation and differentiation. Activation of LXRs also improves permeability barrier homeostasis by a number of mechanisms, including stimulating epidermal lipid synthesis, increasing lamellar body formation and secretion, and increasing the activity of enzymes required for the extracellular processing of lipids in the stratum corneum, leading to the formation of lamellar membranes that mediate permeability barrier function. LXR activation is also anti-inflammatory, reducing inflammation in animal models of allergic and irritant contact dermatitis. (Schmuth et al. 2008, Journal of Lipid Research, 49, 499-509).

Examples of conditions that involve or give rise to a disrupted or dysfunctional epidermal barrier are: inflammation to mucous membranes, such as cheilitis, chapped lips, nasal irritation and vulvovaginitis; eczematous dermnatitides, such as atopic and seborrheic dermatitis, allergic or irritant contact dermatitis, eczema craquelee, photo allergic dermatitis, phototoxic dermatitis, phytophotodermatitis, radiation dermatitis, and stasis dermatitis; ulcers and erosions resulting from trauma, burns, bullous disorders, or ischemia of the skin or mucous membranes; several forms of ichthyoses; epidermolysis bullosae; psoriasis; hypertrophic scars and keloids and cutaneous changes of intrinsic aging and photoaging.

Topical formulations containing LXR activators or activators described herein are applied to beneficial effect to skin and/or mucus membranes. The activators are formulated as lotions, solutions, gels, creams, emollient creams, unguents, sprays, or any other form that will permit topical application. The formulation may also contain one or more agents that promote the spreading of the formulation over the affected area, but are otherwise biologically inactive. Examples of these agents are surfactants, humectants, wetting agents, emulsifiers, or propellants.

Amounts that are referred to herein as effective in enhancing barrier development are any amount that will cause a substantial relief of the symptoms of a disrupted or dysfunctional epidermal permeability barrier when applied repeatedly over time. The optimum amounts in any given instance will be readily apparent to those skilled in the art or are capable of determination by routine experimentation.

Examples of skin conditions that are susceptible to topical treatment with LXR activators are: atopic and seborrheic dermatitis; inflammation to mucous membranes, such as cheilitis, chapped lips, nasal irritation and vulvovaginitis; eczematous dermatitis resulting from allergic and irritant contact, eczema craquelee, radiation and stasis dermatitis; ulcers and erosions due to chemical or thermal burns, bullous disorders, or vascular compromise or ischemia including venous, arterial, embolic or diabetic ulcers; ichthyoses, with or without an associated barrier abnormality; epidermolysis bullosa; psoriasis; hypertrophic scars and keloids; intrinsic aging, photoaging and/or dermatoheliosus; melanoma and non-melanoma skin cancer, including lignin melanoma, basal cell carcinoma, squamous cell carcinoma, actinic keratoses, and virally induced neoplasia (warts and condylomata accuminata).

Compositions

Within the scope of this invention is a composition that contains a suitable carrier and one or more of the therapeutic agents described above. The composition can be a pharmaceutical composition that contains a pharmaceutically acceptable carrier, a dietary composition that contains a dietarily acceptable suitable carrier, or a cosmetic composition that contains a cosmetically acceptable carrier.

The term "pharmaceutical composition" refers to the combination of an active agent with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active compound. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, sodium lauryl sulfate, and D&C Yellow #10.

As used herein, the term "pharmaceutically acceptable salt" refers to those salts which are, within the scope of sound medical judgment, suitable for use in contact with the tissues of humans and lower animals without undue toxicity, irritation, or allergic response, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J. Pharmaceutical Sciences, 66:1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts, include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. Representative alkali or alkaline earth metal salts include sodium, lithium, potassium, calcium, and magnesium. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutical compositions of the present invention additionally include a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, and lubricants, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; natural and synthetic phospholipids, such as soybean and egg yolk phosphatides, lecithin, hydrogenated soy lecithin, dimyristoyl lecithin, dipalmitoyl lecithin, distearoyl lecithin, dioleoyl lecithin, hydroxylated lecithin, lysophosphatidylcholine, cardiolipin, sphingomyelin, phosphatidylcholine, phosphatidyl ethanolamine, diastearoyl phosphatidylethanolamine (DSPE) and its pegylated esters, such as DSPE-PEG750 and, DSPE-PEG2000, phosphatidic acid, phosphatidyl glycerol and phosphatidyl serine. Commercial grades of lecithin which are preferred include those which are available under the trade name Phosal® or Phospholipon® and include Phosal 53 MCT, Phosal 50 PG, Phosal 75 SA, Phospholipon 90H, Phospholipon 90G and Phospholipon 90 NG; soy-phosphatidylcholine (SoyPC) and DSPE-PEG2000 are particularly preferred; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The above-described composition, in any of the forms described above, can be used for treating melanoma, or any other disease or condition described herein. An effective amount refers to the amount of an active compound/agent that is required to confer a therapeutic effect on a treated subject. Effective doses will vary, as recognized by those skilled in the art, depending on the types of diseases treated, route of administration, excipient usage, and the possibility of co-usage with other therapeutic treatment.

A pharmaceutical composition of this invention can be administered parenterally, orally, nasally, rectally, topically, or buccally. The term "parenteral" as used herein refers to subcutaneous, intracutaneous, intravenous, intrmuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent. Such solutions include, but are not limited to, 1,3-butanediol, mannitol, water, Ringer's solution, and isotonic sodium chloride solution. In addition, fixed oils are conventionally employed as a solvent or suspending medium (e.g., synthetic mono- or diglycerides). Fatty acid, such as, but not limited to, oleic acid and its glyceride derivatives, are useful in the preparation of injectables, as are natural pharmaceutically acceptable oils, such as, but not limited to, olive oil or castor oil, polyoxyethylated versions thereof. These oil solutions or suspensions also can contain a long chain alcohol diluent or dispersant such as, but not limited to, carboxymethyl cellulose, or similar dispersing agents. Other commonly used surfactants, such as, but not limited to, Tweens or Spans or other similar emulsifying agents or bioavailability enhancers, which are commonly used in the manufacture of pharmaceutically acceptable solid, liquid, or other dosage forms also can be used for the purpose of formulation.

A composition for oral administration can be any orally acceptable dosage form including capsules, tablets, emulsions and aqueous suspensions, dispersions, and solutions. In the case of tablets, commonly used carriers include, but are not limited to, lactose and corn starch. Lubricating agents, such as, but not limited to, magnesium stearate, also are typically added. For oral administration in a capsule form, useful diluents include, but are not limited to, lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

Pharmaceutical compositions for topical administration according to the described invention can be formulated as solutions, ointments, creams, suspensions, lotions, powders, pastes, gels, sprays, aerosols, or oils. Alternatively, topical formulations can be in the form of patches or dressings impregnated with active ingredient(s), which can optionally include one or more excipients or diluents. In some preferred embodiments, the topical formulations include a material that would enhance absorption or penetration of the active agent(s) through the skin or other affected areas.

A topical composition contains a safe and effective amount of a dermatologically acceptable carrier suitable for application to the skin. A "cosmetically acceptable" or "dermatologically-acceptable" composition or component refers a composition or component that is suitable for use in contact with human skin without undue toxicity, incompatibility, instability, or allergic response. The carrier enables an active agent and optional component to be delivered to the skin at an appropriate concentration(s). The carrier thus can act as a diluent, dispersant, solvent, or the like to ensure that the active materials are applied to and distributed evenly over the selected target at an appropriate concentration. The carrier can be solid, semi-solid, or liquid. The carrier can be in the form of a lotion, a cream, or a gel, in particular one that has a sufficient thickness or yield point to prevent the active materials from sedimenting. The carrier can be inert or possess dermatological benefits. It also should be physically and chemically compatible with the active components described herein, and should not unduly impair stability, efficacy, or other use benefits associated with the composition.

Combination Therapies

In some embodiments, the pharmaceutical composition may further include an additional compound having antiproliferative activity. The additional compound having antiproliferative activity can be selected from a group of antiproliferative agents including those shown in Table 3.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder, or they may achieve different effects (e.g., control of any adverse effects).

By "antiproliferative agent" is meant any antiproliferative agent, including those antiproliferative agents listed in Table 3, any of which can be used in combination with a LXR agonist to treat the medical conditions recited herein. Antiproliferative agents also include organo-platine derivatives, naphtoquinone and benzoquinone derivatives, chrysophanic acid and anthroquinone derivatives thereof.

TABLE 3

| | | |
|---|---|---|
| Alkylating agents | Busulfan | Chlorambucil |
| | dacarbazine | procarbazine |
| | ifosfamide | altretamine |
| | hexamethylmelamine | estramustine phosphate |
| | thiotepa | mechlorethamine |
| | lomustine | streptozocin |
| | cyclophosphamide | temozolomide |
| | | Semustine |
| Platinum agents | spiroplatin | lobaplatin (Aeterna) |
| | tetraplatin | satraplatin (Johnson Matthey) |
| | ormaplatin | BBR-3464 (Hoffmann-La Roche) |
| | iproplatin | SM-11355 (Sumitomo) |
| | ZD-0473 (AnorMED) | AP-5280 (Access) |
| | oxaliplatin | cisplatin |
| | carboplatin | |
| Antimetabolites | azacytidine | trimetrexate |
| | Floxuridine | deoxycoformycin |
| | 2-chlorodeoxyadenosine | pentostatin |
| | 6-mercaptopurine | hydroxyurea |
| | 6-thioguanine | decitabine (SuperGen) |
| | cytarabine | clofarabine (Bioenvision) |
| | 2-fluorodeoxy cytidine | irofulven (MGI Pharma) |
| | methotrexate | DMDC (Hoffmann-La Roche) |
| | tomudex | ethynylcytidine (Taiho) |
| | fludarabine | gemcitabine |
| | raltitrexed | capecitabine |
| Topoisomerase inhibitors | amsacrine | exatecan mesylate (Daiichi) |
| | epirubicin | quinamed (ChemGenex) |
| | etoposide | gimatecan (Sigma-Tau) |
| | teniposide or mitoxantrone | diflomotecan (Beaufour-Ipsen) |
| | 7-ethyl-10-hydroxy-camptothecin | TAS-103 (Taiho) |
| | dexrazoxanet (TopoTarget) | elsamitrucin (Spectrum) |
| | pixantrone (Novuspharma) | J-107088 (Merck & Co) |
| | rebeccamycin analogue (Exelixis) | BNP-1350 (BioNumerik) |
| | BBR-3576 (Novuspharma) | CKD-602 (Chong Kun Dang) |
| | rubitecan (SuperGen) | KW-2170 (Kyowa Hakko) |
| | irinotecan (CPT-11) | hydroxycamptothecin (SN-38) |
| | topotecan | |

TABLE 3-continued

| Category | Agents |
|---|---|
| Antitumor antibiotics | valrubicin, therarubicin, idarubicin, rubidazone, plicamycin, porfiromycin, mitoxantrone (novantrone), amonafide, azonafide, anthrapyrazole, oxantrazole, losoxantrone, MEN-10755 (Menarini), GPX-100 (Gem Pharmaceuticals), Epirubicin, mitoxantrone, doxorubicin |
| Antimitotic agents | colchicine, vinblastine, vindesine, dolastatin 10 (NCI), rhizoxin (Fujisawa), mivobulin (Warner-Lambert), cemadotin (BASF), RPR 109881A (Aventis), TXD 258 (Aventis), epothilone B (Novartis), T 900607 (Tularik), T 138067 (Tularik), cryptophycin 52 (Eli Lilly), vinflunine (Fabre), auristatin PE (Teikoku Hormone), BMS 247550 (BMS), BMS 184476 (BMS), BMS 188797 (BMS), taxoprexin (Protarga), SB 408075 (GlaxoSmithKline), Vinorelbine, Trichostatin A, E7010 (Abbott), PG-TXL (Cell Therapeutics), IDN 5109 (Bayer), A 105972 (Abbott), A 204197 (Abbott), LU 223651 (BASF), D 24851 (ASTAMedica), ER-86526 (Eisai), combretastatin A4 (BMS), isohomohalichondrin-B (PharmaMar), ZD 6126 (AstraZeneca), AZ10992 (Asahi), IDN-5109 (Indena), AVLB (Prescient NeuroPharma), azaepothilone B (BMS), BNP-7787 (BioNumerik), CA-4 prodrug (OXiGENE), dolastatin-10 (NIH), CA-4 (OXiGENE), docetaxel, vincristine, paclitaxel |
| Aromatase inhibitors | aminoglutethimide, atamestane (BioMedicines), letrozole, anastrazole, YM-511 (Yamanouchi), formestane, exemestane |
| Thymidylate synthase inhibitors | pemetrexed (Eli Lilly), ZD-9331 (BTG), nolatrexed (Eximias), CoFactor™ (BioKeys) |
| DNA antagonists | trabectedin (PharmaMar), glufosfamide (Baxter International), albumin + 32P (Isotope Solutions), thymectacin (NewBiotics), edotreotide (Novartis), mafosfamide (Baxter International), apaziquone (Spectrum Pharmaceuticals), O6 benzyl guanine (Paligent) |
| Farnesyltransferase inhibitors | arglabin (NuOncology Labs), lonafarnib (Schering-Plough), BAY-43-9006 (Bayer), tipifarnib (Johnson & Johnson), perillyl alcohol (DOR BioPharma) |
| Pump inhibitors | CBT-1 (CBA Pharma), tariquidar (Xenova), MS-209 (Schering AG), zosuquidar trihydrochloride (Eli Lilly), biricodar dicitrate (Vertex) |
| Histone acetyltransferase inhibitors | tacedinaline (Pfizer), SAHA (Aton Pharma), MS-275 (Schering AG), pivaloyloxymethyl butyrate (Titan), depsipeptide (Fujisawa) |
| Metalloproteinase inhibitors | Neovastat (Aeterna Laboratories), marimastat (British Biotech), CMT-3 (CollaGenex), BMS-275291 (Celltech) |
| Ribonucleoside reductase inhibitors | gallium maltolate (Titan), triapine (Vion), tezacitabine (Aventis), didox (Molecules for Health) |
| TNF alpha agonists/antagonists | virulizin (Lorus Therapeutics), CDC-394 (Celgene), revimid (Celgene) |
| Endothelin A receptor antagonist | atrasentan (Abbott), ZD-4054 (AstraZeneca), YM-598 (Yamanouchi) |
| Retinoic acid receptor agonists | fenretinide (Johnson & Johnson), LGD-1550 (Ligand), alitretinoin (Ligand) |
| Immuno-modulators | interferon, oncophage (Antigenics), GMK (Progenics), adenocarcinoma vaccine (Biomira), CTP-37 (AVI BioPharma), IRX-2 (Immuno-Rx), PEP-005 (Peplin Biotech), synchrovax vaccines (CTL Immuno), melanoma vaccine (CTL Immuno), p21 RAS vaccine (GemVax), MAGE-A3 (GSK), nivolumab (BMS), abatacept (BMS), pembrolizumab (Merck), dexosome therapy (Anosys), pentrix (Australian Cancer Technology), ISF-154 (Tragen), cancer vaccine (Intercell), norelin (Biostar), BLP-25 (Biomira), MGV (Progenics), β-alethine (Dovetail), CLL therapy (Vasogen), Ipilimumab (BMS), CM-10 (cCam Biotherapeutics), MPDL3280A (Genentech) |

TABLE 3-continued

| Category | | |
|---|---|---|
| Hormonal and antihormonal agents | estrogens<br>conjugated estrogens<br>ethinyl estradiol<br>chlortrianisen<br>idenestrol<br>hydroxyprogesterone caproate<br>medroxyprogesterone<br>testosterone<br>testosterone propionate;<br>fluoxymesterone<br>methyltestosterone<br>diethylstilbestrol<br>megestrol<br>bicalutamide<br>flutamide<br>nilutamide | dexamethasone<br>prednisone<br>methylprednisolone<br>prednisolone<br>aminoglutethimide<br>leuprolide<br>octreotide<br>mitotane<br>P-04 (Novogen)<br>2-methoxyestradiol (EntreMed)<br>arzoxifene (Eli Lilly)<br>tamoxifen<br>toremofine<br>goserelin<br>Leuporelin<br>bicalutamide |
| Photodynamic agents | talaporfin (Light Sciences)<br>Theralux (Theratechnologies)<br>motexafin gadolinium (Pharmacyclics) | Pd-bacteriopheophorbide (Yeda)<br>lutetium texaphyrin (Pharmacyclics)<br>hypericin |
| Kinase Inhibitors | imatinib (Novartis)<br>leflunomide (Sugen/Pharmacia)<br>ZD1839 (AstraZeneca)<br>erlotinib (Oncogene Science)<br>canertinib (Pfizer)<br>squalamine (Genaera)<br>SU5416 (Pharmacia)<br>SU6668 (Pharmacia)<br>ZD4190 (AstraZeneca)<br>ZD6474 (AstraZeneca)<br>vatalanib (Novartis)<br>PKI166 (Novartis)<br>GW2016 (GlaxoSmithKline)<br>EKB-509 (Wyeth)<br>trastuzumab (Genentech)<br>OSI-774 (Tarceva ™)<br>CI-1033 (Pfizer)<br>SU11248 (Pharmacia)<br>RH3 (York Medical)<br>Genistein<br>Radicinol<br>Met-MAb (Roche)<br>SR-27897 (CCK A inhibitor, Sanofi-Synthelabo)<br>tocladesine (cyclic AMP agonist, Ribapharm)<br>alvocidib (CDK inhibitor, Aventis)<br>CV-247 (COX-2 inhibitor, Ivy Medical)<br>P54 (COX-2 inhibitor, Phytopharm)<br>CapCell ™ (CYP450 stimulant, Bavarian Nordic)<br>GCS-100 (gal3 antagonist, GlycoGenesys)<br>G17DT immunogen (gastrin inhibitor, Aphton)<br>efaproxiral (oxygenator, Allos Therapeutics)<br>PI-88 (heparanase inhibitor, Progen)<br>tesmilifene (histamine antagonist, YM BioSciences)<br>histamine (histamine H2 receptor agonist, Maxim)<br>tiazofurin (IMPDH inhibitor, Ribapharm)<br>cilengitide (integrin antagonist, Merck KGaA)<br>SR-31747 (IL-1 antagonist, Sanofi-Synthelabo)<br>CCI-779 (mTOR kinase inhibitor, Wyeth)<br>exisulind (PDE V inhibitor, Cell Pathways)<br>CP-461 (PDE V inhibitor, Cell Pathways)<br>AG-2037 (GART inhibitor, Pfizer)<br>WX-UK1 (plasminogen activator inhibitor, Wilex)<br>PBI-1402 (PMN stimulant, ProMetic LifeSciences)<br>bortezomib (proteasome inhibitor, Millennium)<br>SRL-172 (T cell stimulant, SR Pharma)<br>TLK-286 (glutathione S transferase inhibitor, Telik)<br>PT-100 (growth factor agonist, Point Therapeutics)<br>midostaurin (PKC inhibitor, Novartis)<br>bryostatin-1 (PKC stimulant, GPC Biotech)<br>CDA-II (apoptosis promotor, Everlife)<br>SDX-101 (apoptosis promotor, Salmedix)<br>rituximab (CD20 antibody, Genentech)<br>carmustine<br>Mitoxantrone<br>Bleomycin<br>Absinthin<br>Chrysophanic acid | EKB-569 (Wyeth)<br>kahalide F (PharmaMar)<br>CEP-701 (Cephalon)<br>CEP-751 (Cephalon)<br>MLN518 (Millenium)<br>PKC412 (Novartis)<br>Phenoxodiol (Novogen)<br>C225 (ImClone)<br>rhu-Mab (Genentech)<br>MDX-H210 (Medarex)<br>2C4 (Genentech)<br>MDX-447 (Medarex)<br>ABX-EGF (Abgenix)<br>IMC-1C11 (ImClone)<br>Tyrphostins<br>Gefitinib (Iressa)<br>PTK787 (Novartis)<br>EMD 72000 (Merck)<br>Emodin<br>Radicinol<br>Vemurafenib (B-Raf enzyme inhibitor, Daiichi Sankyo)<br>ceflatonin (apoptosis promotor, ChemGenex)<br>BCX-1777 (PNP inhibitor, BioCryst)<br>ranpirnase (ribonuclease stimulant, Alfacell)<br>galarubicin (RNA synthesis inhibitor, Dong-A)<br>tirapazamine (reducing agent, SRI International)<br>N-acetylcysteine (reducing agent, Zambon)<br>R-flurbiprofen (NF-kappaB inhibitor, Encore)<br>3CPA (NF-kappaB inhibitor, Active Biotech)<br>seocalcitol (vitamin D receptor agonist, Leo)<br>131-I-TM-601 (DNA antagonist, TransMolecular)<br>eflornithine (ODC inhibitor, ILEX Oncology)<br>minodronic acid (osteoclast inhibitor, Yamanouchi)<br>indisulam (p53 stimulant, Eisai)<br>aplidine (PPT inhibitor, PharmaMar)<br>gemtuzumab (CD33 antibody, Wyeth Ayerst)<br>PG2 (hematopoiesis enhancer, Pharmagenesis)<br>Immunol ™ (triclosan oral rinse, Endo)<br>triacetyluridine (uridine prodrug, Wellstat)<br>SN-4071 (sarcoma agent, Signature BioScience)<br>TransMID-107 ™ (immunotoxin, KS Biomedix)<br>PCK-3145 (apoptosis promotor, Procyon)<br>doranidazole (apoptosis promotor, Pola)<br>CHS-828 (cytotoxic agent, Leo)<br>trans-retinoic acid (differentiator, NIH)<br>MX6 (apoptosis promotor, MAXIA)<br>apomine (apoptosis promotor, ILEX Oncology)<br>urocidin (apoptosis promotor, Bioniche)<br>Ro-31-7453 (apoptosis promotor, La Roche)<br>brostallicin (apoptosis promotor, Pharmacia)<br>β-lapachone<br>gelonin<br>cafestol<br>kahweol |

TABLE 3-continued

| | |
|---|---|
| Cesium oxides | caffeic acid |
| BRAF inhibitors, | Tyrphostin AG |
| PDL1 inhibitors | PD-1 inhibitors |
| MEK inhibitors | CTLA-4 inhibitors |
| bevacizumab | sorafenib |
| angiogenesis inhibitors | BRAF inhibitors |
| dabrafenib | rindopepimut |
| ramucirumab | vedotin |
| glembatumumab | ANG4043 |
| ANG1005 | Demcizumab |
| Revlimid | pertuzumab |
| Thalidomide | Olaparib |
| Optune | Vintafolide |
| Cobimetinib | Cabozantinib |
| Talimogene laherparepvec | |
| Crizotinib | |

EXAMPLES

Example 1: General Synthesis Methods

The compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4th Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compound as disclosed herein may be derived from reactions and the reactions may be modified by the use of appropriate reagents and conditions, for the introduction of the various moieties found in the formulae as provided herein. As a guide the following synthetic methods may be utilized.

Names of all compounds were generated using ChemAxon's Instant JChem v6.1 for Desktop and IUPAC Naming Plugin.

A comprehensive list of abbreviations utilized by organic chemists appears in the first issue of each volume of the *Journal of Organic Chemistry*. The list, which is typically presented in a table entitled "Standard List of Abbreviations", provides definitions for abbreviations not found in the following list of abbreviations:

ACN acetonitrile
AcOH acetic acid
DCM or $CH_2Cl_2$ dichloromethane or methylene chloride
DIPEA diisopropylethylamine
DMAP 4-dimethylaminopyridine or N,N-dimethylaminopyridine
DME 1,2-dimethoxyethane
DMF N,N-dimethylformamide
DMSO dimethylsulfoxide
EtOAc ethyl acetate
EtOH ethanol
HPLC high performance liquid chromatography
h hour(s)
$H_2O_2$ hydrogen peroxide
INT intermediate
IBX 2-iodoxybenzoic acid
LDA lithium diisopropylamide
LiHMDS lithuim bis(trimethylsilyl)amide
mCPBA meta-chloroperbenzoic acid
MeOH methanol
min minute(s)
mL milliliter
mmol millimole
MS mass spectrometry
MTBE methyl tert-butyl ether
NaHMDS sodium bis(trimethylsilyl)amide
Pd(dppf)$Cl_2$ [1,1'-bis(diphenylphosphino)ferrocene]dichloropalladium(II)
$PdCl_2(PPh_3)_2$ bis(triphenylphosphine)palladium(II) dichloride
Pd/C palladium on carbon
RT room temperature
S.E.M. standard error of the mean
S.D. standard deviation
TBAF 3$H_2O$ tetrabutylammonium fluoride trihydrate
TEA triethylamine
TFA trifluoroacetic acid
THF THF
TLC thin layer chromatography Compounds of the present invention can be prepared using methods illustrated in general synthetic schemes and experimental procedures detailed below. These general synthetic schemes and experimental procedures are presented for purposes of illustration and are not intended to be limiting. Starting materials used to prepare compounds of the present invention are commercially available or can be prepared using routine methods known in the art. Three methodologies described below are used to make compounds described herein.

In Scheme 1, an aldehyde A is reacted with an amine B under standard reductive amination conditions using a reducing agent such as borohydride (e.g. sodium cyanoborohydride or sodium triacetoxyborohydride), an acid (e.g. acetic acid or TFA), and a solvent (e.g. THF, DCM, ACN) to afford secondary amines C. These amines are alkylated with various optionally substituted carbon linkers (e.g. 1,3-dibromopropane, 3-bromopropanol, 1,4-dibromobutane, etc.) in polar solvent (e.g. DMF, THF, ACN) to afford tertiary amines D. X represents a leaving group (i.e. chloride, bromide, iodide, methanesulfonate, para-toluenesulfoneate, trifluoromethanesulfonate), if not already part of the original carbon linker reagent, it is installed after the linker is attached, for example through mesylate formation from an alcohol. Finally, the leaving group X is displaced with the appropriate nucleophile (R4OH) using base (e.g. potassium carbonate, cesium carbonate) in polar solvent (e.g. DMF, THF, ACN) to afford the final products E.

Scheme 1

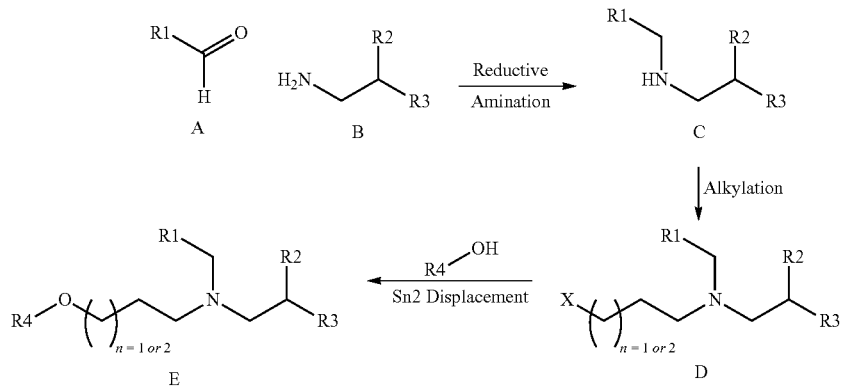

In Scheme 2, amines B are reacted with silyl-protect carbinols F via displacement of the leaving group X (e.g. chloride, bromide, iodide, methanesulfonate, para-toluene-sulfoneate, trifluoromethanesulfonate) in a polar solvent (e.g. DMF, THF, ACN) to afford secondary amines G. These amines are alkylated with various substituted benzyl reagents (e.g. 2-chloro-3-trifluoromethylbenzyl bromide) in polar solvent (e.g. DMF, THF, ACN) to afford tertiary amines H. The silyl-protecting group is removed under standard conditions (e.g. TBAF, HF) in polar solvent (e.g. DMF, THF, ACN) and the resulting alcohol is converted to a leaving group X (e.g. chloride, bromide, iodide, methane-sulfonate, para-toluenesulfoneate, trifluoromethanesul-fonate) to afford intermediates D. Finally, the leaving group X is displaced with the appropriate nucleophile (R4OH) using base (e.g. potassium carbonate, cesium carbonate) and polar solvent (e.g. DMF, THF, ACN) to afford final products E.

Scheme 2

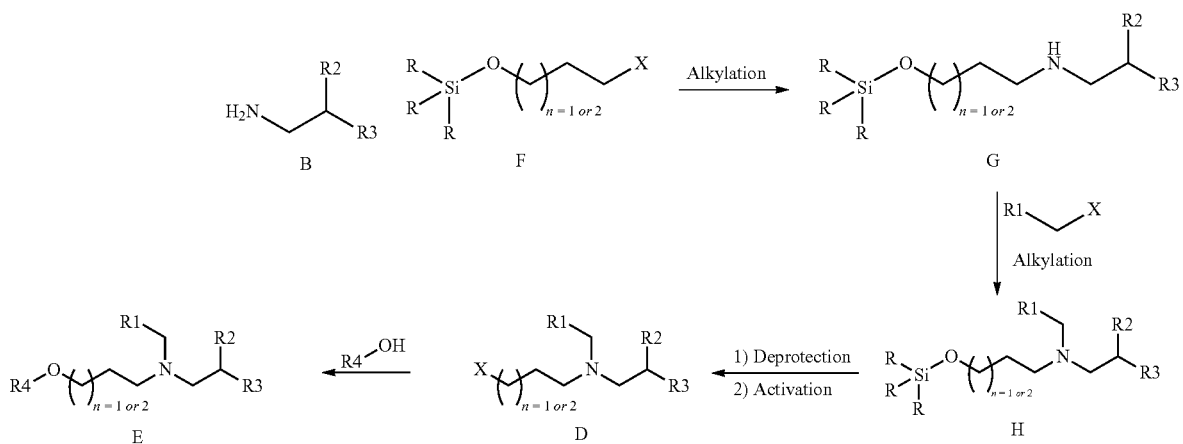

Example 2: Synthesis of Compound 1

Step 1: Synthesis of INT-01

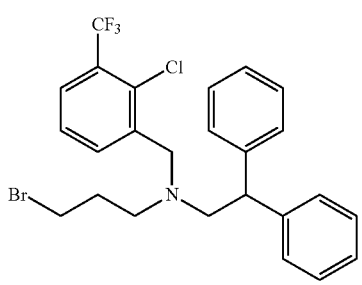

INT-01

Intermediate INT-01 was made as previously described in *Bioorg. Med. Chem. Lett.* 2009, 19, 5617-5621. 2,2-Diphenethylamine and 2-chloro-3-trifluoromethylbenzaldehyde were reacted via reductive amination using sodium triacetoxyborohydride in dichloromethane and acetic acid. The resulting benzyl amine was reacted with 1,3-dibromopropane in refluxing acetonitrile overnight to afford bromide (3-bromopropyl)({[2-chloro-3-(trifluoromethyl)phenyl]methyl})(2,2-diphenylethyDamine (INT-01).

Step 2: Synthesis of INT-02

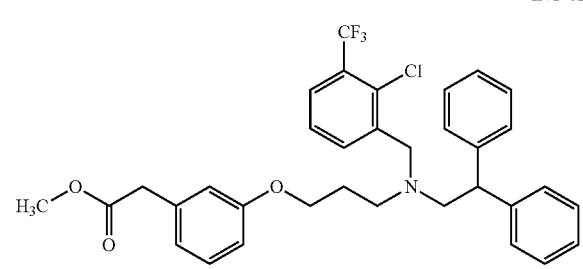

INT-02

To a solution of bromide INT-01 (0.30 g, 0.59 mmol) in acetonitrile (5 mL) was added methyl 3-hydroxyphenylacetic acid (107 mg, 0.65 mmol) and potassium carbonate (0.12 g, 0.9 mmol). The reaction was heated to 70-80° C. overnight. The mixture was cooled, filtered, and the solid was washed with acetonitrile (1 mL) and the combined filtrates were concentrated and purified by silica gel column chromatography to yield methyl-2-{3-[3-({[2-chloro-3-(trifluoromethyl)phenyl]methyl}-(2,2-diphenylethyl)-amino)-propoxy]phenyl}acetate (INT-02) (0.27 g, 76% yield); TLC=20% ethyl acetate/hexanes (0.5 Rf).

Step 3: Synthesis of Compound 1

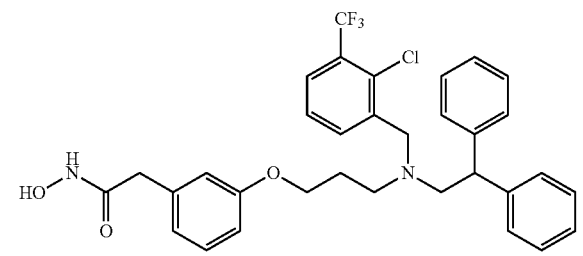

1

INT-02 (190 mg, 0.319 mmol) was dissolved in dry methanol (5 mL). Addition of hydroxylamine hydrochloride (89 mg, 1.27 mmol) and sodium hydroxide (90 mg, 1.60 mmol) was followed by stirring at room temperature for 18 h or until TLC control showed completed conversion. The reaction mixture was poured into ethyl acetate (100 mL) and extracted with water (2×100 mL), dried over magnesium sulfate, filtrated, solvent was evaporated under reduced pressure, and purified by silica gel preparative TLC to afford 2-{3-[3-({[2-chloro-3-(trifluoromethyl)phenyl]methyl}(2,2-diphenylethy)amino)propoxy]phenyl}-N-hydroxyacetamide (1) as a glassy oil (125 mg, 66% yield). ES(pos)MS m/z 597.21 (M+H⁺).

Example 3: Synthesis of Compound 2

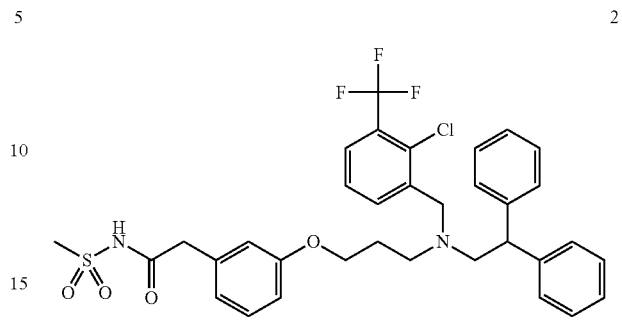

2

GW3965 was made from INT-02 using aqueous base hydrolysis as previously described (U.S. Pat. No. 7,247,748). 1,1-Carbonyldiimidazole (0.1 g, 0.67 mmol) was added to a stirring solution of GW3965 (0.3 g, 0.52 mmol) in THF (5 mL) and the solution was stirred under argon for 3 h. To this solution was added methane sulfonamide (74 mg, 0.78 mmol) and 1,8-diazabicyclo[5.4.0]undec-7-ene (0.12 g, 0.78 mmol) and the reaction was stirred at RT overnight. The mixture was concentrated, dissolved in EtOAc (1 mL), washed with water and brine, and concentrated under reduced pressure. The residue was purified by silica gel preparative TLC to afford 2-{3-[3-({[2-chloro-3-(trifluoromethyl)phenyl]methyl}(2,2-diphenylethyl)amino)propoxy]phenyl}-N-methanesulfonylacetamide (2) as a colorless liquid (0.19 mg, 55% yield); TLC=60% EtOAc/hexanes (0.4 Rf); MS (ESI) 659.2 (M+H⁺).

Example 4: Synthesis of Compound 3

Step 1: Synthesis of INT-03

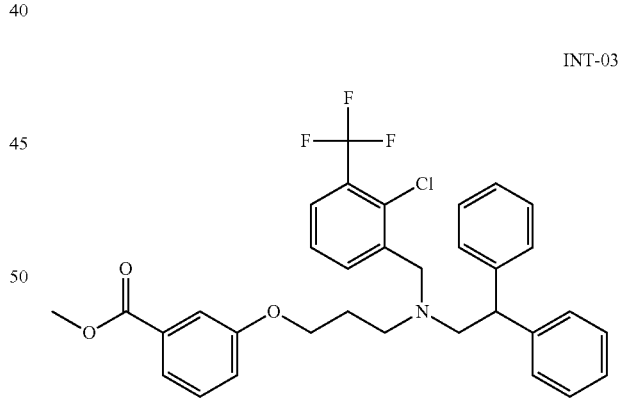

INT-03

To a solution of bromide INT-01 (0.20 g, 0.39 mmol) in ACN (3 mL) was added methyl 3-hydroxybenzoate (60 mg, 0.39 mmol) and potassium carbonate (0.27 g, 1.95 mmol). The reaction was heated to 70-80° C. overnight. The mixture was cooled, filtered, and the solid was washed with ACN (1 mL) and the combined filtrates were concentrated and purified by silica gel column chromatography to yield methyl 3-[3-({[2-chloro-3-(trifluoromethyl)phenyl]methyl}(2,2-diphenylethyl)amino)propoxy]benzoate (INT-03) as a syrup (0.21 g, 91% yield); TLC=10% EtOAc/hexanes (0.4 Rf).

Step 2: Synthesis of Compound 3

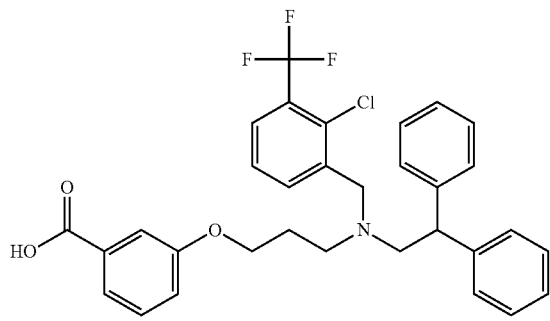

To a solution of ester INT-03 (0.2 g, 0.34 mmol) in a 1:1 mixture of MeOH/THF (3 mL) was added 2N sodium hydroxide (3 mL) drop-wise at 0° C. The resulting solution was stirred at RT overnight. The reaction mixture was acidified with 3N hydrochloric acid (pH ~4) and volatiles were removed under reduced pressure. The reaction mixture was extracted with EtOAc (2×10 mL). The combined organic layers were washed with water and brine, dried over sodium sulfate, filtered, and concentrated under reduced pressure. The residue was purified by silica gel column chromatography to yield 3-[3-({[2-chloro-3-(trifluoromethyl)phenyl]methyl}(2,2-diphenylethyl)amino)propoxy]benzoic acid (3) as a syrup (0.15 g, 89% yield); TLC=30% EtOAc/hexanes (0.2 Rf); MS (ESI) 597.21 (M+H$^+$).

Example 5: Synthesis of Compound 4

Step 1: Synthesis of INT-04

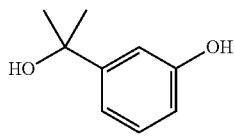

To a 1M solution of methyl magnesium chloride in THF (30 mL, 30.6 mmol) at RT was added a solution of methyl 3-hydroxybenzoate (2.0 g, 13.3 mmol) in THF (10 mL) drop-wise at RT under argon atmosphere. After 2 h the reaction mixture was quenched with a saturated solution of ammonium chloride and extracted with EtOAc (2×15 mL). The organic layer was washed with water and brine, dried over sodium sulfate, filtered, and concentrated. The residue was purified by column chromatography to yield 3-(2-hydroxypropan-2-yl)phenol (INT-04) as a liquid (1.45 g, 72.5% yield); TLC=20% EtOAc/hexanes (0.5 Rf).

Step 2: Synthesis of compound 4

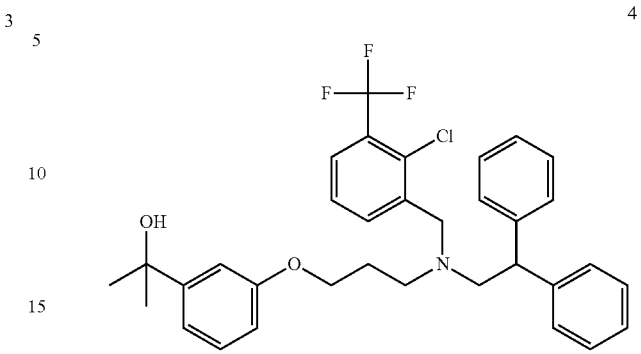

The bromide INT-01 (0.2 g, 0.32 mmol) was reacted with phenol INT-04 (50 mg, 0.38 mmol) in ACN (3 mL) using potassium carbonate (66 mg, 0.48 mmol) as base as described above for compound 3 to yield 2-{3-[3-({[2-chloro-3-(trifluoromethyl)phenyl]methyl}(2,2-diphenylethyl)amino)propoxy]phenyl}propan-2-ol (4) as an oil (0.14 g, 63% yield); TLC=15% EtOAc/hexanes (0.3 Rf); MS (ESI) 582.24 (M+H$^+$).

Example 6: Synthesis of Compound 5

Step 1: Synthesis of INT-05

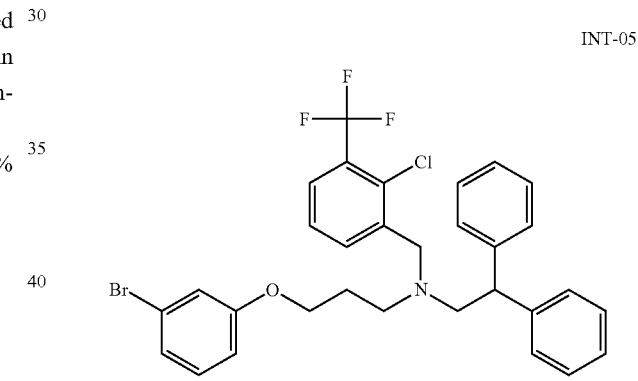

Bromide INT-01 (0.30 mmol) is reacted with 3-bromophenol (0.30 mmol) in ACN (3 mL) using potassium carbonate (0.40 mmol) as base as described above for compound 3 to yield [3-(3-bromophenoxy)propyl]({[2-chloro-3-(trifluoromethyl)phenyl]methyl})(2,2-diphenylethyl)amine (INT-05).

Step 2: Synthesis of Compound 5

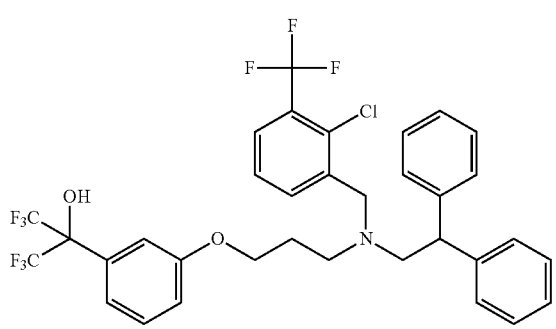

INT-05 (0.2 mmol) is dissolved in THF, cooled to −78° C., and treated with n-butyllithium (0.22 mmol, 1.6 M in hexanes). After 30 min, hexafluoroacetone is bubbled into the solution and the mixture is stirred for an additional 30 min at −78° C. The reaction is quenched with saturated aqueous ammonium chloride solution, extracted with EtOAc (3×50 mL), the combined organic layers are washed with brine, dried over sodium sulfate, filtered, and concentrated under reduced pressure. The residue is purified by silica gel chromatography to afford 2-{3-[3-({[2-chloro-3-(trifluoromethyl)phenyl]methyl}(2,2-diphenylethyl) amino)-propoxy]phenyl}-1,1,1,3,3,3-hexafluoropropan-2-ol (5).

Example 7: Synthesis of Compound 6

Step 1: Synthesis of INT-06

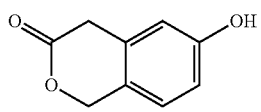

INT-06

6-Methoxy-3,4-dihydro-1H-2-benzopyran-3-one was prepared as described previously (WO2009005998 and *J. Org. Chem.* 1997, 42, 2989).

Step 2: Synthesis of Compound 6

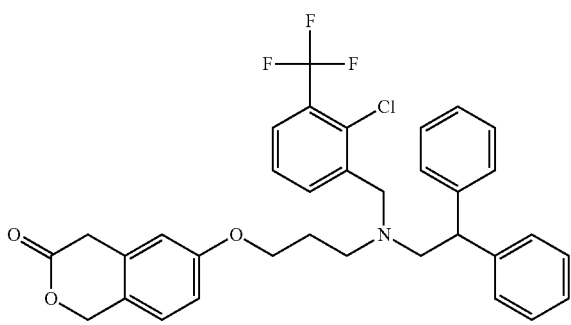

6

The bromide INT-01 (0.3 mmol) was reacted with phenol INT-06 (0.3 mmol) in ACN (3 mL) using potassium carbonate (0.40 mmol) as base as described above for compound 3 to yield 6-[3-({[2-chloro-3-(trifluoromethyl)phenyl]methyl}(2,2-diphenylethyl)amino)propoxy]-3,4-dihydro-1H-2-benzopyran-3-one (6) as a viscous oil (85 mg, 48%). ES(pos)MS m/z 594.20 (M+H⁺).

Example 8: Synthesis of Compound 7

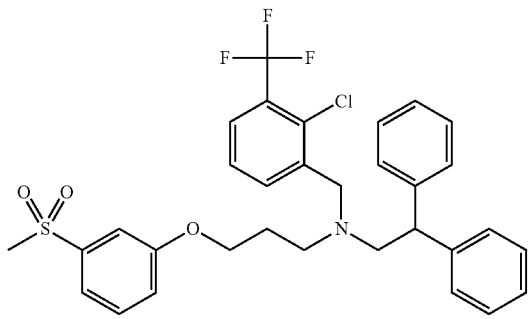

7

To a solution of bromide INT-01 (500 mg, 0.98 mmol) in acetonitrile (10 mL) was added 3-(methylsulfonyl) phenol (168 mg, 0.98 mmol, prepared according to procedures described in *J. Am. Chem. Soc.* 1957, 79, 717-722) and potassium carbonate (202 mg, 1.47 mmol) at RT. The solution was heated to 70° C. for 6 h. The mixture was worked-up as described above for compound 3, and purified by silica gel column chromatography to afford {[2-chloro-3-(trifluoromethyl)phenyl]methyl}(2,2-diphenylethyl)[3-(3-methane sulfonylphenoxy)propyl]amine (7) as a thick syrup (459 mg, 78%); TLC=30% EtOAc/hexanes (0.3 Rf); ES (pos) MS m/z 602.18 (M+H⁺).

Example 9: Synthesis of Compound 8

Step 1: Synthesis of INT-07

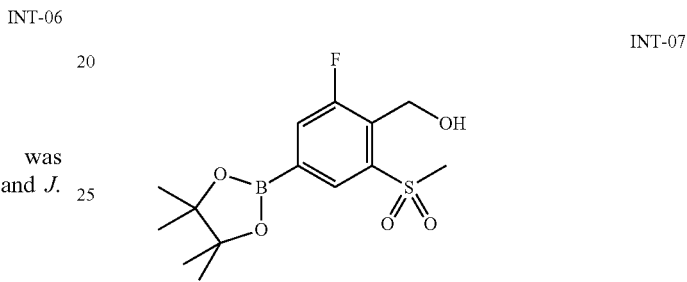

INT-07

INT-07 was made as previously described (WO20100138598). (4-Bromo-2-fluoro-6-methanesulfonyl phenyl)methanol (300 mg, 1.06 mmol), potassium acetate (2.44 mmol, 2.49 mmol), and bis(pinacolato) diborane (350 mg, 1.38 mmol) were suspended in dry DMSO (10 mL). After degassing with argon for 5 min, dichloro((1,1'-biphenylphosphino)ferrocene)palladium (II) dichloromethane complex (43.3 mg, 5 mol %) was added the mixture was degassed for another 5 min. The reaction was heated to 90° C. for 3 h. The cooled reaction mixture was poured into water (100 mL) and extracted with MTBE (2×100 mL). The combined organic layers were washed with water (3×50 mL) and brine (50 mL), dried over magnesium sulfate, filtered, and concentrated under reduced pressure to afford [2-fluoro-6-methanesulfonyl-4-(tetramethyl-1,3,2-dioxaborolan-2-yl) phenyl]methanol (INT-07) as crude material that was used directly in the next step without further purification.

Step 2: Synthesis of INT-08

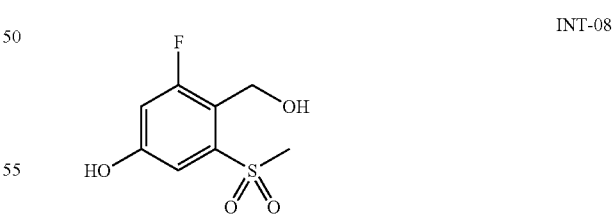

INT-08

The crude mixture of the previous step was dissolved in MeOH (15 mL) and treated with 30% aqueous hydrogen peroxide (5 mL). After addition of iodine (5 mg, catalytic), the mixture was stirred at RT for 3 h or until all starting material had disappeared judged by TLC. The resulting mixture was poured into EtOAc (100 mL) and washed with water (2×100 mL). The combined aqueous layers were re-extracted with EtOAc (100 mL) and this second organic phase was washed with water (100 mL). All organic layers were combined, dried over magnesium sulfate, filtered, concentrated under reduced pressure, and purified by silica gel chromatography (EtOAc/hexanes) to yield 3-fluoro-4-(hydroxymethyl)-5-methanesulfonyl-phenol (INT-08) as an off-white solid (200 mg, 85% yield).

Step 3: Synthesis of Compound 8

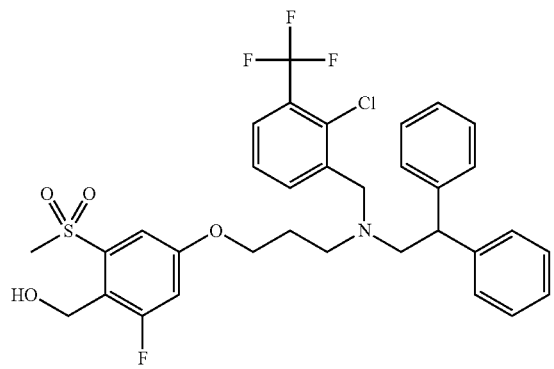

Bromide INT-01 (200 mg, 0.392 mmol), phenol INT-08 (112 mg, 0.509 mmol), and potassium carbonate (325 mg, 2.35 mmol) were suspended in dry ACN (5 mL) and heated to 90° C. for 16 h. The resulting mixture was poured into EtOAc (100 mL) and then washed with water (2×100 mL). The combined aqueous layers were re-extracted with EtOAc (100 mL) and this second organic layer was washed with water (100 mL) again. All organic layers were combined, dried over magnesium sulfate, filtered, concentrated under reduced pressure, and purified by prep-TLC (MeOH/DCM) to yield {4-[3-({[2-chloro-3-(trifluoromethyl)phenyl]methyl}(2,2-diphenylethyl)amino)propoxy]-2-fluoro-6-methanesulfonylphenyl}methanol (8) as a glassy oil (98 mg, 38% yield); ES(pos)MS m/z 650.2 (M+H$^+$).

Example 10: Synthesis of Compound 84

Step 1: Synthesis of INT-09

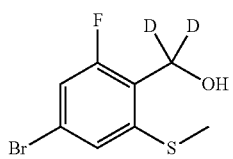

INT-09 was made using a modified protocol previously described for [4-bromo-2-fluoro-6-(methylsulfanyl)phenyl]methanol (see WO20100138598) by replacing sodium borohydride with sodium borodeuteride for the reduction of the acid.

Sodium borodeuteride (483 mg, 11.54 mmol) was suspended to dry THF (10 mL) and to this slurry was added 4-bromo-2-fluoro-6-(methylsulfanyl)benzoic acid (1.53 g, 5.77 mmol) dissolved in dry THF (10 mL) over 5 min. After gas evolution was complete, iodine (2.56 g, 10.07 mmol) dissolved in dry THF (15 mL) was slowly added over 30 min. The reaction mixture was then refluxed for 6 h and most of the solvent was removed under reduced pressure. The residue was taken up in EtOAc (100 mL), washed with saturated sodium bicarbonate (100 mL), water (100 mL), and the combined aqueous layers were re-extracted with EtOAc (100 mL). The second organic layer was washed with water (100 mL) and the combined organic layers were dried over magnesium sulfate, filtered, concentrated under reduced pressure, and purified by silica gel column chromatography (DCM/MeOH=100/1) to afford INT-09 as a white solid (1.25 g, 86%).

Step 2: Synthesis of INT-10

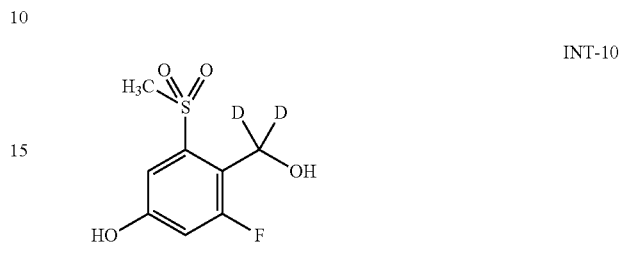

Synthesis of INT-10 followed the protocol outlined for compound INT-08 substituting [4-bromo-2-fluoro-6-(methylsulfanyl)phenyl]methanol with INT-09.

Step 3: Synthesis of Compound 84

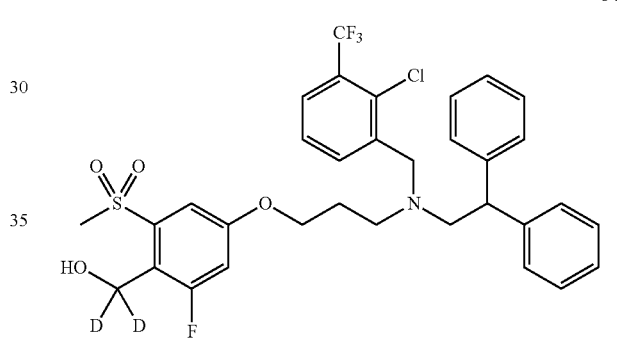

The synthesis of 84 followed the previously described synthesis of compound 8. Bromide INT-01 (260 mg, 0.51 mmol) and INT-10 (130 mg, 0.585 mmol) were reacted in presence of potassium carbonate (210 mg, 1.5 mmol) to afford {4-[3-({[2-chloro-3-(trifluoromethyl)phenyl]methyl}(2,2-diphenylethyl)amino) propoxy]-2-fluoro-6-methanesulfonylphenyl}($^2$H$_2$)methanol (84) as a white solid (284 mg, 86%). ES(pos)MS m/z 652.18 (M+H$^+$).

Example 11: Synthesis of Compound 78

Step 1: Synthesis of INT-11

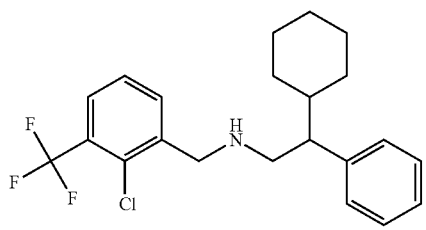

2-Cyclohexyl-2-phenylethylamine (0.5 g, 2.5 mmol) and 2-chloro-3-trifluoromethyl benzaldehyde (0.52 g, 2.5 mmol)

were dissolved in DCM (12 mL) and reacted under reductive amination conditions using sodium triacetoxyborohydride (0.53 g, 2.5 mmol) and acetic acid (0.5 mL) as described in *Bioorg. Med. Chem. Lett.* 2009, 19, 5617-5621 for INT-01 to yield {[2-chloro-3-(trifluoromethyl)phenyl]methyl}(2-cyclohexyl-2-phenylethyl)amine (INT-11) (0.75 g, 76%); TLC=30% EtOAc/hexanes (0.3 Rf).

Step 2: Synthesis of INT-12

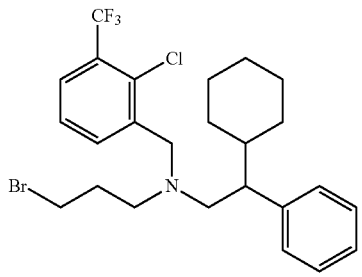

The amine INT-11 (0.5 g, 1.26 mmol) was reacted with 1,3-dibromopropane (2.5 g, 10 eq) in refluxing acetonitrile (25 mL) overnight as described for INT-01 to afford (3-bromopropyl)({[2-chloro-3-(trifluoromethyl)phenyl]methyl})(2-cyclohexyl-2-phenylethyl)amine (INT-12) (0.46 g, 70%); TLC=5% EtOAc/hexanes (0.8 Rf).

Step 3: Synthesis of Compound 78

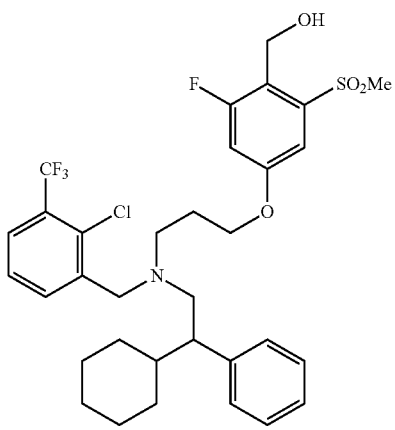

Bromide INT-12 (250 mg, 0.48 mmol), phenol INT-08 (105 mg, 0.48 mmol), and potassium carbonate (132 mg, 0.96 mmol) were suspended in dry ACN (5 mL) and heated to reflux for 12 h. The resulting mixture was poured into EtOAc (50 mL), washed with water (2×50 mL), and the combined aqueous layers were re-extracted with EtOAc (25 mL). The second organic layer was washed with water (100 mL) and the combined organic layers were dried over magnesium sulfate, filtered, concentrated under reduced pressure, and purified by silica gel preparative TLC (30% EtOAc/hexanes) to afford {4-[3-({[2-chloro-3-(trifluoromethyl)phenyl]methyl}(2-cyclohexyl-2-phenylethyl)amino)propoxy]-2-fluoro-6-methanesulfonylphenyl}methanol (78) as a glassy oil (250 mg, 80% yield); TLC=30% EtOAc/hexanes (0.6 Rf); ES(pos)MS m/z 656.6 (M+H$^+$).

Example 12: Synthesis of Compound 79

Step 1: Synthesis of INT-13

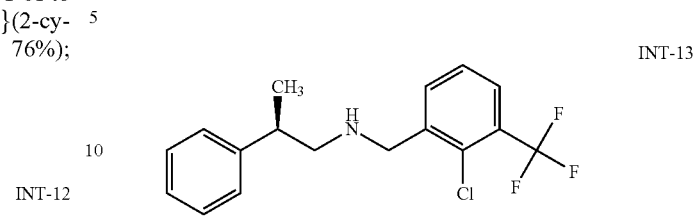

(R)-2-Phenylpropan-1-amine (200 mg, 1.48 mmol) was reacted with 2-chloro-3-trifluoromethyl benzaldehyde (308 mg, 1.48 mmol) as described above for INT-11 to afford {[2-chloro-3-(trifluoromethyl)phenyl]methyl}[(2R)-2-phenylpropyl]amine (INT-13) (300 mg, 62%).

Step 2: Synthesis of INT-14

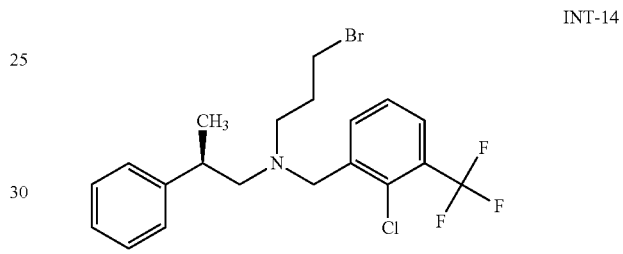

INT-13 (150 mg, 0.46 mmol) was reacted with 1,3-dibromopropane (920 mg, 10 eq) in refluxing acetonitrile as described above for INT-12 to (3-bromopropyl)({[2-chloro-3-(trifluoromethyl)phenyl]methyl})[(2R)-2-phenylpropyl]amine (INT-14) as colorless oil (137 mg, 67%); TLC=5% EtOAc/hexanes (0.8 Rf).

Step 3: Synthesis of Compound 79

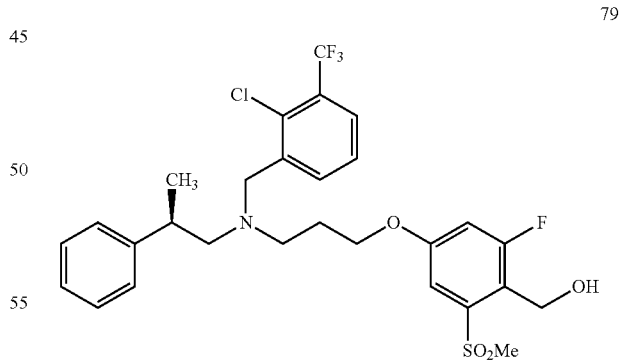

Bromide INT-14 (125 mg, 0.28 mmol) was reacted with phenol INT-08 (62 mg, 0.28 mmol) as described above for compound 78 and purified by silica gel preparative TLC (30% EtOAc/hexanes) to afford {4-[3-({[2-chloro-3-(trifluoromethyl)phenyl]methyl}[(2R)-2-phenylpropyl]amino)propoxy]-2-fluoro-6-methanesulfonylphenyl}methanol (79) as colorless oil (128 mg, 78% yield); TLC=30% EtOAc/hexanes (0.6 Rf); ES(pos) MS m/z 588.5 (M+H$^+$).

Example 13: Synthesis of Compound 80

Step 1: Synthesis of INT-15

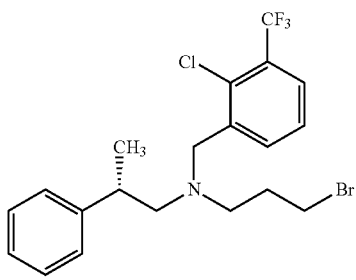

(S)-2-Phenylpropan-1-amine (100 mg, 0.74 mmol) was reacted with 2-chloro-3-trifluoromethyl benzaldehyde (153 mg, 0.74 mmol) as described above for INT-13 to yield {[2-chloro-3-(trifluoromethyl)phenyl]methyl}[(2S)-2-phenylpropyl]amine (150 mg, 62%). This amine (150 mg, 0.46 mmol) was reacted with 1,3-dibromopropane (920 mg, 10 eq) in refluxing acetonitrile as described above for INT-14 to afford (3-bromopropyl)({[2-chloro-3-(trifluoromethyl)phenyl]methyl})[(2S)-2-phenylpropyl]amine (INT-15) as colorless oil (137 mg, 68%); TLC=5% EtOAc/hexanes (0.8 Rf).

Step 2: Synthesis of compound 80

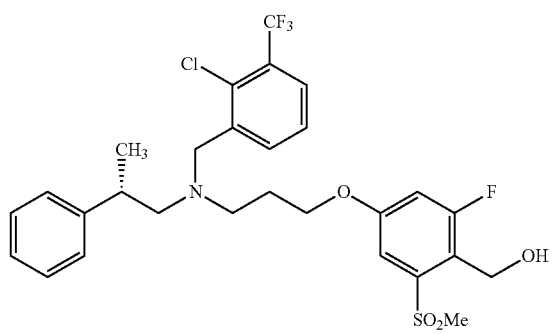

Bromide INT-15 (125 mg, 0.28 mmol) was reacted with phenol INT-08 (62 mg, 0.28 mmol) as described above for compound 78 and purified by silica gel preparative TLC (30% EtOAc/hexanes) to afford {4-[3-({[2-chloro-3-(trifluoromethyl)phenyl]methyl}[(2S)-2-phenylpropyl]amino)propoxy]-2-fluoro-6-methanesulfonylphenyl}methanol (80) as colorless oil (128 mg, 78% yield); TLC=30% EtOAc/hexanes (0.6 Rf); ES(pos) MS m/z 588.5 (M+H⁺).

Example 14: Synthesis of Compound 81

Step 1: Synthesis of INT-16

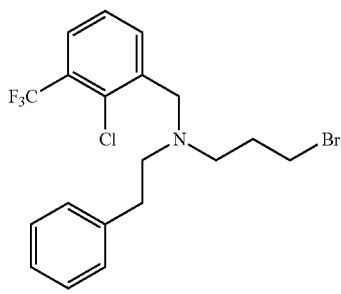

2-Phenylethanamine (150 mg, 1.23 mmol) was reacted with 2-chloro-3-trifluoromethyl benzaldehyde (0.26 g, 1.23 mmol) as described above for INT-11 to yield {[2-chloro-3-(trifluoromethyl) phenyl]methyl}(2-phenylethyl)amine (223 mg, 58%). This amine (150 mg, 0.48 mmol) was reacted with 1,3-dibromopropane (970 mg, 10 eq) in refluxing acetonitrile as described above for INT-12 to afford (3-bromopropyl)({[2-chloro-3-(trifluoromethyl)phenyl]methyl})(2-phenylethyl)amine (INT-16) as thick syrup (150 mg, 72%); TLC=5% EtOAc/hexanes (0.8 Rf).

Step 2: Synthesis of Compound 81

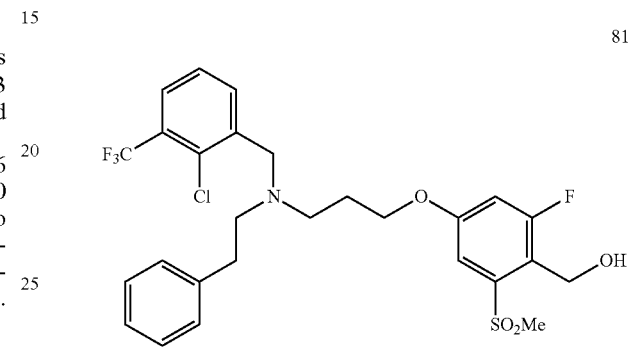

Bromide INT-16 (160 mg, 0.37 mmol) was reacted with phenol INT-08 (82 mg, 0.37 mmol) as described above for compound 78 and purified by silica gel preparative TLC (30% EtOAc/hexanes) to afford {4-[3-({[2-chloro-3-(trifluoromethyl)phenyl]methyl}(2-phenylethyl)amino)propoxy]-2-fluoro-6-methanesulfonylphenyl}methanol (81) as colorless oil (161 mg, 76% yield); TLC=30% EtOAc/hexanes (0.55 Rf); ES(pos) MS m/z 574.5 (M+H⁺).

Example 15: Synthesis of Compound 82

Step 1: Synthesis of INT-17

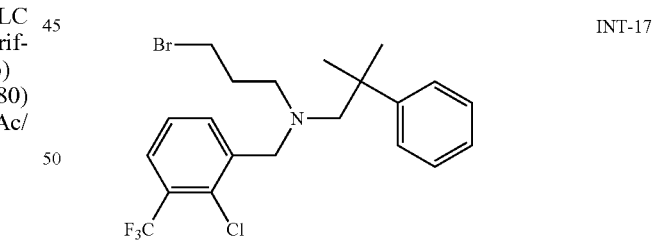

2-Methyl-2-phenylpropan-1-amine (150 mg, 1.0 mmol) was reacted with 2-chloro-3-trifluoromethyl benzaldehyde (207 mg, 1.0 mmol) as described above for INT-11 to yield {[2-chloro-3-(trifluoromethyl) phenyl]methyl}(2-methyl-2-phenylpropyl)amine (184 mg, 54%). The amine (150 mg, 0.43 mmol) was reacted with 1,3-dibromopropane (869 mg, 10 eq) in refluxing acetonitrile as described above for INT-12 to afford (3-bromopropyl)({[2-chloro-3-(trifluoromethyl)phenyl]methyl})(2-methyl-2-phenylpropyl)amine (INT-17) as colorless oil (147 mg, 74%); TLC=5% EtOAc/hexanes (0.85 Rf).

Step 2: Synthesis of Compound 82

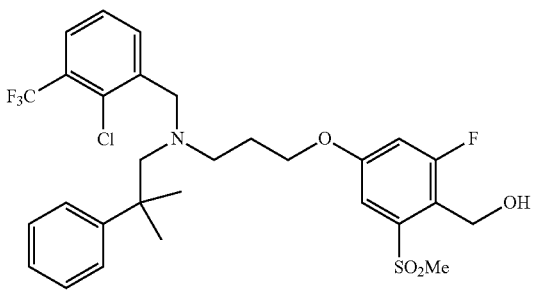

Bromide INT-17 (100 mg, 0.22 mmol) was reacted with phenol INT-08 (48 mg, 0.22 mmol) as described above for compound 78 and purified by silica gel preparative TLC (30% EtOAc/hexanes) to afford {4-[3-({[2-chloro-3-(trifluoromethyl)phenyl]methyl}(2-methyl-2-phenylpropyl)amino)propoxy]-2-fluoro-6-methanesulfonylphenyl}methanol (82) as colorless thick syrup (99 mg, 75% yield); TLC=30% EtOAc/hexanes (0.6 Rf); ES(pos) MS m/z 602.5 (M+H$^+$).

Example 16: Synthesis of Compound 83

Step 1: Synthesis of INT-18

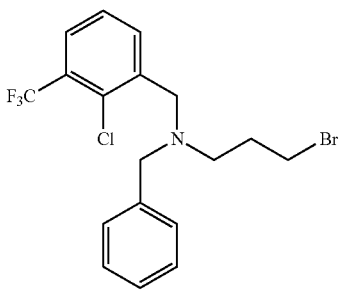

Benzylamine (200 mg, 1.87 mmol) was reacted with 2-chloro-3-trifluoromethyl benzaldehyde (0.38 g, 1.87 mmol) as described above for INT-11 to yield benzyl({[2-chloro-3-(trifluoromethyl)phenyl]methyl})amine (381 mg, 68%). The amine (200 mg, 0.67 mmol) was reacted with 1,3-dibromopropane (1.4 g, 10 eq) in refluxing acetonitrile as described above for INT-12 to afford benzyl(3-bromopropyl){[2-chloro-3-(trifluoromethyl)phenyl]methyl}amine (INT-18) as colorless oil (205 mg, 73%); TLC=5% EtOAc/hexanes (0.85 Rf).

Step 2: Synthesis of Compound 83

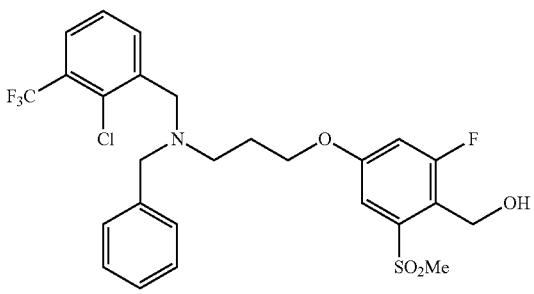

Bromide INT-18 (150 mg, 0.36 mmol) was reacted with phenol INT-08 (78 mg, 0.36 mmol) as described above for compound 78 and purified by silica gel preparative TLC (30% EtOAc/hexanes) to afford (4-{3-[benzyl({[2-chloro-3-(trifluoromethyl)phenyl]methyl})amino]propoxy}-2-fluoro-6-methanesulfonylphenyl) methanol (83) as colorless oil (156 mg, 78% yield); TLC=30% EtOAc/hexanes (0.6 Rf); ES(pos)MS m/z 560.5 (M+H$^+$).

Example 17: Synthesis of Compound 9

Step 1: Synthesis of INT-21

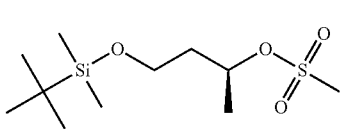

Crude (2S)-4-[(tert-butyldimethylsilyl)oxy]butan-2-ol was made as described WO0166534A2 using (S)-1,3-butanediol (2.1 g, 23.3 mmol). The crude product was dissolved in dry dichloromethane (40 mL) and then reacted with methanesulfonyl chloride (1.81 mL, 23.4 mmol) and triethylamine (3.5 mL, 25.1 mmol) at 0° C. The mixture was allowed to warm to RT over 1 h and then stirred an additional 2 h. Upon completion, judged by TLC, the reaction mixture was poured into EtOAc and washed with 1N hydrochloric acid (2×100 mL), water (100 mL), and brine (50 mL). The mixture was dried over magnesium sulfate, filtrated, and concentrated under reduced pressure to yield crude (2S)-4-[(tert-butyldimethylsilyl)oxy]-butan-2-yl methanesulfonate (INT-21) as a yellowish oil in quantitative yield.

Step 2: Synthesis of INT-22

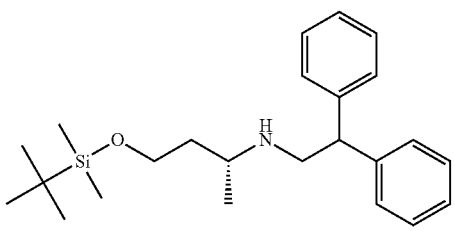

Crude INT-21 (1.0 g, 3.54 mmol) and 2,2-diphenylethylamine (770 mg, 3.89 mmol) were dissolved in dry ACN (10 mL), followed by addition of potassium carbonate (2.93 g, 21.2 mmol). The mixture was heated at 90° C. for 48 h until TLC showed very little starting material remaining. The heterogeneous reaction mixture was poured into EtOAc (100 mL) and washed with water (2×100 mL).

The combined aqueous layers were extracted with EtOAc (100 mL) and this second organic layer was in turn washed with water (100 mL). The combined organic layers were dried over magnesium sulfate, filtered, and concentrated under reduced pressure. The residue was purified by silica gel chromatography (EtOAc/hexane) to afford [(2R)-4-[(tert-butyldimethylsilyl)oxy]butan-2-yl](2,2-diphenylethyl)amine (INT-22) as a slightly yellowish oil (1.06 g, 78% yield).

Step 3: Synthesis of INT-23

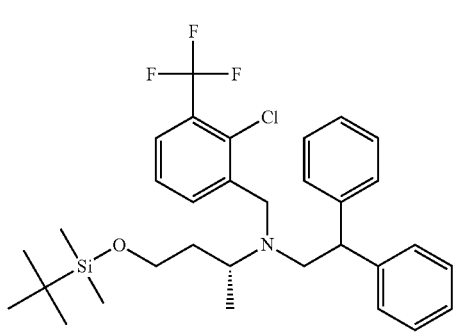

INT-23

Amine INT-22 (1.3 g, 3.39 mmol), 2-chloro-3-(trifluoromethyl)benzyl bromide (1.18 g, 4.31 mmol), and potassium carbonate (1.87 g, 13.6 mmol) were suspended in dry acetonitrile (13 mL). After 12 h at 90° C., the reaction was deemed complete by TLC and poured into MTBE (100 mL). The organic mixture was washed with water (2×100 mL). The combined aqueous layers were extracted with MTBE (100 mL) and this second organic layer was in turn washed with water (100 mL). The combined organic layers were dried over magnesium sulfate, filtered, and concentrated under reduced pressure to afford [(2R)-4-[(tert-butyldimethylsilyl)oxy]butan-2-yl]({[2-chloro-3-(trifluoromethyl)phenyl]methyl})(2,2-diphenylethyl)amine (INT-23) as a brownish oil which was used directly in the following step without further purification.

Step 4: Synthesis of INT-24

INT-24

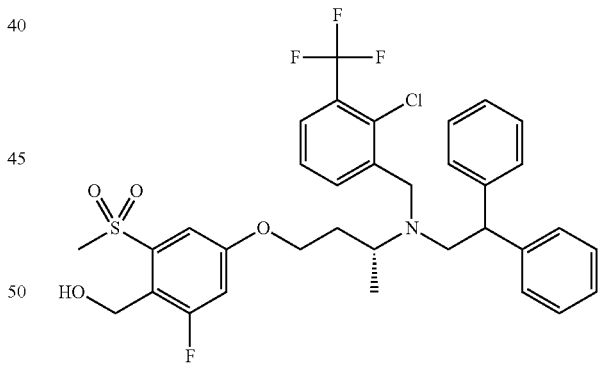

Crude INT-23 (3.39 mmol) was dissolved in dry THF (15 mL) and subsequently treated with tetrabutylammonium fluoride (1.0 M in THF, 6.8 mL, 6.8 mmol). After stirring for 20 h at RT, TLC showed no starting material remaining. The homogeneous mixture was poured into EtOAc (100 mL) and washed with water (2×100 mL). The combined aqueous layers were extracted with EtOAc (100 mL) and this second organic layer was in turn washed with water (100 mL). The combined organic layers were then dried over magnesium sulfate, filtered, and concentrated under reduced pressure. The residue was purified by silica gel chromatography (EtOAc/hexane) to afford (3R)-3-({[2-chloro-3-(trifluoromethyl) phenyl]methyl}(2,2-diphenylethyl)amino)butan-1-ol (INT-24) as a viscous oil (1.33 g, 68% yield over 2 steps).

Step 5: Synthesis of INT-25

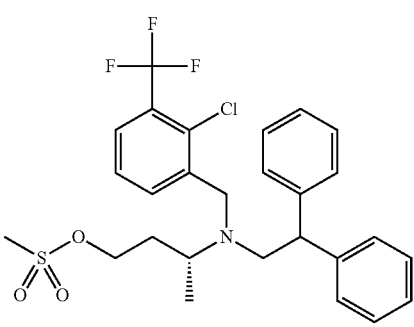

INT-25

INT-24 (1.30 g, 2.81 mmol) and triethylamine (1.18 mL, 8.44 mmol) were dissolved in dry DCM (20 mL). The mixture was cooled to 0° C. and then treated with methanesulfonyl chloride (0.326 mL, 4.22 mmol). The reaction mixture was allowed to warm to RT overnight and then poured into EtOAc (100 mL) and washed with water (2×100 mL). The combined aqueous layers were extracted with EtOAc (100 mL) and this second organic layer was in turn washed with water (100 mL). The combined organic layers were dried over magnesium sulfate, filtered, and concentrated under reduced pressure to yield (3R)-3-({[2-chloro-3-(trifluoromethyl)phenyl]methyl}(2,2-diphenylethyl) amino)butyl methanesulfonate (INT-25) as a crude oil in quantitative yield which was used directly in the following step without further purification.

Step 6: Synthesis of Compound 9

9

INT-08 (183 mg, 0.832 mmol), crude mesylate INT-25 (0.693 mmol), and potassium carbonate (575 mmol, 4.16 mmol) were heated in dry ACN (3 mL) for 16 h at 90° C. After cooling to RT, the mixture was poured into EtOAc (100 mL) and washed with water (2×100 mL). The combined aqueous layers were re-extracted with EtOAc (100 mL) and this second organic layer was washed with water (100 mL) again. All organic layers were combined, dried over magnesium sulfate, filtered, concentrated under reduced pressure, and purified by silica gel chromatography (EtOAc/hexanes) to yield a mixture of isomers as an off-white solid (256 mg, 56% yield). The two isomers were separated by silica preparative TLC purification by running the plates multiple times with EtOAc/hexanes. The isolation of the bottom spot afforded {4-[(3R)-3-({[2-chloro-3-(trifluoromethyl) phenyl]methyl}(2,2-diphenylethyl)amino)butoxy]-2-fluoro-6-methanesulfonylphenyl}methanol (9) as a white solid (6 mg, 30% yield); ES(pos)MS m/z 664.2 (M+H+).

Example 18: Synthesis of Compound 59

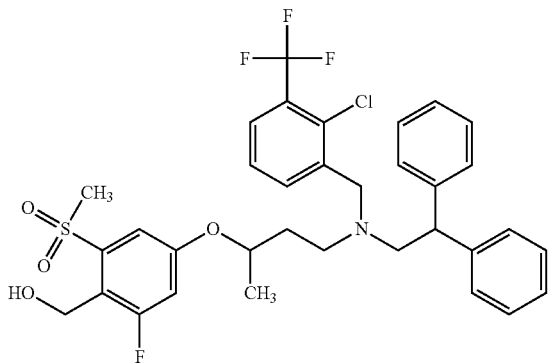

Preparative TLC purification to isolate compound 10 also afforded a pure top spot (4-{[4-({[2-chloro-3-(trifluoromethyl)phenyl]methyl}(2,2-diphenylethyl)amino)butan-2-yl]oxy}-2-fluoro-6-methanesulfonylphenyl)methanol (59); ES(pos)MS m/z 664 (M+H+).

Example 19: Synthesis of Compound 71

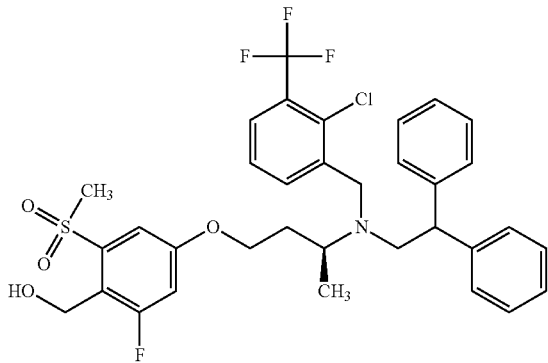

The synthesis of 71 follows the same sequence of procedures described for the synthesis of compound 9 but starting from (2R)-4-[(tert-butyldimethylsilyl)oxy]butan-2-ol to afford the opposite enantiomer {4-[(3S)-3-({[2-chloro-3-(trifluoromethyl)phenyl]methyl}(2,2-diphenylethyl)amino) butoxy]-2-fluoro-6-methanesulfonylphenyl}methanol (71).

Example 20: Synthesis of Compound 10

Step 1: Synthesis of INT-26

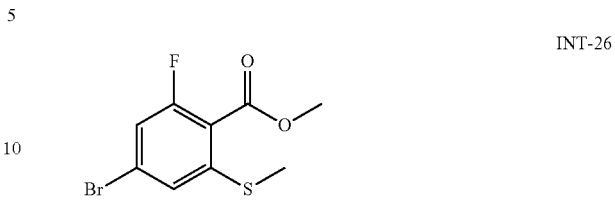

4-Bromo-2,6-difluorobenzoic acid (4.23 g, 17.85 mmol) was converted into the corresponding methylsulfide as described previously (WO20100138598). A portion of the crude residue (3.0 g of 4.7 g) was suspended in dry DCM (50 mL), oxalyl chloride (1.15 mL, 13.6 mmol) and a catalytic amount of dry DMF were added resulting in a bubbling suspension that was stirred for 1 h at RT. The clear solution was concentrated under reduced pressure and the brown oil was dissolved in dry DCM (50 mL). Triethylamine (6.27 mL, 45 mmol) was added and the mixture was cooled to 0° C. followed by slow addition of dry MeOH (5 mL, large excess). The reaction was warmed to RT over 30 min and then stirred for 1 h. The reaction was poured into water (200 mL), the pH was adjusted to pH ~1 with 1N hydrochloric acid, extracted with EtOAc (200 mL), the organic layer was washed with water (100 mL), and the combined aqueous layers were extracted with EtOAc (100 mL). The second organic layer was also washed with water (100 mL). All organic layers were combined, dried over magnesium sulfate, filtrated, and concentrated under reduced pressure to yield crude methyl 4-bromo-2-fluoro-6-(methylsulfanyl)-benzoate (INT-26) that was used directly in the next step without further purification.

Step 2: Synthesis of INT-27

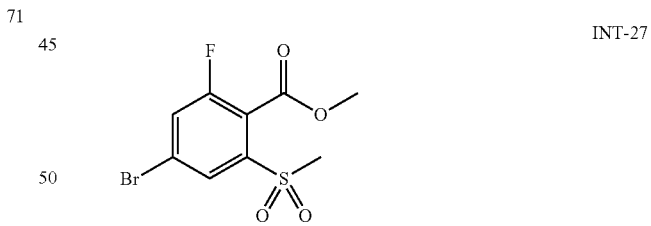

The crude mixture of INT-26 in DCM (100 mL) was treated with mCPBA (77%, 5.07 g, 22.6 mmol). The resulting biphasic mixture was stirred overnight at RT. The organic solvent was removed under reduced pressure and the resulting slurry was dissolved in EtOAc (200 mL). The light yellowish solution was washed with 1N sodium hydroxide (2×200 mL) and water (2×100 mL). The organic layer was dried over magnesium sulfate, filtered, concentrated under reduced pressure, and the yellow residue was purified by silica gel chromatography (MeOH/DCM) to yield methyl 4-bromo-2-fluoro-6-methanesulfonylbenzoate (INT-27) as an off-white solid (1.35 g, 38% over 4 steps).

Step 3: Synthesis of INT-28

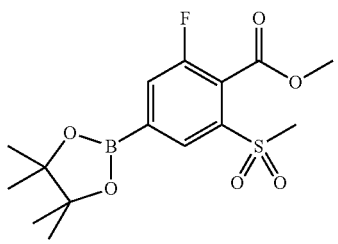

INT-28

Bromide INT-27 (1.0 g, 3.21 mmol) was converted to methyl 2-fluoro-6-methanesulfonyl-4-(tetramethyl-1,3,2-dioxaborolan-2-yl)-benzoate (INT-28) as described for INT-07, which was used in the next step without further purification.

Step 4: Synthesis of INT-28

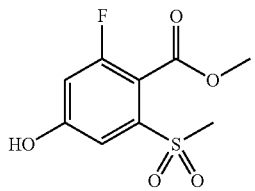

INT-28

The crude boronic ester INT-28 was dissolved in MeOH (20 mL) and treated with hydrogen peroxide (30% in water, 10 mL). The mixture was stirred overnight at RT and poured into EtOAc (100 mL) and then washed with water (2×100 mL). The combined aqueous layers were re-extracted with EtOAc (100 mL) and this second organic phase was washed with water (100 mL). All organic layers were combined and dried over magnesium sulfate, filtered, concentrated under reduced pressure and purified by silica gel chromatography (MeOH/DCM) to yield a brown oil. This residue was suspended in DCM (10 mL), hexanes (10 mL) were added and the mixture was stirred overnight at RT. The slurry was filtrated and washed with DCM/hexanes (1:1) to afford methyl 2-fluoro-4-hydroxy-6-methanesulfonylbenzoate (INT-28) as an off-white solid (256 mg, 58% 2 steps).

Step 5: Synthesis of Compound 10

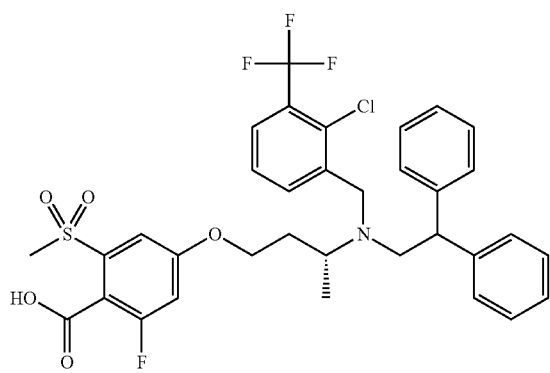

10

The mesylate INT-25 (0.3 mmol) is reacted with phenol INT-28 (0.3 mmol) in ACN (3 mL) using potassium carbonate (0.40 mmol) as base as described above for compound 9. The resulting product is hydrolyzed as described for compound 3 to afford 4-[(3R)-3-({[2-chloro-3-(trifluoromethyl)phenyl]methyl}(2,2-diphenylethyl)amino)butoxy]-2-fluoro-6-methanesulfonylbenzoic acid (10).

Example 21: Synthesis of Compound 37

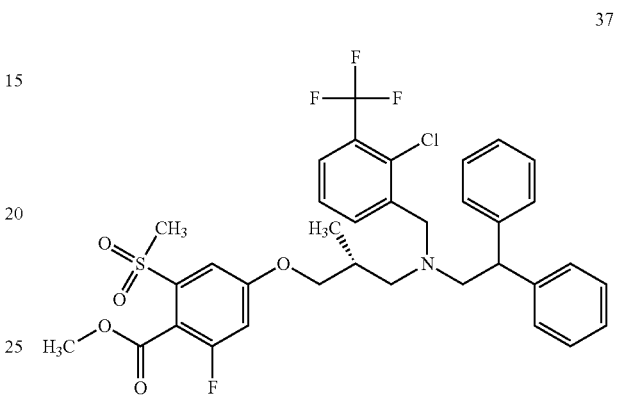

37

The synthesis of 37 is accomplished using procedures described in *Bioorg. Med. Chem. Lett.* 2009, 19, 5617-5621 by replacing methyl 3-hydroxyphenylacetic acid with INT-28 to afford methyl 4-[(2R)-3-({[2-chloro-3-(trifluoromethyl)phenyl]methyl}(2,2-diphenylethyl)amino)-2-methylpropoxy]-2-fluoro-6-methanesulfonylbenzoate (37).

Example 22: Synthesis of Compound 70

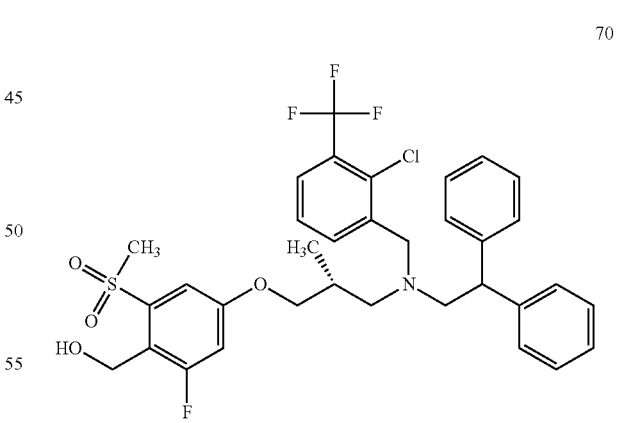

70

Compound 37 is hydrolyzed as described for compound 3 and subsequent benzoic acid reduction is accomplished as described for the synthesis of INT-09 using sodium borohydride and catalytic iodine. Work-up and purification affords {4-[(2R)-3-({[2-chloro-3-(trifluoromethyl)phenyl]methyl}(2,2-diphenylethyl)amino)-2-methylpropoxy]-2-fluoro-6-methanesulfonylphenyl}methanol (70).

Example 23: Synthesis of Compound 39

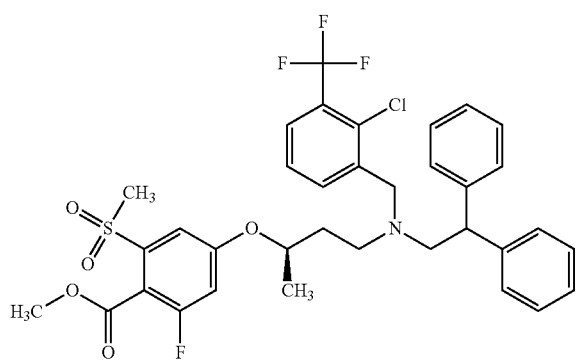

39

The synthesis of 39 is accomplished using procedures described in *Bioorg. Med. Chem. Lett.* 2009, 19, 5617-5621 by replacing methyl 3-hydroxyphenylacetic acid with INT-28 and using chiral (S)-1,3-butanediol to afford methyl 4-{[(2R)-4-({[2-chloro-3-(trifluoromethyl)phenyl]methyl} (2,2-diphenylethyl) amino)butan-2-yl]oxy}-2-fluoro-6-methanesulfonylbenzoate (39).

Example 24: Synthesis of Compound 69

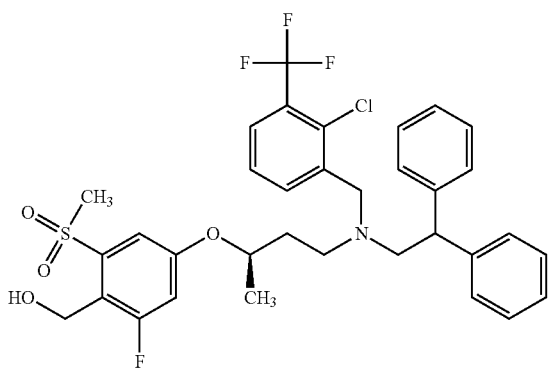

69

Compound 39 is hydrolyzed as described for compound 3 and subsequent benzoic acid reduction is accomplished as described for the synthesis of INT-09 using sodium borohydride and catalytic iodine. Work-up and purification affords (4-{[(2R)-4-({[2-chloro-3-(trifluoromethyl)phenyl] methyl}(2,2-diphenylethyl)amino)butan-2-yl]oxy}-2-fluoro-6-methanesulfonylphenyl)methanol (69).

Example 25: Synthesis of Compound 68

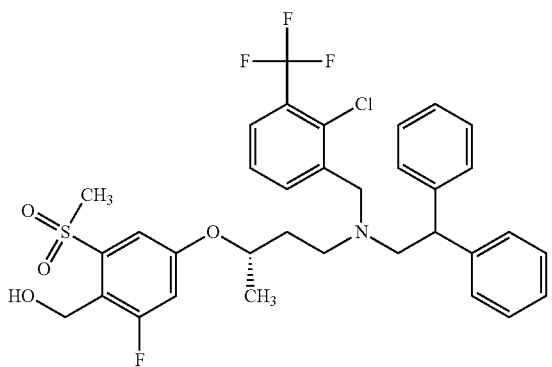

68

The synthesis of 68 is accomplished as described for compound 69 but using (R)-1,3-butanediol as the starting material to afford (4-{[(2S)-4-({[2-chloro-3-(trifluoromethyl)phenyl]methyl}(2,2-diphenylethyl)amino)butan-2-yl] oxy}-2-fluoro-6-methanesulfonylphenyl)methanol (68).

Example 26: Synthesis of Compound 64

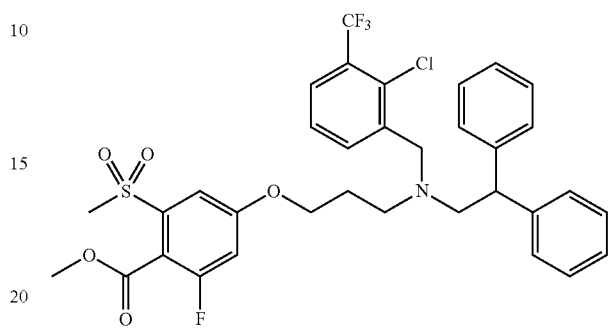

64

To a solution of bromide INT-01 (374 mg, 0.81 mmol) in ACN (8 mL) were added phenol INT-28 (200 mg, 0.73 mmol) and potassium carbonate (607 mg, 4.39 mmol). The reaction was heated to 90° C. overnight, cooled, and diluted with EtOAc (100 mL). The organic layer was washed with water (2×100 mL), and the combined aqueous layers were re-extracted with EtOAc (100 mL). The second organic layer was washed with water (100 mL) and the combined organic layers were dried over magnesium sulfate, filtered, concentrated under reduced pressure, and purified by silica gel column chromatography (EtOAc/hexanes=1/3) to afford methyl 4-[3-({[2-chloro-3-(trifluoromethyl)phenyl]methyl} (2,2-diphenylethyl)amino)propoxy]-2-fluoro-6-methanesulfonylbenzoate (64) as a colorless solid foam (315 mg, 63%). ES(pos)MS m/z 678.13 (M+H⁺).

Example 27: Synthesis of Compound 35

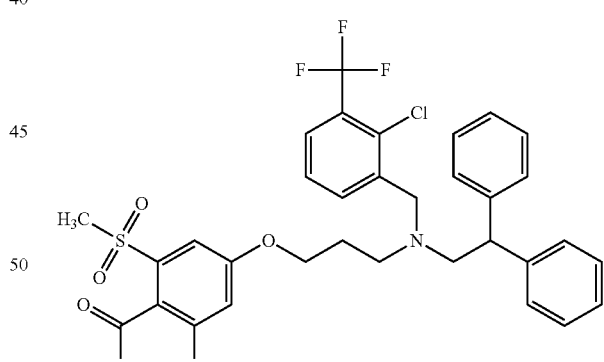

35

Ester 64 (80 mg, 0.118 mmol) was dissolved in THF (10 mL) and treated with a solution of 2.0 N lithium hydroxide (2 mL). After stirring for 16 h, the reaction mixture was quenched with water (100 mL) and 2N aqueous hydrochloric acid to adjust the pH to between 2-3. The mixture was extracted with EtOAc (3×100 mL), dried over magnesium sulfate, and purified by silica gel column chromatography (DCM/MeOH=10/1) to afford 4-[3-({[2-chloro-3-(trifluoromethyl)phenyl]methyl}(2,2-diphenylethyl)amino) propoxy]-2-fluoro-6-methanesulfonylbenzoic acid (35) as a white solid (51 mg, 65% yield). ES(pos)MS m/z 664.15 (M+H⁺).

Example 28: Synthesis of Compound 60

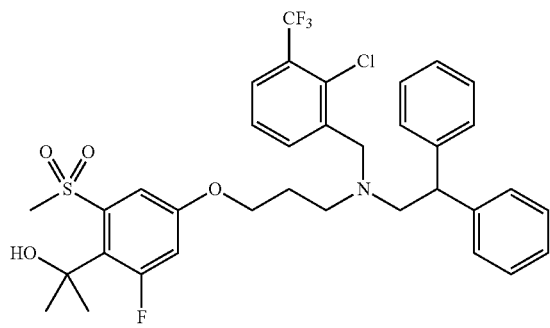

60

Ester 64 (100 mg, 0.148 mmol) was dissolved in dry THF (5 mL) and treated with 3.0 M methylmagnesium bromide solution in diethyl ether (0.45 mL, 1.35 mmol). The reaction was heated for 2 days at 60° C. HPLC analysis showed 60-70% conversion. The reaction was cooled and the mixture was poured into diethyl ether (100 mL), washed with half-saturated sodium bicarbonate solution (100 mL) and water (100 mL). The combined aqueous layers were re-extracted with diethyl ether (100 mL). The second organic layer was washed with water (100 mL) and the combined organic layers were dried over magnesium sulfate, filtered, and concentrated under reduced pressure to yield an inseparable mixture of starting material and product. This mixture was dissolved in THF (5 mL), treated with 2N lithium hydroxide solution (0.5 mL, 1.0 mmol), and the reaction was stirred at RT overnight. The reaction was diluted with EtOAc (100 mL), washed with water (2×100 mL), and the combined aqueous layers were re-extracted with EtOAc (100 mL). The second organic layer was washed with water (100 mL) and the combined organic layers were dried over magnesium sulfate, filtered, concentrated under reduced pressure, and purified by silica gel column chromatography (EtOAc/hexanes=1/3) to afford 2-{4-[3-({[2-chloro-3-(trifluoromethyl)phenyl]methyl}(2,2-diphenylethyl)amino)propoxy]-2-fluoro-6-methanesulfonylphenyl}propan-2-ol (60) as a slightly yellow oil (31 mg, 31%). ES(pos)MS m/z 678.16 (M+H$^+$).

Example 29: Synthesis of Compound 65

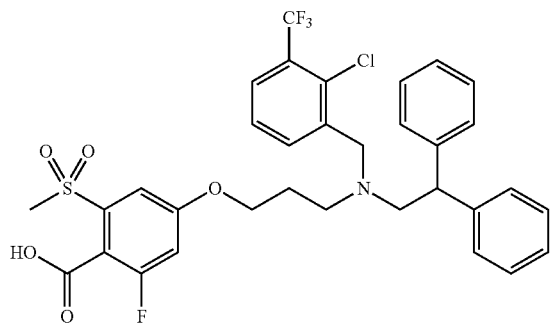

65

Chromium trioxide (75 mg, 0.75 mmol) was slurried in concentrated sulfuric acid (0.075 mL) for 5 min. Water (0.225 mL) was then added to the mixture resulting in a bright red solution. Silica gel (1.0 g) was added followed by stirring the orange powder for 10 min. Compound 8 (325 mg, 0.50 mmol) was added in DCM (15 mL) and the slurry was stirred for 30 min at RT or until TLC indicated consumption of starting materials. The remaining oxidant was quenched with MeOH (5 mL) and the mixture was stirred for 10 min (the slurry becomes dark green). The solids were filtered off, the filtrate was diluted with EtOAc (100 mL), washed with water (2×100 mL), and the combined aqueous layers were re-extracted with EtOAc (100 mL). The second organic layer was washed with water (100 mL) and the combined organic layers were dried over magnesium sulfate, filtered, concentrated under reduced pressure, and purified by silica gel column chromatography (EtOAc/hexanes=1/5 to 1/2) to afford 4-[3-({[2-chloro-3-(trifluoromethyl)phenyl]methyl}(2,2-diphenylethyl)amino)propoxy]-2-fluoro-6-methanesulfonyl-benzaldehyde (65) as a colorless solid foam (90%). ES(pos)MS m/z 648.16 (M+H$^+$).

Example 30: Synthesis of Compound 85

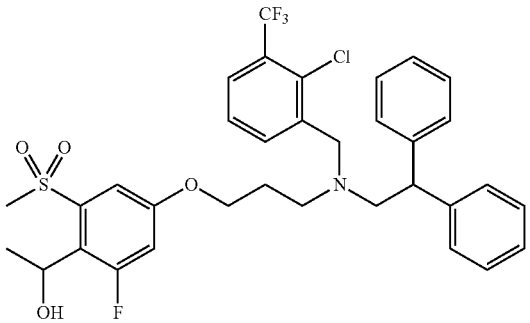

85

Compound 65 (150 mg, 0.231 mmol) was dissolved in dry THF (10 mL) and treated with 3.0 M methylmagnesium bromide solution in diethyl ether (0.31 mL, 0.93 mmol). After stirring at RT for 1 h, an additional amount of methylmagnesium bromide (0.31 mL, 0.93 mmol) was added and the reaction was stirred overnight. The mixture was quenched with saturated sodium bicarbonate solution (5 mL), diluted with EtOAc (100 mL), washed with water (2×100 mL), and the combined aqueous layers were re-extracted with EtOAc (100 mL). The second organic layer was washed with water (100 mL) and the combined organic layers were dried over magnesium sulfate, filtered, concentrated under reduced pressure, and purified by silica gel preparative TLC (2×2000 micron plates, EtOAc/hexanes=1/1 and then again with DCM/MeOH=50/1) to afford 1-{4-[3-({[2-chloro-3-(trifluoromethyl)phenyl]methyl}(2,2-diphenylethyl)amino)propoxy]-2-fluoro-6-methanesulfonylphenyl}ethan-1-ol (85) as a colorless foam (35 mg, 22%). ES(pos)MS m/z 664.19 (M+H$^+$).

Example 31: Synthesis of Compound 87

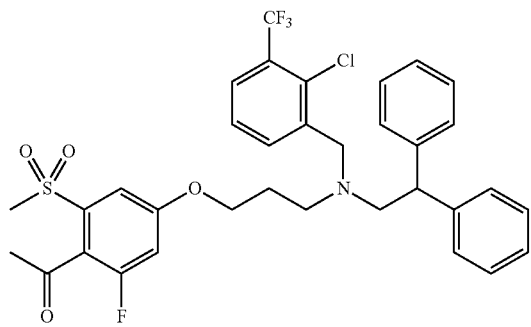

Silica gel supported Jones Reagent was synthesized as described for compound 65 (0.5 mmol).

The resulting orange powder was slurried in DCM (3 mL) and alcohol 85 (25 mg, 0.038 mmol) was added. After stirring for 10 min at RT or until TLC indicated consumption of starting materials, the excess oxidant was quenched with MeOH (5 mL) and the mixture was stirred for 10 min (slurry becomes dark green). The solids were filtered off, the filtrate was diluted with EtOAc (100 mL), washed with water (2×100 mL), and the combined aqueous layers were re-extracted with EtOAc (100 mL). The second organic layer was washed with water (100 mL) and the combined organic layers were dried over magnesium sulfate, filtered, concentrated under reduced pressure, and purified by silica gel preparative TLC (2000 micron plate, EtOAc/hexanes=1/1) to afford 1-{4-[3-({[2-chloro-3-(trifluoromethyl)phenyl]methyl}(2,2-diphenylethyl)amino)propoxy]-2-fluoro-6-methanesulfonylphenyl}ethan-1-one (87) as a colorless solid foam (15 mg, 60%). ES(pos)MS m/z 662.17 (M+H$^+$).

Example 32: Synthesis of Compound 88

Step 1: Synthesis of INT-29

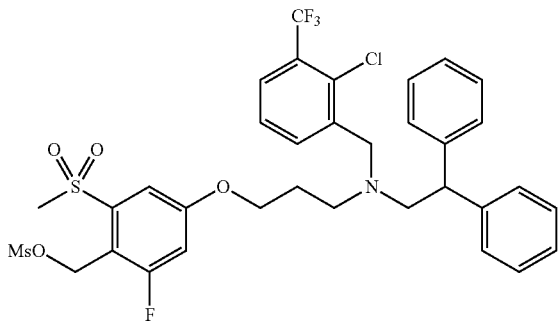

Alcohol 8 (325 mg, 0.50 mmol) was dissolved in dry DCM (10 mL) and treated with triethylamine (0.21 mL, 3.0 mmol) and methanesulfonyl chloride (0.058 mL, 1.5 mmol). The reaction was stirred overnight, diluted with EtOAc (100 mL), washed with water (2×100 mL), and the combined aqueous layers were re-extracted with EtOAc (100 mL). The second organic layer was washed with water (100 mL) and the combined organic layers were dried over magnesium sulfate, filtered, concentrated under reduced pressure to yield the crude mesylate INT-29, which was used in the next step without further purification.

Step 2: Synthesis of INT-30

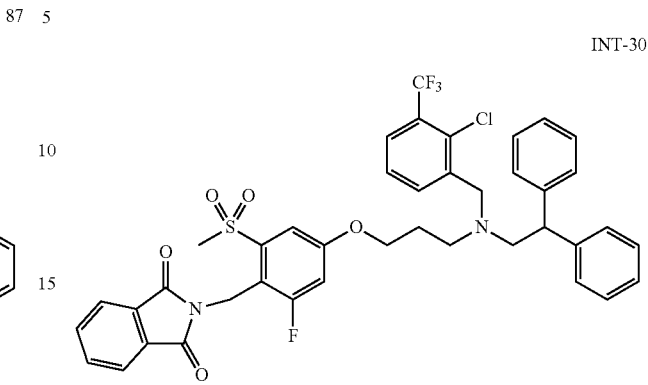

Crude mesylate INT-29 was dissolved in dry DMF (5 mL) and treated with potassium phthalate (278 mg, 1.5 mmol). The reaction was heated at 90° C. for 3 h until TLC indicated complete consumption of the starting material. The mixture was cooled, diluted with EtOAc (100 mL), washed with water (2×100 mL), and the combined aqueous layers were re-extracted with EtOAc (100 mL). The second organic layer was washed with water (100 mL) and the combined organic layers were dried over magnesium sulfate, filtered, concentrated under reduced pressure, and purified by silica gel column chromatography (DCM/MeOH=200/1) to afford the desired phthalate (INT-30) as a white solid (72% over 2 steps).

Step 3: Synthesis of Compound 88

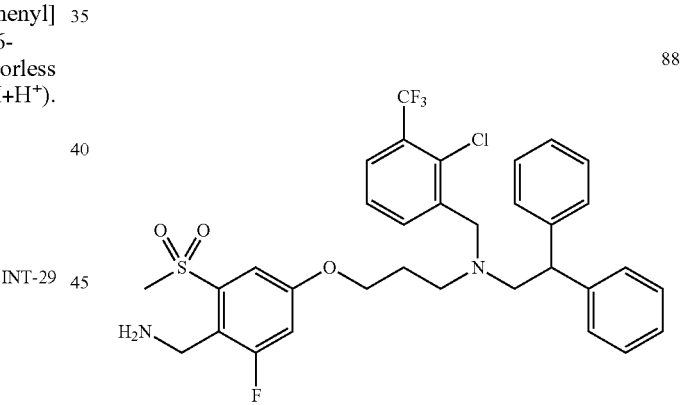

Phthalate INT-30 (280 mg, 0.359 mmol) was suspended in ethanol (5 mL) and treated with hydrazine monohydrate (1.0 mL). The mixture was heated at 70° C. for 3 h resulting in a clear solution, followed by precipitate formation at which point TLC showed complete consumption of the starting material. The reaction was diluted with EtOAc (100 mL), washed with water (2×100 mL), and the combined aqueous layers were then re-extracted with EtOAc (100 mL). The second organic layer was washed with water (100 mL) and the combined organic layers were dried over magnesium sulfate, filtered, concentrated under reduced pressure, and purified by silica gel column chromatography (DCM/MeOH (7.0 N ammonia)=50/1) to afford {4-[3-({[2-chloro-3-(trifluoromethyl)phenyl]methyl}(2,2-diphenylethyl)amino)propoxy]-2-fluoro-6-methanesulfonylphenyl}methanamine (88) as a white colorless oil (185 mg, 79%). ES(pos)MS m/z 649.19 (M+H$^+$).

Example 33: Synthesis of Compound 89

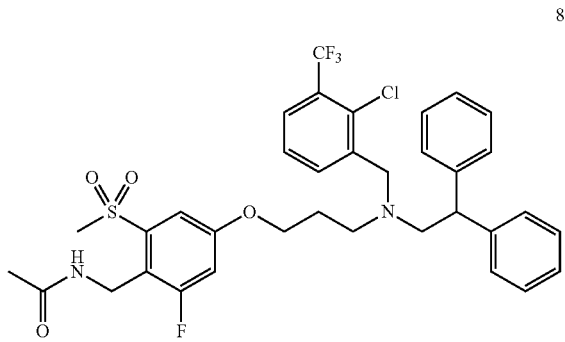

89

Primary amine 88 (73 mg, 0.112 mmol) was dissolved in dry DCM (3 mL) and treated with triethylamine (0.063 mL, 0.45 mmol) and acetyl chloride (0.017 mL, 0.225 mmol). After stirring for 2 h, the reaction mixture was diluted with EtOAc (100 mL), washed with water (2×100 mL), and the combined aqueous layers were re-extracted with EtOAc (100 mL). The second organic layer was washed with water (100 mL) and the combined organic layers were dried over magnesium sulfate, filtered, concentrated under reduced pressure, and purified by silica gel column chromatography (EtOAc/hexanes=5/1) to afford N-({4-[3-({[2-chloro-3-(trifluoromethyl)phenyl]methyl}(2,2-diphenylethyl)amino)propoxy]-2-fluoro-6-methanesulfonylphenyl}methyl)acetamide (89) as a white solid foam (70 mg, 90%). ES(pos)MS m/z 691.20 (M+H$^+$).

Example 34: Synthesis of Compound 91

Step 1: Synthesis of INT-31

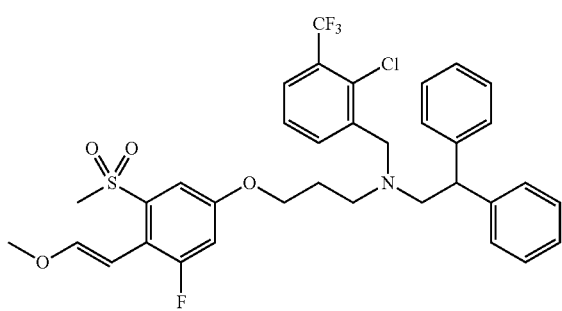

INT-31

(Methoxymethyl)triphenylphosphonium chloride (68.6 mg, 0.20 mmol) was suspended in dry THF (1.0 mL) and cooled to 0° C. A solution of 1.0 M LiHMDS in THF (0.186 mg, 0.185 mmol) was added to the reaction and the mixture was stirred for 30 min at the same temperature. The resulting bright orange solution was cooled to −78° C. and aldehyde 65 (120 mg, 0.185 mmol) dissolved in dry THF (2 mL) was slowly added to the reaction over 5 min. The mixture was warmed to RT over 1 h and stirred at this temperature for an additional 2 h. The yellow mixture was quenched with saturated sodium bicarbonate solution, diluted with EtOAc (100 mL), washed water (2×100 mL), and the combined aqueous layers were re-extracted with EtOAc (100 mL). The second organic layer was washed with water (100 mL) and the combined organic layers were dried over magnesium sulfate, filtered, concentrated under reduced pressure, and purified by silica gel column chromatography (EtOAc/hexanes=1/1) to afford INT-31 as a mixture of E/Z-isomers and as a colorless solid foam (120 mg, 96%).

Step 2: Synthesis of Compound 91

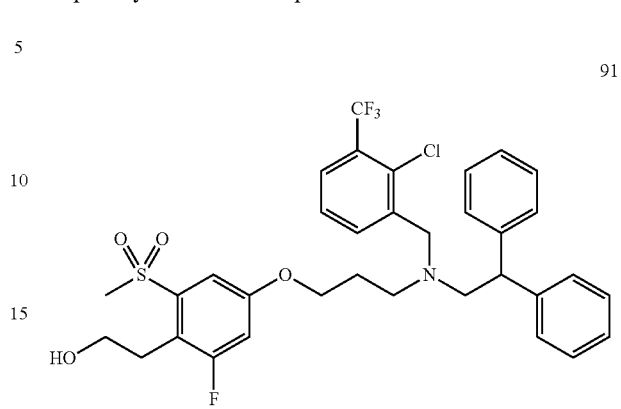

91

INT-31 (115 mg, 0.17 mmol) was dissolved in THF (3 mL) and treated with 6N hydrochloric acid (2 mL). The reaction was stirred for 3.5 h at RT, or until TLC showed complete consumption of starting material. The mixture was carefully quenched with saturated potassium carbonate solution to adjust the pH to 8-9. The mixture was diluted with EtOAc (100 mL), washed with water (2×100 mL), and the combined aqueous layers were re-extracted with EtOAc (100 mL). The second organic layer was washed with water (100 mL) and the combined organic layers were dried over magnesium sulfate, filtered, and concentrated under reduced pressure to afford the crude aldehyde.

The crude residue was dissolved in MeOH (5 mL) and treated with solid sodium borohydride (13 mg, 0.34 mmol). After stirring for 15 min at RT, TLC showed no starting material remained. The mixture was diluted with EtOAc (100 mL), washed with water (2×100 mL), and the combined aqueous layers were re-extracted with EtOAc (100 mL). The second organic layer was washed with water (100 mL) and the combined organic layers were dried over magnesium sulfate, filtered, concentrated under reduced pressure, and purified by silica gel column chromatography (EtOAc/hexanes=1/1) to afford semi-pure product. This lower spot was re-purified by silica gel preparative TLC (2000 micron plate, DCM/MeOH=50/1) to yield 2-{4-[3-({[2-chloro-3-(trifluoromethyl)phenyl]methyl}(2,2-diphenylethyl)amino)propoxy]-2-fluoro-6-methanesulfonylphenyl} ethan-1-ol (91) as a white foam (31 mg, 27%). ES(pos) MS m/z 664.19 (M+H$^+$).

Example 35: Synthesis of Compound 95

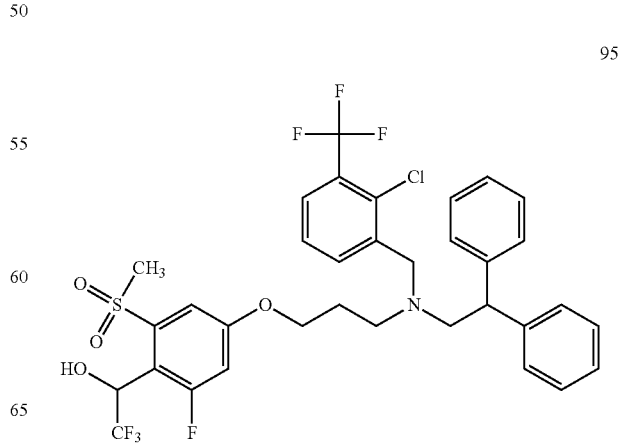

95

The reaction was performed according to *J. Med. Chem.* 2009, 52 (19) 6097-6106. To a solution of aldehyde 65 (0.3 g, 0.46 mmol) in anhydrous THF (5 mL) under nitrogen atmosphere was added trifluoromethyltrimethylsilane (78 mg, 0.55 mmol) and cesium fluoride (10 mg, 0.06 mmol). The resulting solution was sonicated for 15 min to initiate the reaction and then stirred at RT for 6 h. Aqueous 1 M hydrochloric acid (2 mL) was added and the mixture was stirred for an additional 2 h. The reaction was poured into EtOAc (25 mL), washed with saturated sodium bicarbonate, brine, dried over sodium sulfate and concentrated under reduced pressure. The residue was purified by silica gel preparative TLC (30% EtOAC/hexanes) to afford 1-{4-[3-({[2-chloro-3-(trifluoromethyl)phenyl]methyl}(2,2-diphenylethyl)amino) propoxy]-2-fluoro-6-methanesulfonylphenyl}-2,2,2-trifluoroethan-1-ol (95) as a white solid (171 mg, 52%); TLC=30% EtOAc/hexanes (0.5 Rf); ES(pos)MS m/z 718.5 (M+H⁺).

Example 36: Synthesis of Compound 93

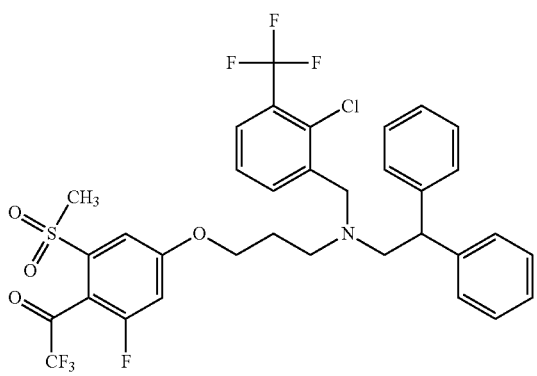

93

Compound 95 (200 mg, 0.28 mmol) was oxidized as described for compound 65 and purified by silica gel preparative TLC to afford 1-{4-[3-({[2-chloro-3-(trifluoromethyl)phenyl]methyl}(2,2-diphenylethyl) amino)propoxy]-2-fluoro-6-methanesulfonylphenyl}-2,2,2-trifluoroethan-1-one (93) as a semi solid (70 mg, 35%); TLC=30% EtOAc/hexanes (0.65 Rf); ES (pos) MS m/z 716.5 (M+H⁺).

Example 37: Synthesis of Compound 94

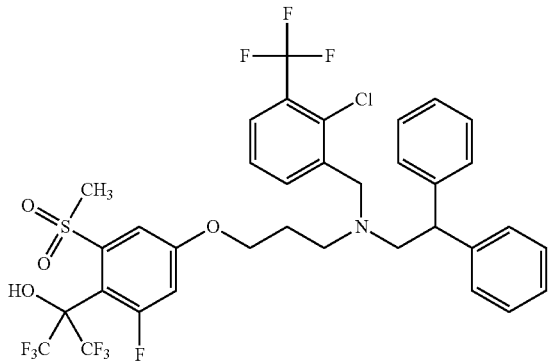

94

To a solution of aldehyde 93 (0.2 mmol) in anhydrous THF (2 mL) under nitrogen atmosphere is added trifluoromethyltrimethylsilane (0.25 mmol) and cesium fluoride (0.02 mmol). The resulting solution is sonicated for 15 min to initiate the reaction and then stirred at RT for 6 h. Aqueous 1 M hydrochloric acid (2 mL) is added and the mixture is stirred for an additional 2 h. The reaction is poured into EtOAc (25 mL), washed with saturated sodium bicarbonate, brine, dried over sodium sulfate and concentrated under reduced pressure. The residue is purified by silica gel preparative TLC (30% EtOAC/hexanes) to afford 2-{4-[3-({[2-chloro-3-(trifluoromethyl)phenyl]methyl}(2,2-diphenylethyl)amino)propoxy]-2-fluoro-6-methanesulfonylphenyl}-1,1,1,3,3,3-hexafluoropropan-2-ol (94).

Example 38: Synthesis of Compound 97

Step 1: Synthesis of INT-64

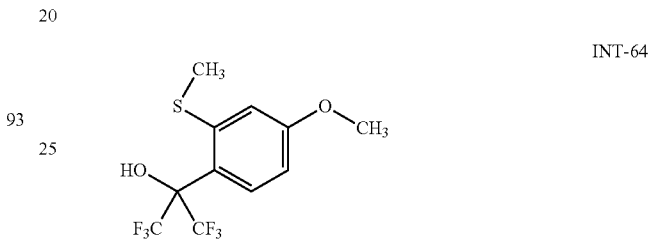

INT-64

1-Bromo-4-methoxy-2-(methylsulfanyl)benzene is prepared as described in *Organic Process Research & Development* 2004, 8(1), 33-44. 1-Bromo-4-methoxy-2-(methylsulfanyl)benzene (5.0 mmol) is dissolved in THF (50 mL), cooled to −78° C., and treated with n-butyllithium (5.3 mmol, 1.6 M in hexanes). After 30 min, hexafluoroacetone is bubbled into the solution and the mixture is stirred for an additional 30 min at −78° C. The reaction is quenched with saturated aqueous ammonium chloride solution, extracted with EtOAc (3×100 mL), the combined organic layers are washed with brine, dried over sodium sulfate, filtered, and concentrated under reduced pressure. The residue is purified by silica gel chromatography to afford 1,1,1,3,3,3-hexafluoro-2-[4-methoxy-2-(methylsulfanyl)phenyl]propan-2-ol (INT-64).

Step 2: Synthesis of INT-65

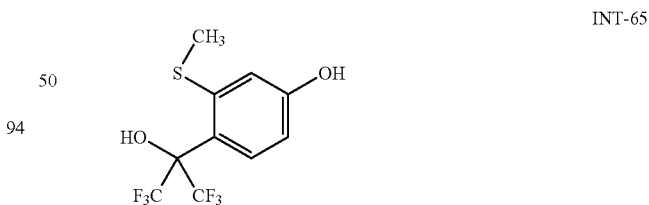

INT-65

To a suspension of INT-64 (2.0 mmol) and sodium iodide (20.0 mmol) in acetonitrile (15 mL) is added trimethylsilyl chloride (10 mmol) at RT. The mixture is heated to reflux for 48 h, cooled to RT, diluted with water (100 mL) and extracted into EtOAc (2×100 mL). The combined EtOAc extracts are washed with saturated sodium thiosulfate solution (100 mL) to remove the iodine color, washed with brine (100 mL), dried over anhydrous magnesium sulfate, filtered, and concentrated under reduced pressure. The crude residue is purified by silica gel chromatography to afford 4-(1,1,1,3,3,3-hexafluoro-2-hydroxypropan-2-yl)-3-(methylsulfanyl)phenol (INT-65).

Step 3: Synthesis of INT-66

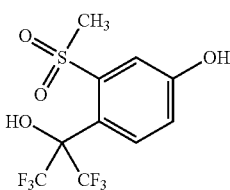

INT-65 (1.0 mmol) is dissolved in DCM (10 mL) and treated with mCPBA (77%, 3.0 mmol). The resulting mixture is stirred overnight at RT. The organic solvent is removed under reduced pressure and the residue is dissolved in EtOAc (50 mL). The solution is washed with 1N sodium hydroxide (2×50 mL) and water (2×50 mL). The organic layer is dried over magnesium sulfate, filtered, concentrated under reduced pressure, and the residue is purified by silica gel chromatography (MeOH/DCM) to yield 4-(1,1,1,3,3,3-hexafluoro-2-hydroxypropan-2-yl)-3-methanesulfonylphenol (INT-66).

Step 4: Synthesis of Compound 97

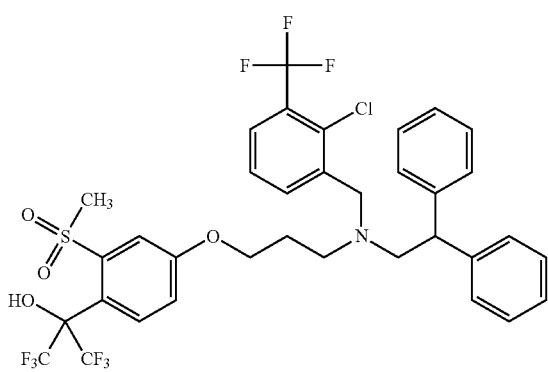

Bromide INT-01 (0.50 mmol) and INT-66 (0.55 mmol) are dissolved in DMF (2 mL) and potassium carbonate (1.5 mmol) is added. After 6 h at RT the reaction is poured into EtOAc (25 mL), washed with saturated sodium bicarbonate, brine, dried over sodium sulfate and concentrated under reduced pressure. The residue is purified by silica gel preparative TLC to afford 2-{4-[3-({[2-chloro-3-(trifluoromethyl)phenyl]methyl}(2,2-diphenylethyl)amino)propoxy]-2-methanesulfonylphenyl}-1,1,1,3,3,3-hexafluoropropan-2-ol (97).

Example 39: Synthesis of Compound 90

Step 1: Synthesis of INT-32

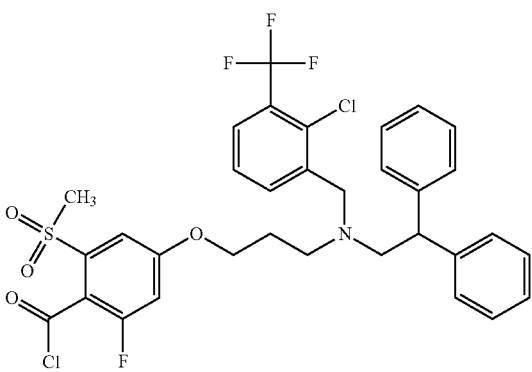

To benzoic acid 35 (850 mg, 1.28 mmol) in DCM (10 mL) was added oxalyl chloride (131 μL, 1.54 mmol) and a catalytic amount of DMF under nitrogen atmosphere. The reaction mixture was stirred for 1 h and concentrated under reduced pressure and the residue 4-[3-({[2-chloro-3-(trifluoromethyl)phenyl]methyl}(2,2-diphenylethyl)amino)propoxy]-2-fluoro-6-methanesulfonylbenzoyl chloride (INT-32) (840 mg, crude) was used in the next step without further purification.

Step 2: Synthesis of Compound 90

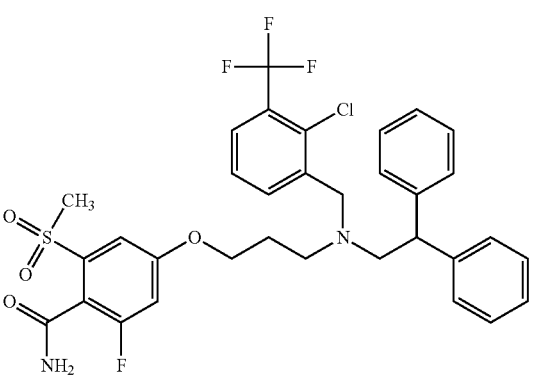

To a solution of acid chloride INT-32 (150 mg, 0.22 mmol) in DCM (5 mL) at 0° C. was added methanolic ammonia (5 mL, 17%) in large excess and the solution was slowly warmed to RT. After 1 h, the volatiles were removed under reduced pressure and the residue was purified by silica gel preparative TLC (40% EtOAc/hexanes) to afford 4-[3-({[2-chloro-3-(trifluoromethyl)phenyl]methyl}(2,2-diphenylethyl) amino)-propoxy]-2-fluoro-6-methanesulfonylbenzamide (90) as a white solid (90 mg, 63%). TLC=30% EtOAc/hexanes (0.2 Rf); ES (pos) MS m/z 663.5 (M+H$^+$).

Example 40: Synthesis of Compound 92

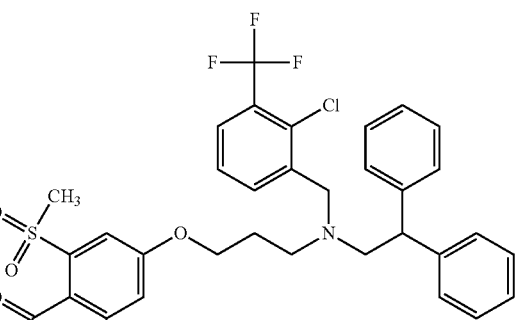

To a solution of acid chloride INT-32 (150 mg, 0.22 mmol) in DCM (5 mL) at 0° C. was added methanolic methylamine (8 mL, 10%) in large excess and the solution was slowly warmed to RT. After 1 h, the volatiles were removed and the residue was purified by silica gel preparative TLC (30% EtOAc/hexanes) to afford 4-[3-({[2-chloro- 3-(trifluoromethyl)phenyl]methyl}(2,2-diphenylethyl) amino)-propoxy]-2-fluoro-6-methanesulfonyl-N-methylbenzamide (92) as a thick syrup (90 mg, 64%). TLC=30% EtOAc/hexanes (0.25 Rf); ES(pos)MS m/z 677.5 (M+H⁺).

Example 41: Synthesis of Compound 96

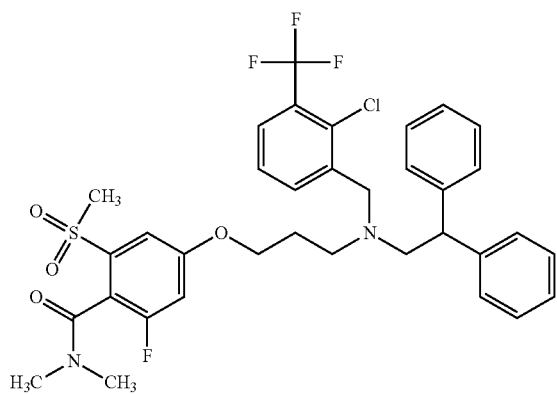

96

To a solution of acid chloride INT-32 (150 mg, 0.22 mmol) in DCM (5 mL) at 0° C. was added triethylamine (140 µL, 1.0 mmol) and dimethylamine hydrochloride (82 mg, 1.0 mmol). The solution was slowly warmed to RT and stirred for 1 h. The reaction mixture was concentrated under reduced pressure and EtOAc (15 mL) and water were added. The organic layer was separated and the water layer was back extracted with EtOAc (10 mL) The combined organic layers were washed with brine, dried over sodium sulfate and concentrated under reduced pressure and the residue was purified by silica gel preparative TLC (30% EtOAc/hexanes) to afford 4-[3-({[2-chloro-3-(trifluoromethyl)phenyl]methyl}(2,2-diphenylethyl)amino) propoxy]-2-fluoro-6-methanesulfonyl-N,N-dimethylbenzamide (96) as a thick syrup (62 mg, 41%). TLC=30% EtOAc/hexanes (0.3 Rf); ES (pos) MS m/z 691.6 (M+H⁺).

Example 42: Synthesis of Compound 11

Step 1: Synthesis of INT-33

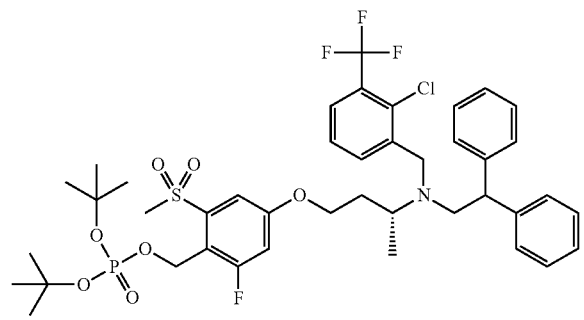

INT-33

To a solution of compound 9 (2.0 mmol) in DCM (2 mL) is added di-tert-butyl diisopropylphosphoramidite (1.35 g, 2.5 mmol) in DCM (2 mL) and tetrazole (5.0 mmol). The resulting suspension is stirred at RT for 16 h. Hydrogen peroxide (30%, 4.0 mmol) is added drop-wise and the resulting mixture is stirred for 2 h. The reaction mixture is diluted with DCM (10 mL), washed with brine, dried, concentrated under reduced pressure, and purified by silica gel chromatography to afford di-tert-butyl {4-[(3R)-3-({[2-chloro-3-(trifluoromethyl)phenyl]methyl}(2,2-diphenyl-ethyl)amino)-butoxy]-2-fluoro-6-methanesulfonylphenyl} methyl phosphate (INT-33).

Step 2: Synthesis of Compound 11

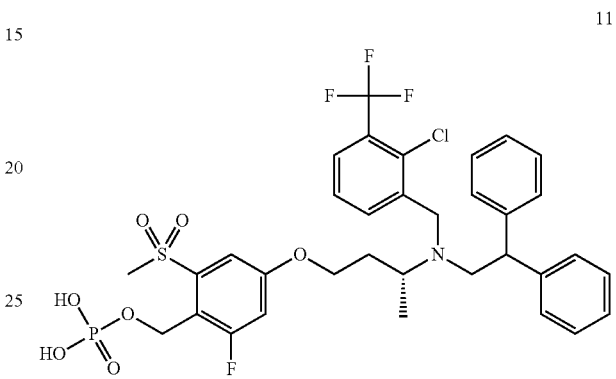

11

INT-33 (1.0 mmol) is dissolved in toluene (5 mL), TFA (10 mmol) is added, and the reaction is stirred for 2.5 h at RT. The mixture is concentrated under reduced pressure, and purified by preparatory reverse phase preparative HPLC to afford ({4-[(3R)-3-({[2-chloro-3-(trifluoromethyl)phenyl] methyl}(2,2-diphenylethyl)amino)butoxy]-2-fluoro-6-methanesulfonylphenyl}methoxy)phosphonic acid (11).

Example 43: Synthesis of Compound 12

Step 1: Synthesis of INT-34

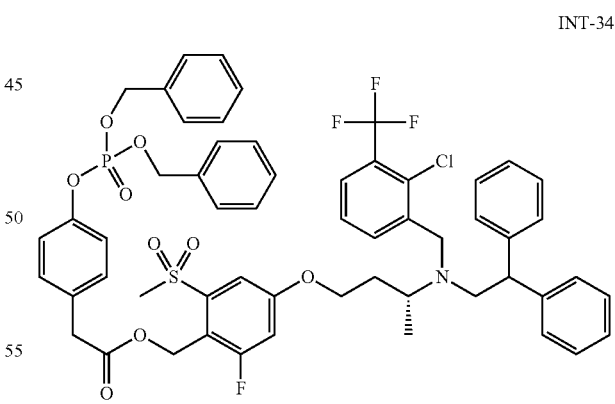

INT-34

2-(4-(Bis(benzyloxy)phosphoryloxy)phenyl)acetic acid (1.0 mmol) is prepared as previously described (WO20120135082) and added to a solution of compound 9 (0.5 mmol) and DMAP (1.0 mmol) in DCM (5 mL). N,N'-dicyclohexylcarbodiimide (1.2 mmol) in DCM (5 mL) is added to the reaction and the mixture is stirred at RT for 30 min. The solution is filtered and concentrated under reduced pressure to yield crude product. The residue is purified by silica gel chromatography to afford {4-[(3R)-3-

({[2-chloro-3-(trifluoromethyl)phenyl]methyl}(2,2-diphenylethyl)amino)-butoxy]-2-fluoro-6-methanesulfonylphenyl} methyl 2-(4-{[bis(benzyloxy)phosphoryl]oxy}phenyl)acetate (INT-34).

Step 2: Synthesis of Compound 12

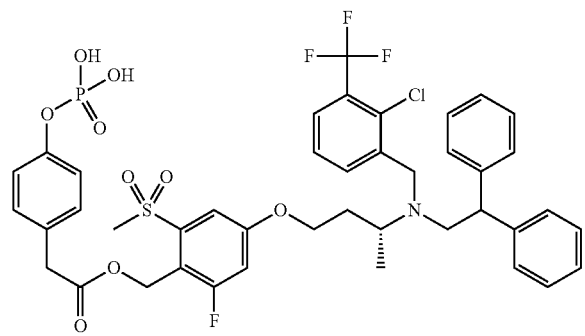

To a solution of INT-34 (0.25 mmol) in MeOH (5 mL) is added Pd/C (10% w/w) under an atmosphere of hydrogen at RT for 15 min. The mixture is filtered, concentrated under reduced pressure, and purified by reverse phase preparative HPLC to afford {4-[2-({4-[(3R)-3-({[2-chloro-3-(trifluoromethyl)-phenyl]methyl}-(2,2-diphenylethyl)amino)butoxy]-2-fluoro-6-methanesulfonylphenyl}methoxy)-2-oxoethyl]phenoxy} phosphonic acid (12).

Example 44: Synthesis of Compound 13

Step 1: Synthesis of INT-35

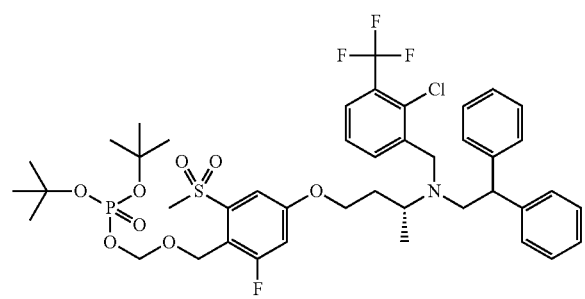

To a solution of compound 9 (1 mmol) in DME (5 mL) is added sodium hydride (60% in mineral oil, 1.5 mmol) at 0° C. and then the reaction is cooled to −60° C. Chloromethylditertiarybutylphosphate (1.5 mmol) is prepared as previously described (WO20120135082) and sodium iodide (1.5 mmol) are added to the reaction. The temperature is maintained at −60° C. for 2 hours, and then the reaction is warmed to RT. The reaction is stirred for 2 h, poured into cold water (10 mL), extracted with EtOAc (3×15 mL), dried over sodium sulfate, filtered, and concentrated under reduced pressure to afford crude di-tert-butyl ({4-[(3R)-3-({[2-chloro-3-(trifluoromethyl)-phenyl]-methyl}-(2,2-diphenylethyl)amino)-butoxy]-2-fluoro-6-methanesulfonylphenyl}methoxy)methyl phosphate (INT-35).

Step 2: Synthesis of Compound 13

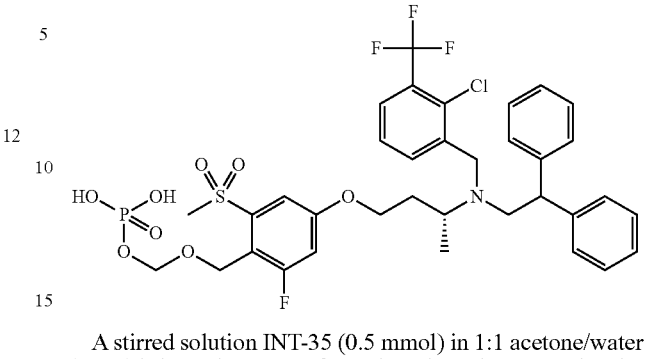

A stirred solution INT-35 (0.5 mmol) in 1:1 acetone/water (4 mL) is heated to 60° C. for 16 h. Solvent is removed under reduced pressure and the crude product is purified by reverse phase preparative HPLC to afford [({4-[(3R)-3-({[2-chloro-3-(trifluoromethyl)-phenyl]methyl}-(2,2-diphenylethyl)amino)-butoxy]-2-fluoro-6-methanesulfonylphenyl}-methoxy)methoxy]phosphonic acid (13).

Example 45: Synthesis of Compound 14

Step 1: Synthesis of INT-36

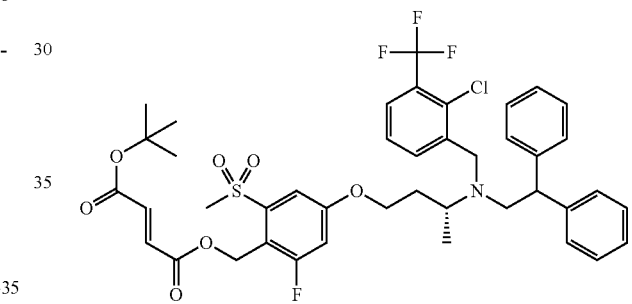

To a solution of compound 9 (1.0 mmol), mono-tert-butylfumerate ester (1.0 mmol), and DMAP (0.5 mmol) in DCM (5 mL) is added N,N'-dicyclohexylcarbodiimide (1.2 mmol) in DCM (5 mL). The mixture is stirred at RT overnight, diluted with DCM (10 mL), washed with water (3×3 mL), dried over sodium sulfate, filtered, and concentrated under reduced pressure. The residue is purified by silica gel chromatography to afford 1-tert-butyl 4-{4-[(3R)-3-({[2-chloro-3-(trifluoromethyl)phenyl]methyl}-(2,2-diphenylethyl)amino)butoxy]-2-fluoro-6-methanesulfonylphenyl}methyl (2E)-but-2-enedioate (INT-36).

Step 2: Synthesis of Compound 14

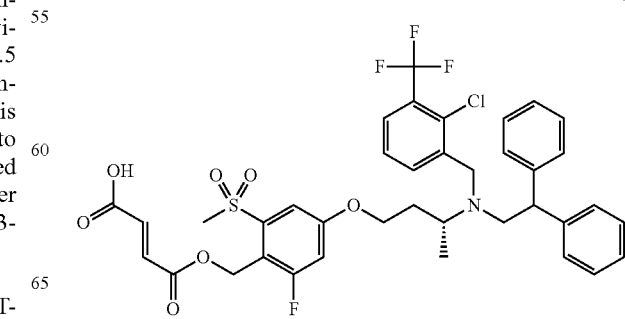

INT-36 (0.50 mmol) in DCM (2 mL) is added TFA (0.2 mL) drop-wise over a period of 10 min at 0° C. The mixture is warmed to RT, stirred for 4 h, and the solvent removed under reduced pressure. The residue is purified by reverse phase preparative HPLC to afford (2E)-4-({4-[(3R)-3-({[2-chloro-3-(trifluoromethyl)-phenyl]methyl}-(2,2-diphenyl-ethyl)amino)butoxy]-2-fluoro-6-methanesulfonylphenyl)-methoxy)-4-oxobut-2-enoic acid (14).

Example 46: Synthesis of Compound 15

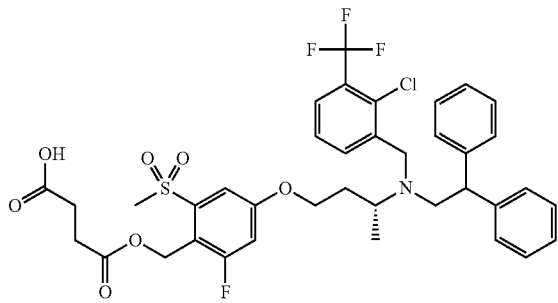

To a stirred solution of compound 9 (0.50 mmol) in pyridine (1 mL) is added DMAP (0.05 mmol) and succinic anhydride (0.5 mmol) at RT. The reaction is stirred at RT overnight, solvent is removed under reduced pressure, and the crude product is purified by reverse phase preparative HPLC to afford 4-({4-[(3R)-3-({[2-chloro-3-(trifluoromethyl)phenyl]methyl}(2,2-diphenylethyl)amino)butoxy]-2-fluoro-6-methanesulfonylphenyl}methoxy)-4-oxobutanoic acid (15).

Example 47: Synthesis of Compound 16

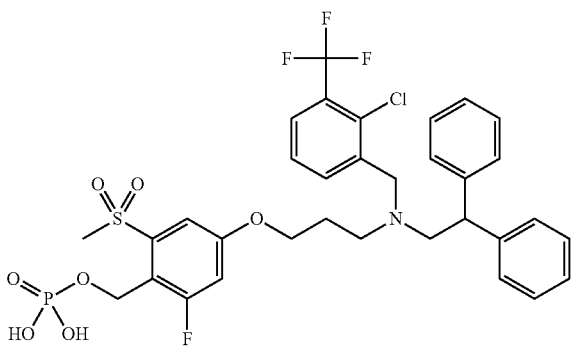

Using a similar procedure to prepare compound 11, starting material compound 9 is replaced with compound 8 to afford ({4-[3-({[2-chloro-3-(trifluoromethyl)phenyl]methyl}-(2,2-diphenylethyl)amino)-propoxy]-2-fluoro-6-methanesulfonylphenyl}methoxy)phosphonic acid (16).

Example 48: Synthesis of Compound 17

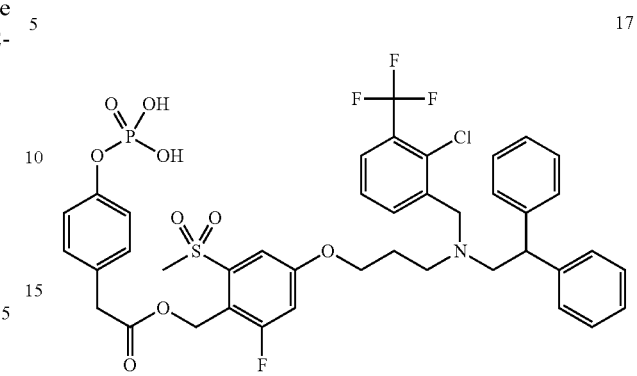

Using a similar procedure to prepare compound 12, starting material compound 9 is replaced with compound 8 to afford {4-[2-({4-[3-({[2-chloro-3-(trifluoromethyl)phenyl]methyl}-(2,2-diphenylethyl)amino)-propoxy]-2-fluoro-6-methanesulfonylphenyl}methoxy)-2-oxoethyl]phenoxy}phosphonic acid (17).

Example 49: Synthesis of Compound 18

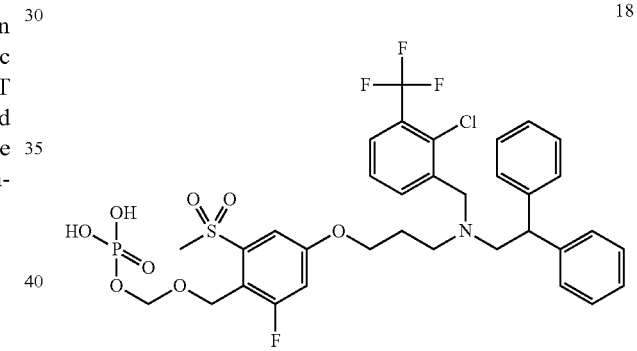

Using a similar procedure to prepare compound 13, starting material compound 9 is replaced with compound 8 to afford [({4-[3-({[2-chloro-3-(trifluoromethyl)phenyl]methyl}-(2,2-diphenylethyl)amino)-propoxy]-2-fluoro-6-methanesulfonylphenyl}methoxy)methoxy]phosphonic acid (18).

Example 50: Synthesis of Compound 19

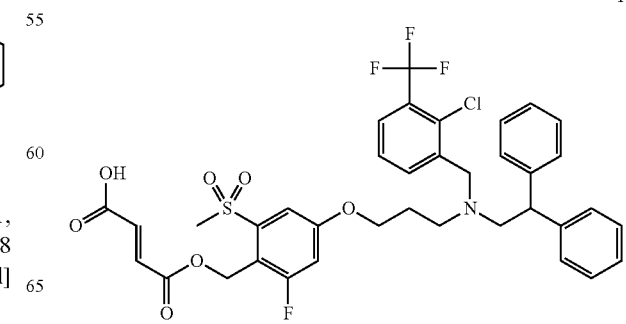

Using a similar procedure to prepare compound 14, starting material compound 9 is replaced with compound 8 to afford (2E)-4-({4-[3-({[2-chloro-3-(trifluoromethyl)phenyl]methyl}(2,2-diphenylethyl) amino)-propoxy]-2-fluoro-6-methanesulfonylphenyl}methoxy)-4-oxobut-2-enoic acid (19).

Example 51: Synthesis of Compound 20

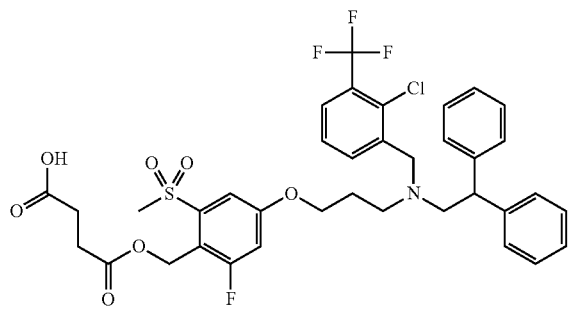

Using a similar procedure to prepare compound 15, starting material compound 9 is replaced with compound 8 to afford 4-({4-[3-({[2-chloro-3-(trifluoromethyl)phenyl]methyl}(2,2-diphenylethyl)amino)-propoxy]-2-fluoro-6-methanesulfonylphenyl}methoxy)-4-oxobutanoic acid (20).

Example 52: Synthesis of Compound 21

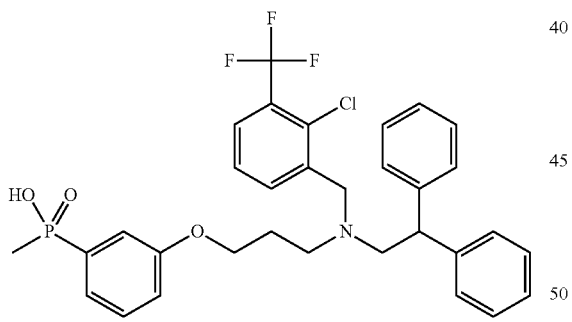

Ethyl (3-hydroxyphenyl)methylphosphinate (0.5 mmol) is prepared as previously described (WO2010036613) and dissolved in ACN (3 mL). Bromide INT-01 (0.5 mmol) and potassium carbonate (0.60 mmol) are added as described above for compound 9. The resulting product is isolated and purified by chromatography and then the ester is hydrolyzed in dioxane (0.5 mL) with 5N sodium hydroxide (0.2 mL) at reflux temperature overnight. The reaction is concentrated under reduced pressure, treated with TFA (0.5 mL), and concentrated. The residue is purified by reverse phase preparative HPLC to afford {3-[3-({[2-chloro-3-(trifluoromethyl)phenyl]methyl}(2,2-diphenylethyl)amino)propoxy]-phenyl}(methyl)-phosphinic acid (21).

Example 53: Synthesis of Compound 22

Step 1: Synthesis of INT-37

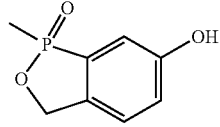

Methods to make benzoxaphosphol-1-ones have been previously described (*Tetrahedron Lett.* 1985, 26(39), 4771; *J. Org. Chem.* 1982, 47(9), 1677; and *J. Org. Chem.* 1981, 46(17), 3486). Using similar protocols, 6-hydroxy-1-methyl-1,3-dihydro-2,1λ-benzoxaphosphol-1-one (INT-37) is made from 3-bromo-4-methyl-phenol (U.S. Pat. No. 6,414,002).

Step 2: Synthesis of Compound 22

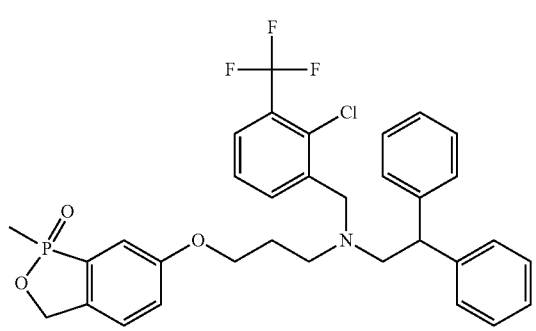

INT-37 (0.5 mmol) and bromide INT-01 (0.5 mmol) are dissolved in ACN (3 mL) and potassium carbonate (0.60 mmol) is added as base as described above for compound 9. The resulting product is isolated and purified by chromatography to afford 6-[3-({[2-chloro-3-(trifluoromethyl)phenyl]methyl}(2,2-diphenylethyl)-amino)-propoxy]-1-methyl-1,3-dihydro-2,1λ-benzoxaphosphol-1-one (22).

Example 54: Synthesis of Compound 23

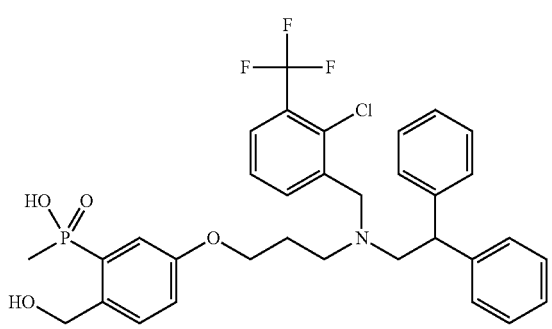

Compound 22 is hydrolyzed in dioxane (0.5 mL) with 5N sodium hydroxide (0.2 mL) at reflux temperature overnight. The reaction is concentrated under reduced pressure, treated with TFA (0.5 mL), and concentrated. The residue is purified by reverse phase preparative HPLC to afford {5-[3-({[2-chloro-3-(trifluoromethyl)phenyl]methyl}(2,2-diphenylethyl)amino)propoxy]-2-(hydroxymethyl)phenyl}-(methyl)-phosphinic acid (23).

Example 55: Synthesis of Compound 24

Step 1: Synthesis of INT-38

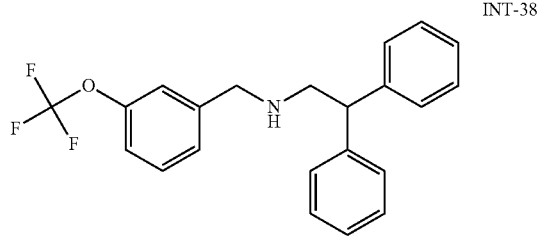 [SMILES: FC(F)(F)Oc1cccc(CNCC(c2ccccc2)c2ccccc2)c1]

3-(Trifluoromethoxy)benzaldehyde (975 mg, 5.13 mmol) and 2,2-diphenylethylamine (920 mg, 4.66 mmol) were dissolved in dry DCM (10 mL). Subsequent addition of sodium triacetoxyborohydride (988 mg, 4.66 mmol) and acetic acid (1 mL) was followed by stirring at RT overnight or until TLC showed no starting material remained. The reaction mixture was poured into saturated sodium bicarbonate solution (150 mL) and then extracted with EtOAc (3×100 mL). The organic layers were dried over magnesium sulfate, filtered, concentrated under reduced pressure, and the residue was purified by silica gel chromatography (MeOH/DCM/7N ammonium hydroxide) to afford the desired (2,2-diphenylethyl)({[3-(trifluoromethoxy)-phenyl]methyl})amine (INT-38) as a viscous oil (1.13 g, 65% yield).

Step 2: Synthesis of INT-39

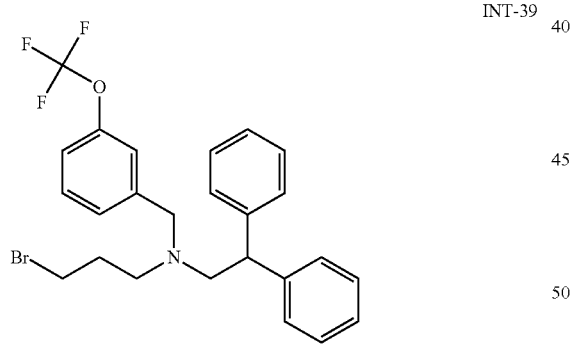

INT-38 (1.1 g, 2.96 mmol) and 1,3-dibromopropane (5.98 g, 29.6 mmol) were dissolved in dry ACN (24 mL). Potassium carbonate (613 mg, 4.44 mmol) was added and the reaction was heated to 90° C. for 16 h. The reaction mixture was poured into saturated sodium bicarbonate solution (100 mL) and then extracted with EtOAc (3×100 mL). The organic layers were dried over magnesium sulfate, filtered, concentrated under reduced pressure, and the residue was purified by silica gel chromatography (DCM/hexanes) to afford (3-bromopropyl)(2,2-diphenylethyl){[3-(trifluoromethoxy)phenyl]methyl}amine (INT-39) as a slightly yellowish oil (1.5 g, 76% yield) contaminated with 1,3-dibromopropane according to $^1$H-NMR.

Step 3: Synthesis of INT-40

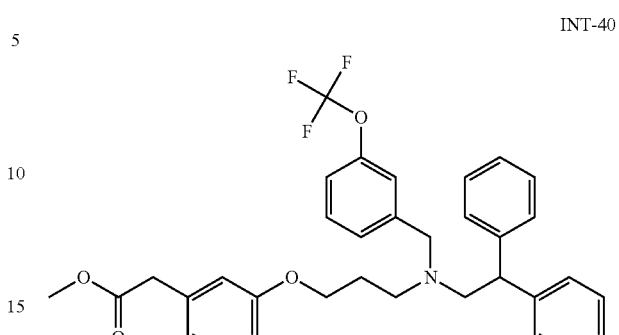

INT-39 (270 mg, 0.406 mmol), methyl 3-hydroxyphenyl acetate (202 mg, 1.22 mmol), and potassium carbonate (561 mg, 4.06 mmol) were suspended in dry ACN and heated to 90° C. for 18 h. The reaction mixture was poured into saturated sodium bicarbonate solution (75 mL) and extracted with EtOAc (3×75 mL). The organic layers were dried over magnesium sulfate, filtered, concentrated, under reduced pressure, and the residue was purified by silica gel chromatography (EtOAc/hexanes) to afford the desired coupled ester methyl 2-(3-{3-[(2,2-diphenylethyl)({[3-(trifluoromethoxy)phenyl]methyl})-amino]propoxy}phenyl)acetate (INT-40) as a glassy oil (165 mg, 67% yield).

Step 4: Synthesis of Compound 24

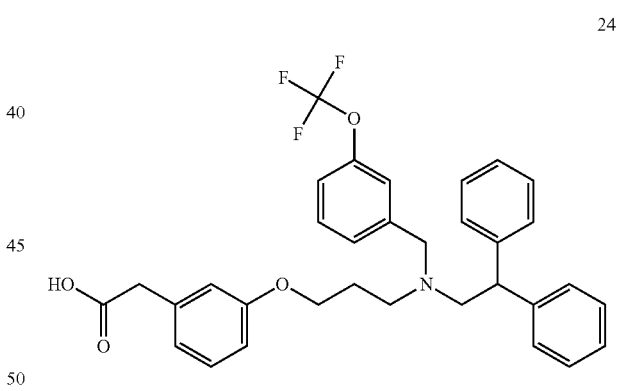

INT-40 (150 mg, 0.260 mmol) was dissolved in MeOH (30 mL) and then treated with 2.5 N sodium hydroxide (2.5 mL). Stirring at RT for 18 h resulted in completed conversion to the acid as judged by TLC. The solvent was removed under reduced pressure, the residue was dissolved in water (20 mL), the pH of the solution was adjusted to pH 2 with 1N hydrochloric acid, and the mixture was extracted with EtOAc (3×50 mL). The combined organic layers were dried over magnesium sulfate, filtered, concentrated under reduced pressure, and purified by prep-TLC (MeOH/DCM) to yield 2-(3-{3(2,2-diphenylethyl)({[3-(trifluoromethoxy)phenyl]methyl})amino]propoxy}phenyl)acetic acid (24) as a glassy oil (98 mg, 67% yield); ES(pos)MS m/z 564.23 (M+H$^+$).

Example 56: Synthesis of Compound 25

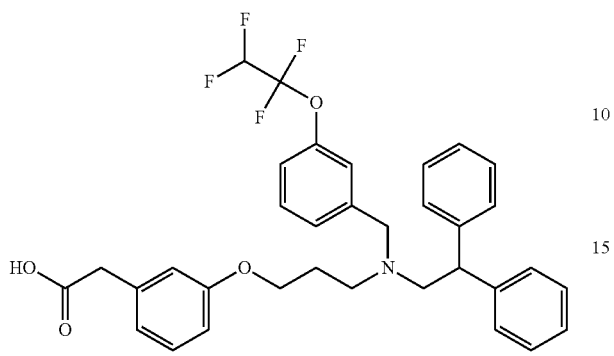

25

Using a similar protocol to make compound 24, 3-(trifluoromethoxy)benzaldehyde was replaced with 3-(1,1,2,2-tetrafluoroethoxy)benzaldehyde to make 2-(3-{3[(2,2-diphenylethyl)({[3-(1,1,2,2-tetrafluoroethoxy)phenyl]methyl})amino]propoxy}phenyl)acetic acid (25) as a glassy oil (115 mg, 56% yield); ES(pos)MS m/z 596.24 (M+H⁺).

Example 57: Synthesis of Compound 26

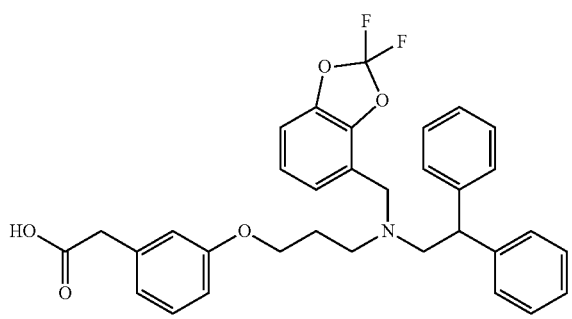

26

Using a similar protocol to make compound 24, 3-(trifluoromethoxy)benzaldehyde was replaced with 2,2-difluoro-2H-1,3-benzodioxole-4-carbaldehyde to make 2[3-(3-{[(2,2-difluoro-2H-1,3-benzodioxol-4-yl)methyl](2,2-diphenylethyl)amino}propoxy)phenyl]acetic acid (26) as a viscous oil (105 mg, 49% yield); ES(pos)MS m/z 560.23 (M+H⁺).

Example 58: Synthesis of Compound 27

Step 1: Synthesis of INT-41

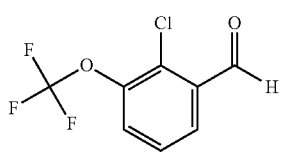

INT-41

To a solution of 1-chloro-2-(trifluoromethoxy)benzene (2.5 mmol) in THF (10 mL) is added 2.5 M n-butyllithium in hexanes (1.4 mmol) at −78° C. After 40 min, a solution of DMF (2.8 mmol) in THF (2.5 mL) is added and the mixture is stirred to room overnight. The reaction is quenched with water at 0° C., extracted with EtOAc (3×50 mL), the combined organic layers are dried over magnesium sulfate, filtered, and concentrated under reduced pressure. Purification by silica gel chromatography provides 2-chloro-3-(trifluoromethoxy)benzaldehyde (INT-41).

Step 2: Synthesis of Compound 27

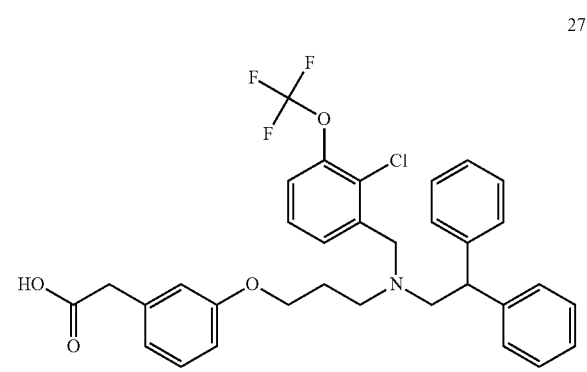 [SMILES: O=C(O)Cc1cccc(OCCCN(Cc2cccc(OC(F)(F)F)c2Cl)CC(c2ccccc2)c2ccccc2)c1]

27

Using a similar protocol to make compound 24, 3-(trifluoromethoxy)benzaldehyde is replaced with INT-41 to make 2-{3-[3-({[2-chloro-3-(trifluoromethoxy)phenyl]methyl}(2,2-diphenylethyl)amino)-propoxy]-phenyl}-acetic acid (27).

Example 59: Synthesis of Compound 28

Step 1: Synthesis of INT-42

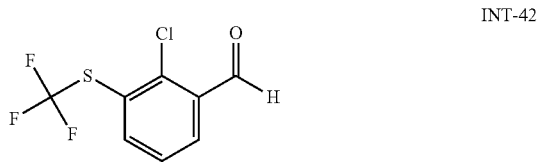 [SMILES: O=Cc1cccc(SC(F)(F)F)c1Cl]

INT-42

Using a similar protocol to make INT-41, 1-chloro-2-(trifluoromethoxy)benzene is replaced with 1-chloro-2-[(trifluoromethyl)sulfanyl]benzene to make 2-chloro-3-[(trifluoromethyl)sulfanyl]benzaldehyde (INT-42).

Step 2: Synthesis of Compound 28

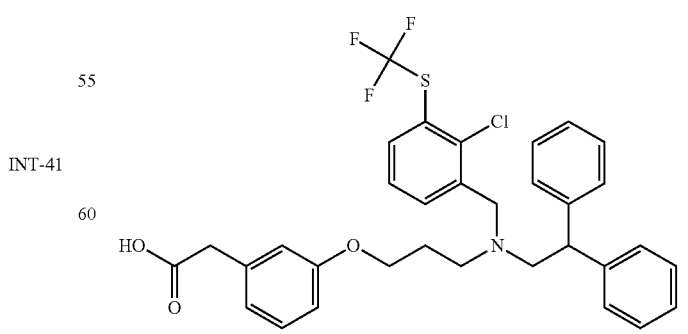

28

Using a similar protocol to make compound 24, 3-(trifluoromethoxy)benzaldehyde is replaced with INT-42 to make 2-(3-{3-[({2-chloro-3-[(trifluoromethyl)sulfanyl]phenyl}methyl)(2,2-diphenylethyl)amino]propoxy}-phenyl)-acetic acid (28).

Example 60: Synthesis of Compound 72

Step 1: Synthesis of INT-43

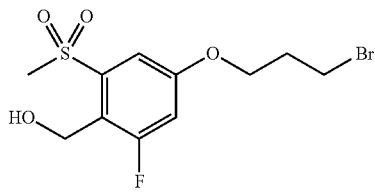

INT-43

Phenol INT-08 (50 mg, 0.227 mmol) and 1,3-dibromopropane (0.23 mL, 2.27 mmol) were dissolved in dry ACN (2 mL). Potassium carbonate (94 mg, 0.681 mmol) was added followed by heating at 40° C. overnight or until TLC showed complete consumption of the starting material. The reaction was diluted with EtOAc (100 mL), washed with water (2×100 mL), and the combined aqueous layers were re-extracted with EtOAc (100 mL). The second organic layer was washed with water (100 mL) and the combined organic layers were dried over magnesium sulfate, filtered, concentrated under reduced pressure, and purified by silica gel column chromatography (DCM/MeOH=50/1) to afford [4-(3-bromopropoxy)-2-fluoro-6-methanesulfonylphenyl]methanol (INT-43) as a white solid (55 mg, 71%).

Step 2: Synthesis of INT-44

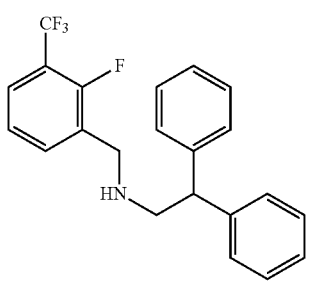

INT-44

2-2-Diphenylethylamine (500 mg, 2.6 mmol) and 2-fluoro-3-trifluoromethylbenzaldehyde (467 mg, 2.37 mmol) were dissolved in dry DCM (11 mL). Sodium triacetoxyborohydride (703 mg, 3.32 mmol) and acetic acid (0.136 mL, 2.37 mmol) were added and the reaction was stirred at RT overnight or until TLC showed consumption of the starting material. The reaction was diluted with EtOAc (100 mL), washed with half-saturated potassium carbonate solution (100 mL), water (100 mL), and the combined aqueous layers were re-extracted with EtOAc (100 mL). The second organic layer was washed with water (100 mL) and the combined organic layers were dried over magnesium sulfate, filtered, concentrated under reduced pressure, and purified by silica gel column chromatography (EtOAc/hexanes=1/3) to afford (2,2-diphenylethyl)({[2-fluoro-3-(trifluoromethyl)phenyl]methyl})amine (INT-44) as a yellow viscous oil (736 mg, 83%).

Step 3: Synthesis of 72

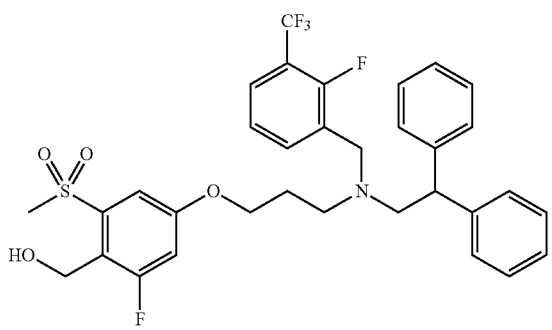

72

Secondary amine INT-44 (98 mg, 0.264 mmol) and bromide INT-43 (60 mg, 0.176 mmol) were dissolved in dry ACN (2 mL). Potassium carbonate (73 mg, 0.53 mmol) was added and the reaction was heated at 90° C. overnight. The mixture was diluted with EtOAc (100 mL), washed with water (2×100 mL), and the combined aqueous layers were re-extracted with EtOAc (100 mL). The second organic layer was washed with water (100 mL) and the combined organic layers were dried over magnesium sulfate, filtered, concentrated under reduced pressure, and purified by silica gel preparative TLC (2000 micron plate, EtOAc/hexanes=1/2 then a second purification using DCM/MeOH 50/1) to afford (4-{3-[(2,2-diphenylethyl)({[2-fluoro-3-(trifluoromethyl)phenyl]methyl})amino]propoxy}-2-fluoro-6-methanesulfonylphenyl)methanol (72) as a slightly yellow foam (59 mg, 53%). ES(pos)MS m/z 634.21 (M+H$^+$).

Example 61: Synthesis of Compound 73

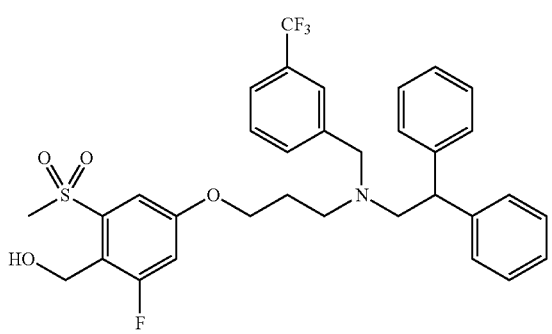

73

Synthesis of 73 followed the protocol outlined for compound 72 substituting 3-trifluromethylbenzaldehyde for 2-fluoro-3-trifluromethylbenzaldehyde. The reaction sequence yielded (4-{3-[(2,2-diphenylethyl)({[3-(trifluoromethyl)phenyl]methyl})amino]propoxy}-2-fluoro-6-methanesulfonylphenyl)methanol (73) as a viscous oil (65 mg, 60%). ES(pos)MS m/z 616.21 (M+H$^+$).

Example 62: Synthesis of Compound 74

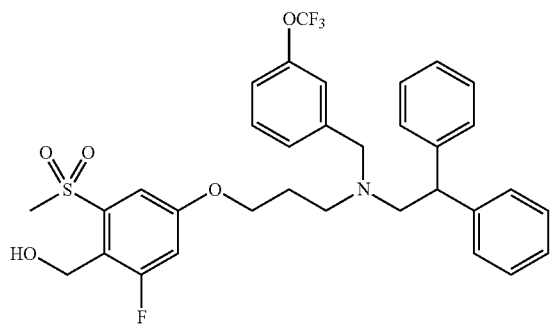

Synthesis of compound 74 followed the protocol outlined for compound 72 substituting 3-trifluromethoxybenzaldehyde for 2-fluoro-3-trifluromethylbenzaldehyde. The reaction sequence yielded (4-{3-[(2,2-diphenylethyl)({[3-(trifluoromethoxy)phenyl]methyl})amino]propoxy}-2-fluoro-6-methanesulfonylphenyl)methanol (74) as a viscous oil (70 mg, 63%). ES(pos)MS m/z 632.21 (M+H$^+$).

Example 63: Synthesis of Compound 75

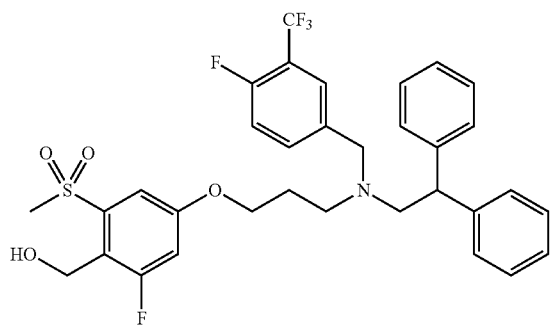

Synthesis of compound 75 followed the protocol outlined for compound 72 substituting 4-fluoro-3-trifluoromethylbenzaldehyde for 2-fluoro-3-trifluoromethylbenzaldehyde. The reaction sequence yielded (4-{3-[(2,2-diphenylethyl)({[4-fluoro-3-(trifluoromethyl)phenyl]methyl})amino]propoxy}-2-fluoro-6-methanesulfonylphenyl)methanol (75) as a viscous oil (68 mg, 61%). ES(pos)MS m/z 634.21 (M+H$^+$).

Example 64: Synthesis of Compound 29

Step 1: Synthesis of INT-45

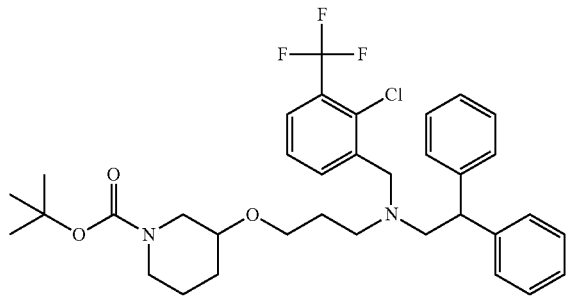

To a solution of tert-butyl 3-hydroxypiperidine-1-carboxylate (0.24 g, 1.17 mmol) in DMF (3 mL) was added sodium hydride (0.05 mg, 1.17 mg) in portions at 0° C. over 30 min. A solution of bromide INT-01 (0.5 g, 0.98 mmol) was added and the solution was stirred at RT for 3 h. The reaction mixture was quenched with ice and extracted into diethyl ether (2×10 mL). The organic layer was washed with brine, dried over sodium sulfate, filtered, and concentrated under reduced pressure. The residue was purified by silica gel chromatography to yield tert-butyl 3-[3-({[2-chloro-3-(trifluoromethyl)phenyl]methyl}(2,2-diphenylethyl)amino)propoxy]piperidine-1-carboxylate (INT-45) as a colorless liquid (0.3 g, 55% yield); TLC=30% EtOAc/hexanes (0.4 Rf).

Step 2: Synthesis of INT-46

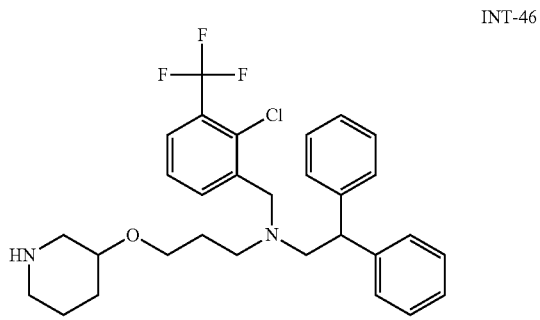 [SMILES: FC(F)(F)c1cccc(CN(CCCOC2CCCNC2)CC(c2ccccc2)c2ccccc2)c1Cl]

To a solution of INT-45 (0.25 g, 0.39 mmol) in DCM (2.5 mL) was added TFA (0.045 mL, 0.59 mmol) and the solution was stirred at RT for 3 h. The reaction mixture was concentrated under reduced pressure. The residue was re-dissolved in fresh DCM (5 mL) and re-concentrated under reduced pressure. The process was repeated 3 times and the residue {[2-chloro-3-(trifluoromethyl)phenyl]methyl}(2,2-diphenylethyl)[3-(piperidin-3-yloxy)propyl]amine (INT-46) was used in the next step without further purification.

Step 3: Synthesis of Compound 29

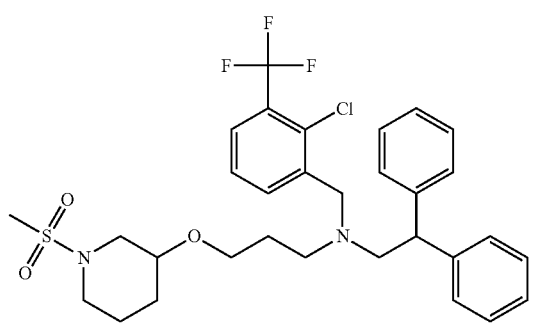

To amine INT-46 (0.2 g, 0.38 mmol) in DCM (3 mL) was added triethylamine (79 µL, 0.56 mmol) and methanesulfonyl chloride (28 µL, 0.38 mmol) at 0° C. After 2 h stirring at RT, the reaction mixture was diluted with DCM (5 mL), washed with saturated sodium bicarbonate, brine, dried over sodium sulfate, filtered, and concentrated under reduced pressure. The residue was purified by preparative TLC to yield {[2-chloro-3-(trifluoromethyl)phenyl]methyl}(2,2-diphenylethyl){3-[(1-methanesulfonylpiperidin-3-yl)oxy]propyl}amine (29) as thick syrup (0.16 g, 72% yield); MS (ESI) 609.1 (M+H$^+$).

Example 65: Synthesis of Compound 30

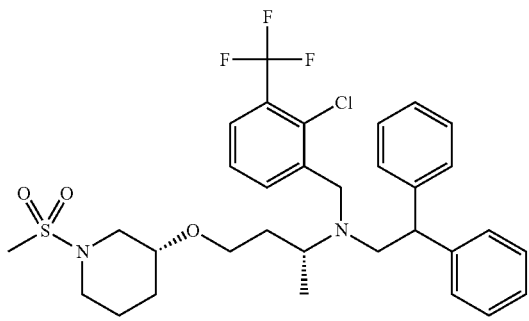

Using a similar protocol to make compound 29, tert-butyl 3-hydroxypiperidine-1-carboxylate was replaced with (R)-tert-butyl 3-hydroxypiperidine-1-carboxylate and INT-01 was replaced with INT-25 to make {[2-chloro-3-(trifluoromethyl)phenyl]methyl}(2,2-diphenylethyl)[(2R)-4-{[(3R)-1-methanesulfonylpiperidin-3-yl]oxy}butan-2-yl]amine (30) as a glassy oil (56 mg, 48% yield); MS (ESI) 623.23 (M+H$^+$).

Example 66: Synthesis of Compound 31

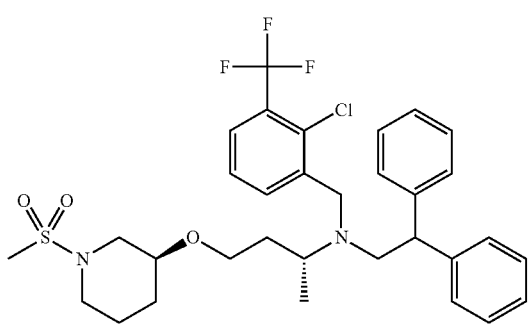

Using a similar protocol to make compound 29, tert-butyl 3-hydroxypiperidine-1-carboxylate was replaced with (S)-tert-butyl 3-hydroxypiperidine-1-carboxylate and INT-01 was replaced with INT-25 to make {[2-chloro-3-(trifluoromethyl)phenyl]methyl}(2,2-diphenylethyl)[(2R)-4-{[(3S)-1-methanesulfonylpiperidin-3-yl]oxy}butan-2-yl]amine (31) as a glassy oil (63 mg, 51% yield); MS (ESI) 623.22 (M+H$^+$).

Example 67: Synthesis of Compound 32

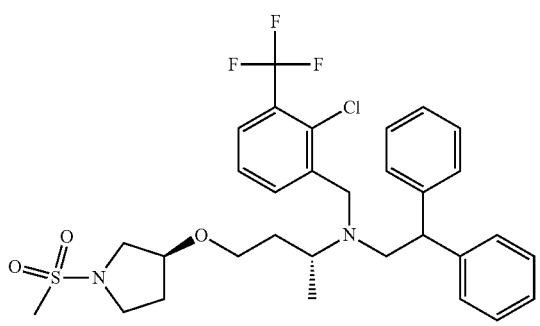

Using a similar protocol to make compound 29, tert-butyl 3-hydroxypiperidine-1-carboxylate is replaced with (3S)-1-methanesulfonylpyrrolidin-3-ol and INT-01 is replaced with INT-25 to make {[2-chloro-3-(trifluoromethyl)phenyl]methyl}(2,2-diphenylethyl)[(2R)-4-{[(3S)-1-methanesulfonylpyrrolidin-3-yl]oxy}butan-2-yl]amine (32).

Example 68: Synthesis of Compound 33

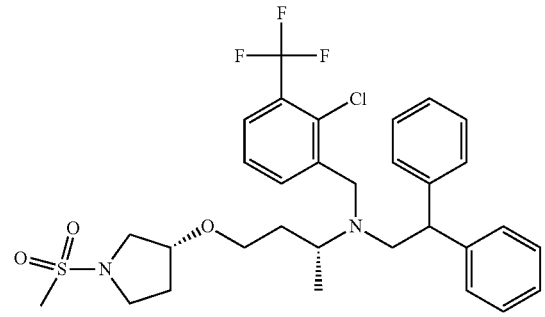

Using a similar protocol to make compound 29, tert-butyl 3-hydroxypiperidine-1-carboxylate is replaced with (3R)-1-methanesulfonylpyrrolidin-3-ol and INT-01 is replaced with INT-25 to make {[2-chloro-3-(trifluoromethyl)phenyl]methyl}(2,2-diphenylethyl)[(2R)-4-{[(3R)-1-methanesulfonylpyrrolidin-3-yl]oxy}butan-2-yl]amine (33).

Example 69: Synthesis of Compound 34

Step 1: Synthesis of INT-47

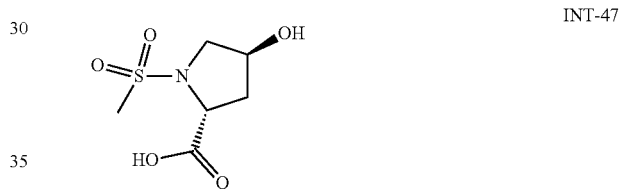

(2R,4S)-4-Hydroxypyrrolidine-2-carboxylic acid (0.5 mmol) is dissolved in DCM (2.5 mL) and triethylamine (1.0 mmol) is added followed by methanesulfonyl chloride (0.5 mmol). After stirring for 2 h at RT the reaction is poured into 1N aqueous hydrochloric acid (25 mL), and extracted with EtOAc (3×25 mL). The combined organic layers are washed with brine, dried over sodium sulfate, filtered, concentrated under reduced pressure to afford crude (2R,4S)-4-hydroxy-1-methanesulfonylpyrrolidine-2-carboxylic acid (INT-47) which is used in the next reaction without further purification.

Step 2: Synthesis of Compound 34

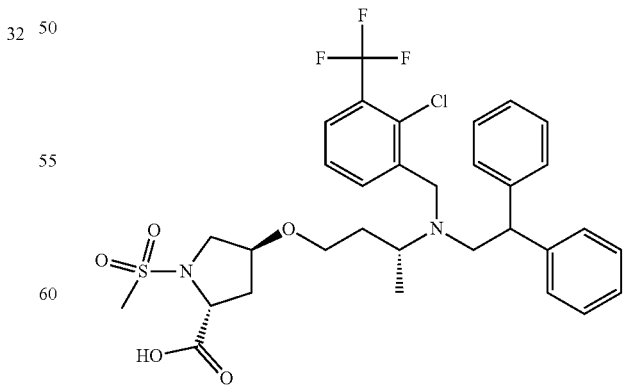

To a solution of INT-47 (0.25 mmol) in DMF (3 mL) is added sodium hydride (0.5 mmol) in portions at 0° C. over 30 min. A solution of INT-25 (0.25 mmol) is added and the solution is stirred at RT for 3 h. The reaction mixture is quenched with ice, the pH is adjusted to pH ~3 using 1N aqueous hydrochloric acid, and the mixture is extracted into EtOAc (2×25 mL). The combined organic layers are washed with brine, dried over sodium sulfate, filtered, and concentrated under reduced pressure. The residue is purified by silica gel chromatography to yield (2R,4S)-4-[3R)-3-({[2-chloro-3-(trifluoromethyl)phenyl]methyl}-(2,2-diphenylethyl)amino)butoxy]-1-methanesulfonylpyrrolidine-2-carboxylic acid (34).

Example 70: Synthesis of Compound 36

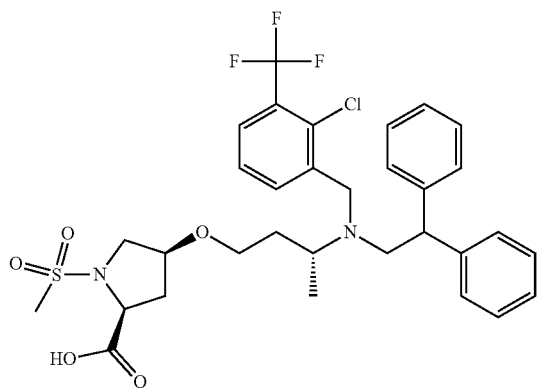

Using a similar protocol to make compound 34, (2R,4S)-4-hydroxypyrrolidine-2-carboxylic acid is replaced with (2S,4S)-4-hydroxypyrrolidine-2-carboxylic acid to make (2S,4S)-4-[3R)-3-({[2-chloro-3-(trifluoromethyl)phenyl]methyl}(2,2-diphenylethyl)amino)butoxy]-1-methanesulfonylpyrrolidine-2-carboxylic acid (36).

Example 71: Synthesis of Compound 38

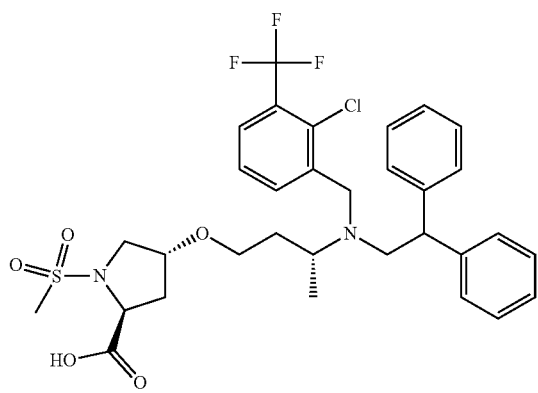

Using a similar protocol to make compound 34, (2R,4S)-4-hydroxypyrrolidine-2-carboxylic acid is replaced with (2S,4R)-4-hydroxypyrrolidine-2-carboxylic acid to make (2S,4R)-4-[(3R)-3-({[2-chloro-3-(trifluoromethyl)phenyl]methyl}(2,2-diphenylethyl)amino)-butoxy]-1-methanesulfonylpyrrolidine-2-carboxylic acid (38).

Example 72: Synthesis of Compound 40

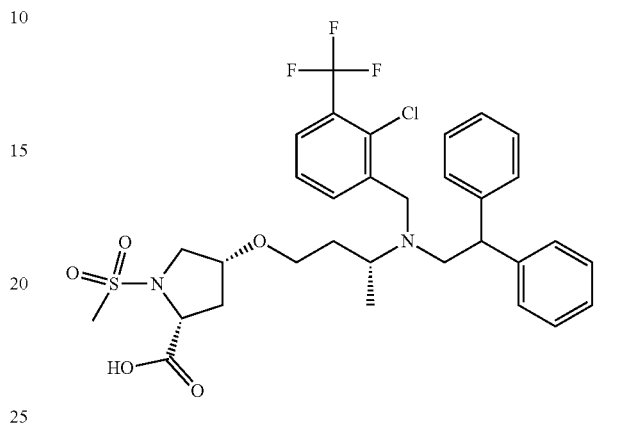

Using a similar protocol to make compound 34, (2R,4S)-4-hydroxypyrrolidine-2-carboxylic acid is replaced with (2R,4R)-4-hydroxypyrrolidine-2-carboxylic acid to make (2R,4R)-4-[(3R)-3-({[2-chloro-3-(trifluoromethyl)phenyl]methyl}(2,2-diphenylethyl)amino)-butoxy]-1-methanesulfonylpyrrolidine-2-carboxylic acid (40).

Example 73: Synthesis of Compound 61

Step 1: Synthesis of INT-48

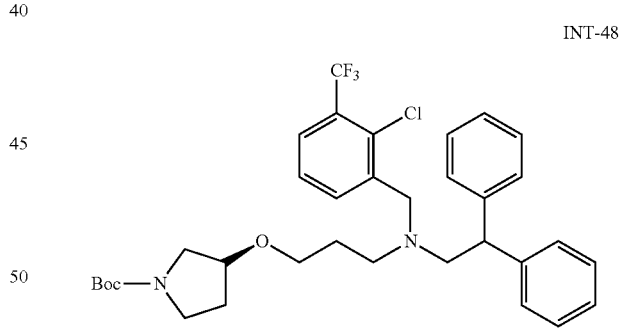

Bromide INT-01 (200 mg, 0.395 mmol) and (S)—N-Boc-3-pyrrolidinol (147 mg, 0.783 mmol) were dissolved in dry DMF (3 mL). Sodium hydride (60% in mineral oil, 28.2 mg, 0.706 mmol) was added and the reaction was stirred at 45° C. overnight or until TLC showed the bromide was mostly consumed. The reaction was quenched by addition of saturated sodium bicarbonate solution, extracted with 1:1 EtOAc/hexanes (3×100 mL), dried over magnesium sulfate, the solvent was concentrated under reduced pressure, and the material was purified by silica gel column chromatography (EtOAc/hexanes=1/5 to 1/3) to afford INT-48 as a slightly yellow oil (206 mg, 52%).

Step 2: Synthesis of INT-49

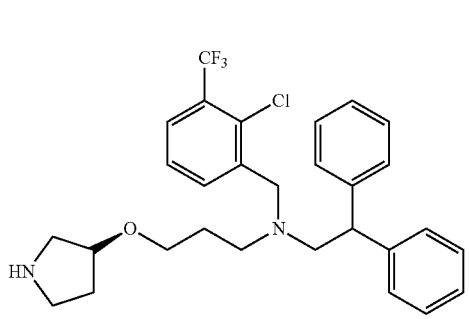
INT-49

Protected amine INT-48 (127 mg, 0.206 mmol) was dissolved in dry DCM (10 mL) and treated with trifluoroacetic acid (0.80 mL). The mixture was stirred at RT for 3 h or until TLC confirmed full removal of the protecting group. The reaction was carefully quenched with saturated potassium carbonate solution (100 mL), extracted with DCM (3×100 mL), dried over magnesium sulfate, and solvent was concentrated under reduced pressure to afford the crude amine INT-49 that was used in the next step without further purification.

Step 3: Synthesis of 61

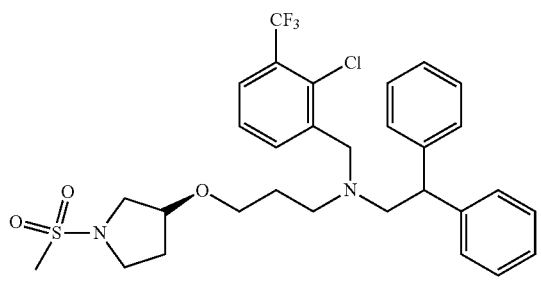
61

INT-49 was dissolved in dry DCM (5 mL), and treated with triethylamine (0.142 mL, 1.01 mmol) and methanesulfonyl chloride (0.039 mL, 0.5 mmol). The reaction was stirred at RT overnight or until TLC showed complete consumption of the starting material. The mixture was diluted with EtOAc (100 mL), washed with 10:1 water/saturated sodium bicarbonate solution (100 mL) and water (100 mL), and the combined aqueous layers were re-extracted with EtOAc (100 mL). The second organic layer was washed with water (100 mL) and the combined organic layers were dried over magnesium sulfate, filtered, concentrated under reduced pressure, and purified by silica gel preparative TLC (2×2000 micron plates, EtOAc/hexanes=2/3) to afford {[2-chloro-3-(trifluoromethyl)phenyl]methyl}(2,2-diphenylethyl)(3-{[(3S)-1-methanesulfonylpyrrolidin-3-yl]oxy}propyl)amine (61) as a slightly yellow foam (86 mg, 70% over two steps). ES(pos)MS m/z 595.20 (M+H⁺).

Example 74: Synthesis of Compound 62

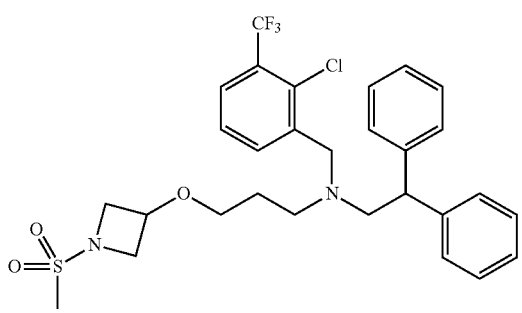
62

Synthesis of 62 followed the protocol outlined for compound 61 substituting 1-N-Boc-3-hydroxyazetidine for (S)—N-Boc-3-pyrrolidinol. The reaction sequence yielded {[2-chloro-3-(trifluoromethyl)phenyl]methyl} (2,2-diphenylethyl){3-[(1-methanesulfonylazetidin-3-yl)oxy]propyl}amine (62) as a viscous oil (215 mg, 63% over three steps). ES(pos)MS m/z 581.18 (M+H⁺).

Example 75: Synthesis of Compound 63

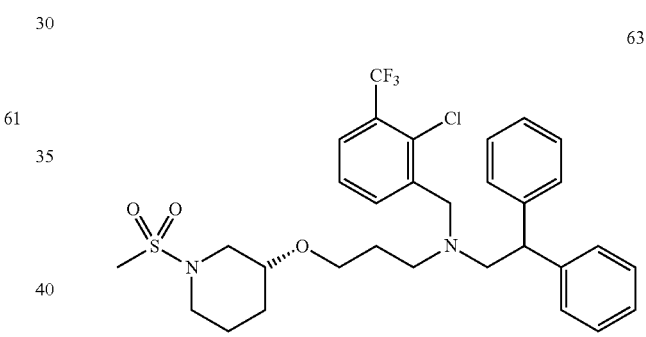
63

Synthesis of compound 63 followed the protocol outlined for compound 61 substituting (R)—N-Boc-3-piperidinol for (S)—N-Boc-3-pyrrolidinol. The reaction sequence yielded {[2-chloro-3-(trifluoromethyl)phenyl]methyl}(2,2-diphenylethyl)(3-{[(3R)-1-methanesulfonylpiperidin-3-yl]oxy}propyl)amine (63) as a viscous oil (105 mg, 33% over three steps). ES(pos)MS m/z 609.21 (M+H⁺).

Example 76: Synthesis of Compound 66

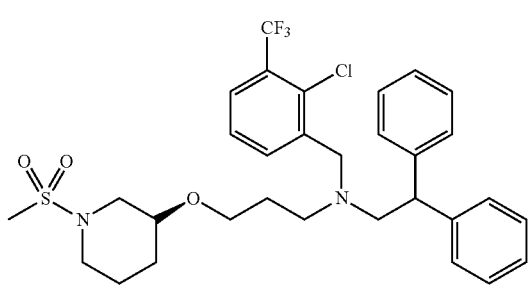
66

Synthesis of compound 66 followed the protocol outlined for compound 61 substituting (S)—N-Boc-3-piperidinol for (S)—N-Boc-3-pyrrolidinol. The reaction sequence yielded {[2-chloro-3-(trifluoromethyl)phenyl]methyl}(2,2-diphenylethyl)(3-{[(3S)-1-methanesulfonylpiperidin-3-yl]oxy}propyl)amine (66) as a viscous oil (91 mg, 29% over three steps). ES(pos)MS m/z 609.21 (M+H⁺).

Example 77: Synthesis of Compound 67

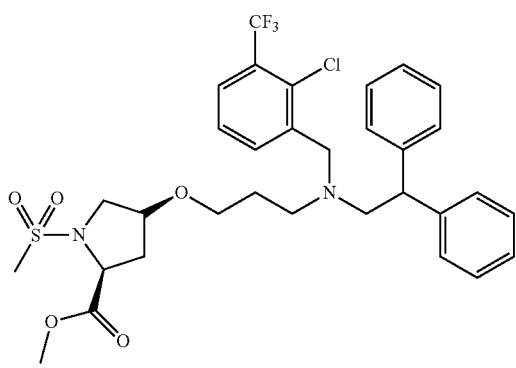

67

Synthesis of compound 67 followed the protocol outlined for compound 61 substituting N—Boc-cis-4-hydroxy-L-proline for (S)—N-Boc-3-pyrrolidinol. The reaction sequence yielded (2S,4S)-4-[3-({[2-chloro-3-(trifluoromethyl)phenyl]methyl}(2,2-diphenylethyl)amino)propoxy]-1-methanesulfonylpyrrolidine-2-carboxylic acid (67) as a viscous oil (163 mg, 26% over three steps). ES(pos)MS m/z 653.17 (M+H⁺).

Example 78: Synthesis of Compound 42

Step 1: Synthesis of INT-50

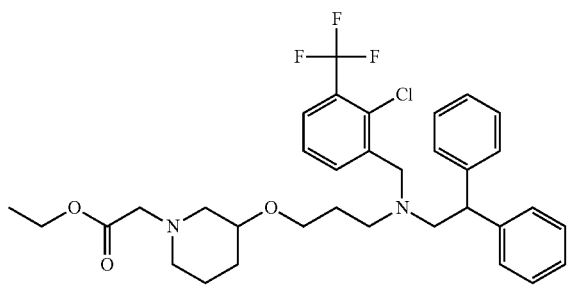

INT-50

To a solution of INT-46 (0.2 g, 0.37 mmol) in DCM (5 mL) was added DIPEA (96 µL, 0.55 mmol) and ethyl bromoacetate (49 µL, 0.44 mmol) at 0° C. The reaction was stirred at RT for 4 h, concentrated under reduced pressure, and purified by silica gel chromatography to yield ethyl 2-{3-[3-({[2-chloro-3-(trifluoromethyl)phenyl]methyl}(2,2-diphenylethyl)amino)propoxy]-piperidin-1-yl}acetate (INT-50) as syrup (0.19 g, 83% yield); TLC=30% EtOAc/hexanes (0.6 Rf).

Step 2: Synthesis of Compound 42

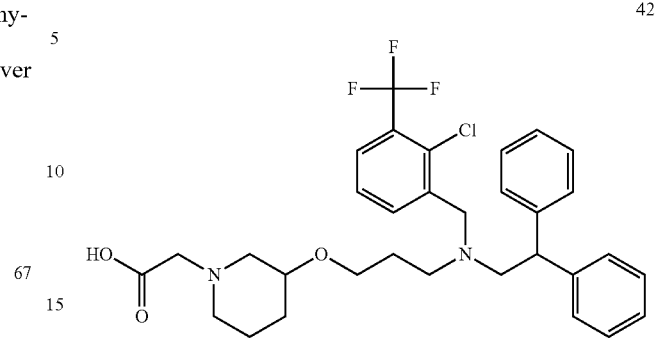

42

INT-50 (0.15 g, 0.24 mmol) was dissolved in 1:1 MeOH and THF (3 mL) and treated with 2N sodium hydroxide (0.5 mL) at 0° C. The mixture was stirred at RT overnight and then concentration under reduced pressure. The residue was dissolved in DCM (5 mL) and water (5 mL), carefully neutralized with 1N hydrochloric acid to pH ~7, transferred into a separating funnel, and the organic layer was separated. The water layer was re-extracted with DCM (2×5 mL). The combined DCM layers were washed with brine, dried over sodium sulfate, filtered, and concentrated under reduced pressure. The residue was purified by preparative TLC to yield 2-{3-[3-({[2-chloro-3-(trifluoromethyl)phenyl]methyl}-(2,2-diphenylethyl)amino)propoxy]piperidin-1-yl}acetic acid (42) as a syrup (0.12 g, 86% yield); TLC=5% MeOH/DCM (0.3 Rf); MS (ESI) 589.1 (M+H⁺).

Example 79: Synthesis of Compound 43

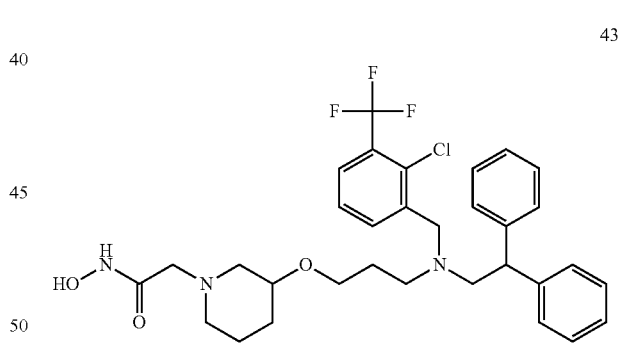

43

To a solution of hydroxylamine hydrochloride (0.05 g, 0.68 mmol) in MeOH (2.5 mL) is added potassium hydroxide (0.04 g, 0.68 mmol) in an ice-bath for 1 h. The salts are filtered off and the filtrate containing free hydroxylamine in MeOH is collected. INT-50 (0.2 mmol) in THF (2 mL) is added to the above solution and stirred at RT for 3 h. The reaction is concentrated under reduced pressure, the residue is diluted with water (10 mL) and acidified with 2N aqueous hydrochloric acid to pH ~4. The mixture is extracted with EtOAc (2×10 mL). The organic layers are separated, washed with brine, dried over sodium sulfate, filtered, and concentrated under reduced pressure. The residue is purified by preparative TLC to yield 2-{3-[3-({[2-chloro-3-(trifluoromethyl)phenyl]methyl}(2,2-diphenylethyl)amino)propoxy]-piperidin-1-yl}-N-hydroxyacetamide (43).

Example 80: Synthesis of Compound 44

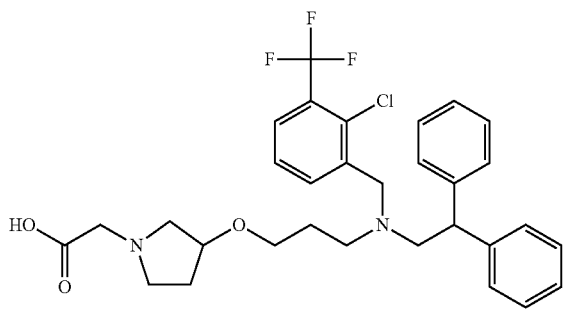

44

Using a similar protocol to make compound 42, tert-butyl 3-hydroxypiperidine-1-carboxylate is replaced with tert-butyl 3-hydroxypyrrolidine-1-carboxylate to make 2-{3[3-({[2-chloro-3-(trifluoromethyl)-phenyl]methyl}(2,2-diphenylethyl)amino)propoxy]pyrrolidin-1-yl}acetic acid (44).

Example 81: Synthesis of Compound 45

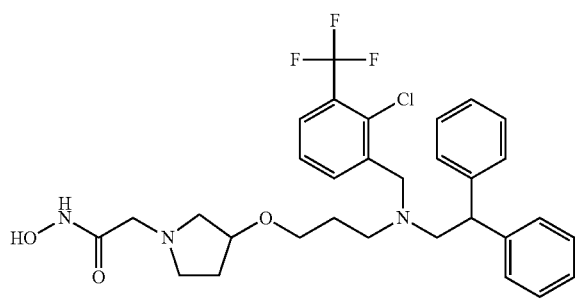

45

Using a similar protocol to make compound 43, reaction of compound 44 with hydroxylamine affords 2-{3-[3-({[2-chloro-3-(trifluoromethyl)phenyl]methyl}(2,2-diphenylethyl)amino)propoxy]pyrrolidin-1-yl}-N-hydroxyacetamide (45).

Example 82: Synthesis of Compound 77

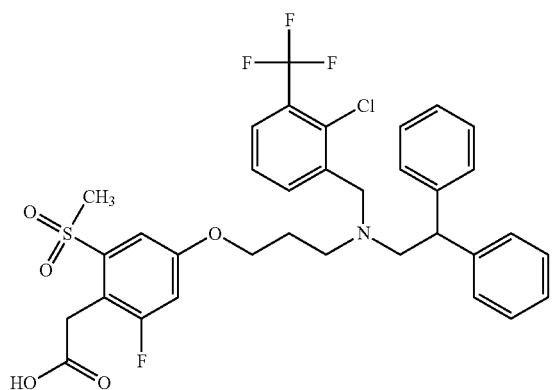

77

INT-31 (0.15 mmol) is dissolved in THF (3 mL) and treated with 6N hydrochloric acid (2 mL). The reaction is stirred for 3.5 h at RT, or until TLC showed complete consumption of starting material. The reaction is carefully quenched with saturated potassium carbonate solution to adjust the pH to 8-9. The mixture is diluted with EtOAc (50 mL), washed with water (2×50 mL), and the combined aqueous layers are re-extracted with EtOAc (50 mL). The second organic layer is washed with water (50 mL) and the combined organic layers are dried over magnesium sulfate, filtered, and concentrated under reduced pressure to afford the crude aldehyde which is oxidized directly to the carboxylic acid without further purification and using known literature protocols (e.g. Org. Lett. 2003, 5, 1031-1034).

The crude aldehyde (0.15 mmol) is dissolved in DMF (3 mL) and treated with methanesulfonic acid (0.15 mmol) and Oxone® (0.15 mmol). The reaction is stirred for 3 h at RT, the mixture is diluted with EtOAc (50 mL), washed with water (2×50 mL), and the combined aqueous layers are extracted with EtOAc (50 mL). The second organic layer is washed with water (50 mL) and the combined organic layers are dried over magnesium sulfate, filtered, concentrated under reduced pressure, and purified by silica gel column chromatography to afford 2-{4-[3-({[2-chloro-3-(trifluoromethyl)phenyl]methyl}(2,2-diphenylethyl)amino)propoxy]-2-fluoro-6-methanesulfonylphenyl}acetic acid (77).

Example 83: Selected LXR Agonists of the Invention

Exemplary LXR agonists of the invention that are synthesized by combining intermediates and methods described herein are listed in Table 4.

To make certain fluoridated compounds, starting materials for described syntheses are replaced as follows: 2-(phenyl)propan-1-amine is replaced by 2-(4-fluorophenyl)propan-1-amine [456-01-9]; phenethylamine is replaced with 2-(4-fluorophenyl)ethylamine [1583-88-6]; benzylamine is replaced with 4-fluorobenzylamine [140-75-0]; 2-phenyl-2-methylpropan-1-amine is replaced with 2-(4-fluorophenyl)-2-methylpropan-1-amine [40377-35-3]; and phenethylamine is replaced 2,2-difluoro-2-(4-fluorophenyl)ethan-1-amine which is made by standard lithium aluminum hydride reduction of 2,2-difluoro-2-(4-fluorophenyl)acetamide (Enamine #EN300-96772).

To make certain desfluoridated compounds, INT-08 is replaced by INT-67 which is made from 4-bromo-2-(methylsulfonyl)benzaldehyde [849035-77-4] by standard sodium borohydride reduction and following a similar sequence of steps described for INT-08.

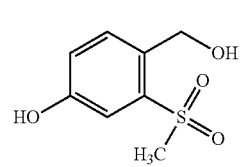

INT-67

TABLE 4

Additional LXR agonists of the Invention.

| # | Name |
|---|------|
| 98 | (2-fluoro-6-methanesulfonyl-4-{3-[(2-methyl-2-phenylpropyl)({[3-(trifluoromethyl)phenyl]methyl})amino]propoxy}phenyl)methanol |
| 99 | (2-fluoro-6-methanesulfonyl-4-{3-[(2-phenylethyl)({[3-(trifluoromethyl)phenyl]methyl})amino]propoxy}phenyl)methanol |
| 100 | (2-fluoro-6-methanesulfonyl-4-{3-[(2-phenylpropyl)({[3-(trifluoromethyl)phenyl]methyl})amino]propoxy}phenyl)methanol |
| 101 | (4-{3-[benzyl({[2-fluoro-3-(trifluoromethyl)phenyl]methyl})amino]propoxy}-2-fluoro-6-methanesulfonylphenyl)methanol |
| 102 | (4-{3-[benzyl({[3-(trifluoromethyl)phenyl]methyl})amino]propoxy}-2-fluoro-6-methanesulfonylphenyl)methanol |
| 103 | [2-fluoro-4-(3-{[(4-fluorophenyl)methyl]({[3-(trifluoromethyl)phenyl]methyl})amino}propoxy)-6-methanesulfonylphenyl]methanol |
| 104 | [2-fluoro-4-(3-{[2-(4-fluorophenyl)-2-methylpropyl]({[3-(trifluoromethyl)phenyl]methyl})amino}propoxy)-6-methanesulfonylphenyl]methanol |
| 105 | [2-fluoro-4-(3-{[2-(4-fluorophenyl)ethyl]({[3-(trifluoromethyl)phenyl]methyl})amino}propoxy)-6-methanesulfonylphenyl]methanol |
| 106 | [2-fluoro-4-(3-{[2-(4-fluorophenyl)propyl]({[3-(trifluoromethyl)phenyl]methyl})amino}propoxy)-6-methanesulfonylphenyl]methanol |
| 107 | {4-[3-({[2-chloro-3-(trifluoromethyl)phenyl]methyl}[2,2-difluoro-2-(4-fluorophenyl)ethyl]amino)propoxy]-2-fluoro-6-methanesulfonylphenyl}methanol |
| 108 | [4-(3-{[2,2-difluoro-2-(4-fluorophenyl)ethyl]({[2-fluoro-3-(trifluoromethyl)phenyl]methyl})amino}propoxy)-2-fluoro-6-methanesulfonylphenyl]methanol |
| 109 | [4-(3-{[2,2-difluoro-2-(4-fluoropheny)ethyl]({[3-(trifluoromethyl)phenyl]methyl})amino}propoxy)-2-fluoro-6-methanesulfonylphenyl]methanol |
| 110 | {4-[3-({[2-chloro-3-(trifluoromethyl)phenyl]methyl}[(4-fluorophenyl)methyl]amino)propoxy]-2-fluoro-6-methanesulfonylphenyl}methanol |
| 111 | {4-[3-({[2-chloro-3-(trifluoromethyl)phenyl]methyl}[2-(4-fluorophenyl)-2-methylpropyl]amino)propoxy]-2-fluoro-6-methanesulfonylphenyl}methanol |
| 112 | {4-[3-({[2-chloro-3-(trifluoromethyl)phenyl]methyl}[2-(4-fluoropheny)ethyl]amino)propoxy]-2-fluoro-6-methanesulfonylphenyl}methanol |
| 113 | {4-[3-({[2-chloro-3-(trifluoromethyl)phenyl]methyl}[2-(4-fluorophenyl)propyl]amino)propoxy]-2-fluoro-6-methanesulfonylphenyl}methanol |
| 114 | {2-fluoro-4-[3-({[2-fluoro-3-(trifluoromethyl)phenyl]methyl}(2-methyl-2-phenylpropyl)amino)propoxy]-6-methanesulfonylphenyl}methanol |
| 115 | {2-fluoro-4-[3-({[2-fluoro-3-(trifluoromethyl)phenyl]methyl}(2-phenylethyl)amino)propoxy]-6-methanesulfonylphenyl}methanol |
| 116 | {2-fluoro-4-[3-({[2-fluoro-3-(trifluoromethyl)phenyl]methyl}(2-phenylpropyl)amino)propoxy]-6-methanesulfonylphenyl}methanol |
| 117 | {2-fluoro-4-[3-({[2-fluoro-3-(trifluoromethyl)phenyl]methyl}[(4-fluorophenyl)methyl]amino)propoxy]-6-methanesulfonylphenyl}methanol |
| 118 | {2-fluoro-4-[3-({[2-fluoro-3-(trifluoromethyl)phenyl]methyl}[2-(4-fluorophenyl)-2-methylpropyl]amino)propoxy]-6-methanesulfonylphenyl}methanol |
| 119 | {2-fluoro-4-[3-({[2-fluoro-3-(trifluoromethyl)phenyl]methyl}[2-(4-fluoropheny)ethyl]amino)propoxy]-6-methanesulfonylphenyl}methanol |
| 120 | {2-fluoro-4-[3-({[2-fluoro-3-(trifluoromethyl)phenyl]methyl}[2-(4-fluorophenyl)propyl]amino)propoxy]-6-methanesulfonylphenyl}methanol |
| 121 | (2-methanesulfonyl-4-{3-[(2-methyl-2-phenylpropyl)({[3-(trifluoromethyl)phenyl]methyl})amino]propoxy}phenyl)methanol |
| 122 | (2-methanesulfonyl-4-{3-[(2-phenylethyl)({[3-(trifluoromethyl)phenyl]methyl})amino]propoxy}phenyl)methanol |
| 123 | (2-methanesulfonyl-4-{3-[(2-phenylpropyl)({[3-(trifluoromethyl)phenyl]methyl})amino]propoxy}phenyl)methanol |
| 124 | {4-[3-({[2-chloro-3-(trifluoromethyl)phenyl]methyl}(2,2-diphenylethyl)amino)propoxy]-2-methanesulfonylphenyl}methanol |
| 125 | (4-{3-[(2,2-diphenylethyl)({[2-fluoro-3-(trifluoromethyl)phenyl]methyl})amino]propoxy}-2-methanesulfonylphenyl)methanol |
| 126 | (4-{3-[(2,2-diphenylethyl)({[3-(trifluoromethyl)phenyl]methyl})amino]propoxy}-2-methanesulfonylphenyl)methanol |
| 127 | (4-{3-[benzyl({[2-chloro-3-(trifluoromethyl)phenyl]methyl})amino]propoxy}-2-methanesulfonylphenyl)methanol |
| 128 | (4-{3-[benzyl({[2-fluoro-3-(trifluoromethyl)phenyl]methyl})amino]propoxy}-2-methanesulfonylphenyl)methanol |
| 129 | (4-{3-[benzyl({[3-(trifluoromethyl)phenyl]methyl})amino]propoxy}-2-methanesulfonylphenyl)methanol |
| 130 | [4-(3-{[(4-fluorophenyl)methyl]({[3-(trifluoromethyl)phenyl]methyl})amino}propoxy)-2-methanesulfonylphenyl]methanol |
| 131 | [4-(3-{[2-(4-fluorophenyl)-2-methylpropyl]({[3-(trifluoromethyl)phenyl]methyl})amino}propoxy)-2-methanesulfonylphenyl]methanol |
| 132 | [4-(3-{[2-(4-fluorophenyl)ethyl]({[3-(trifluoromethyl)phenyl]methyl})amino}propoxy)-2-methanesulfonylphenyl]methanol |
| 133 | [4-(3-{[2-(4-fluorophenyl)propyl]({[3-(trifluoromethyl)phenyl]methyl})amino}propoxy)-2-methanesulfonylphenyl]methanol |
| 134 | {4-[3-({[2-chloro-3-(trifluoromethyl)phenyl]methyl}[2,2-difluoro-2-(4-fluorophenyl)ethyl]amino)propoxy]-2-methanesulfonylphenyl}methanol |

TABLE 4-continued

Additional LXR agonists of the Invention.

| # | Name |
|---|------|
| 135 | [4-(3-{[2,2-difluoro-2-(4-fluoropheny)ethyl]({[2-fluoro-3-(trifluoromethyl)phenyl]methyl})amino}propoxy)-2-methanesulfonylphenyl]methanol |
| 136 | [4-(3-{[2,2-difluoro-2-(4-fluoropheny)ethyl]({[3-(trifluoromethyl)phenyl]methyl})amino}propoxy)-2-methanesulfonylphenyl]methanol |
| 137 | {4-[3-({[2-chloro-3-(trifluoromethyl)phenyl]methyl}(2-methyl-2-phenylpropyl)amino)propoxy]-2-methanesulfonylphenyl}methanol |
| 138 | {4-[3-({[2-chloro-3-(trifluoromethyl)phenyl]methyl}(2-phenylethyl)amino)propoxy]-2-methanesulfonylphenyl}methanol |
| 139 | {4-[3-({[2-chloro-3-(trifluoromethyl)phenyl]methyl}(2-phenylpropyl)amino)propoxy]-2-methanesulfonylphenyl}methanol |
| 140 | {4-[3-({[2-chloro-3-(trifluoromethyl)phenyl]methyl}[(4-fluorophenyl)methyl]amino)propoxy]-2-methanesulfonylphenyl}methanol |
| 141 | {4-[3-({[2-chloro-3-(trifluoromethyl)phenyl]methyl}[2-(4-fluorophenyl)-2-methylpropyl]amino)propoxy]-2-methanesulfonylphenyl}methanol |
| 142 | {4-[3-({[2-chloro-3-(trifluoromethyl)phenyl]methyl}[2-(4-fluorophenyl)ethyl]amino)propoxy]-2-methanesulfonylphenyl}methanol |
| 143 | {4-[3-({[2-chloro-3-(trifluoromethyl)phenyl]methyl}[2-(4-fluorophenyl)propyl]amino)propoxy]-2-methanesulfonylphenyl}methanol |
| 144 | {4-[3-({[2-fluoro-3-(trifluoromethyl)phenyl]methyl}(2-methyl-2-phenylpropyl)amino)propoxy]-2-methanesulfonylphenyl}methanol |
| 145 | {4-[3-({[2-fluoro-3-(trifluoromethyl)phenyl]methyl}(2-phenylethyl)amino)propoxy]-2-methanesulfonylphenyl}methanol |
| 146 | {4-[3-({[2-fluoro-3-(trifluoromethyl)phenyl]methyl}(2-phenylpropyl)amino)propoxy]-2-methanesulfonylphenyl}methanol |
| 147 | {4-[3-({[2-fluoro-3-(trifluoromethyl)phenyl]methyl}[(4-fluorophenyl)methyl]amino)propoxy]-2-methanesulfonylphenyl}methanol |
| 148 | {4-[3-({[2-fluoro-3-(trifluoromethyl)phenyl]methyl}[2-(4-fluorophenyl)-2-methylpropyl]amino)propoxy]-2-methanesulfonylphenyl}methanol |
| 149 | {4-[3-({[2-fluoro-3-(trifluoromethyl)phenyl]methyl}[2-(4-fluorophenyl)ethyl]amino)propoxy]-2-methanesulfonylphenyl}methanol |
| 150 | {4-[3-({[2-fluoro-3-(trifluoromethyl)phenyl]methyl}[2-(4-fluorophenyl)propyl]amino)propoxy]-2-methanesulfonylphenyl}methanol |
| 151 | [3-(3-methanesulfonylphenoxy)propyl](2-methyl-2-phenylpropyl){[3-(trifluoromethyl)phenyl]methyl}amine |
| 152 | [3-(3-methanesulfonylphenoxy)propyl](2-phenylethyl){[3-(trifluoromethyl)phenyl]methyl}amine |
| 153 | [3-(3-methanesulfonylphenoxy)propyl](2-phenylpropyl){[3-(trifluoromethyl)phenyl]methyl}amine |
| 154 | (2,2-diphenylethyl)({[2-fluoro-3-(trifluoromethyl)phenyl]methyl})[3-(3-methanesulfonylphenoxy)propyl]amine |
| 155 | (2,2-diphenylethyl)[3-(3-methanesulfonylphenoxy)propyl]{[3-(trifluoromethyl)phenyl]methyl}amine |
| 156 | benzyl({[2-chloro-3-(trifluoromethyl)phenyl]methyl})[3-(3-methanesulfonylphenoxy)propyl]amine |
| 157 | benzyl({[2-fluoro-3-(trifluoromethyl)phenyl]methyl})[3-(3-methanesulfonylphenoxy)propyl]amine |
| 158 | benzyl[3-(3-methanesulfonylphenoxy)propyl]{[3-(trifluoromethyl)phenyl]methyl}amine |
| 159 | [(4-fluorophenyl)methyl][3-(3-methanesulfonylphenoxy)propyl]{[3-(trifluoromethyl)phenyl]methyl}amine |
| 160 | [2-(4-fluorophenyl)-2-methylpropyl][3-(3-methanesulfonylphenoxy)propyl]{[3-(trifluoromethyl)phenyl]methyl}amine |
| 161 | [2-(4-fluorophenyl)ethyl][3-(3-methanesulfonylphenoxy)propyl]{[3-(trifluoromethyl)phenyl]methyl}amine |
| 162 | [2-(4-fluorophenyl)propyl][3-(3-methanesulfonylphenoxy)propyl]{[3-(trifluoromethyl)phenyl]methyl}amine |
| 163 | {[2-chloro-3-(trifluoromethyl)phenyl]methyl}[2,2-difluoro-2-(4-fluoropheny)ethyl][3-(3-methanesulfonylphenoxy)propyl]amine |
| 164 | [2,2-difluoro-2-(4-fluoropheny)ethyl]({[2-fluoro-3-(trifluoromethyl)phenyl]methyl})[3-(3-methanesulfonylphenoxy)propyl]amine |
| 165 | [2,2-difluoro-2-(4-fluoropheny)ethyl][3-(3-methanesulfonylphenoxy)propyl]{[3-(trifluoromethyl)phenyl]methyl}amine |
| 166 | {[2-chloro-3-(trifluoromethyl)phenyl]methyl}[3-(3-methanesulfonylphenoxy)propyl](2-methyl-2-phenylpropyl)amine |
| 167 | {[2-chloro-3-(trifluoromethyl)phenyl]methyl}[3-(3-methanesulfonylphenoxy)propyl](2-phenylethyl)amine |
| 168 | {[2-chloro-3-(trifluoromethyl)phenyl]methyl}[3-(3-methanesulfonylphenoxy)propyl](2-phenylpropyl)amine |
| 169 | {[2-chloro-3-(trifluoromethyl)phenyl]methyl}[(4-fluorophenyl)methyl][3-(3-methanesulfonylphenoxy)propyl]amine |
| 170 | {[2-chloro-3-(trifluoromethyl)phenyl]methyl}[2-(4-fluorophenyl)-2-methylpropyl][3-(3-methanesulfonylphenoxy)propyl]amine |
| 171 | {[2-chloro-3-(trifluoromethyl)phenyl]methyl}[2-(4-fluoropheny)ethyl][3-(3-methanesulfonylphenoxy)propyl]amine |
| 172 | {[2-chloro-3-(trifluoromethyl)phenyl]methyl}[2-(4-fluorophenyl)propyl][3-(3-methanesulfonylphenoxy)propyl]amine |

TABLE 4-continued

Additional LXR agonists of the Invention.

| # | Name |
|---|---|
| 173 | {[2-fluoro-3-(trifluoromethyl)phenyl]methyl}[3-(3-methanesulfonylphenoxy)propyl](2-methyl-2-phenylpropyl)amine |
| 174 | {[2-fluoro-3-(trifluoromethyl)phenyl]methyl}[3-(3-methanesulfonylphenoxy)propyl](2-phenylethyl)amine |
| 175 | {[2-fluoro-3-(trifluoromethyl)phenyl]methyl}[3-(3-methanesulfonylphenoxy)propyl](2-phenylpropyl)amine |
| 176 | {[2-fluoro-3-(trifluoromethyl)phenyl]methyl}[(4-fluorophenyl)methyl][3-(3-methanesulfonylphenoxy)propyl]amine |
| 177 | {[2-fluoro-3-(trifluoromethyl)phenyl]methyl}[2-(4-fluorophenyl)-2-methylpropyl][3-(3-methanesulfonylphenoxy)propyl]amine |
| 178 | {[2-fluoro-3-(trifluoromethyl)phenyl]methyl}[2-(4-fluoropheny)ethyl][3-(3-methanesulfonylphenoxy)propyl]amine |
| 179 | {[2-fluoro-3-(trifluoromethyl)phenyl]methyl}[2-(4-fluorophenyl)propyl][3-(3-methanesulfonylphenoxy)propyl]amine |
| 180 | 1-(2-fluoro-6-methanesulfonyl-4-{3-[(2-phenylethyl)({[3-(trifluoromethyl)phenyl]methyl})amino]propoxy}phenyl)ethan-1-ol |
| 181 | 1-(2-fluoro-6-methanesulfonyl-4-{3-[(2-methyl-2-phenylpropyl)({[3-(trifluoromethyl)phenyl]methyl})amino]propoxy}phenyl)ethan-1-ol |
| 182 | 1-(2-fluoro-6-methanesulfonyl-4-{3-[(2-phenylpropyl)({[3-(trifluoromethyl)phenyl]methyl})amino]propoxy}phenyl)ethan-1-ol |
| 183 | 1-(4-{3-[(2,2-diphenylethyl)({[2-fluoro-3-(trifluoromethyl)phenyl]methyl})amino]propoxy}-2-fluoro-6-methanesulfonylphenyl)ethan-1-ol |
| 184 | 1-(4-{3-[(2,2-diphenylethyl)({[3-(trifluoromethyl)phenyl]methyl})amino]propoxy}-2-fluoro-6-methanesulfonylphenyl)ethan-1-ol |
| 185 | 1-(4-{3-[benzyl({[2-chloro-3-(trifluoromethyl)phenyl]methyl})amino]propoxy}-2-fluoro-6-methanesulfonylphenyl)ethan-1-ol |
| 186 | 1-(4-{3-[benzyl({[2-fluoro-3-(trifluoromethyl)phenyl]methyl})amino]propoxy}-2-fluoro-6-methanesulfonylphenyl)ethan-1-ol |
| 187 | 1-(4-{3-[benzyl({[3-(trifluoromethyl)phenyl]methyl})amino]propoxy}-2-fluoro-6-methanesulfonylphenyl)ethan-1-ol |
| 188 | 1-[2-fluoro-4-(3-{[(4-fluorophenyl)methyl]({[3-(trifluoromethyl)phenyl]methyl})amino}propoxy)-6-methanesulfonylphenyl]ethan-1-ol |
| 189 | 1-[2-fluoro-4-(3-{[2-(4-fluorophenyl)-2-methylpropyl]({[3-(trifluoromethyl)phenyl]methyl})amino}propoxy)-6-methanesulfonylphenyl]ethan-1-ol |
| 190 | 1-[2-fluoro-4-(3-{[2-(4-fluoropheny)ethyl]({[3-(trifluoromethyl)phenyl]methyl})amino}propoxy)-6-methanesulfonylphenyl]ethan-1-ol |
| 191 | 1-[2-fluoro-4-(3-{[2-(4-fluorophenyl)propyl]({[3-(trifluoromethyl)phenyl]methyl})amino}propoxy)-6-methanesulfonylphenyl]ethan-1-ol |
| 192 | 1-{4-[3-({[2-chloro-3-(trifluoromethyl)phenyl]methyl}[2,2-difluoro-2-(4-fluoropheny)ethyl]amino)propoxy]-2-fluoro-6-methanesulfonylphenyl}ethan-1-ol |
| 193 | 1-[4-(3-{[2-difluoro-2-(4-fluoropheny)ethyl]({[2-fluoro-3-(trifluoromethyl)phenyl]methyl})amino}propoxy)-2-fluoro-6-methanesulfonylphenyl]ethan-1-ol |
| 194 | 1-[4-(3-{[2,2-difluoro-2-(4-fluorophenyl)ethyl]({[3-(trifluoromethyl)phenyl]methyl})amino}propoxy)-2-fluoro-6-methanesulfonylphenyl]ethan-1-ol |
| 195 | 1-{4-[3-({[2-chloro-3-(trifluoromethyl)phenyl]methyl}(2-methyl-2-phenylpropyl)amino)propoxy]-2-fluoro-6-methanesulfonylphenyl}ethan-1-ol |
| 196 | 1-{4-[3-({[2-chloro-3-(trifluoromethyl)phenyl]methyl}(2-phenylpropyl)amino)propoxy]-2-fluoro-6-methanesulfonylphenyl}ethan-1-ol |
| 197 | 1-{4-[3-({[2-chloro-3-(trifluoromethyl)phenyl]methyl}[2-(4-fluorophenyl)-2-methylpropyl]amino)propoxy]-2-fluoro-6-methanesulfonylphenyl}ethan-1-ol |
| 198 | 1-{4-[3-({[2-chloro-3-(trifluoromethyl)phenyl]methyl}[(4-fluorophenyl)methyl]amino)propoxy]-2-fluoro-6-methanesulfonylphenyl}ethan-1-ol |
| 199 | 1-{4-[3-({[2-chloro-3-(trifluoromethyl)phenyl]methyl}[2-(4-fluorophenyl)ethyl]amino)propoxy]-2-fluoro-6-methanesulfonylphenyl}ethan-1-ol |
| 200 | 1-{2-fluoro-4-[3-({[2-fluoro-3-(trifluoromethyl)phenyl]methyl}(2-methyl-2-phenylpropyl)amino)propoxy]-6-methanesulfonylphenyl}ethan-1-ol |
| 201 | 1-{4-[3-({[2-chloro-3-(trifluoromethyl)phenyl]methyl}[2-(4-fluorophenyl)propyl]amino)propoxy]-2-fluoro-6-methanesulfonylphenyl}ethan-1-ol |
| 202 | 1-{2-fluoro-4-[3-({[2-fluoro-3-(trifluoromethyl)phenyl]methyl}(2-phenylethyl)amino)propoxy]-6-methanesulfonylphenyl}ethan-1-ol |
| 203 | 1-{2-fluoro-4-[3-({[2-fluoro-3-(trifluoromethyl)phenyl]methyl}(2-phenylpropyl)amino)propoxy]-6-methanesulfonylphenyl}ethan-1-ol |
| 204 | 1-{2-fluoro-4-[3-({[2-fluoro-3-(trifluoromethyl)phenyl]methyl}[(4-fluorophenyl)methyl]amino)propoxy]-6-methanesulfonylphenyl}ethan-1-ol |
| 205 | 1-{4-[3-({[2-chloro-3-(trifluoromethyl)phenyl]methyl}(2-phenylethyl)amino)propoxy]-2-fluoro-6-methanesulfonylphenyl}ethan-1-ol |
| 206 | 1-{2-fluoro-4-[3-({[2-fluoro-3-(trifluoromethyl)phenyl]methyl}[2-(4-fluorophenyl)-2-methylpropyl]amino)propoxy]-6-methanesulfonylphenyl}ethan-1-ol |
| 207 | 1-{2-fluoro-4-[3-({[2-fluoro-3-(trifluoromethyl)phenyl]methyl}[2-(4-fluorophenyl)ethyl]amino)propoxy]-6-methanesulfonylphenyl}ethan-1-ol |
| 208 | 1-{2-fluoro-4-[3-({[2-fluoro-3-(trifluoromethyl)phenyl]methyl}[2-(4-fluorophenyl)propyl]amino)propoxy]-6-methanesulfonylphenyl}ethan-1-ol |
| 209 | 1-(2-methanesulfonyl-4-{3-[(2-methyl-2-phenylpropyl)({[3-(trifluoromethyl)phenyl]methyl})amino]propoxy}phenyl)ethan-1-ol |

TABLE 4-continued

Additional LXR agonists of the Invention.

| # | Name |
|---|---|
| 210 | 1-(2-methanesulfonyl-4-{3-[(2-phenylethyl)({[3-(trifluoromethyl)phenyl]methyl})amino]propoxy}phenyl)ethan-1-ol |
| 211 | 1-(2-methanesulfonyl-4-{3-[(2-phenylpropyl)({[3-(trifluoromethyl)phenyl]methyl})amino]propoxy}phenyl)ethan-1-ol |
| 212 | 1-(4-{3-[(2,2-diphenylethyl)({[2-fluoro-3-(trifluoromethyl)phenyl]methyl})amino]propoxy}-2-methanesulfonylphenyl)ethan-1-ol |
| 213 | 1-(4-{3-[(2,2-diphenylethyl)({[3-(trifluoromethyl)phenyl]methyl})amino]propoxy}-2-methanesulfonylphenyl)ethan-1-ol |
| 214 | 1-(4-{3-[benzyl({[2-chloro-3-(trifluoromethyl)phenyl]methyl})amino]propoxy}-2-methanesulfonylphenyl)ethan-1-ol |
| 215 | 1-(4-{3-[benzyl({[2-fluoro-3-(trifluoromethyl)phenyl]methyl})amino]propoxy}-2-methanesulfonylphenyl)ethan-1-ol |
| 216 | 1-(4-{3-[benzyl({[3-(trifluoromethyl)phenyl]methyl})amino]propoxy}-2-methanesulfonylphenyl)ethan-1-ol |
| 217 | 1-[4-(3-{[(4-fluorophenyl)methyl]({[3-(trifluoromethyl)phenyl]methyl})amino}propoxy)-2-methanesulfonylphenyl]ethan-1-ol |
| 218 | 1-[4-(3-{[2-(4-fluorophenyl)-2-methylpropyl]({[3-(trifluoromethyl)phenyl]methyl})amino}propoxy)-2-methanesulfonylphenyl]ethan-1-ol |
| 219 | 1-[4-(3-{[2-(4-fluorophenyl)ethyl]({[3-(trifluoromethyl)phenyl]methyl})amino}propoxy)-2-methanesulfonylphenyl]ethan-1-ol |
| 220 | 1-[4-(3-{[2-(4-fluorophenyl)propyl]({[3-(trifluoromethyl)phenyl]methyl})amino}propoxy)-2-methanesulfonylphenyl]ethan-1-ol |
| 221 | 1-{4-[3-({[2-chloro-3-(trifluoromethyl)phenyl]methyl}[2,2-difluoro-2-(4-fluorophenyl)ethyl]amino)propoxy]-2-methanesulfonylphenyl}ethan-1-ol |
| 222 | 1-[4-(3-{[2,2-difluoro-2-(4-fluorophenyl)ethyl]({[2-fluoro-3-(trifluoromethyl)phenyl]methyl})amino}propoxy)-2-methanesulfonylphenyl]ethan-1-ol |
| 223 | 1-[4-(3-{[2,2-difluoro-2-(4-fluorophenyl)ethyl]({[3-(trifluoromethyl)phenyl]methyl})amino}propoxy)-2-methanesulfonylphenyl]ethan-1-ol |
| 224 | 1-{4-[3-({[2-chloro-3-(trifluoromethyl)phenyl]methyl}(2-methyl-2-phenylpropyl)amino)propoxy]-2-methanesulfonylphenyl}ethan-1-ol |
| 225 | 1-{4-[3-({[2-chloro-3-(trifluoromethyl)phenyl]methyl}(2-phenylethyl)amino)propoxy]-2-methanesulfonylphenyl}ethan-1-ol |
| 226 | 1-{4-[3-({[2-chloro-3-(trifluoromethyl)phenyl]methyl}(2-phenylpropyl)amino)propoxy]-2-methanesulfonylphenyl}ethan-1-ol |
| 227 | 1-{4-[3-({[2-chloro-3-(trifluoromethyl)phenyl]methyl}[(4-fluorophenyl)methyl]amino)propoxy]-2-methanesulfonylphenyl}ethan-1-ol |
| 228 | 1-{4-[3-({[2-chloro-3-(trifluoromethyl)phenyl]methyl}[2-(4-fluorophenyl)-2-methylpropyl]amino)propoxy]-2-methanesulfonylphenyl}ethan-1-ol |
| 229 | 1-{4-[3-({[2-chloro-3-(trifluoromethyl)phenyl]methyl}[2-(4-fluorophenyl)ethyl]amino)propoxy]-2-methanesulfonylphenyl}ethan-1-ol |
| 230 | 1-{4-[3-({[2-chloro-3-(trifluoromethyl)phenyl]methyl}[2-(4-fluorophenyl)propyl]amino)propoxy]-2-methanesulfonylphenyl}ethan-1-ol |
| 231 | 1-{4-[3-({[2-fluoro-3-(trifluoromethyl)phenyl]methyl}(2-methyl-2-phenylpropyl)amino)propoxy]-2-methanesulfonylphenyl}ethan-1-ol |
| 232 | 1-{4-[3-({[2-fluoro-3-(trifluoromethyl)phenyl]methyl}(2-phenylethyl)amino)propoxy]-2-methanesulfonylphenyl}ethan-1-ol |
| 233 | 1-{4-[3-({[2-fluoro-3-(trifluoromethyl)phenyl]methyl}(2-phenylpropyl)amino)propoxy]-2-methanesulfonylphenyl}ethan-1-ol |
| 234 | 1-{4-[3-({[2-fluoro-3-(trifluoromethyl)phenyl]methyl}[(4-fluorophenyl)methyl]amino)propoxy]-2-methanesulfonylphenyl}ethan-1-ol |
| 235 | 1-{4-[3-({[2-fluoro-3-(trifluoromethyl)phenyl]methyl}[2-(4-fluorophenyl)-2-methylpropyl]amino)propoxy]-2-methanesulfonylphenyl}ethan-1-ol |
| 236 | 1-{4-[3-({[2-fluoro-3-(trifluoromethyl)phenyl]methyl}[2-(4-fluorophenyl)ethyl]amino)propoxy]-2-methanesulfonylphenyl}ethan-1-ol |
| 237 | 1-{4-[3-({[2-fluoro-3-(trifluoromethyl)phenyl]methyl}[2-(4-fluorophenyl)propyl]amino)propoxy]-2-methanesulfonylphenyl}ethan-1-ol |
| 238 | 1-{4-[3-({[2-chloro-3-(trifluoromethyl)phenyl]methyl}(2,2-diphenylethyl)amino)propoxy]-2-methanesulfonylphenyl}ethan-1-ol |
| 239 | 2-fluoro-6-methanesulfonyl-4-{3-[(2-phenylethyl)({[3-(trifluoromethyl)phenyl]methyl})amino]propoxy}benzaldehyde |
| 240 | 4-{3-[(2,2-diphenylethyl)({[2-fluoro-3-(trifluoromethyl)phenyl]methyl})amino]propoxy}-2-fluoro-6-methanesulfonylbenzaldehyde |
| 241 | 2-fluoro-6-methanesulfonyl-4-{3-[(2-methyl-2-phenylpropyl)({[3-(trifluoromethyl)phenyl]methyl})amino]propoxy}benzaldehyde |
| 242 | 4-{3-[(2,2-diphenylethyl)({[3-(trifluoromethyl)phenyl]methyl})amino]propoxy}-2-fluoro-6-methanesulfonylbenzaldehyde |
| 243 | 4-{3-[benzyl({[2-chloro-3-(trifluoromethyl)phenyl]methyl})amino]propoxy}-2-fluoro-6-methanesulfonylbenzaldehyde |
| 244 | 4-{3-[benzyl({[2-fluoro-3-(trifluoromethyl)phenyl]methyl})amino]propoxy}-2-fluoro-6-methanesulfonylbenzaldehyde |
| 245 | 4-{3-[benzyl({[3-(trifluoromethyl)phenyl]methyl})amino]propoxy}-2-fluoro-6-methanesulfonylbenzaldehyde |
| 246 | 2-fluoro-4-(3-{[(4-fluorophenyl)methyl]({[3-(trifluoromethyl)phenyl]methyl})amino}propoxy)-6-methanesulfonylbenzaldehyde |
| 247 | 2-fluoro-4-(3-{[2-(4-fluorophenyl)-2-methylpropyl]({[3-(trifluoromethyl)phenyl]methyl})amino}propoxy)-6-methanesulfonylbenzaldehyde |

TABLE 4-continued

Additional LXR agonists of the Invention.

| # | Name |
|---|------|
| 248 | 2-fluoro-4-(3-{[2-(4-fluorophenyl)ethyl]({[3-(trifluoromethyl)phenyl]methyl})amino}propoxy)-6-methanesulfonylbenzaldehyde |
| 249 | 2-fluoro-4-(3-{[2-(4-fluorophenyl)propyl]({[3-(trifluoromethyl)phenyl]methyl})amino}propoxy)-6-methanesulfonylbenzaldehyde |
| 250 | 4-(3-{[2,2-difluoro-2-(4-fluorophenyl)ethyl]({[2-fluoro-3-(trifluoromethyl)phenyl]methyl})amino}propoxy)-2-fluoro-6-methanesulfonylbenzaldehyde |
| 251 | 4-[3-({[2-chloro-3-(trifluoromethyl)phenyl]methyl}[2,2-difluoro-2-(4-fluorophenyl)ethyl]amino)propoxy]-2-fluoro-6-methanesulfonylbenzaldehyde |
| 252 | 4-(3-{[2,2-difluoro-2-(4-fluorophenyl)ethyl]({[3-(trifluoromethyl)phenyl]methyl})amino}propoxy)-2-fluoro-6-methanesulfonylbenzaldehyde |
| 253 | 4-[3-({[2-chloro-3-(trifluoromethyl)phenyl]methyl}(2-methyl-2-phenylpropyl)amino)propoxy]-2-fluoro-6-methanesulfonylbenzaldehyde |
| 254 | 4-[3-({[2-chloro-3-(trifluoromethyl)phenyl]methyl}(2-phenylethyl)amino)propoxy]-2-fluoro-6-methanesulfonylbenzaldehyde |
| 255 | 4-[3-({[2-chloro-3-(trifluoromethyl)phenyl]methyl}(2-phenylpropyl)amino)propoxy]-2-fluoro-6-methanesulfonylbenzaldehyde |
| 256 | 4-[3-({[2-chloro-3-(trifluoromethyl)phenyl]methyl}[(4-fluorophenyl)methyl]amino)propoxy]-2-fluoro-6-methanesulfonylbenzaldehyde |
| 257 | 4-[3-({[2-chloro-3-(trifluoromethyl)phenyl]methyl}[2-(4-fluorophenyl)-2-methylpropyl]amino)propoxy]-2-fluoro-6-methanesulfonylbenzaldehyde |
| 258 | 2-fluoro-4-[3-({[2-fluoro-3-(trifluoromethyl)phenyl]methyl}(2-methyl-2-phenylpropyl)amino)propoxy]-6-methanesulfonylbenzaldehyde |
| 259 | 4-[3-({[2-chloro-3-(trifluoromethyl)phenyl]methyl}[2-(4-fluorophenyl)propyl]amino)propoxy]-2-fluoro-6-methanesulfonylbenzaldehyde |
| 260 | 2-fluoro-4-[3-({[2-fluoro-3-(trifluoromethyl)phenyl]methyl}(2-phenylethyl)amino)propoxy]-6-methanesulfonylbenzaldehyde |
| 261 | 2-fluoro-4-[3-({[2-fluoro-3-(trifluoromethyl)phenyl]methyl}(2-phenylpropyl)amino)propoxy]-6-methanesulfonylbenzaldehyde |
| 262 | 2-fluoro-4-[3-({[2-fluoro-3-(trifluoromethyl)phenyl]methyl}[(4-fluorophenyl)methyl]amino)propoxy]-6-methanesulfonylbenzaldehyde |
| 263 | 2-fluoro-4-[3-({[2-fluoro-3-(trifluoromethyl)phenyl]methyl}[2-(4-fluorophenyl)-2-methylpropyl]amino)propoxy]-6-methanesulfonylbenzaldehyde |
| 264 | 2-fluoro-6-methanesulfonyl-4-{3-[(2-phenylpropyl)({[3-(trifluoromethyl)phenyl]methyl})amino]propoxy}benzaldehyde |
| 265 | 2-fluoro-4-[3-({[2-fluoro-3-(trifluoromethyl)phenyl]methyl}[2-(4-fluorophenyl)ethyl]amino)propoxy]-6-methanesulfonylbenzaldehyde |
| 266 | 2-fluoro-4-[3-({[2-fluoro-3-(trifluoromethyl)phenyl]methyl}[2-(4-fluorophenyl)propyl]amino)propoxy]-6-methanesulfonylbenzaldehyde |
| 267 | 4-[3-({[2-chloro-3-(trifluoromethyl)phenyl]methyl}[2-(4-fluorophenyl)ethyl]amino)propoxy]-2-fluoro-6-methanesulfonylbenzaldehyde |
| 268 | 2-methanesulfonyl-4-{3-[(2-methyl-2-phenylpropyl)({[3-(trifluoromethyl)phenyl]methyl})amino]propoxy}benzaldehyde |
| 269 | 2-methanesulfonyl-4-{3-[(2-phenylethyl)({[3-(trifluoromethyl)phenyl]methyl})amino]propoxy}benzaldehyde |
| 270 | 2-methanesulfonyl-4-{3-[(2-phenylpropyl)({[3-(trifluoromethyl)phenyl]methyl})amino]propoxy}benzaldehyde |
| 271 | 4-{3-[(2,2-diphenylethyl)({[2-fluoro-3-(trifluoromethyl)phenyl]methyl})amino]propoxy}-2-methanesulfonylbenzaldehyde |
| 272 | 4-{3-[(2,2-diphenylethyl)({[3-(trifluoromethyl)phenyl]methyl})amino]propoxy}-2-methanesulfonylbenzaldehyde |
| 273 | 4-{3-[benzyl({[2-chloro-3-(trifluoromethyl)phenyl]methyl})amino]propoxy}-2-methanesulfonylbenzaldehyde |
| 274 | 4-{3-[benzyl({[2-fluoro-3-(trifluoromethyl)phenyl]methyl})amino]propoxy}-2-methanesulfonylbenzaldehyde |
| 275 | 4-{3-[benzyl({[3-(trifluoromethyl)phenyl]methyl})amino]propoxy}-2-methanesulfonylbenzaldehyde |
| 276 | 4-(3-{[(4-fluorophenyl)methyl]({[3-(trifluoromethyl)phenyl]methyl})amino}propoxy)-2-methanesulfonylbenzaldehyde |
| 277 | 4-(3-{[2-(4-fluorophenyl)-2-methylpropyl]({[3-(trifluoromethyl)phenyl]methyl})amino}propoxy)-2-methanesulfonylbenzaldehyde |
| 278 | 4-(3-{[2-(4-fluorophenyl)ethyl]({[3-(trifluoromethyl)phenyl]methyl})amino}propoxy)-2-methanesulfonylbenzaldehyde |
| 279 | 4-(3-{[2-(4-fluorophenyl)propyl]({[3-(trifluoromethyl)phenyl]methyl})amino}propoxy)-2-methanesulfonylbenzaldehyde |
| 280 | 4-[3-({[2-chloro-3-(trifluoromethyl)phenyl]methyl}[2,2-difluoro-2-(4-fluorophenyl)ethyl]amino)propoxy]-2-methanesulfonylbenzaldehyde |
| 281 | 4-(3-{[2,2-difluoro-2-(4-fluorophenyl)ethyl]({[2-fluoro-3-(trifluoromethyl)phenyl]methyl})amino}propoxy)-2-methanesulfonylbenzaldehyde |
| 282 | 4-(3-{[2,2-difluoro-2-(4-fluorophenyl)ethyl]({[3-(trifluoromethyl)phenyl]methyl})amino}propoxy)-2-methanesulfonylbenzaldehyde |
| 283 | 4-[3-({[2-chloro-3-(trifluoromethyl)phenyl]methyl}(2-methyl-2-phenylpropyl)amino)propoxy]-2-methanesulfonylbenzaldehyde |
| 284 | 4-[3-({[2-chloro-3-(trifluoromethyl)phenyl]methyl}(2-phenylethyl)amino)propoxy]-2-methanesulfonylbenzaldehyde |

TABLE 4-continued

Additional LXR agonists of the Invention.

| # | Name |
|---|------|
| 285 | 4-[3-({[2-chloro-3-(trifluoromethyl)phenyl]methyl}(2-phenylpropyl)amino)propoxy]-2-methanesulfonylbenzaldehyde |
| 286 | 4-[3-({[2-chloro-3-(trifluoromethyl)phenyl]methyl}(2,2-diphenylethyl)amino)propoxy]-2-methanesulfonylbenzaldehyde |
| 287 | 4-[3-({[2-chloro-3-(trifluoromethyl)phenyl]methyl}[(4-fluorophenyl)methyl]amino)propoxy]-2-methanesulfonylbenzaldehyde |
| 288 | 4-[3-({[2-chloro-3-(trifluoromethyl)phenyl]methyl}[2-(4-fluorophenyl)-2-methylpropyl]amino)propoxy]-2-methanesulfonylbenzaldehyde |
| 289 | 4-[3-({[2-chloro-3-(trifluoromethyl)phenyl]methyl}[2-(4-fluorophenyl)ethyl]amino)propoxy]-2-methanesulfonylbenzaldehyde |
| 290 | 4-[3-({[2-chloro-3-(trifluoromethyl)phenyl]methyl}[2-(4-fluorophenyl)propyl]amino)propoxy]-2-methanesulfonylbenzaldehyde |
| 291 | 4-[3-({[2-fluoro-3-(trifluoromethyl)phenyl]methyl}(2-methyl-2-phenylpropyl)amino)propoxy]-2-methanesulfonylbenzaldehyde |
| 292 | 4-[3-({[2-fluoro-3-(trifluoromethyl)phenyl]methyl}(2-phenylethyl)amino)propoxy]-2-methanesulfonylbenzaldehyde |
| 293 | 4-[3-({[2-fluoro-3-(trifluoromethyl)phenyl]methyl}(2-phenylpropyl)amino)propoxy]-2-methanesulfonylbenzaldehyde |
| 294 | 4-[3-({[2-fluoro-3-(trifluoromethyl)phenyl]methyl}[(4-fluorophenyl)methyl]amino)propoxy]-2-methanesulfonylbenzaldehyde |
| 295 | 4-[3-({[2-fluoro-3-(trifluoromethyl)phenyl]methyl}[2-(4-fluorophenyl)-2-methylpropyl]amino)propoxy]-2-methanesulfonylbenzaldehyde |
| 296 | 4-[3-({[2-fluoro-3-(trifluoromethyl)phenyl]methyl}[2-(4-fluorophenyl)ethyl]amino)propoxy]-2-methanesulfonylbenzaldehyde |
| 297 | 4-[3-({[2-fluoro-3-(trifluoromethyl)phenyl]methyl}[2-(4-fluorophenyl)propyl]amino)propoxy]-2-methanesulfonylbenzaldehyde |
| 298 | methyl 2-fluoro-6-methanesulfonyl-4-{3-[(2-methyl-2-phenylpropyl)({[3-(trifluoromethyl)phenyl]methyl})amino]propoxy}benzoate |
| 299 | methyl 2-fluoro-6-methanesulfonyl-4-{3-[(2-phenylpropyl)({[3-(trifluoromethyl)phenyl]methyl})amino]propoxy}benzoate |
| 300 | methyl 4-{3-[(2,2-diphenylethyl)({[3-(trifluoromethyl)phenyl]methyl})amino]propoxy}-2-fluoro-6-methanesulfonylbenzoate |
| 301 | methyl 2-fluoro-6-methanesulfonyl-4-{3-[(2-phenylethyl)({[3-(trifluoromethyl)phenyl]methyl})amino]propoxy}benzoate |
| 302 | methyl 4-{3-[(2,2-diphenylethyl)({[2-fluoro-3-(trifluoromethyl)phenyl]methyl})amino]propoxy}-2-fluoro-6-methanesulfonylbenzoate |
| 303 | methyl 4-{3-[benzyl({[2-chloro-3-(trifluoromethyl)phenyl]methyl})amino]propoxy}-2-fluoro-6-methanesulfonylbenzoate |
| 304 | methyl 4-{3-[benzyl({[2-fluoro-3-(trifluoromethyl)phenyl]methyl})amino]propoxy}-2-fluoro-6-methanesulfonylbenzoate |
| 305 | methyl 4-{3-[benzyl({[3-(trifluoromethyl)phenyl]methyl})amino]propoxy}-2-fluoro-6-methanesulfonylbenzoate |
| 306 | methyl 2-fluoro-4-(3-{[(4-fluorophenyl)methyl]({[3-(trifluoromethyl)phenyl]methyl})amino}propoxy)-6-methanesulfonylbenzoate |
| 307 | methyl 2-fluoro-4-(3-{[2-(4-fluorophenyl)-2-methylpropyl]({[3-(trifluoromethyl)phenyl]methyl})amino}propoxy)-6-methanesulfonylbenzoate |
| 308 | methyl 2-fluoro-4-(3-{[2-(4-fluorophenyl)ethyl]({[3-(trifluoromethyl)phenyl]methyl})amino}propoxy)-6-methanesulfonylbenzoate |
| 309 | methyl 2-fluoro-4-(3-{[2-(4-fluorophenyl)propyl]({[3-(trifluoromethyl)phenyl]methyl})amino}propoxy)-6-methanesulfonylbenzoate |
| 310 | methyl 4-[3-({[2-chloro-3-(trifluoromethyl)phenyl]methyl}[2,2-difluoro-2-(4-fluorophenyl)ethyl]amino)propoxy]-2-fluoro-6-methanesulfonylbenzoate |
| 311 | methyl 4-(3-{[2,2-difluoro-2-(4-fluorophenyl)ethyl]({[2-fluoro-3-(trifluoromethyl)phenyl]methyl})amino}propoxy)-2-fluoro-6-methanesulfonylbenzoate |
| 312 | methyl 4-(3-{[2,2-difluoro-2-(4-fluorophenyl)ethyl]({[3-(trifluoromethyl)phenyl]methyl})amino}propoxy)-2-fluoro-6-methanesulfonylbenzoate |
| 313 | methyl 4-[3-({[2-chloro-3-(trifluoromethyl)phenyl]methyl}(2-methyl-2-phenylpropyl)amino)propoxy]-2-fluoro-6-methanesulfonylbenzoate |
| 314 | methyl 4-[3-({[2-chloro-3-(trifluoromethyl)phenyl]methyl}(2-phenylethyl)amino)propoxy]-2-fluoro-6-methanesulfonylbenzoate |
| 315 | methyl 4-[3-({[2-chloro-3-(trifluoromethyl)phenyl]methyl}[2-(4-fluorophenyl)-2-methylpropyl]amino)propoxy]-2-fluoro-6-methanesulfonylbenzoate |
| 316 | methyl 4-[3-({[2-chloro-3-(trifluoromethyl)phenyl]methyl}[(4-fluorophenyl)methyl]amino)propoxy]-2-fluoro-6-methanesulfonylbenzoate |
| 317 | methyl 4-[3-({[2-chloro-3-(trifluoromethyl)phenyl]methyl}(2-phenylpropyl)amino)propoxy]-2-fluoro-6-methanesulfonylbenzoate |
| 318 | methyl 4-[3-({[2-chloro-3-(trifluoromethyl)phenyl]methyl}[2-(4-fluorophenyl)propyl]amino)propoxy]-2-fluoro-6-methanesulfonylbenzoate |
| 319 | methyl 4-[3-({[2-chloro-3-(trifluoromethyl)phenyl]methyl}[2-(4-fluorophenyl)ethyl]amino)propoxy]-2-fluoro-6-methanesulfonylbenzoate |
| 320 | methyl 2-fluoro-4-[3-({[2-fluoro-3-(trifluoromethyl)phenyl]methyl}(2-methyl-2-phenylpropyl)amino)propoxy]-6-methanesulfonylbenzoate |
| 321 | methyl 2-fluoro-4-[3-({[2-fluoro-3-(trifluoromethyl)phenyl]methyl}(2-phenylethyl)amino)propoxy]-6-methanesulfonylbenzoate |
| 322 | methyl 2-fluoro-4-[3-({[2-fluoro-3-(trifluoromethyl)phenyl]methyl}(2-phenylpropyl)amino)propoxy]-6-methanesulfonylbenzoate |

TABLE 4-continued

Additional LXR agonists of the Invention.

| # | Name |
|---|---|
| 323 | methyl 2-fluoro-4-[3-({[2-fluoro-3-(trifluoromethyl)phenyl]methyl}[(4-fluorophenyl)methyl]amino)propoxy]-6-methanesulfonylbenzoate |
| 324 | methyl 2-fluoro-4-[3-({[2-fluoro-3-(trifluoromethyl)phenyl]methyl}[2-(4-fluorophenyl)-2-methylpropyl]amino)propoxy]-6-methanesulfonylbenzoate |
| 325 | methyl 2-fluoro-4-[3-({[2-fluoro-3-(trifluoromethyl)phenyl]methyl}[2-(4-fluorophenyl)ethyl]amino)propoxy]-6-methanesulfonylbenzoate |
| 326 | methyl 2-fluoro-4-[3-({[2-fluoro-3-(trifluoromethyl)phenyl]methyl}[2-(4-fluorophenyl)propyl]amino)propoxy]-6-methanesulfonylbenzoate |
| 327 | methyl 2-methanesulfonyl-4-{3-[(2-methyl-2-phenylpropyl)({[3-(trifluoromethyl)phenyl]methyl})amino]propoxy}benzoate |
| 328 | methyl 2-methanesulfonyl-4-{3-[(2-phenylethyl)({[3-(trifluoromethyl)phenyl]methyl})amino]propoxy}benzoate |
| 329 | methyl 2-methanesulfonyl-4-{3-[(2-phenylpropyl)({[3-(trifluoromethyl)phenyl]methyl})amino]propoxy}benzoate |
| 330 | methyl 4-{3-[(2,2-diphenylethyl)({[2-fluoro-3-(trifluoromethyl)phenyl]methyl})amino]propoxy}-2-methanesulfonylbenzoate |
| 331 | methyl 4-{3-[(2,2-diphenylethyl)({[3-(trifluoromethyl)phenyl]methyl})amino]propoxy}-2-methanesulfonylbenzoate |
| 332 | methyl 4-{3-[benzyl({[2-chloro-3-(trifluoromethyl)phenyl]methyl})amino]propoxy}-2-methanesulfonylbenzoate |
| 333 | methyl 4-{3-[benzyl({[2-fluoro-3-(trifluoromethyl)phenyl]methyl})amino]propoxy}-2-methanesulfonylbenzoate |
| 334 | methyl 4-{3-[benzyl({[3-(trifluoromethyl)phenyl]methyl})amino]propoxy}-2-methanesulfonylbenzoate |
| 335 | methyl 4-(3-{[(4-fluorophenyl)methyl]({[3-(trifluoromethyl)phenyl]methyl})amino}propoxy)-2-methanesulfonylbenzoate |
| 336 | methyl 4-(3-{[2-(4-fluorophenyl)-2-methylpropyl]({[3-(trifluoromethyl)phenyl]methyl})amino}propoxy)-2-methanesulfonylbenzoate |
| 337 | methyl 4-(3-{[2-(4-fluorophenyl)ethyl]({[3-(trifluoromethyl)phenyl]methyl})amino}propoxy)-2-methanesulfonylbenzoate |
| 338 | methyl 4-(3-{[2-(4-fluorophenyl)propyl]({[3-(trifluoromethyl)phenyl]methyl})amino}propoxy)-2-methanesulfonylbenzoate |
| 339 | methyl 4-[3-({[2-chloro-3-(trifluoromethyl)phenyl]methyl}[2,2-difluoro-2-(4-fluorophenyl)ethyl]amino)propoxy]-2-methanesulfonylbenzoate |
| 340 | methyl 4-(3-{[2,2-difluoro-2-(4-fluorophenyl)ethyl]({[2-fluoro-3-(trifluoromethyl)phenyl]methyl})amino}propoxy)-2-methanesulfonylbenzoate |
| 341 | methyl 4-(3-{[2,2-difluoro-2-(4-fluorophenyl)ethyl]({[3-(trifluoromethyl)phenyl]methyl})amino}propoxy)-2-methanesulfonylbenzoate |
| 342 | methyl 4-[3-({[2-chloro-3-(trifluoromethyl)phenyl]methyl}(2-methyl-2-phenylpropyl)amino)propoxy]-2-methanesulfonylbenzoate |
| 343 | methyl 4-[3-({[2-chloro-3-(trifluoromethyl)phenyl]methyl}(2-phenylethyl)amino)propoxy]-2-methanesulfonylbenzoate |
| 344 | methyl 4-[3-({[2-chloro-3-(trifluoromethyl)phenyl]methyl}(2-phenylpropyl)amino)propoxy]-2-methanesulfonylbenzoate |
| 345 | methyl 4-[3-({[2-chloro-3-(trifluoromethyl)phenyl]methyl}(2,2-diphenylethyl)amino)propoxy]-2-methanesulfonylbenzoate |
| 346 | methyl 4-[3-({[2-chloro-3-(trifluoromethyl)phenyl]methyl}[(4-fluorophenyl)methyl]amino)propoxy]-2-methanesulfonylbenzoate |
| 347 | methyl 4-[3-({[2-chloro-3-(trifluoromethyl)phenyl]methyl}[2-(4-fluorophenyl)-2-methylpropyl]amino)propoxy]-2-methanesulfonylbenzoate |
| 348 | methyl 4-[3-({[2-chloro-3-(trifluoromethyl)phenyl]methyl}[2-(4-fluorophenyl)ethyl]amino)propoxy]-2-methanesulfonylbenzoate |
| 349 | methyl 4-[3-({[2-chloro-3-(trifluoromethyl)phenyl]methyl}[2-(4-fluorophenyl)propyl]amino)propoxy]-2-methanesulfonylbenzoate |
| 350 | methyl 4-[3-({[2-fluoro-3-(trifluoromethyl)phenyl]methyl}(2-methyl-2-phenylpropyl)amino)propoxy]-2-methanesulfonylbenzoate |
| 351 | methyl 4-[3-({[2-fluoro-3-(trifluoromethyl)phenyl]methyl}(2-phenylethyl)amino)propoxy]-2-methanesulfonylbenzoate |
| 352 | methyl 4-[3-({[2-fluoro-3-(trifluoromethyl)phenyl]methyl}(2-phenylpropyl)amino)propoxy]-2-methanesulfonylbenzoate |
| 353 | methyl 4-[3-({[2-fluoro-3-(trifluoromethyl)phenyl]methyl}[(4-fluorophenyl)methyl]amino)propoxy]-2-methanesulfonylbenzoate |
| 354 | methyl 4-[3-({[2-fluoro-3-(trifluoromethyl)phenyl]methyl}[2-(4-fluorophenyl)-2-methylpropyl]amino)propoxy]-2-methanesulfonylbenzoate |
| 355 | methyl 4-[3-({[2-fluoro-3-(trifluoromethyl)phenyl]methyl}[2-(4-fluorophenyl)ethyl]amino)propoxy]-2-methanesulfonylbenzoate |
| 356 | methyl 4-[3-({[2-fluoro-3-(trifluoromethyl)phenyl]methyl}[2-(4-fluorophenyl)propyl]amino)propoxy]-2-methanesulfonylbenzoate |
| 357 | 2-(2-fluoro-6-methanesulfonyl-4-{3-[(2-phenylpropyl)({[3-(trifluoromethyl)phenyl]methyl})amino]propoxy}phenyl)ethan-1-ol |
| 358 | 2-(2-fluoro-6-methanesulfonyl-4-{3-[(2-phenylethyl)({[3-(trifluoromethyl)phenyl]methyl})amino]propoxy}phenyl)ethan-1-ol |
| 359 | 2-(2-fluoro-6-methanesulfonyl-4-{3-[(2-methyl-2-phenylpropyl)({[3-(trifluoromethyl)phenyl]methyl})amino]propoxy}phenyl)ethan-1-ol |
| 360 | 2-(4-{3-[(2,2-diphenylethyl)({[2-fluoro-3-(trifluoromethyl)phenyl]methyl})amino]propoxy}-2-fluoro-6-methanesulfonylphenyl)ethan-1-ol |

TABLE 4-continued

Additional LXR agonists of the Invention.

| # | Name |
|---|---|
| 361 | 2-(4-{3-[benzyl({[2-chloro-3-(trifluoromethyl)phenyl]methyl})amino]propoxy}-2-fluoro-6-methanesulfonylphenyl)ethan-1-ol |
| 362 | 2-(4-{3-[benzyl({[3-(trifluoromethyl)phenyl]methyl})amino]propoxy}-2-fluoro-6-methanesulfonylphenyl)ethan-1-ol |
| 363 | 2-(4-{3-[benzyl({[2-fluoro-3-(trifluoromethyl)phenyl]methyl})amino]propoxy}-2-fluoro-6-methanesulfonylphenyl)ethan-1-ol |
| 364 | 2-[2-fluoro-4-(3-{[2-(4-fluorophenyl)ethyl]({[3-(trifluoromethyl)phenyl]methyl})amino}propoxy)-6-methanesulfonylphenyl]ethan-1-ol |
| 365 | 2-[2-fluoro-4-(3-{[2-(4-fluorophenyl)-2-methylpropyl]({[3-(trifluoromethyl)phenyl]methyl})amino}propoxy)-6-methanesulfonylphenyl]ethan-1-ol |
| 366 | 2-[2-fluoro-4-(3-{[2-(4-fluorophenyl)propyl]({[3-(trifluoromethyl)phenyl]methyl})amino}propoxy)-6-methanesulfonylphenyl]ethan-1-ol |
| 367 | 2-{4-[3-({[2-chloro-3-(trifluoromethyl)phenyl]methyl}[2,2-difluoro-2-(4-fluorophenyl)ethyl]amino)propoxy]-2-fluoro-6-methanesulfonylphenyl}ethan-1-ol |
| 368 | 2-[2-fluoro-4-(3-{[(4-fluorophenyl)methyl]({[3-(trifluoromethyl)phenyl]methyl})amino}propoxy)-6-methanesulfonylphenyl]ethan-1-ol |
| 369 | 2-[4-(3-{[2,2-difluoro-2-(4-fluorophenyl)ethyl]({[3-(trifluoromethyl)phenyl]methyl})amino}propoxy)-2-fluoro-6-methanesulfonylphenyl]ethan-1-ol |
| 370 | 2-{4-[3-({[2-chloro-3-(trifluoromethyl)phenyl]methyl}(2-methyl-2-phenylpropyl)amino)propoxy]-2-fluoro-6-methanesulfonylphenyl}ethan-1-ol |
| 371 | 2-(4-{3-[(2,2-diphenylethyl)({[3-(trifluoromethyl)phenyl]methyl})amino]propoxy}-2-fluoro-6-methanesulfonylphenyl)ethan-1-ol |
| 372 | 2-{4-[3-({[2-chloro-3-(trifluoromethyl)phenyl]methyl}(2-phenylethyl)amino)propoxy]-2-fluoro-6-methanesulfonylphenyl}ethan-1-ol |
| 373 | 2-{4-[3-({[2-chloro-3-(trifluoromethyl)phenyl]methyl}(2-phenylpropyl)amino)propoxy]-2-fluoro-6-methanesulfonylphenyl}ethan-1-ol |
| 374 | 2-{4-[3-({[2-chloro-3-(trifluoromethyl)phenyl]methyl}[2-(4-fluorophenyl)-2-methylpropyl]amino)propoxy]-2-fluoro-6-methanesulfonylphenyl}ethan-1-ol |
| 375 | 2-{4-[3-({[2-chloro-3-(trifluoromethyl)phenyl]methyl}[(4-fluorophenyl)methyl]amino)propoxy]-2-fluoro-6-methanesulfonylphenyl}ethan-1-ol |
| 376 | 2-{4-[3-({[2-chloro-3-(trifluoromethyl)phenyl]methyl}[2-(4-fluorophenyl)ethyl]amino)propoxy]-2-fluoro-6-methanesulfonylphenyl}ethan-1-ol |
| 377 | 2-{4-[3-({[2-chloro-3-(trifluoromethyl)phenyl]methyl}[2-(4-fluorophenyl)propyl]amino)propoxy]-2-fluoro-6-methanesulfonylphenyl}ethan-1-ol |
| 378 | 2-{2-fluoro-4-[3-({[2-fluoro-3-(trifluoromethyl)phenyl]methyl}(2-methyl-2-phenylpropyl)amino)propoxy]-6-methanesulfonylphenyl}ethan-1-ol |
| 379 | 2-[4-(3-{[2,2-difluoro-2-(4-fluorophenyl)ethyl]({[2-fluoro-3-(trifluoromethyl)phenyl]methyl})amino}propoxy)-2-fluoro-6-methanesulfonylphenyl]ethan-1-ol |
| 380 | 2-{2-fluoro-4-[3-({[2-fluoro-3-(trifluoromethyl)phenyl]methyl}(2-phenylpropyl)amino)propoxy]-6-methanesulfonylphenyl}ethan-1-ol |
| 381 | 2-{2-fluoro-4-[3-({[2-fluoro-3-(trifluoromethyl)phenyl]methyl}[(4-fluorophenyl)methyl]amino)propoxy]-6-methanesulfonylphenyl}ethan-1-ol |
| 382 | 2-{2-fluoro-4-[3-({[2-fluoro-3-(trifluoromethyl)phenyl]methyl}(2-phenylethyl)amino)propoxy]-6-methanesulfonylphenyl}ethan-1-ol |
| 383 | 2-{2-fluoro-4-[3-({[2-fluoro-3-(trifluoromethyl)phenyl]methyl}[2-(4-fluorophenyl)-2-methylpropyl]amino)propoxy]-6-methanesulfonylphenyl}ethan-1-ol |
| 384 | 2-{2-fluoro-4-[3-({[2-fluoro-3-(trifluoromethyl)phenyl]methyl}[2-(4-fluorophenyl)ethyl]amino)propoxy]-6-methanesulfonylphenyl}ethan-1-ol |
| 385 | 2-{2-fluoro-4-[3-({[2-fluoro-3-(trifluoromethyl)phenyl]methyl}[2-(4-fluorophenyl)propyl]amino)propoxy]-6-methanesulfonylphenyl}ethan-1-ol |
| 386 | 2-(2-methanesulfonyl-4-{3-[(2-methyl-2-phenylpropyl)({[3-(trifluoromethyl)phenyl]methyl})amino]propoxy}phenyl)ethan-1-ol |
| 387 | 2-(2-methanesulfonyl-4-{3-[(2-phenylethyl)({[3-(trifluoromethyl)phenyl]methyl})amino]propoxy}phenyl)ethan-1-ol |
| 388 | 2-(2-methanesulfonyl-4-{3-[(2-phenylpropyl)({[3-(trifluoromethyl)phenyl]methyl})amino]propoxy}phenyl)ethan-1-ol |
| 389 | 2-(4-{3-[(2,2-diphenylethyl)({[2-fluoro-3-(trifluoromethyl)phenyl]methyl})amino]propoxy}-2-methanesulfonylphenyl)ethan-1-ol |
| 390 | 2-(4-{3-[(2,2-diphenylethyl)({[3-(trifluoromethyl)phenyl]methyl})amino]propoxy}-2-methanesulfonylphenyl)ethan-1-ol |
| 391 | 2-(4-{3-[benzyl({[2-chloro-3-(trifluoromethyl)phenyl]methyl})amino]propoxy}-2-methanesulfonylphenyl)ethan-1-ol |
| 392 | 2-(4-{3-[benzyl({[2-fluoro-3-(trifluoromethyl)phenyl]methyl})amino]propoxy}-2-methanesulfonylphenyl)ethan-1-ol |
| 393 | 2-(4-{3-[benzyl({[3-(trifluoromethyl)phenyl]methyl})amino]propoxy}-2-methanesulfonylphenyl)ethan-1-ol |
| 394 | 2-[4-(3-{[(4-fluorophenyl)methyl]({[3-(trifluoromethyl)phenyl]methyl})amino}propoxy)-2-methanesulfonylphenyl]ethan-1-ol |
| 395 | 2-[4-(3-{[2-(4-fluorophenyl)-2-methylpropyl]({[3-(trifluoromethyl)phenyl]methyl})amino}propoxy)-2-methanesulfonylphenyl]ethan-1-ol |
| 396 | 2-[4-(3-{[2-(4-fluorophenyl)ethyl]({[3-(trifluoromethyl)phenyl]methyl})amino}propoxy)-2-methanesulfonylphenyl]ethan-1-ol |
| 397 | 2-[4-(3-{[2-(4-fluorophenyl)propyl]({[3-(trifluoromethyl)phenyl]methyl})amino}propoxy)-2-methanesulfonylphenyl]ethan-1-ol |

TABLE 4-continued

Additional LXR agonists of the Invention.

| # | Name |
|---|------|
| 398 | 2-{4-[3-({[2-chloro-3-(trifluoromethyl)phenyl]methyl}[2,2-difluoro-2-(4-fluorophenyl)ethyl]amino)propoxy]-2-methanesulfonylphenyl}ethan-1-ol |
| 399 | 2-[4-(3-{[2,2-difluoro-2-(4-fluorophenyl)ethyl]({[2-fluoro-3-(trifluoromethyl)phenyl]methyl})amino}propoxy)-2-methanesulfonylphenyl]ethan-1-ol |
| 400 | 2-[4-(3-{[2,2-difluoro-2-(4-fluorophenyl)ethyl]({[3-(trifluoromethyl)phenyl]methyl})amino}propoxy)-2-methanesulfonylphenyl]ethan-1-ol |
| 401 | 2-{4-[3-({[2-chloro-3-(trifluoromethyl)phenyl]methyl}(2-methyl-2-phenylpropyl)amino)propoxy]-2-methanesulfonylphenyl}ethan-1-ol |
| 402 | 2-{4-[3-({[2-chloro-3-(trifluoromethyl)phenyl]methyl}(2-phenylethyl)amino)propoxy]-2-methanesulfonylphenyl}ethan-1-ol |
| 403 | 2-{4-[3-({[2-chloro-3-(trifluoromethyl)phenyl]methyl}(2-phenylpropyl)amino)propoxy]-2-methanesulfonylphenyl}ethan-1-ol |
| 404 | 2-{4-[3-({[2-chloro-3-(trifluoromethyl)phenyl]methyl}(2,2-diphenylethyl)amino)propoxy]-2-methanesulfonylphenyl}ethan-1-ol |
| 405 | 2-{4-[3-({[2-chloro-3-(trifluoromethyl)phenyl]methyl}[(4-fluorophenyl)methyl]amino)propoxy]-2-methanesulfonylphenyl}ethan-1-ol |
| 406 | 2-{4-[3-({[2-chloro-3-(trifluoromethyl)phenyl]methyl}[2-(4-fluorophenyl)-2-methylpropyl]amino)propoxy]-2-methanesulfonylphenyl}ethan-1-ol |
| 407 | 2-{4-[3-({[2-chloro-3-(trifluoromethyl)phenyl]methyl}[2-(4-fluorophenyl)ethyl]amino)propoxy]-2-methanesulfonylphenyl}ethan-1-ol |
| 408 | 2-{4-[3-({[2-chloro-3-(trifluoromethyl)phenyl]methyl}[2-(4-fluorophenyl)propyl]amino)propoxy]-2-methanesulfonylphenyl}ethan-1-ol |
| 409 | 2-{4-[3-({[2-fluoro-3-(trifluoromethyl)phenyl]methyl}(2-methyl-2-phenylpropyl)amino)propoxy]-2-methanesulfonylphenyl}ethan-1-ol |
| 410 | 2-{4-[3-({[2-fluoro-3-(trifluoromethyl)phenyl]methyl}(2-phenylethyl)amino)propoxy]-2-methanesulfonylphenyl}ethan-1-ol |
| 411 | 2-{4-[3-({[2-fluoro-3-(trifluoromethyl)phenyl]methyl}(2-phenylpropyl)amino)propoxy]-2-methanesulfonylphenyl}ethan-1-ol |
| 412 | 2-{4-[3-({[2-fluoro-3-(trifluoromethyl)phenyl]methyl}[(4-fluorophenyl)methyl]amino)propoxy]-2-methanesulfonylphenyl}ethan-1-ol |
| 413 | 2-{4-[3-({[2-fluoro-3-(trifluoromethyl)phenyl]methyl}[2-(4-fluorophenyl)-2-methylpropyl]amino)propoxy]-2-methanesulfonylphenyl}ethan-1-ol |
| 414 | 2-{4-[3-({[2-fluoro-3-(trifluoromethyl)phenyl]methyl}[2-(4-fluorophenyl)ethyl]amino)propoxy]-2-methanesulfonylphenyl}ethan-1-ol |
| 415 | 2-{4-[3-({[2-fluoro-3-(trifluoromethyl)phenyl]methyl}[2-(4-fluorophenyl)propyl]amino)propoxy]-2-methanesulfonylphenyl}ethan-1-ol |
| 416 | 2-(2-fluoro-6-methanesulfonyl-4-{3-[(2-phenylethyl)({[3-(trifluoromethyl)phenyl]methyl})amino]propoxy}phenyl)acetic acid |
| 417 | 2-(2-fluoro-6-methanesulfonyl-4-{3-[(2-phenylpropyl)({[3-(trifluoromethyl)phenyl]methyl})amino]propoxy}phenyl)acetic acid |
| 418 | 2-(4-{3-[(2,2-diphenylethyl)({[2-fluoro-3-(trifluoromethyl)phenyl]methyl})amino]propoxy}-2-fluoro-6-methanesulfonylphenyl)acetic acid |
| 419 | 2-(4-{3-[benzyl({[2-chloro-3-(trifluoromethyl)phenyl]methyl})amino]propoxy}-2-fluoro-6-methanesulfonylphenyl)acetic acid |
| 420 | 2-(4-{3-[benzyl({[2-fluoro-3-(trifluoromethyl)phenyl]methyl})amino]propoxy}-2-fluoro-6-methanesulfonylphenyl)acetic acid |
| 421 | 2-(4-{3-[benzyl({[3-(trifluoromethyl)phenyl]methyl})amino]propoxy}-2-fluoro-6-methanesulfonylphenyl)acetic acid |
| 422 | 2-[2-fluoro-4-(3-{[(4-fluorophenyl)methyl]({[3-(trifluoromethyl)phenyl]methyl})amino}propoxy)-6-methanesulfonylphenyl]acetic acid |
| 423 | 2-[2-fluoro-4-(3-{[2-(4-fluorophenyl)-2-methylpropyl]({[3-(trifluoromethyl)phenyl]methyl})amino}propoxy)-6-methanesulfonylphenyl]acetic acid |
| 424 | 2-[2-fluoro-4-(3-{[2-(4-fluorophenyl)ethyl]({[3-(trifluoromethyl)phenyl]methyl})amino}propoxy)-6-methanesulfonylphenyl]acetic acid |
| 425 | 2-[2-fluoro-4-(3-{[2-(4-fluorophenyl)propyl]({[3-(trifluoromethyl)phenyl]methyl})amino}propoxy)-6-methanesulfonylphenyl]acetic acid |
| 426 | 2-{4-[3-({[2-chloro-3-(trifluoromethyl)phenyl]methyl}[2,2-difluoro-2-(4-fluorophenyl)ethyl]amino)propoxy]-2-fluoro-6-methanesulfonylphenyl}acetic acid |
| 427 | 2-[4-(3-{[2,2-difluoro-2-(4-fluorophenyl)ethyl]({[2-fluoro-3-(trifluoromethyl)phenyl]methyl})amino}propoxy)-2-fluoro-6-methanesulfonylphenyl]acetic acid |
| 428 | 2-[4-(3-{[2,2-difluoro-2-(4-fluorophenyl)ethyl]({[3-(trifluoromethyl)phenyl]methyl})amino}propoxy)-2-fluoro-6-methanesulfonylphenyl]acetic acid |
| 429 | 2-{4-[3-({[2-chloro-3-(trifluoromethyl)phenyl]methyl}(2-methyl-2-phenylpropyl)amino)propoxy]-2-fluoro-6-methanesulfonylphenyl}acetic acid |
| 430 | 2-{4-[3-({[2-chloro-3-(trifluoromethyl)phenyl]methyl}(2-phenylethyl)amino)propoxy]-2-fluoro-6-methanesulfonylphenyl}acetic acid |
| 431 | 2-{4-[3-({[2-chloro-3-(trifluoromethyl)phenyl]methyl}(2-phenylpropyl)amino)propoxy]-2-fluoro-6-methanesulfonylphenyl}acetic acid |
| 432 | 2-{4-[3-({[2-chloro-3-(trifluoromethyl)phenyl]methyl}(2,2-diphenylethyl)amino)propoxy]-2-fluoro-6-methanesulfonylphenyl}acetic acid |
| 433 | 2-{4-[3-({[2-chloro-3-(trifluoromethyl)phenyl]methyl}[(4-fluorophenyl)methyl]amino)propoxy]-2-fluoro-6-methanesulfonylphenyl}acetic acid |
| 434 | 2-{4-[3-({[2-chloro-3-(trifluoromethyl)phenyl]methyl}[2-(4-fluorophenyl)-2-methylpropyl]amino)propoxy]-2-fluoro-6-methanesulfonylphenyl}acetic acid |

TABLE 4-continued

Additional LXR agonists of the Invention.

| # | Name |
|---|---|
| 435 | 2-{4-[3-({[2-chloro-3-(trifluoromethyl)phenyl]methyl}[2-(4-fluorophenyl)ethyl]amino)propoxy]-2-fluoro-6-methanesulfonylphenyl}acetic acid |
| 436 | 2-{4-[3-({[2-chloro-3-(trifluoromethyl)phenyl]methyl}[2-(4-fluorophenyl)propyl]amino)propoxy]-2-fluoro-6-methanesulfonylphenyl}acetic acid |
| 437 | 2-(4-{3-[(2,2-diphenylethyl)({[3-(trifluoromethyl)phenyl]methyl})amino]propoxy}-2-fluoro-6-methanesulfonylphenyl)acetic acid |
| 438 | 2-{2-fluoro-4-[3-({[2-fluoro-3-(trifluoromethyl)phenyl]methyl}(2-methyl-2-phenylpropyl)amino)propoxy]-6-methanesulfonylphenyl}acetic acid |
| 439 | 2-(2-fluoro-6-methanesulfonyl-4-{3-[(2-methyl-2-phenylpropyl)({[3-(trifluoromethyl)phenyl]methyl})amino]propoxy}phenyl)acetic acid |
| 440 | 2-{2-fluoro-4-[3-({[2-fluoro-3-(trifluoromethyl)phenyl]methyl}(2-phenylpropyl)amino)propoxy]-6-methanesulfonylphenyl}acetic acid |
| 441 | 2-{2-fluoro-4-[3-({[2-fluoro-3-(trifluoromethyl)phenyl]methyl}[(4-fluorophenyl)methyl]amino)propoxy]-6-methanesulfonylphenyl}acetic acid |
| 442 | 2-{2-fluoro-4-[3-({[2-fluoro-3-(trifluoromethyl)phenyl]methyl}[2-(4-fluorophenyl)-2-methylpropyl]amino)propoxy]-6-methanesulfonylphenyl}acetic acid |
| 443 | 2-{2-fluoro-4-[3-({[2-fluoro-3-(trifluoromethyl)phenyl]methyl}[2-(4-fluorophenyl)ethyl]amino)propoxy]-6-methanesulfonylphenyl}acetic acid |
| 444 | 2-{2-fluoro-4-[3-({[2-fluoro-3-(trifluoromethyl)phenyl]methyl}(2-phenylethyl)amino)propoxy]-6-methanesulfonylphenyl}acetic acid |
| 445 | 2-{2-fluoro-4-[3-({[2-fluoro-3-(trifluoromethyl)phenyl]methyl}[2-(4-fluorophenyl)propyl]amino)propoxy]-6-methanesulfonylphenyl}acetic acid |
| 446 | 2-(2-methanesulfonyl-4-{3-[(2-methyl-2-phenylpropyl)({[3-(trifluoromethyl)phenyl]methyl})amino]propoxy}phenyl)acetic acid |
| 447 | 2-(2-methanesulfonyl-4-{3-[(2-phenylethyl)({[3-(trifluoromethyl)phenyl]methyl})amino]propoxy}phenyl)acetic acid |
| 448 | 2-(2-methanesulfonyl-4-{3-[(2-phenylpropyl)({[3-(trifluoromethyl)phenyl]methyl})amino]propoxy}phenyl)acetic acid |
| 449 | 2-(4-{3-[(2,2-diphenylethyl)({[2-fluoro-3-(trifluoromethyl)phenyl]methyl})amino]propoxy}-2-methanesulfonylphenyl)acetic acid |
| 450 | 2-(4-{3-[(2,2-diphenylethyl)({[3-(trifluoromethyl)phenyl]methyl})amino]propoxy}-2-methanesulfonylphenyl)acetic acid |
| 451 | 2-(4-{3-[benzyl({[2-chloro-3-(trifluoromethyl)phenyl]methyl})amino]propoxy}-2-methanesulfonylphenyl)acetic acid |
| 452 | 2-(4-{3-[benzyl({[2-fluoro-3-(trifluoromethyl)phenyl]methyl})amino]propoxy}-2-methanesulfonylphenyl)acetic acid |
| 453 | 2-(4-{3-[benzyl({[3-(trifluoromethyl)phenyl]methyl})amino]propoxy}-2-methanesulfonylphenyl)acetic acid |
| 454 | 2-[4-(3-{[(4-fluorophenyl)methyl]({[3-(trifluoromethyl)phenyl]methyl})amino}propoxy)-2-methanesulfonylphenyl]acetic acid |
| 455 | 2-[4-(3-{[2-(4-fluorophenyl)-2-methylpropyl]({[3-(trifluoromethyl)phenyl]methyl})amino}propoxy)-2-methanesulfonylphenyl]acetic acid |
| 456 | 2-[4-(3-{[2-(4-fluorophenyl)ethyl]({[3-(trifluoromethyl)phenyl]methyl})amino}propoxy)-2-methanesulfonylphenyl]acetic acid |
| 457 | 2-[4-(3-{[2-(4-fluorophenyl)propyl]({[3-(trifluoromethyl)phenyl]methyl})amino}propoxy)-2-methanesulfonylphenyl]acetic acid |
| 458 | 2-{4-[3-({[2-chloro-3-(trifluoromethyl)phenyl]methyl}[2,2-difluoro-2-(4-fluorophenyl)ethyl]amino)propoxy]-2-methanesulfonylphenyl}acetic acid |
| 459 | 2-[4-(3-{[2,2-difluoro-2-(4-fluorophenyl)ethyl]({[2-fluoro-3-(trifluoromethyl)phenyl]methyl})amino}propoxy)-2-methanesulfonylphenyl]acetic acid |
| 460 | 2-[4-(3-{[2,2-difluoro-2-(4-fluorophenyl)ethyl]({[3-(trifluoromethyl)phenyl]methyl})amino}propoxy)-2-methanesulfonylphenyl]acetic acid |
| 461 | 2-{4-[3-({[2-chloro-3-(trifluoromethyl)phenyl]methyl}(2-methyl-2-phenylpropyl)amino)propoxy]-2-methanesulfonylphenyl}acetic acid |
| 462 | 2-{4-[3-({[2-chloro-3-(trifluoromethyl)phenyl]methyl}(2-phenylethyl)amino)propoxy]-2-methanesulfonylphenyl}acetic acid |
| 463 | 2-{4-[3-({[2-chloro-3-(trifluoromethyl)phenyl]methyl}(2-phenylpropyl)amino)propoxy]-2-methanesulfonylphenyl}acetic acid |
| 464 | 2-{4-[3-({[2-chloro-3-(trifluoromethyl)phenyl]methyl}(2,2-diphenylethyl)amino)propoxy]-2-methanesulfonylphenyl}acetic acid |
| 465 | 2-{4-[3-({[2-chloro-3-(trifluoromethyl)phenyl]methyl}[(4-fluorophenyl)methyl]amino)propoxy]-2-methanesulfonylphenyl}acetic acid |
| 466 | 2-{4-[3-({[2-chloro-3-(trifluoromethyl)phenyl]methyl}[2-(4-fluorophenyl)-2-methylpropyl]amino)propoxy]-2-methanesulfonylphenyl}acetic acid |
| 467 | 2-{4-[3-({[2-chloro-3-(trifluoromethyl)phenyl]methyl}[2-(4-fluorophenyl)ethyl]amino)propoxy]-2-methanesulfonylphenyl}acetic acid |
| 468 | 2-{4-[3-({[2-chloro-3-(trifluoromethyl)phenyl]methyl}[2-(4-fluorophenyl)propyl]amino)propoxy]-2-methanesulfonylphenyl}acetic acid |
| 469 | 2-{4-[3-({[2-fluoro-3-(trifluoromethyl)phenyl]methyl}(2-methyl-2-phenylpropyl)amino)propoxy]-2-methanesulfonylphenyl}acetic acid |
| 470 | 2-{4-[3-({[2-fluoro-3-(trifluoromethyl)phenyl]methyl}(2-phenylethyl)amino)propoxy]-2-methanesulfonylphenyl}acetic acid |
| 471 | 2-{4-[3-({[2-fluoro-3-(trifluoromethyl)phenyl]methyl}(2-phenylpropyl)amino)propoxy]-2-methanesulfonylphenyl}acetic acid |
| 472 | 2-{4-[3-({[2-fluoro-3-(trifluoromethyl)phenyl]methyl}[(4-fluorophenyl)methyl]amino)propoxy]-2-methanesulfonylphenyl}acetic acid |

TABLE 4-continued

Additional LXR agonists of the Invention.

| # | Name |
|---|------|
| 473 | 2-{4-[3-({[2-fluoro-3-(trifluoromethyl)phenyl]methyl}[2-(4-fluorophenyl)-2-methylpropyl]amino)propoxy]-2-methanesulfonylphenyl}acetic acid |
| 474 | 2-{4-[3-({[2-fluoro-3-(trifluoromethyl)phenyl]methyl}[2-(4-fluorophenyl)ethyl]amino)propoxy]-2-methanesulfonylphenyl}acetic acid |
| 475 | 2-{4-[3-({[2-fluoro-3-(trifluoromethyl)phenyl]methyl}[2-(4-fluorophenyl)propyl]amino)propoxy]-2-methanesulfonylphenyl}acetic acid |
| 476 | N-[(2-fluoro-6-methanesulfonyl-4-{3-[(2-phenylethyl)({[3-(trifluoromethyl)phenyl]methyl})amino]propoxy}phenyl)methyl]acetamide |
| 477 | N-[(4-{3-[(2,2-diphenylethyl)({[2-fluoro-3-(trifluoromethyl)phenyl]methyl})amino]propoxy}-2-fluoro-6-methanesulfonylphenyl)methyl]acetamide |
| 478 | N-[(2-fluoro-6-methanesulfonyl-4-{3-[(2-phenylpropyl)({[3-(trifluoromethyl)phenyl]methyl})amino]propoxy}phenyl)methyl]acetamide |
| 479 | N-[(2-fluoro-6-methanesulfonyl-4-{3-[(2-methyl-2-phenylpropyl)({[3-(trifluoromethyl)phenyl]methyl})amino]propoxy}phenyl)methyl]acetamide |
| 480 | N-[(4-{3-[(2,2-diphenylethyl)({[3-(trifluoromethyl)phenyl]methyl})amino]propoxy}-2-fluoro-6-methanesulfonylphenyl)methyl]acetamide |
| 481 | N-[(4-{3-[benzyl({[2-chloro-3-(trifluoromethyl)phenyl]methyl})amino]propoxy}-2-fluoro-6-methanesulfonylphenyl)methyl]acetamide |
| 482 | N-[(4-{3-[benzyl({[3-(trifluoromethyl)phenyl]methyl})amino]propoxy}-2-fluoro-6-methanesulfonylphenyl)methyl]acetamide |
| 483 | N-{[2-fluoro-4-(3-{[(4-fluorophenyl)methyl]({[3-(trifluoromethyl)phenyl]methyl})amino}propoxy)-6-methanesulfonylphenyl]methyl}acetamide |
| 484 | N-{[2-fluoro-4-(3-{[2-(4-fluorophenyl)-2-methylpropyl]({[3-(trifluoromethyl)phenyl]methyl})amino}propoxy)-6-methanesulfonylphenyl]methyl}acetamide |
| 485 | N-{[2-fluoro-4-(3-{[2-(4-fluorophenyl)propyl]({[3-(trifluoromethyl)phenyl]methyl})amino}propoxy)-6-methanesulfonylphenyl]methyl}acetamide |
| 486 | N-{[4-(3-{[2,2-difluoro-2-(4-fluorophenyl)ethyl]({[2-fluoro-3-(trifluoromethyl)phenyl]methyl})amino}propoxy)-2-fluoro-6-methanesulfonylphenyl]methyl}acetamide |
| 487 | N-({4-[3-({[2-chloro-3-(trifluoromethyl)phenyl]methyl}[2,2-difluoro-2-(4-fluorophenyl)ethyl]amino)propoxy]-2-fluoro-6-methanesulfonylphenyl}methyl)acetamide |
| 488 | N-{[4-(3-{[2,2-difluoro-2-(4-fluorophenyl)ethyl]({[3-(trifluoromethyl)phenyl]methyl})amino}propoxy)-2-fluoro-6-methanesulfonylphenyl]methyl}acetamide |
| 489 | N-({4-[3-({[2-chloro-3-(trifluoromethyl)phenyl]methyl}(2-methyl-2-phenylpropyl)amino)propoxy]-2-fluoro-6-methanesulfonylphenyl}methyl)acetamide |
| 490 | N-({4-[3-({[2-chloro-3-(trifluoromethyl)phenyl]methyl}(2-phenylethyl)amino)propoxy]-2-fluoro-6-methanesulfonylphenyl}methyl)acetamide |
| 491 | N-({4-[3-({[2-chloro-3-(trifluoromethyl)phenyl]methyl}(2-phenylpropyl)amino)propoxy]-2-fluoro-6-methanesulfonylphenyl}methyl)acetamide |
| 492 | N-({4-[3-({[2-chloro-3-(trifluoromethyl)phenyl]methyl}[(4-fluorophenyl)methyl]amino)propoxy]-2-fluoro-6-methanesulfonylphenyl}methyl)acetamide |
| 493 | N-({4-[3-({[2-chloro-3-(trifluoromethyl)phenyl]methyl}[2-(4-fluorophenyl)-2-methylpropyl]amino)propoxy]-2-fluoro-6-methanesulfonylphenyl}methyl)acetamide |
| 494 | N-({4-[3-({[2-chloro-3-(trifluoromethyl)phenyl]methyl}[2-(4-fluorophenyl)ethyl]amino)propoxy]-2-fluoro-6-methanesulfonylphenyl}methyl)acetamide |
| 495 | N-({4-[3-({[2-chloro-3-(trifluoromethyl)phenyl]methyl}[2-(4-fluorophenyl)propyl]amino)propoxy]-2-fluoro-6-methanesulfonylphenyl}methyl)acetamide |
| 496 | N-({2-fluoro-4-[3-({[2-fluoro-3-(trifluoromethyl)phenyl]methyl}(2-methyl-2-phenylpropyl)amino)propoxy]-6-methanesulfonylphenyl}methyl)acetamide |
| 497 | N-({2-fluoro-4-[3-({[2-fluoro-3-(trifluoromethyl)phenyl]methyl}(2-phenylethyl)amino)propoxy]-6-methanesulfonylphenyl}methyl)acetamide |
| 498 | N-({2-fluoro-4-[3-({[2-fluoro-3-(trifluoromethyl)phenyl]methyl}(2-phenylpropyl)amino)propoxy]-6-methanesulfonylphenyl}methyl)acetamide |
| 499 | N-{[2-fluoro-4-(3-{[2-(4-fluorophenyl)ethyl]({[3-(trifluoromethyl)phenyl]methyl})amino}propoxy)-6-methanesulfonylphenyl]methyl}acetamide |
| 500 | N-[(4-{3-[benzyl({[2-fluoro-3-(trifluoromethyl)phenyl]methyl})amino]propoxy}-2-fluoro-6-methanesulfonylphenyl)methyl]acetamide |
| 501 | N-({2-fluoro-4-[3-({[2-fluoro-3-(trifluoromethyl)phenyl]methyl}[(4-fluorophenyl)methyl]amino)propoxy]-6-methanesulfonylphenyl}methyl)acetamide |
| 502 | N-({2-fluoro-4-[3-({[2-fluoro-3-(trifluoromethyl)phenyl]methyl}[2-(4-fluorophenyl)-2-methylpropyl]amino)propoxy]-6-methanesulfonylphenyl}methyl)acetamide |
| 503 | N-({2-fluoro-4-[3-({[2-fluoro-3-(trifluoromethyl)phenyl]methyl}[2-(4-fluorophenyl)ethyl]amino)propoxy]-6-methanesulfonylphenyl}methyl)acetamide |
| 504 | N-({2-fluoro-4-[3-({[2-fluoro-3-(trifluoromethyl)phenyl]methyl}[2-(4-fluorophenyl)propyl]amino)propoxy]-6-methanesulfonylphenyl}methyl)acetamide |
| 505 | N-[(2-methanesulfonyl-4-{3-[(2-methyl-2-phenylpropyl)({[3-(trifluoromethyl)phenyl]methyl})amino]propoxy}phenyl)methyl]acetamide |
| 506 | N-[(2-methanesulfonyl-4-{3-[(2-phenylethyl)({[3-(trifluoromethyl)phenyl]methyl})amino]propoxy}phenyl)methyl]acetamide |

TABLE 4-continued

Additional LXR agonists of the Invention.

| # | Name |
|---|---|
| 507 | N-[(2-methanesulfonyl-4-{3-[(2-phenylpropyl)({[3-(trifluoromethyl)phenyl]methyl})amino]propoxy}phenyl)methyl]acetamide |
| 508 | N-[(4-{3-[(2,2-diphenylethyl)({[2-fluoro-3-(trifluoromethyl)phenyl]methyl})amino]propoxy}-2-methanesulfonylphenyl)methyl]acetamide |
| 509 | N-[(4-{3-[(2,2-diphenylethyl)({[3-(trifluoromethyl)phenyl]methyl})amino]propoxy}-2-methanesulfonylphenyl)methyl]acetamide |
| 510 | N-[(4-{3-[benzyl({[2-chloro-3-(trifluoromethyl)phenyl]methyl})amino]propoxy}-2-methanesulfonylphenyl)methyl]acetamide |
| 511 | N-[(4-{3-[benzyl({[2-fluoro-3-(trifluoromethyl)phenyl]methyl})amino]propoxy}-2-methanesulfonylphenyl)methyl]acetamide |
| 512 | N-[(4-{3-[benzyl({[3-(trifluoromethyl)phenyl]methyl})amino]propoxy}-2-methanesulfonylphenyl)methyl]acetamide |
| 513 | N-{[4-(3-{[(4-fluorophenyl)methyl]({[3-(trifluoromethyl)phenyl]methyl})amino}propoxy)-2-methanesulfonylphenyl]methyl}acetamide |
| 514 | N-{[4-(3-{[2-(4-fluorophenyl)-2-methylpropyl]({[3-(trifluoromethyl)phenyl]methyl})amino}propoxy)-2-methanesulfonylphenyl]methyl}acetamide |
| 515 | N-{[4-(3-{[2-(4-fluorophenyl)ethyl]({[3-(trifluoromethyl)phenyl]methyl})amino}propoxy)-2-methanesulfonylphenyl]methyl}acetamide |
| 516 | N-{[4-(3-{[2-(4-fluorophenyl)propyl]({[3-(trifluoromethyl)phenyl]methyl})amino}propoxy)-2-methanesulfonylphenyl]methyl}acetamide |
| 517 | N-({4-[3-({[2-chloro-3-(trifluoromethyl)phenyl]methyl}[2,2-difluoro-2-(4-fluorophenyl)ethyl]amino)propoxy]-2-methanesulfonylphenyl}methyl)acetamide |
| 518 | N-{[4-(3-{[2,2-difluoro-2-(4-fluorophenyl)ethyl]({[2-fluoro-3-(trifluoromethyl)phenyl]methyl})amino}propoxy)-2-methanesulfonylphenyl]methyl}acetamide |
| 519 | N-{[4-(3-{[2,2-difluoro-2-(4-fluorophenyl)ethyl]({[3-(trifluoromethyl)phenyl]methyl})amino}propoxy)-2-methanesulfonylphenyl]methyl}acetamide |
| 520 | N-({4-[3-({[2-chloro-3-(trifluoromethyl)phenyl]methyl}(2-methyl-2-phenylpropyl)amino)propoxy]-2-methanesulfonylphenyl}methyl)acetamide |
| 521 | N-({4-[3-({[2-chloro-3-(trifluoromethyl)phenyl]methyl}(2-phenylethyl)amino)propoxy]-2-methanesulfonylphenyl}methyl)acetamide |
| 522 | N-({4-[3-({[2-chloro-3-(trifluoromethyl)phenyl]methyl}(2-phenylpropyl)amino)propoxy]-2-methanesulfonylphenyl}methyl)acetamide |
| 523 | N-({4-[3-({[2-chloro-3-(trifluoromethyl)phenyl]methyl}(2,2-diphenylethyl)amino)propoxy]-2-methanesulfonylphenyl}methyl)acetamide |
| 524 | N-({4-[3-({[2-chloro-3-(trifluoromethyl)phenyl]methyl}[(4-fluorophenyl)methyl]amino)propoxy]-2-methanesulfonylphenyl}methyl)acetamide |
| 525 | N-({4-[3-({[2-chloro-3-(trifluoromethyl)phenyl]methyl}[2-(4-fluorophenyl)-2-methylpropyl]amino)propoxy]-2-methanesulfonylphenyl}methyl)acetamide |
| 526 | N-({4-[3-({[2-chloro-3-(trifluoromethyl)phenyl]methyl}[2-(4-fluorophenyl)ethyl]amino)propoxy]-2-methanesulfonylphenyl}methyl)acetamide |
| 527 | N-({4-[3-({[2-chloro-3-(trifluoromethyl)phenyl]methyl}[2-(4-fluorophenyl)propyl]amino)propoxy]-2-methanesulfonylphenyl}methyl)acetamide |
| 528 | N-({4-[3-({[2-fluoro-3-(trifluoromethyl)phenyl]methyl}(2-methyl-2-phenylpropyl)amino)propoxy]-2-methanesulfonylphenyl}methyl)acetamide |
| 529 | N-({4-[3-({[2-fluoro-3-(trifluoromethyl)phenyl]methyl}(2-phenylethyl)amino)propoxy]-2-methanesulfonylphenyl}methyl)acetamide |
| 530 | N-({4-[3-({[2-fluoro-3-(trifluoromethyl)phenyl]methyl}(2-phenylpropyl)amino)propoxy]-2-methanesulfonylphenyl}methyl)acetamide |
| 531 | N-({4-[3-({[2-fluoro-3-(trifluoromethyl)phenyl]methyl}[(4-fluorophenyl)methyl]amino)propoxy]-2-methanesulfonylphenyl}methyl)acetamide |
| 532 | N-({4-[3-({[2-fluoro-3-(trifluoromethyl)phenyl]methyl}[2-(4-fluorophenyl)-2-methylpropyl]amino)propoxy]-2-methanesulfonylphenyl}methyl)acetamide |
| 533 | N-({4-[3-({[2-fluoro-3-(trifluoromethyl)phenyl]methyl}[2-(4-fluorophenyl)ethyl]amino)propoxy]-2-methanesulfonylphenyl}methyl)acetamide |
| 534 | N-({4-[3-({[2-fluoro-3-(trifluoromethyl)phenyl]methyl}[2-(4-fluorophenyl)propyl]amino)propoxy]-2-methanesulfonylphenyl}methyl)acetamide |
| 535 | 2-(2-fluoro-6-methanesulfonyl-4-{3-[(2-methyl-2-phenylpropyl)({[3-(trifluoromethyl)phenyl]methyl})amino]propoxy}phenyl)propan-2-ol |
| 536 | 2-(2-fluoro-6-methanesulfonyl-4-{3-[(2-phenylethyl)({[3-(trifluoromethyl)phenyl]methyl})amino]propoxy}phenyl)propan-2-ol |
| 537 | 2-(2-fluoro-6-methanesulfonyl-4-{3-[(2-phenylpropyl)({[3-(trifluoromethyl)phenyl]methyl})amino]propoxy}phenyl)propan-2-ol |
| 538 | 2-(4-{3-[(2,2-diphenylethyl)({[3-(trifluoromethyl)phenyl]methyl})amino]propoxy}-2-fluoro-6-methanesulfonylphenyl)propan-2-ol |
| 539 | 2-(4-{3-[benzyl({[2-chloro-3-(trifluoromethyl)phenyl]methyl})amino]propoxy}-2-fluoro-6-methanesulfonylphenyl)propan-2-ol |
| 540 | 2-(4-{3-[benzyl({[2-fluoro-3-(trifluoromethyl)phenyl]methyl})amino]propoxy}-2-fluoro-6-methanesulfonylphenyl)propan-2-ol |
| 541 | 2-(4-{3-[benzyl({[3-(trifluoromethyl)phenyl]methyl})amino]propoxy}-2-fluoro-6-methanesulfonylphenyl)propan-2-ol |
| 542 | 2-(4-{3-[(2,2-diphenylethyl)({[2-fluoro-3-(trifluoromethyl)phenyl]methyl})amino]propoxy}-2-fluoro-6-methanesulfonylphenyl)propan-2-ol |

TABLE 4-continued

Additional LXR agonists of the Invention.

| # | Name |
|---|---|
| 543 | 2-[2-fluoro-4-(3-{[(4-fluorophenyl)methyl]({[3-(trifluoromethyl)phenyl]methyl})amino}propoxy)-6-methanesulfonylphenyl]propan-2-ol |
| 544 | 2-[2-fluoro-4-(3-{[2-(4-fluorophenyl)ethyl]({[3-(trifluoromethyl)phenyl]methyl})amino}propoxy)-6-methanesulfonylphenyl]propan-2-ol |
| 545 | 2-[2-fluoro-4-(3-{[2-(4-fluorophenyl)-2-methylpropyl]({[3-(trifluoromethyl)phenyl]methyl})amino}propoxy)-6-methanesulfonylphenyl]propan-2-ol |
| 546 | 2-[2-fluoro-4-(3-{[2-(4-fluorophenyl)propyl]({[3-(trifluoromethyl)phenyl]methyl})amino}propoxy)-6-methanesulfonylphenyl]propan-2-ol |
| 547 | 2-{4-[3-({[2-chloro-3-(trifluoromethyl)phenyl]methyl}[2,2-difluoro-2-(4-fluorophenyl)ethyl]amino)propoxy]-2-fluoro-6-methanesulfonylphenyl}propan-2-ol |
| 548 | 2-[4-(3-{[2,2-difluoro-2-(4-fluorophenyl)ethyl]({[3-(trifluoromethyl)phenyl]methyl})amino}propoxy)-2-fluoro-6-methanesulfonylphenyl]propan-2-ol |
| 549 | 2-[4-(3-{[2,2-difluoro-2-(4-fluorophenyl)ethyl]({[2-fluoro-3-(trifluoromethyl)phenyl]methyl})amino}propoxy)-2-fluoro-6-methanesulfonylphenyl]propan-2-ol |
| 550 | 2-{4-[3-({[2-chloro-3-(trifluoromethyl)phenyl]methyl}(2-methyl-2-phenylpropyl)amino)propoxy]-2-fluoro-6-methanesulfonylphenyl}propan-2-ol |
| 551 | 2-{4-[3-({[2-chloro-3-(trifluoromethyl)phenyl]methyl}(2-phenylethyl)amino)propoxy]-2-fluoro-6-methanesulfonylphenyl}propan-2-ol |
| 552 | 2-{4-[3-({[2-chloro-3-(trifluoromethyl)phenyl]methyl}[(4-fluorophenyl)methyl]amino)propoxy]-2-fluoro-6-methanesulfonylphenyl}propan-2-ol |
| 553 | 2-{4-[3-({[2-chloro-3-(trifluoromethyl)phenyl]methyl}(2-phenylpropyl)amino)propoxy]-2-fluoro-6-methanesulfonylphenyl}propan-2-ol |
| 554 | 2-{4-[3-({[2-chloro-3-(trifluoromethyl)phenyl]methyl}[2-(4-fluorophenyl)-2-methylpropyl]amino)propoxy]-2-fluoro-6-methanesulfonylphenyl}propan-2-ol |
| 555 | 2-{4-[3-({[2-chloro-3-(trifluoromethyl)phenyl]methyl}[2-(4-fluorophenyl)ethyl]amino)propoxy]-2-fluoro-6-methanesulfonylphenyl}propan-2-ol |
| 556 | 2-{2-fluoro-4-[3-({[2-fluoro-3-(trifluoromethyl)phenyl]methyl}(2-methyl-2-phenylpropyl)amino)propoxy]-6-methanesulfonylphenyl}propan-2-ol |
| 557 | 2-{4-[3-({[2-chloro-3-(trifluoromethyl)phenyl]methyl}[2-(4-fluorophenyl)propyl]amino)propoxy]-2-fluoro-6-methanesulfonylphenyl}propan-2-ol |
| 558 | 2-{2-fluoro-4-[3-({[2-fluoro-3-(trifluoromethyl)phenyl]methyl}(2-phenylethyl)amino)propoxy]-6-methanesulfonylphenyl}propan-2-ol |
| 559 | 2-{2-fluoro-4-[3-({[2-fluoro-3-(trifluoromethyl)phenyl]methyl}(2-phenylpropyl)amino)propoxy]-6-methanesulfonylphenyl}propan-2-ol |
| 560 | 2-{2-fluoro-4-[3-({[2-fluoro-3-(trifluoromethyl)phenyl]methyl}[(4-fluorophenyl)methyl]amino)propoxy]-6-methanesulfonylphenyl}propan-2-ol |
| 561 | 2-{2-fluoro-4-[3-({[2-fluoro-3-(trifluoromethyl)phenyl]methyl}[2-(4-fluorophenyl)-2-methylpropyl]amino)propoxy]-6-methanesulfonylphenyl}propan-2-ol |
| 562 | 2-{2-fluoro-4-[3-({[2-fluoro-3-(trifluoromethyl)phenyl]methyl}[2-(4-fluorophenyl)ethyl]amino)propoxy]-6-methanesulfonylphenyl}propan-2-ol |
| 563 | 2-{2-fluoro-4-[3-({[2-fluoro-3-(trifluoromethyl)phenyl]methyl}[2-(4-fluorophenyl)propyl]amino)propoxy]-6-methanesulfonylphenyl}propan-2-ol |
| 564 | 2-(2-methanesulfonyl-4-{3-[(2-methyl-2-phenylpropyl)({[3-(trifluoromethyl)phenyl]methyl})amino]propoxy}phenyl)propan-2-ol |
| 565 | 2-(2-methanesulfonyl-4-{3-[(2-phenylethyl)({[3-(trifluoromethyl)phenyl]methyl})amino]propoxy}phenyl)propan-2-ol |
| 566 | 2-(2-methanesulfonyl-4-{3-[(2-phenylpropyl)({[3-(trifluoromethyl)phenyl]methyl})amino]propoxy}phenyl)propan-2-ol |
| 567 | 2-(4-{3-[(2,2-diphenylethyl)({[2-fluoro-3-(trifluoromethyl)phenyl]methyl})amino]propoxy}-2-methanesulfonylphenyl)propan-2-ol |
| 568 | 2-(4-{3-[(2,2-diphenylethyl)({[3-(trifluoromethyl)phenyl]methyl})amino]propoxy}-2-methanesulfonylphenyl)propan-2-ol |
| 569 | 2-(4-{3-[benzyl({[2-chloro-3-(trifluoromethyl)phenyl]methyl})amino]propoxy}-2-methanesulfonylphenyl)propan-2-ol |
| 570 | 2-(4-{3-[benzyl({[2-fluoro-3-(trifluoromethyl)phenyl]methyl})amino]propoxy}-2-methanesulfonylphenyl)propan-2-ol |
| 571 | 2-(4-{3-[benzyl({[3-(trifluoromethyl)phenyl]methyl})amino]propoxy}-2-methanesulfonylphenyl)propan-2-ol |
| 572 | 2-[4-(3-{[(4-fluorophenyl)methyl]({[3-(trifluoromethyl)phenyl]methyl})amino}propoxy)-2-methanesulfonylphenyl]propan-2-ol |
| 573 | 2-[4-(3-{[2-(4-fluorophenyl)-2-methylpropyl]({[3-(trifluoromethyl)phenyl]methyl})amino}propoxy)-2-methanesulfonylphenyl]propan-2-ol |
| 574 | 2-[4-(3-{[2-(4-fluorophenyl)ethyl]({[3-(trifluoromethyl)phenyl]methyl})amino}propoxy)-2-methanesulfonylphenyl]propan-2-ol |
| 575 | 2-[4-(3-{[2-(4-fluorophenyl)propyl]({[3-(trifluoromethyl)phenyl]methyl})amino}propoxy)-2-methanesulfonylphenyl]propan-2-ol |
| 576 | 2-{4-[3-({[2-chloro-3-(trifluoromethyl)phenyl]methyl}[2,2-difluoro-2-(4-fluorophenyl)ethyl]amino)propoxy]-2-methanesulfonylphenyl}propan-2-ol |
| 577 | 2-[4-(3-{[2,2-difluoro-2-(4-fluorophenyl)ethyl]({[2-fluoro-3-(trifluoromethyl)phenyl]methyl})amino}propoxy)-2-methanesulfonylphenyl]propan-2-ol |
| 578 | 2-[4-(3-{[2,2-difluoro-2-(4-fluorophenyl)ethyl]({[3-(trifluoromethyl)phenyl]methyl})amino}propoxy)-2-methanesulfonylphenyl]propan-2-ol |
| 579 | 2-{4-[3-({[2-chloro-3-(trifluoromethyl)phenyl]methyl}(2-methyl-2-phenylpropyl)amino)propoxy]-2-methanesulfonylphenyl}propan-2-ol |

TABLE 4-continued

Additional LXR agonists of the Invention.

| # | Name |
|---|---|
| 580 | 2-{4-[3-({[2-chloro-3-(trifluoromethyl)phenyl]methyl}(2-phenylethyl)amino)propoxy]-2-methanesulfonylphenyl}propan-2-ol |
| 581 | 2-{4-[3-({[2-chloro-3-(trifluoromethyl)phenyl]methyl}(2-phenylpropyl)amino)propoxy]-2-methanesulfonylphenyl}propan-2-ol |
| 582 | 2-{4-[3-({[2-chloro-3-(trifluoromethyl)phenyl]methyl}[(4-fluorophenyl)methyl]amino)propoxy]-2-methanesulfonylphenyl}propan-2-ol |
| 583 | 2-{4-[3-({[2-chloro-3-(trifluoromethyl)phenyl]methyl}[2-(4-fluorophenyl)-2-methylpropyl]amino)propoxy]-2-methanesulfonylphenyl}propan-2-ol |
| 584 | 2-{4-[3-({[2-chloro-3-(trifluoromethyl)phenyl]methyl}[2-(4-fluorophenyl)ethyl]amino)propoxy]-2-methanesulfonylphenyl}propan-2-ol |
| 585 | 2-{4-[3-({[2-chloro-3-(trifluoromethyl)phenyl]methyl}[2-(4-fluorophenyl)propyl]amino)propoxy]-2-methanesulfonylphenyl}propan-2-ol |
| 586 | 2-{4-[3-({[2-fluoro-3-(trifluoromethyl)phenyl]methyl}(2-methyl-2-phenylpropyl)amino)propoxy]-2-methanesulfonylphenyl}propan-2-ol |
| 587 | 2-{4-[3-({[2-fluoro-3-(trifluoromethyl)phenyl]methyl}(2-phenylethyl)amino)propoxy]-2-methanesulfonylphenyl}propan-2-ol |
| 588 | 2-{4-[3-({[2-fluoro-3-(trifluoromethyl)phenyl]methyl}(2-phenylpropyl)amino)propoxy]-2-methanesulfonylphenyl}propan-2-ol |
| 589 | 2-{4-[3-({[2-fluoro-3-(trifluoromethyl)phenyl]methyl}[(4-fluorophenyl)methyl]amino)propoxy]-2-methanesulfonylphenyl}propan-2-ol |
| 590 | 2-{4-[3-({[2-fluoro-3-(trifluoromethyl)phenyl]methyl}[2-(4-fluorophenyl)-2-methylpropyl]amino)propoxy]-2-methanesulfonylphenyl}propan-2-ol |
| 591 | 2-{4-[3-({[2-fluoro-3-(trifluoromethyl)phenyl]methyl}[2-(4-fluorophenyl)ethyl]amino)propoxy]-2-methanesulfonylphenyl}propan-2-ol |
| 592 | 2-{4-[3-({[2-fluoro-3-(trifluoromethyl)phenyl]methyl}[2-(4-fluorophenyl)propyl]amino)propoxy]-2-methanesulfonylphenyl}propan-2-ol |
| 593 | 2-{4-[3-({[2-chloro-3-(trifluoromethyl)phenyl]methyl}(2,2-diphenylethyl)amino)propoxy]-2-methanesulfonylphenyl}propan-2-ol |
| 594 | 6-(3-{[(4-fluorophenyl)methyl]({[3-(trifluoromethyl)phenyl]methyl})amino}propoxy)-3,4-dihydro-1H-2-benzopyran-3-one |
| 595 | 6-(3-{[2-(4-fluorophenyl)-2-methylpropyl]({[3-(trifluoromethyl)phenyl]methyl})amino}propoxy)-3,4-dihydro-1H-2-benzopyran-3-one |
| 596 | 6-(3-{[2-(4-fluorophenyl)ethyl]({[3-(trifluoromethyl)phenyl]methyl})amino}propoxy)-3,4-dihydro-1H-2-benzopyran-3-one |
| 597 | 6-(3-{[2-(4-fluorophenyl)propyl]({[3-(trifluoromethyl)phenyl]methyl})amino}propoxy)-3,4-dihydro-1H-2-benzopyran-3-one |
| 598 | 6-[3-({[2-chloro-3-(trifluoromethyl)phenyl]methyl}[2,2-difluoro-2-(4-fluorophenyl)ethyl]amino)propoxy]-3,4-dihydro-1H-2-benzopyran-3-one |
| 599 | 6-(3-{[2,2-difluoro-2-(4-fluorophenyl)ethyl]({[2-fluoro-3-(trifluoromethyl)phenyl]methyl})amino}propoxy)-3,4-dihydro-1H-2-benzopyran-3-one |
| 600 | 6-(3-{[2,2-difluoro-2-(4-fluorophenyl)ethyl]({[3-(trifluoromethyl)phenyl]methyl})amino}propoxy)-3,4-dihydro-1H-2-benzopyran-3-one |
| 601 | 6-[3-({[2-chloro-3-(trifluoromethyl)phenyl]methyl}(2-methyl-2-phenylpropyl)amino)propoxy]-3,4-dihydro-1H-2-benzopyran-3-one |
| 602 | 6-[3-({[2-chloro-3-(trifluoromethyl)phenyl]methyl}(2-phenylethyl)amino)propoxy]-3,4-dihydro-1H-2-benzopyran-3-one |
| 603 | 6-[3-({[2-chloro-3-(trifluoromethyl)phenyl]methyl}(2-phenylpropyl)amino)propoxy]-3,4-dihydro-1H-2-benzopyran-3-one |
| 604 | 6-[3-({[2-chloro-3-(trifluoromethyl)phenyl]methyl}[(4-fluorophenyl)methyl]amino)propoxy]-3,4-dihydro-1H-2-benzopyran-3-one |
| 605 | 6-[3-({[2-chloro-3-(trifluoromethyl)phenyl]methyl}[2-(4-fluorophenyl)-2-methylpropyl]amino)propoxy]-3,4-dihydro-1H-2-benzopyran-3-one |
| 606 | 6-[3-({[2-chloro-3-(trifluoromethyl)phenyl]methyl}[2-(4-fluorophenyl)ethyl]amino)propoxy]-3,4-dihydro-1H-2-benzopyran-3-one |
| 607 | 6-[3-({[2-chloro-3-(trifluoromethyl)phenyl]methyl}[2-(4-fluorophenyl)propyl]amino)propoxy]-3,4-dihydro-1H-2-benzopyran-3-one |
| 608 | 6-[3-({[2-fluoro-3-(trifluoromethyl)phenyl]methyl}(2-methyl-2-phenylpropyl)amino)propoxy]-3,4-dihydro-1H-2-benzopyran-3-one |
| 609 | 6-[3-({[2-fluoro-3-(trifluoromethyl)phenyl]methyl}(2-phenylethyl)amino)propoxy]-3,4-dihydro-1H-2-benzopyran-3-one |
| 610 | 6-[3-({[2-fluoro-3-(trifluoromethyl)phenyl]methyl}(2-phenylpropyl)amino)propoxy]-3,4-dihydro-1H-2-benzopyran-3-one |
| 611 | 6-[3-({[2-fluoro-3-(trifluoromethyl)phenyl]methyl}[(4-fluorophenyl)methyl]amino)propoxy]-3,4-dihydro-1H-2-benzopyran-3-one |
| 612 | 6-[3-({[2-fluoro-3-(trifluoromethyl)phenyl]methyl}[2-(4-fluorophenyl)-2-methylpropyl]amino)propoxy]-3,4-dihydro-1H-2-benzopyran-3-one |
| 613 | 6-[3-({[2-fluoro-3-(trifluoromethyl)phenyl]methyl}[2-(4-fluorophenyl)ethyl]amino)propoxy]-3,4-dihydro-1H-2-benzopyran-3-one |
| 614 | 6-[3-({[2-fluoro-3-(trifluoromethyl)phenyl]methyl}[2-(4-fluorophenyl)propyl]amino)propoxy]-3,4-dihydro-1H-2-benzopyran-3-one |
| 615 | 6-{3-[(2-methyl-2-phenylpropyl)({[3-(trifluoromethyl)phenyl]methyl})amino]propoxy}-3,4-dihydro-1H-2-benzopyran-3-one |
| 616 | 6-{3-[(2-phenylethyl)({[3-(trifluoromethyl)phenyl]methyl})amino]propoxy}-3,4-dihydro-1H-2-benzopyran-3-one |
| 617 | 6-{3-[(2-phenylpropyl)({[3-(trifluoromethyl)phenyl]methyl})amino]propoxy}-3,4-dihydro-1H-2-benzopyran-3-one |

TABLE 4-continued

Additional LXR agonists of the Invention.

| # | Name |
|---|------|
| 618 | 6-{3-[(2,2-diphenylethyl)({[2-fluoro-3-(trifluoromethyl)phenyl]methyl})amino]propoxy}-3,4-dihydro-1H-2-benzopyran-3-one |
| 619 | 6-{3-[(2,2-diphenylethyl)({[3-(trifluoromethyl)phenyl]methyl})amino]propoxy}-3,4-dihydro-1H-2-benzopyran-3-one |
| 620 | 6-{3-[benzyl({[2-chloro-3-(trifluoromethyl)phenyl]methyl})amino]propoxy}-3,4-dihydro-1H-2-benzopyran-3-one |
| 621 | 6-{3-[benzyl({[2-fluoro-3-(trifluoromethyl)phenyl]methyl})amino]propoxy}-3,4-dihydro-1H-2-benzopyran-3-one |
| 622 | 6-{3-[benzyl({[3-(trifluoromethyl)phenyl]methyl})amino]propoxy}-3,4-dihydro-1H-2-benzopyran-3-one |
| 623 | {3-[(1-methanesulfonylpiperidin-3-yl)oxy]propyl}(2-methyl-2-phenylpropyl){[3-(trifluoromethyl)phenyl]methyl}amine |
| 624 | {3-[(1-methanesulfonylpiperidin-3-yl)oxy]propyl}(2-phenylethyl){[3-(trifluoromethyl)phenyl]methyl}amine |
| 625 | {3-[(1-methanesulfonylpiperidin-3-yl)oxy]propyl}(2-phenylpropyl){[3-(trifluoromethyl)phenyl]methyl}amine |
| 626 | (2,2-diphenylethyl)({[2-fluoro-3-(trifluoromethyl)phenyl]methyl}){3-[(1-methanesulfonylpiperidin-3-yl)oxy]propyl}amine |
| 627 | (2,2-diphenylethyl)({3-[(1-methanesulfonylpiperidin-3-yl)oxy]propyl}){[3-(trifluoromethyl)phenyl]methyl}amine |
| 628 | benzyl({[2-chloro-3-(trifluoromethyl)phenyl]methyl}){3-[(1-methanesulfonylpiperidin-3-yl)oxy]propyl}amine |
| 629 | benzyl({[2-fluoro-3-(trifluoromethyl)phenyl]methyl}){3-[(1-methanesulfonylpiperidin-3-yl)oxy]propyl}amine |
| 630 | benzyl({3-[(1-methanesulfonylpiperidin-3-yl)oxy]propyl}){[3-(trifluoromethyl)phenyl]methyl}amine |
| 631 | [(4-fluorophenyl)methyl]({3-[(1-methanesulfonylpiperidin-3-yl)oxy]propyl}){[3-(trifluoromethyl)phenyl]methyl}amine |
| 632 | [2-(4-fluorophenyl)-2-methylpropyl]({3-[(1-methanesulfonylpiperidin-3-yl)oxy]propyl}){[3-(trifluoromethyl)phenyl]methyl}amine |
| 633 | [2-(4-fluorophenyl)ethyl]({3-[(1-methanesulfonylpiperidin-3-yl)oxy]propyl}){[3-(trifluoromethyl)phenyl]methyl}amine |
| 634 | [2-(4-fluorophenyl)propyl]({3-[(1-methanesulfonylpiperidin-3-yl)oxy]propyl}){[3-(trifluoromethyl)phenyl]methyl}amine |
| 635 | {[2-chloro-3-(trifluoromethyl)phenyl]methyl}[2,2-difluoro-2-(4-fluorophenyl)ethyl]{3-[(1-methanesulfonylpiperidin-3-yl)oxy]propyl}amine |
| 636 | [2,2-difluoro-2-(4-fluorophenyl)ethyl]({[2-fluoro-3-(trifluoromethyl)phenyl]methyl}){3-[(1-methanesulfonylpiperidin-3-yl)oxy]propyl}amine |
| 637 | [2,2-difluoro-2-(4-fluorophenyl)ethyl]({3-[(1-methanesulfonylpiperidin-3-yl)oxy]propyl}){[3-(trifluoromethyl)phenyl]methyl}amine |
| 638 | {[2-chloro-3-(trifluoromethyl)phenyl]methyl}({3-[(1-methanesulfonylpiperidin-3-yl)oxy]propyl})(2-methyl-2-phenylpropyl)amine |
| 639 | {[2-chloro-3-(trifluoromethyl)phenyl]methyl}({3-[(1-methanesulfonylpiperidin-3-yl)oxy]propyl})(2-phenylethyl)amine |
| 640 | {[2-chloro-3-(trifluoromethyl)phenyl]methyl}({3-[(1-methanesulfonylpiperidin-3-yl)oxy]propyl})(2-phenylpropyl)amine |
| 641 | {[2-chloro-3-(trifluoromethyl)phenyl]methyl}[(4-fluorophenyl)methyl]{3-[(1-methanesulfonylpiperidin-3-yl)oxy]propyl}amine |
| 642 | {[2-chloro-3-(trifluoromethyl)phenyl]methyl}[2-(4-fluorophenyl)-2-methylpropyl]{3-[(1-methanesulfonylpiperidin-3-yl)oxy]propyl}amine |
| 643 | {[2-chloro-3-(trifluoromethyl)phenyl]methyl}[2-(4-fluorophenyl)ethyl]{3-[(1-methanesulfonylpiperidin-3-yl)oxy]propyl}amine |
| 644 | {[2-chloro-3-(trifluoromethyl)phenyl]methyl}[2-(4-fluorophenyl)propyl]{3-[(1-methanesulfonylpiperidin-3-yl)oxy]propyl}amine |
| 645 | {[2-fluoro-3-(trifluoromethyl)phenyl]methyl}({3-[(1-methanesulfonylpiperidin-3-yl)oxy]propyl})(2-methyl-2-phenylpropyl)amine |
| 646 | {[2-fluoro-3-(trifluoromethyl)phenyl]methyl}({3-[(1-methanesulfonylpiperidin-3-yl)oxy]propyl})(2-phenylethyl)amine |
| 647 | {[2-fluoro-3-(trifluoromethyl)phenyl]methyl}({3-[(1-methanesulfonylpiperidin-3-yl)oxy]propyl})(2-phenylpropyl)amine |
| 648 | {[2-fluoro-3-(trifluoromethyl)phenyl]methyl}[(4-fluorophenyl)methyl]{3-[(1-methanesulfonylpiperidin-3-yl)oxy]propyl}amine |
| 649 | {[2-fluoro-3-(trifluoromethyl)phenyl]methyl}[2-(4-fluorophenyl)-2-methylpropyl]{3-[(1-methanesulfonylpiperidin-3-yl)oxy]propyl}amine |
| 650 | {[2-fluoro-3-(trifluoromethyl)phenyl]methyl}[2-(4-fluorophenyl)ethyl]{3-[(1-methanesulfonylpiperidin-3-yl)oxy]propyl}amine |
| 651 | {[2-fluoro-3-(trifluoromethyl)phenyl]methyl}[2-(4-fluorophenyl)propyl]{3-[(1-methanesulfonylpiperidin-3-yl)oxy]propyl}amine |
| 652 | {3-[(1-methanesulfonylazetidin-3-yl)oxy]propyl}(2-methyl-2-phenylpropyl){[3-(trifluoromethyl)phenyl]methyl}amine |
| 653 | {3-[(1-methanesulfonylazetidin-3-yl)oxy]propyl}(2-phenylethyl){[3-(trifluoromethyl)phenyl]methyl}amine |
| 654 | {3-[(1-methanesulfonylazetidin-3-yl)oxy]propyl}(2-phenylpropyl){[3-(trifluoromethyl)phenyl]methyl}amine |
| 655 | (2,2-diphenylethyl)({[2-fluoro-3-(trifluoromethyl)phenyl]methyl}){3-[(1-methanesulfonylazetidin-3-yl)oxy]propyl}amine |

TABLE 4-continued

Additional LXR agonists of the Invention.

| # | Name |
|---|---|
| 656 | (2,2-diphenylethyl)({3-[(1-methanesulfonylazetidin-3-yl)oxy]propyl}){[3-(trifluoromethyl)phenyl]methyl}amine |
| 657 | benzyl({[2-chloro-3-(trifluoromethyl)phenyl]methyl}){3-[(1-methanesulfonylazetidin-3-yl)oxy]propyl}amine |
| 658 | benzyl({[2-fluoro-3-(trifluoromethyl)phenyl]methyl}){3-[(1-methanesulfonylazetidin-3-yl)oxy]propyl}amine |
| 659 | benzyl({3-[(1-methanesulfonylazetidin-3-yl)oxy]propyl}){[3-(trifluoromethyl)phenyl]methyl}amine |
| 660 | [(4-fluorophenyl)methyl]({3-[(1-methanesulfonylazetidin-3-yl)oxy]propyl}){[3-(trifluoromethyl)phenyl]methyl}amine |
| 661 | [2-(4-fluorophenyl)-2-methylpropyl]({3-[(1-methanesulfonylazetidin-3-yl)oxy]propyl}){[3-(trifluoromethyl)phenyl]methyl}amine |
| 662 | [2-(4-fluorophenyl)ethyl]({3-[(1-methanesulfonylazetidin-3-yl)oxy]propyl}){[3-(trifluoromethyl)phenyl]methyl}amine |
| 663 | [2-(4-fluorophenyl)propyl]({3-[(1-methanesulfonylazetidin-3-yl)oxy]propyl}){[3-(trifluoromethyl)phenyl]methyl}amine |
| 664 | {[2-chloro-3-(trifluoromethyl)phenyl]methyl}[2,2-difluoro-2-(4-fluorophenyl)ethyl]{3-[(1-methanesulfonylazetidin-3-yl)oxy]propyl}amine |
| 665 | [2,2-difluoro-2-(4-fluorophenyl)ethyl]({[2-fluoro-3-(trifluoromethyl)phenyl]methyl}){3-[(1-methanesulfonylazetidin-3-yl)oxy]propyl}amine |
| 666 | [2,2-difluoro-2-(4-fluorophenyl)ethyl]({3-[(1-methanesulfonylazetidin-3-yl)oxy]propyl}){[3-(trifluoromethyl)phenyl]methyl}amine |
| 667 | {[2-chloro-3-(trifluoromethyl)phenyl]methyl}({3-[(1-methanesulfonylazetidin-3-yl)oxy]propyl})(2-methyl-2-phenylpropyl)amine |
| 668 | {[2-chloro-3-(trifluoromethyl)phenyl]methyl}({3-[(1-methanesulfonylazetidin-3-yl)oxy]propyl})(2-phenylethyl)amine |
| 669 | {[2-chloro-3-(trifluoromethyl)phenyl]methyl}({3-[(1-methanesulfonylazetidin-3-yl)oxy]propyl})(2-phenylpropyl)amine |
| 670 | {[2-chloro-3-(trifluoromethyl)phenyl]methyl}[(4-fluorophenyl)methyl]{3-[(1-methanesulfonylazetidin-3-yl)oxy]propyl}amine |
| 671 | {[2-chloro-3-(trifluoromethyl)phenyl]methyl}[2-(4-fluorophenyl)-2-methylpropyl]{3-[(1-methanesulfonylazetidin-3-yl)oxy]propyl}amine |
| 672 | {[2-chloro-3-(trifluoromethyl)phenyl]methyl}[2-(4-fluorophenyl)ethyl]{3-[(1-methanesulfonylazetidin-3-yl)oxy]propyl}amine |
| 673 | {[2-chloro-3-(trifluoromethyl)phenyl]methyl}[2-(4-fluorophenyl)propyl]{3-[(1-methanesulfonylazetidin-3-yl)oxy]propyl}amine |
| 674 | {[2-fluoro-3-(trifluoromethyl)phenyl]methyl}({3-[(1-methanesulfonylazetidin-3-yl)oxy]propyl})(2-methyl-2-phenylpropyl)amine |
| 675 | {[2-fluoro-3-(trifluoromethyl)phenyl]methyl}({3-[(1-methanesulfonylazetidin-3-yl)oxy]propyl})(2-phenylethyl)amine |
| 676 | {[2-fluoro-3-(trifluoromethyl)phenyl]methyl}({3-[(1-methanesulfonylazetidin-3-yl)oxy]propyl})(2-phenylpropyl)amine |
| 677 | {[2-fluoro-3-(trifluoromethyl)phenyl]methyl}[(4-fluorophenyl)methyl]{3-[(1-methanesulfonylazetidin-3-yl)oxy]propyl}amine |
| 678 | {[2-fluoro-3-(trifluoromethyl)phenyl]methyl}[2-(4-fluorophenyl)-2-methylpropyl]{3-[(1-methanesulfonylazetidin-3-yl)oxy]propyl}amine |
| 679 | {[2-fluoro-3-(trifluoromethyl)phenyl]methyl}[2-(4-fluorophenyl)ethyl]{3-[(1-methanesulfonylazetidin-3-yl)oxy]propyl}amine |
| 680 | {[2-fluoro-3-(trifluoromethyl)phenyl]methyl}[2-(4-fluorophenyl)propyl]{3-[(1-methanesulfonylazetidin-3-yl)oxy]propyl}amine |

Example 84: ApoE Gene Expression Analysis by qRT-PCR

Cancer cells (MeWo) were treated in presence of drug or control (DMSO) at indicated concentrations for 48 h. RNA was extracted from whole cell lysates using the Total RNA Purification Kit (17200, Norgen, Thorold, Canada). 600 ng of total RNA was then reverse transcribed into cDNA using the Verso cDNA Synthesis Kit (AB-1453/B, Fisher Scientific). 6 ng of the resulting cDNA was then mixed with SYBR green PCR Master Mix (4309155, Applied Biosystems) and the appropriate primers. Each reaction was performed in quadruplicate, and mRNA expression was quantified by performing real-time PCR amplification using a StepOne Plus Real-Time PCR System (Applied Biosystems). GAPDH was used as an endogenous control for normalization. $EC_{50}$ values were calculated using Prism6 software and plotting expression values versus drug concentration.

The following primers were used:

```
ApoE Forward:
                                  (SEQ ID NO: 1)
5'-TGGGTCGCTTTTGGGATTAC-3'

ApoE Reverse:
                                  (SEQ ID NO: 2)
5'-TTCAACTCCTTCATGGTCTCG-3'

GAPDH Forward:
                                  (SEQ ID NO: 3)
5'-AGCCACATCGCTCAGACAC-3'

GAPDH Reverse:
                                  (SEQ ID NO: 4)
5'-GCCCAATACGACCAAATCC-3'
```

Results: The results of ApoE gene expression analysis are shown in Table 5. The results are shown in relation to GW3965 ApoE expression at 1 μM (i.e. 100%). $EC_{50}$ values for selected compounds are shown in Table 6.

TABLE 5

Results of ApoE gene expression analysis

| Compound | 1 μM | 10 μM |
|---|---|---|
| GW3965 | 100% | ++ |
| SB742881 | ++ | ++ |
| WO2007002563 Tb. 1 Ex. 19 | ++ | ++ |
| WO20100138598 Ex. 9 | ++ | ++ |
| WO2013138565 Racemic Ex. E2a | ++ | ++ |
| 1 | +++ | + |
| 2 | ++ | ++ |
| 3 | ++ | + |
| 4 | ++ | ++ |
| 6 | +++ | ++ |
| 7 | +++ | ++ |
| 8 | +++ | +++ |
| 9 | ++ | +++ |
| 24 | ++ | ++ |
| 25 | ++ | + |
| 26 | + | + |
| 29 | ++ | +++ |
| 30 | ++ | +++ |
| 31 | ++ | +++ |
| 35 | + | ++ |
| 59 | ++ | ++ |
| 60 | ++ | +++ |
| 61 | ++ | +++ |
| 62 | +++ | +++ |
| 63 | +++ | +++ |
| 64 | +++ | +++ |
| 65 | +++ | +++ |
| 66 | +++ | +++ |
| 67 | + | + |
| 71 | + | ND |
| 72 | +++ | +++ |
| 73 | +++ | +++ |
| 74 | ++ | ++ |
| 75 | ++ | +++ |
| 78 | ++ | ND |
| 79 | +++ | +++ |
| 80 | +++ | +++ |
| 81 | ++ | ++ |
| 82 | ++ | ND |
| 83 | +++ | ND |
| 84 | ++ | ++ |
| 85 | +++ | ND |
| 87 | ++ | ND |
| 88 | +++ | ND |
| 89 | +++ | +++ |
| 90 | +++ | ND |
| 91 | +++ | ++ |
| 92 | ++ | ND |
| 93 | + | + |
| 95 | ++ | ND |
| 96 | ++ | ND |

"+++" > 80% ApoE induction,
"++" > 40% induction,
and "+" < 40% induction,
ND = Not Determined

TABLE 6

$EC_{50}$ values for ApoE expression for selected compounds

| Compound | $EC_{50}$ (μM) |
|---|---|
| GW3965 | <0.3 |
| SB742881 | <1.0 |
| WO20100138598 Ex. 9 | <1.0 |
| WO2013138565 Racemic Ex. E2a | <0.3 |
| 1 | <1.0 |
| 4 | <1.0 |
| 6 | <0.3 |
| 7 | <1.0 |
| 8 | <1.0 |
| 9 | <0.3 |
| 29 | <0.3 |
| 31 | <1.0 |
| 35 | <3.0 |
| 59 | <0.3 |
| 60 | <0.3 |
| 62 | <1.0 |
| 63 | <3.0 |
| 64 | <1.0 |
| 65 | <1.0 |
| 66 | <3.0 |
| 79 | <1.0 |
| 80 | <1.0 |
| 81 | <0.3 |
| 83 | <1.0 |
| 85 | <1.0 |
| 89 | <1.0 |
| 90 | <1.0 |

Example 85: Matrigel Invasion Assay

Cancer cells (MeWo) were pre-treated in presence of 1 μM drug or control (DMSO) for 72 h after which cancer cells were switched to serum-starvation in 0.2% FBS DMEM-based media for 16 h in the presence of the drug or control, respectively. Trans-well invasion chambers (354480, BD Biosciences, Bedford, Mass.) were pre-equilibrated in DMEM-based media prior to the beginning of the assay by adding 0.5 ml of starvation media to the top and bottom chambers. After 30 min, the media in the top chamber was removed, and 0.5 ml of media containing $1 \times 10^5$ cancer cells in the presence of the drug, was added into each matrigel-coated trans-well insert. Cells were allowed to invade through the matrigel-coated inserts for 24 h at 37° C.

Results: The results of the invasion assay with select compounds are shown in Table 7.

TABLE 7

Invasion assay results

| Compound | % of Cells Migrated Compared to Control |
|---|---|
| GW3965 | <70% |
| SB742881 | <70% |
| WO20100138598 Ex. 9 | <90% |
| DMSO Control | 100% |
| 1 | <95% |
| 8 | <50% |
| 9 | <50% |
| 29 | <50% |
| 31 | <70% |

Example 86: Whole Blood Gene Expression Analysis of ApoE

Six drops of blood are collected from BL6 mice by Submandibular Sampling into serum blood sample collection tubes, inverted 8-10 times before centrifugation at 2,000 g for 10 min. Blood serum is removed and RNA was extracted from whole cell lysates using the Total RNA Purification Kit (17200, Norgen, Thorold, Canada). 600 ng of total RNA is then reverse transcribed into cDNA using the Verso cDNA Synthesis Kit (AB-1453/B, Fisher Scientific). 6 ng of the resulting cDNA is then mixed with SYBR green PCR Master Mix (4309155, Applied Biosystems) and the appropriate primers. Each reaction is performed in quadruplicate, and mRNA expression is quantified by performing real-time PCR amplification using a StepOne Plus Real-Time PCR System (Applied Biosystems). GAPDH is used as an endogenous control for normalization.

The following primers were used:

```
ApoE Forward:
                              (SEQ ID NO: 5)
5'-GACCCTGGAGGCTAAGGACT-3'

ApoE Reverse:
                              (SEQ ID NO: 6)
5'-AGAGCCTTCATCTTCGCAAT-3'

GAPDH Forward:
                              (SEQ ID NO: 7)
5'-GCACAGTCAAGGCCGAGAAT-3'

GAPDH Reverse:
                              (SEQ ID NO: 8)
5'-GCCTTCTCCATGGTGGTGAA-3'
```

Example 87: In Vivo Primary Tumor Growth Assay

For primary tumor growth studies, $5 \times 10^4$ B16F10 melanoma cells were mixed 1:1 with matrigel and subcutaneously injected into the lower flanks of 6-week old C57B16 mice. Upon the formation of palpable tumors, 4-5 days after tumor cell injection, 10 mice were randomly assigned to groups eating a control diet or a diet supplemented with compound 8 (5 and 25 mg/kg). Tumor volume was calculated as (small diameter)$^2$×(large diameter)/2 and tumor growth inhibition was measured relative to vehicle control.

Results: The result of in vivo tumor growth inhibition of compound 8 is shown in Table 8. Compound 8 demonstrated 39% tumor growth inhibition of B16F10 melanoma cells in vivo at 25 mpk.

TABLE 8

In vivo tumor growth inhibition assay results for compound 8.

|  | Control | 5 mg/kg Cmpd 8 | 25 mg/kg Cmpd 8 |
|---|---|---|---|
| Mean tumor volume (mm3) (+/−S.E.M.) | 784 (+/−77) | 686 (+/−97) | 475 (+/−56) |
| Tumor growth inhibition % of control (+/−S.E.M.) | 0% (+/−10%) | 13% (+/−12%) | 39% (+/−7%) |

Example 88: Pharmacodynamic Analysis of ApoE

In Vivo Dosing and Sample Collection: 6-7 week old B16F10 mice received a single dose of Compound 8 at 52.6 mg/kg, formulated in 2% DMSO/20% Propylene Glycol/ 78% 0.5% Methylcellulose (400 cp) at a final concentration of 4.62 mg/mL by oral gavage. Bleeds were taken at 0.5 h, 2 h, 4 h, 8 h, 16 h, 24 h and 48 h. Mice were bled twice, the first bleed was drawn submandibular and the second through intracardiac puncture. Blood was collected in Dipotassium EDTA Microtainer tubes (02-669-38, Fisher). To isolate peripheral blood lymphocytes, blood samples were centrifuged at 2000 g for 5 min. After separation of the plasma, Erythrocytes were lysed in 1 mL Erythrocyte Lysis (EL) buffer (79217, Qiagen) and incubation at room temperature for 20 min. Samples were centrifuged at 400 g for 10 min, and peripheral blood lymphocytes washed once in EL buffer, followed by one wash in PBS.

ApoE Gene Expression Analysis by qRT-PCR: RNA was extracted from peripheral blood lymphocytes using the Total RNA Purification Micro Kit (35300, Norgen, Thorold, Canada). 200-300 ng of total RNA was then reverse transcribed into cDNA using the Verso cDNA synthesis Kit (AB-1453B, Fisher Scientific) and 6 ng of the resulting cDNA was mixed with SYBR Green PCR Mater Mix (4385612, Applied Biosystems) and quantitative real-time PCR amplification was performed using an ABI Prism 7900HT Real-Time PCR System (Applied Biosystems, Austin, Tex.). Each PCR reaction was carried out in quadruplicates. Gene expression was normalized to GAPDH, which was used as an endogenous control. Primers used as described in Example 86.

Results: The results of ApoE induction in vivo by compound 8 is shown in Table 9 where Pre-Dose represents endogenous levels of ApoE induction prior to dosing, n is the number of samples analyzed, and values are expressed as fold induction over pre-dose endogenous ApoE levels (normalized to 1.0). Peak induction of compound 8 is >6-fold over background at 4 h.

TABLE 9

Pharmacodynamic assay results in vivo ApoE induction

| Time Sampling | n | Fold ApoE Induction Over Pre-Dose Level (+/−S.D.) |
|---|---|---|
| Pre-Dose | 3 | 1.0 (+/−0.2) |
| 0.5 h | 2 | 1.3 (+/−0.3) |
| 2 h | 2 | 2.7 (+/−0.5) |
| 4 h | 3 | 6.3 (+/−1.8) |
| 8 h | 4 | 3.8 (+/−2.4) |
| 16 h | 4 | 0.3 (+/−0.4) |
| 24 h | 5 | 0.4 (+/−0.6) |
| 48 h | 4 | 0.1 (+/−0.3) |

Example 89: Immunohistochemistry Analysis of ApoE

Human primary melanoma skin samples are resected from melanoma patients, formalin-fixed, embedded in paraffin, and sectioned into 5-μm-thick increments. To determine ApoE protein expression, the samples are first de-paraffinized by two consecutive xylene washes (5-min each), and rehydrated in a series of ethanol washes (100%, 95%, 80%, and 70% EtOH). ApoE antigen is retrieved by incubating the samples in the presence of proteinase K (5 μg/mL) for 20 min at room temperature. To quench endogenous peroxidase activity, the slides are incubated in 3% $H_2O_2$ solution. The slides are then blocked in three consecutive Avidin, Biotin, and horse serum block solutions for 15 min each at room temperature (SP-2001, Vector Laboratories, Burlingame, Calif.). ApoE is detected by staining with D6E10 anti-ApoE antibody (ab1908, Abcam), which is used at a 1:100 dilution in PBS at 4° C. overnight. The primary antibody is then recognized by incubating the slides in a peroxidase-conjugated secondary antibody (PK-4002, Vector Laboratories) and exposed by DAB (SK-4105, Vector Laboratories) oxidation reaction. The slides are imaged at 10× magnification and analyzed in a double-blinded manner. ApoE expression is quantified by counting the number of DAB-positive cells and measuring the area of extracellular ApoE staining. Total ApoE staining signal is expressed as the percentage staining area per given tumor area, determined based on matched H&E-stained slides for each sample.

Example 90: Western Blot Analysis of ApoE in Plasma Samples

For analysis of ApoE protein levels in plasma samples, 8 µg of plasma is separated by SDS-PAGE and transferred to a PVDF membrane. The membrane is blocked in 5% milk in PBS/0.1% Tween-20 (PBS-T) for 1 h at room temperature (RT), washed three times in PBS-T before incubation with primary antibodies against mouse ApoE (ab20874, Abcam), or human ApoE (ab1906, Abcam) and transferrin (ab82411). Transferrin is used to normalize the ApoE signal. The membrane is washed three times in PBS-T and blotted with secondary antibody (65612, Invitrogen) for 1 h at RT. Following three washes in PBS-T, the membrane is developed using ECL substrate (32106, Pierce) according to the manufacturers instructions.

Example 91: Gene Expression Analysis in Human Peripheral Blood Mononuclear Cells (PBMCs)

Purified PBMC are suspended in culture medium (RPMI+ 10% FBS+1% penicillin/streptomycin/amphotericin B with 1% L-glutamine) and transferred into 6-well culture dishes at $5\times10^6$ cells/well. After one hour, drug or control (DMSO) is added and incubation is continued for 48 h. The conditioned media is removed and centrifuged at 450 g for 5 min. The cell pellet is washed once in PBS before resuspending in lysis buffer (17200, Norgen, Thorold, Canada). The remaining adherent cells are washed once in PBS and directly lysed by the addition of lysis buffer. The fractions are pooled and RNA extracted (17200, Norgen, Thorold, Canada). 600 ng of total RNA is then reverse transcribed into cDNA using the Verso cDNA Synthesis Kit (AB-1453/B, Fisher Scientific). 6 ng of the resulting cDNA is mixed with SYBR green PCR Master Mix (4309155, Applied Biosystems) and the appropriate primers. Each reaction is performed in quadruplicate, and mRNA expression is quantified by performing real-time PCR amplification using a StepOne Plus Real-Time PCR System (Applied Biosystems). GAPDH is used as an endogenous control for normalization.

The following primers are used:

```
ApoE Forward:
                          (SEQ ID NO: 1)
5'-TGGGTCGCTTTTGGGATTAC-3'

ApoE Reverse:
                          (SEQ ID NO: 2)
5'-TTCAACTCCTTCATGGTCTCG-3'

GAPDH Forward:
                          (SEQ ID NO: 3)
5'-AGCCACATCGCTCAGACAC-3'

GAPDH Reverse:
                          (SEQ ID NO: 4)
5'-GCCCAATACGACCAAATCC-3'

ABCG1 Forward:
                          (SEQ ID NO: 9)
5'-GCCACTTTCGTGGGCCCAGTGA-3'

ABCG1 Reverse:
                          (SEQ ID NO: 10)
5'-TCTCATCACCAGCTGTGTTGCA-3'

ABCA1 Forward:
                          (SEQ ID NO: 11)
5'-TGC TGC ATA GTC TTG GGA CTC-3'

ABCA1 Reverse:
                          (SEQ ID NO: 12)
5'-ACC TCC TGT CGC ATG TCA CT
```

Example 92: LXR α/β Agonist Activity and Selectivity Profiling

DiscoveRx PathHunter cells (NR1H2 for β; NR1H3 for α) are seeded in a total volume of 20 µL in white-walled, 384-well microplates and incubated at 37° C. for the appropriate time prior to testing. Assay media contains charcoal-dextran-filtered serum to reduce the level of hormones present. Serial dilution of drug is performed to generate 5× sample in assay buffer and 3.5 µL of each 5× sample is added to cells in the appropriate well. The plate is incubated at 37° C. or RT for 3-16 hours. Final assay vehicle concentration is 1%. Assay signal is generated through a single addition of 12.5 µL or 15 µL (50% v/v) of PathHunter Detection reagent cocktail, followed by incubation for 1 h at RT. Microplates are analyzed by chemiluminescent using a PerkinElmer Envision™ instrument. Compound activity is calculated using CBIS data analysis suite (Chem Innovation, Calif.). Percentage agonist activity is calculated using the following formula:

$$\text{Actvity}=100\%\times(\text{mean of test sample}-\text{mean of vehicle control})/(\text{mean control ligand}-\text{mean of vehicle control})$$

Example 93: Allergic Contact Dermatitis of the Mouse Ear

The mouse contact dermatitis model (ear edema model) has been previously used for the characterization of topical application of LXR activators for their effect on skin inflammation (Fowler et al. J. Invest. Dermatol. 2003, 120, 246).

Briefly, phorbol 12-myristate-13-acetate (PMA) is applied topically to both the inner and outer surface (10 µL each surface, 20 µL total) of the left ears of the mice to induce irritant contact dermatitis. Acetone alone (vehicle) is applied to the right ears. Test compounds (20 µL/side) are applied 30 min prior and 15 min after PMA application to both surfaces of left ear (40 µL total). Identical treatments are performed with 20 µL of the positive control (0.05% clobetasol) and the vehicle group (acetone application alone). Blood samples (approximately 60 µL) are collected from retro-orbital plexus of 5 mice (from each group), at the 6 h time point, into labeled micro-tubes containing $K_2$EDTA solution as an anticoagulant. Plasma is immediately harvested by centrifugation at 4000 rpm for 10 min at 4±2° C. and stored below −70° C. until bioanalysis. The inflammatory insult induced by PMA is assessed as the percentage increase in ear thickness and/or ear weight in the treated left ear versus the vehicle-treated right ear. Ear thickness is measured with a digital caliper followed by whole ear weight to ascertain changes in ear weights. The extent of inflammation is quantitated according to the following equation:

$$\text{ear swelling }(\%)=100\times(a-b)/b$$

where a is the thickness/weight of the left (treated) ear and b is the thickness/weight of the right (untreated control) ear. After obtaining the samples for assessment of ear thickness/ weight, biopsies are obtained from adjacent sites for routine histopathology fixation in 4% freshly prepared paraformaldehyde in phosphate-buffered saline. Ear swelling and ear weight for test compounds are compared to Clobetasol (corticosteroid used to treat various skin disorders).

Example 94: Alzheimer's Disease Mouse Model

A mouse model of Alzheimer's disease has been previously described for the characterization of LXR agonist's ability to reduce Aβ levels and ameliorates plaque burden in Tg2576 mice (*Neuron* 2008, 58 (5), 681-693).

In Vivo Dosing and Sample Collection: Tg2576 mice or wild type littermates (5 animals/group), 12 months of age, are fed AIN-76A standard rodent diet alone or supplemented with test compound (e.g., at 120 mg/kg; 33 mg/kg/day) ad libitum for 4 months. The animals are sacrificed, and the right hemispheres are fixed and processed for immunohistochemical analysis. The left hemispheres are snap-frozen on dry ice and subject to serial extraction of total RNA, DNA and protein. Wild type mice (C57BL/6), Apoe null mice (B6129P2-Apoe$^{tm1Unc/J}$) and Abca1 heterozygote mice (DBA/1-Abca1$^{tm1Jdm/J}$) are obtained from Jackson Laboratory (Bar Harbor, Me.). Abca1 +/+, +/− and −/− mice are bred from Abca1 heterozygote mice (DBA/1-Abca1$^{tm1Jdm/J}$). Tg2576 mice are maintained by crossing to B6SJLF1/J animals. Aβ plaque burden is monitored by 6E10 staining in the hippocampus by quantifying plaque number and plaque area for treated groups vs control. Levels of full-length APP, C99 C-terminal fragment, total Aβ, ABCA1 and ApoE are monitored by Western blot analysis. The results are normalized to β-actin.

Immunohistochemistry and Image Analysis: Post-fixed hemispheres are sectioned sagittally into 10 μm sections using a cryostat. Sections are mounted, air-dried, and then stored at 4° C. until use. For Aβ immunohistochemistry, sections (3 per mouse, about 1.2 mm-1.5 mm from the midline, spaced 0.1 mm apart from each other) are incubated in 70% formic acid for 3 min and the endogenous tissue peroxidase activity is quenched by incubation with 1% peroxide in methanol for 10 min. Sections are then microwaved in distilled water for 3 min, and then incubated with blocking solution (5% normal goat serum and 0.1% Triton X-100 in PBS) for 1 h. Sections are incubated with primary antibody in the blocking solution overnight at 4° C. The antigens are detected by secondary antibodies using standard ABC-DAB methods. Sections are counterstained with hematoxylin. The 6E10 antibody against human Aβ is used to stain Aβ plaques. Images are analyzed using Image Pro-Plus software (Media Cybernetics, Silver Spring, Md.).

Example 95: Gene Expression Analysis in Whole Tissue

Organs (e.g. liver, lung, small intestine, brain, tumor, etc.) are removed from control or drug-treated animals (See Example 99) are snapfrozen in liquid nitrogen until further processing. Frozen tissue (10 mg) is homogenized in 600 μl lysis buffer (17200, Norgen, Thorold, Canada) using a scalpel followed by passing the lysate 5-10 times through a 25G needle attached to a syringe. The lysate is transferred to a microcentrifuge tube and centrifuged for 2 min at 14,000 g. The supernatant is transferred to a new microcentrifuge tube and an equal amount of 70% ethanol is added and mixed by vortexing. 650 μl of the lysate is loaded onto a RNA extraction column and processed according to the manufacturers protocol (17200, Norgen, Thorold, Canada). 600 ng of total RNA is then reverse transcribed into cDNA using the Verso cDNA Synthesis Kit (AB-1453/B, Fisher Scientific). 6 ng of the resulting cDNA is mixed with SYBR green PCR Master Mix (4309155, Applied Biosystems) and the appropriate primers (see Example 98). Each reaction is performed in quadruplicate, and mRNA expression quantified by performing real-time PCR amplification using a StepOne Plus Real-Time PCR System (Applied Biosystems). GAPDH is used as an endogenous control for normalization.

Alternatively, ApoE levels are determined by W-blot analysis, in which case mouse lung and brain tissues are homogenized on ice in RIPA buffer (Sigma-Aldrich). Mouse adipose tissue is homogenized in TNET buffer (1.5 mM Tris [pH 7.5], 150 mM NaCl, 2 mM EDTA, 1% triton, protease inhibitors). Total protein lysates are separated by SDS-PAGE and processed as described in Example 102, with the exception that tubulin (2148, Cell Signaling Technology) is used as an internal loading control.

The following primers were used:

```
ApoE Forward:
5'-GACCCTGGAGGCTAAGGACT-3'

ApoE Reverse:
5'-AGAGCCTTCATCTTCGCAAT-3'

GAPDH Forward:
5'-GCACAGTCAAGGCCGAGAAT-3'

GAPDH Reverse:
5'-GCCTTCTCCATGGTGGTGAA-3'

ABCA1 Forward:
5'-ATGGAGCAGGGAAGACCAC-3'

ABCA1 Reverse:
5'-GTAGGCCGTGCCAGAAGTT-3'

ABCG1 Forward:
5'-TTTCCCAGAGATCCCTTTCA-3'

ABCG1 Reverse:
5'-ATCGAATTCAAGGACCTTTCC-3'
```

Other Embodiments

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

While the methods have been described in conjunction with various embodiments and examples, it is not intended that the methods be limited to such embodiments or examples. On the contrary, the present disclosure encompasses various alternatives, modifications, and equivalents, as will be appreciated by those of skill in the art.

While the methods have been particularly shown and described with reference to specific illustrative embodiments, it should be understood that various changes in form and detail may be made without departing from the spirit and scope of the present disclosure. Therefore, all embodiments that come within the scope and spirit of the present disclosure, and equivalents thereto, are intended to be claimed. The claims, descriptions and diagrams of the methods, systems, and assays of the present disclosure should not be read as limited to the described order of elements unless stated to that effect.

The invention claimed is:

1. A compound of Formula I:

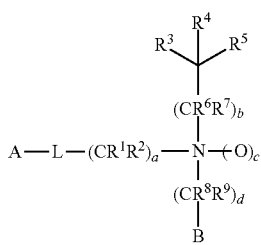

Formula I wherein A is:

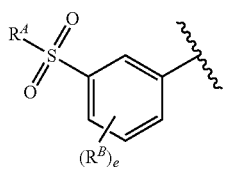

Formula Ia wherein e is 0, 1, 2, 3, or 4;

$R^A$ is optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_4$-$C_{10}$ cycloalkenyl, optionally substituted $C_8$-$C_{12}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, 8F optionally substituted $C_2$-$C_9$ heterocyclyl $C_1$-$C_6$ alkyl;

each $R^B$ is independently hydroxyl, optionally substituted amino, halo, thiol, optionally substituted amino acid, optionally substituted $C_1$-$C_6$ acyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ cycloalkyl, optionally substituted $C_8$-$C_{12}$ cycloalkenyl, optionally substituted $C_4$-$C_{10}$ cycloalkynyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl; and L is —O—;

a is 2 or 3;

b is 1;

c is 0;

d is 1;

each $R^1$, $R^2$, $R^6$, $R^7$, $R^8$, and $R^9$ are independently hydrogen or optionally substituted $C_1$-$C_6$ alkyl;

$R^3$ is hydrogen, halo, or optionally substituted $C_1$-$C_6$ alkyl;

$R^4$ is hydrogen, optionally substituted $C_1$-$C_6$ alkyl, optionally substituted $C_3$-$C_{10}$ cycloalkyl, or optionally substituted $C_6$-$C_{10}$ aryl;

$R^5$ is optionally substituted $C_6$-$C_{10}$ aryl; and

B is optionally substituted $C_6$-$C_{10}$ aryl;

or a pharmaceutically acceptable salt thereof.

2. The compound of claim 1, wherein each $R^6$ and $R^7$ is hydrogen.

3. The compound of claim 1, wherein $R^3$ is hydrogen.

4. The compound of claim 1, wherein $R^4$ is hydrogen, phenyl, cyclohexyl, or methyl.

5. The compound of claim 1, wherein $R^5$ is phenyl.

6. The compound of claim 1, wherein each $R^8$ and $R^9$ is hydrogen.

7. The compound of claim 1, wherein —$(CR^1R^2)_a$— has the structure:

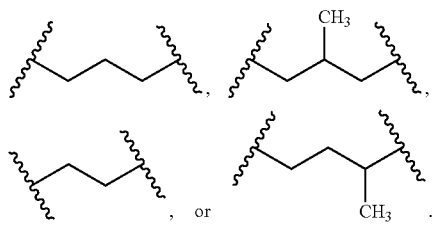

8. The compound of claim 7, wherein —$(CR^1R^2)_3$— has the structure:

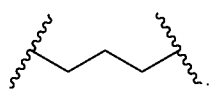 [SMILES: *CCC*]

9. The compound of claim 1, wherein said compound has the structure:

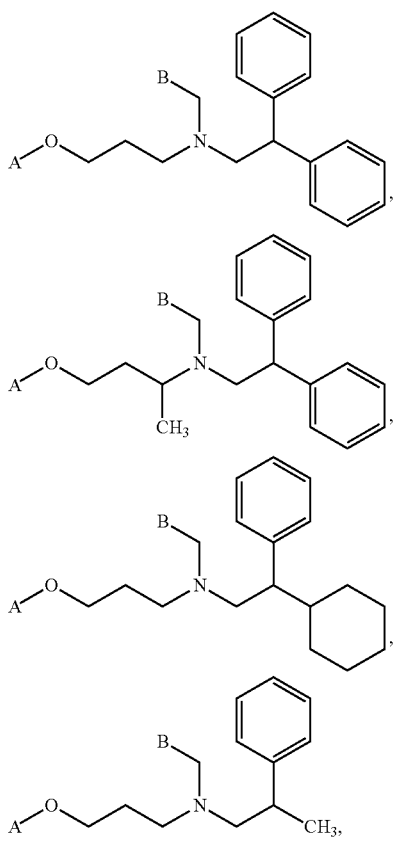

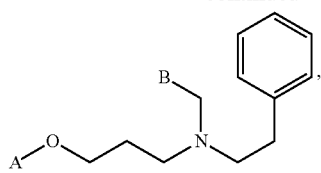

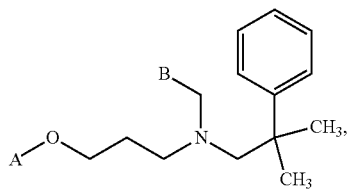

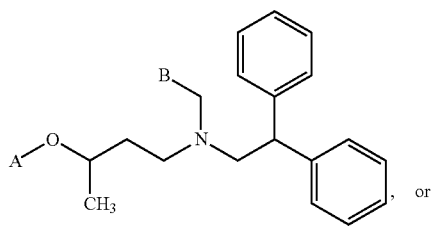

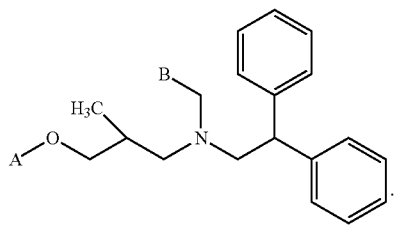

10. The compound of claim 1, wherein said optionally substituted $C_6$-$C_{10}$ aryl is 2-chloro-3-trifluoromethyl-phenyl, 2-fluoro-3-trifluoromethyl-phenyl, 3-(1,1,2,2-tetrafluoroethoxy)-phenyl, 3-trifluoromethyl-phenyl, 3-trifluoromethyl-4-fluoro-phenyl, or 3-trifluoromethoxy-phenyl.

11. The compound of claim 10, wherein B is 2-chloro-3-trifluoromethyl-phenyl, 2-fluoro-3-trifluoromethyl-phenyl, or 3-trifluoromethyl-phenyl.

12. The compound of claim 11, wherein B is 2-chloro-3-trifluoromethyl-phenyl.

13. A compound, or pharmaceutically acceptable salt thereof, selected from:

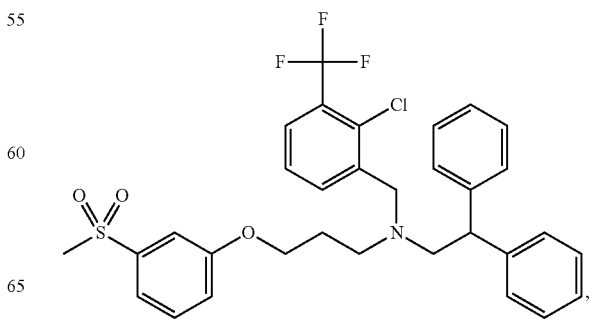

189
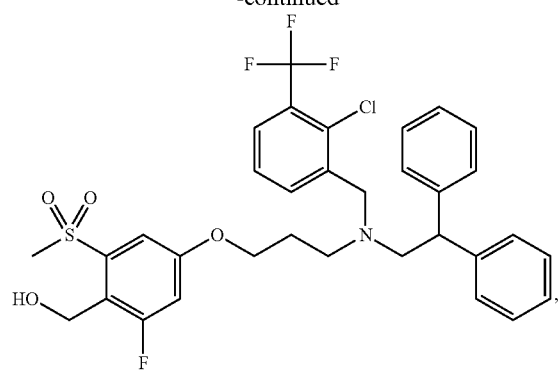
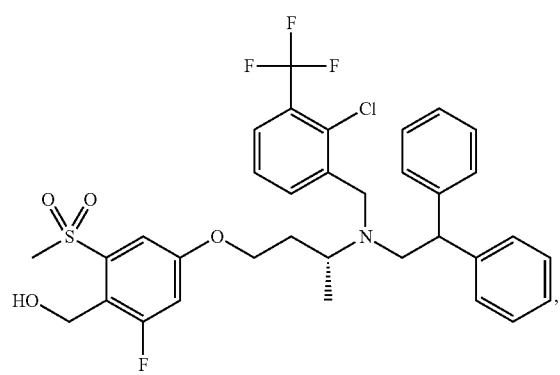
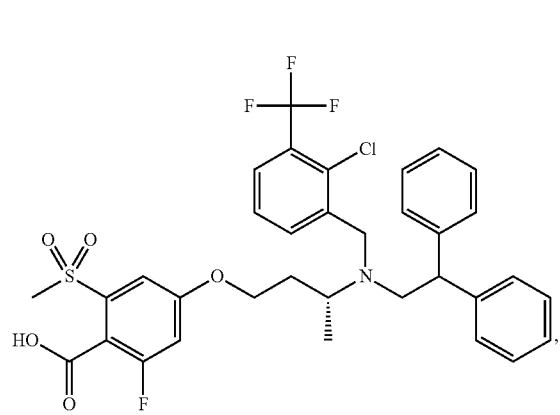
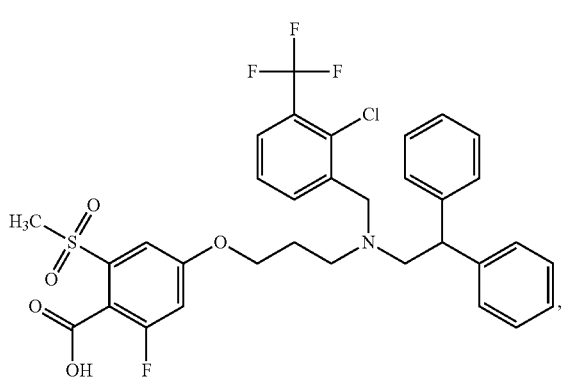
190
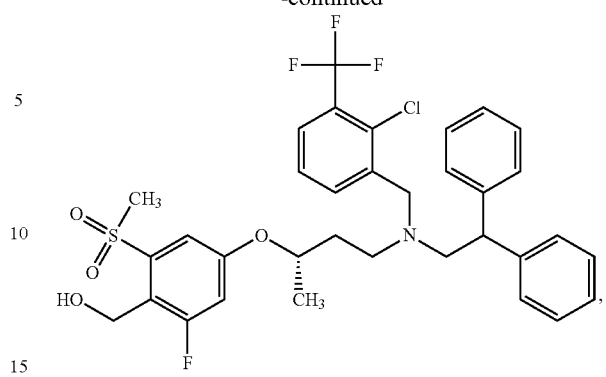
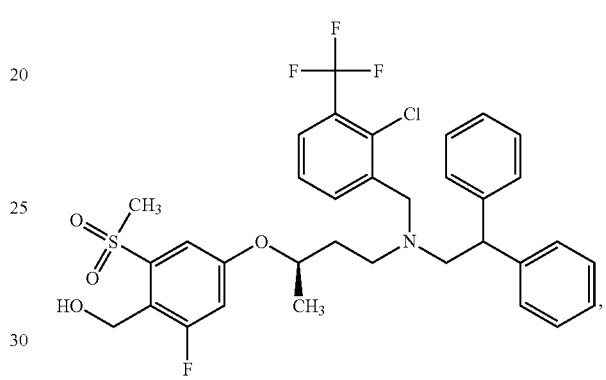
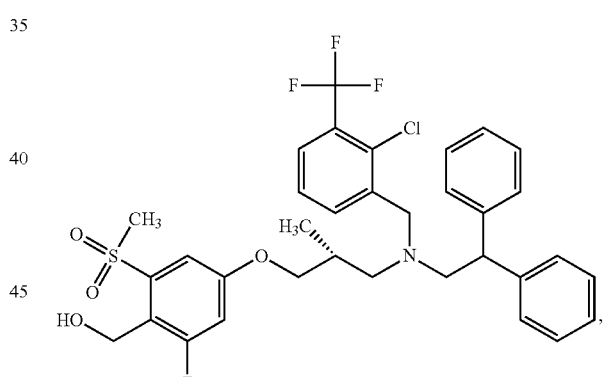
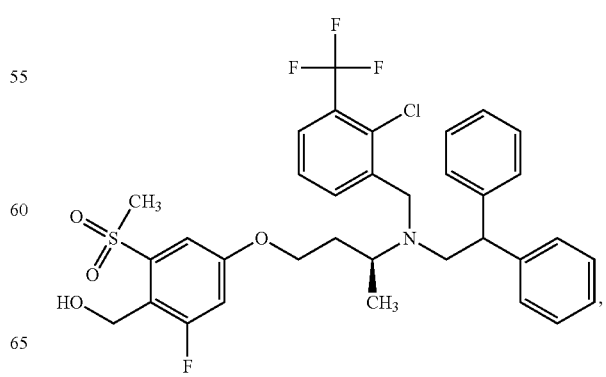

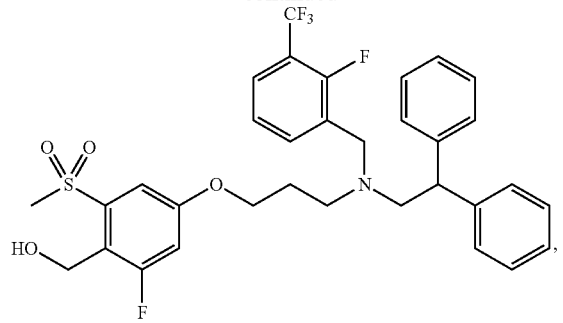
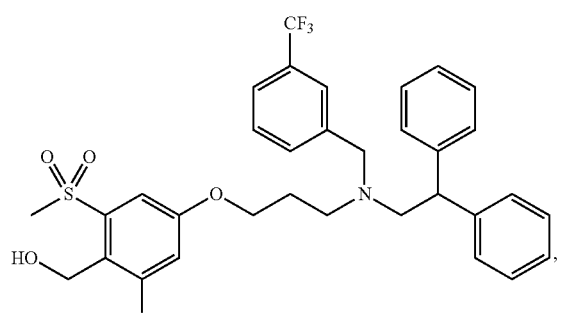
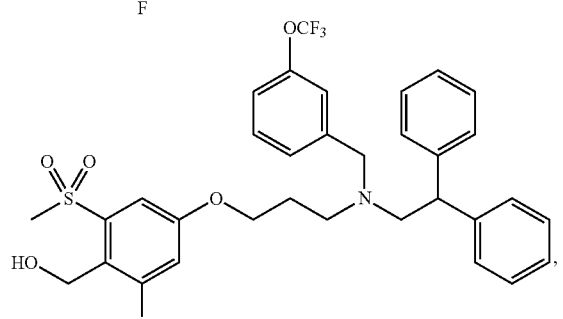
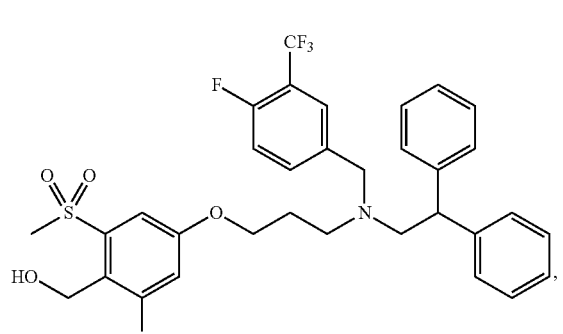
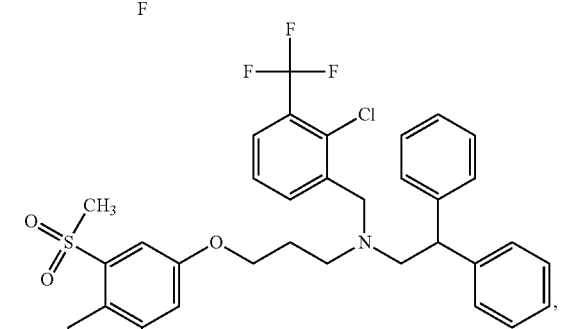
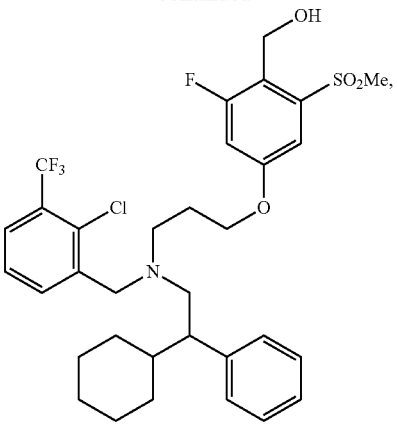
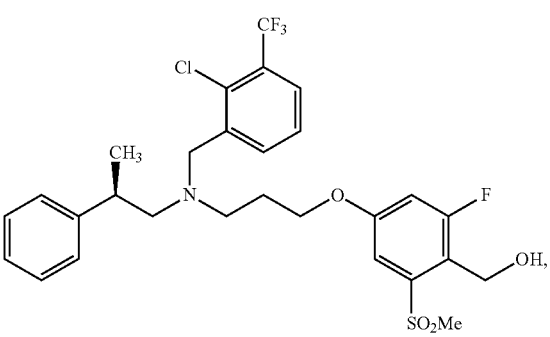
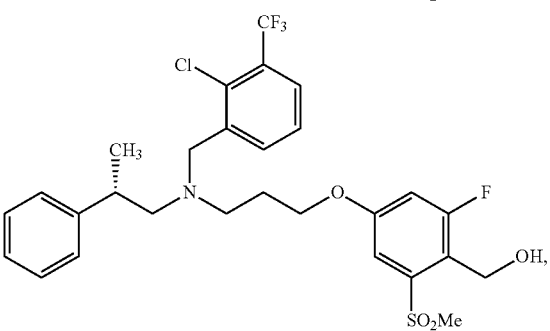
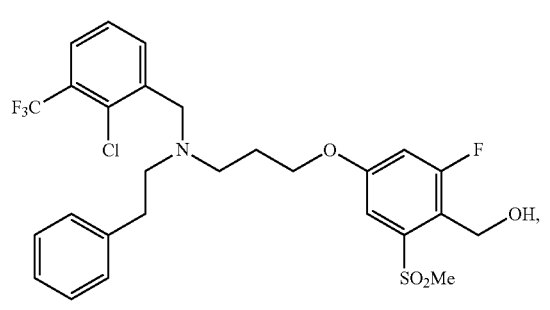
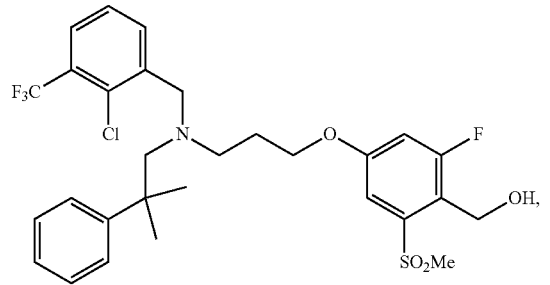

193
-continued
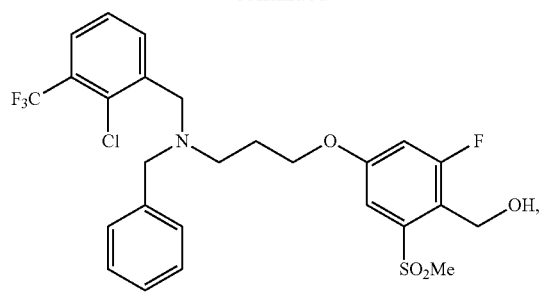
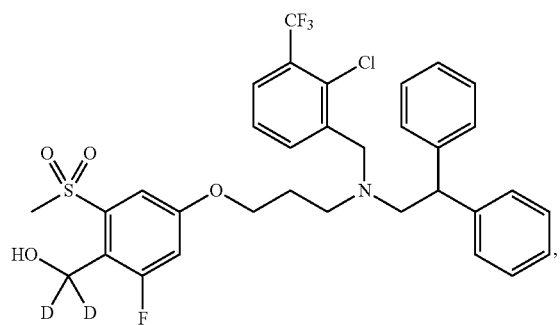
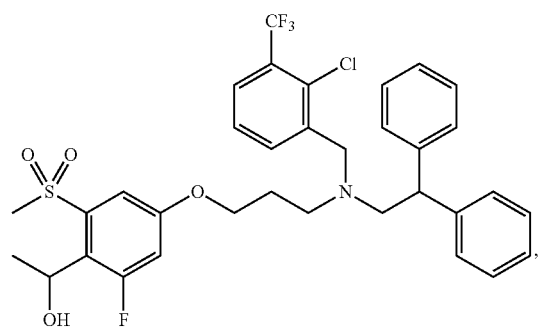
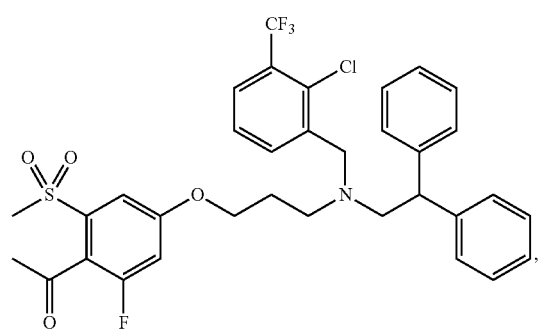
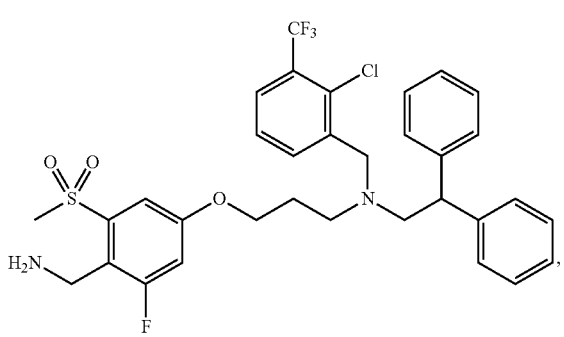
194
-continued
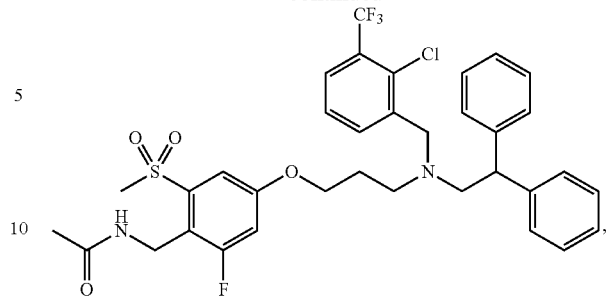
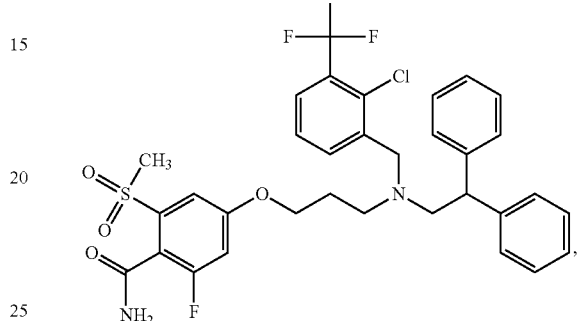
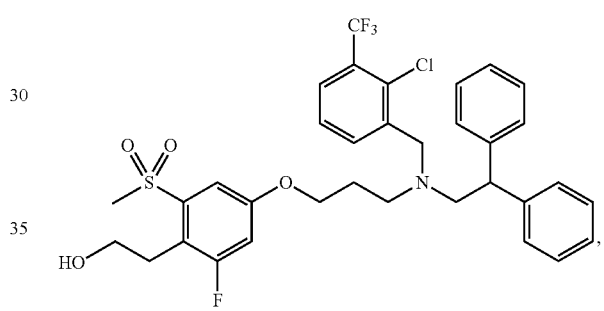
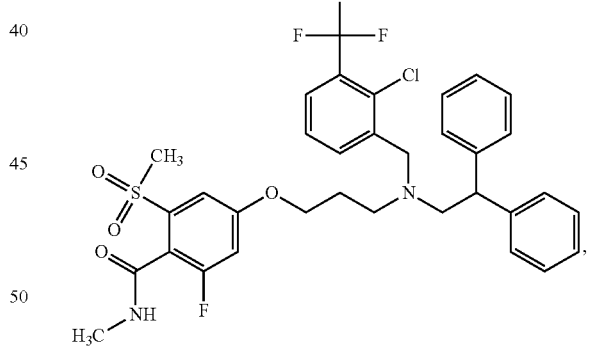
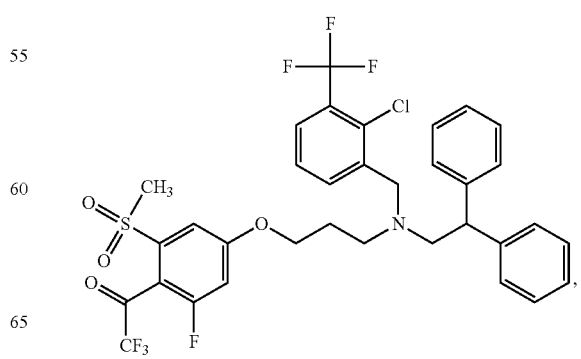

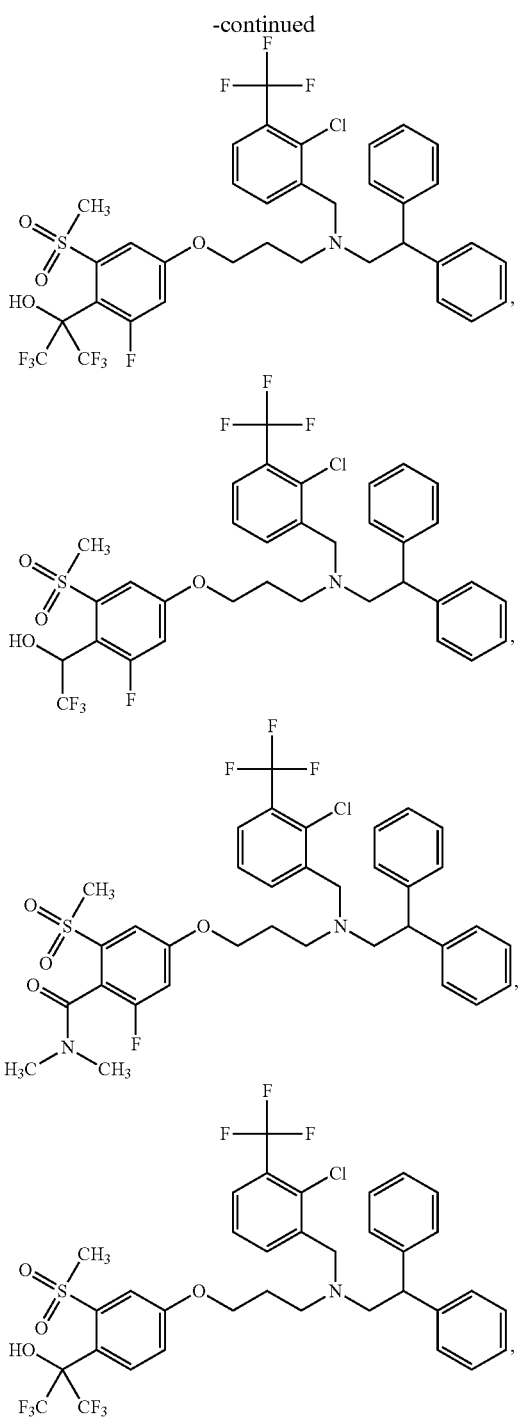

(2-fluoro-6-methanesulfonyl-4-{3-[(2-methyl-2-phenyl-propyl)({[3-(trifluoromethyl)phenyl]methyl})amino]propoxy}phenyl)methanol,
(2-fluoro-6-methanesulfonyl-4-{3-[(2-phenylethyl)({[3-(trifluoromethyl)phenyl]methyl})amino]propoxy}phenyl) methanol,
(2-fluoro-6-methanesulfonyl-4-{3-[(2-phenylpropyl)({[3-(trifluoromethyl)phenyl]methyl})amino]propoxy}phenyl) methanol,
(4-{3-[benzyl({[2-fluoro-3-(trifluoromethyl)phenyl]methyl})amino]propoxy}-2-fluoro-6-methanesulfonylphenyl) methanol,
(4-{3-[benzyl({[3-(trifluoromethyl)phenyl]methyl})amino]propoxy}-2-fluoro-6-methanesulfonylphenyl) methanol,
[2-fluoro-4-(3-{[(4-fluorophenyl)methyl]({[3-(trifluoromethyl)phenyl]methyl})amino}propoxy)-6-methanesulfonylphenyl]methanol,
[2-fluoro-4-(3-{[2-(4-fluorophenyl)-2-methylpropyl]({[3-(trifluoromethyl)phenyl]methyl})amino}propoxy)-6-methanesulfonylphenyl]methanol,
[2-fluoro-4-(3-{[2-(4-fluorophenyl)ethyl]({[3-(trifluoromethyl)phenyl]methyl})amino}propoxy)-6-methanesulfonylphenyl]methanol,
[2-fluoro-4-(3-{[2-(4-fluorophenyl)propyl]({[3-(trifluoromethyl)phenyl]methyl})amino}propoxy)-6-methanesulfonylphenyl]methanol,
{4-[3-({[2-chloro-3-(trifluoromethyl)phenyl]methyl}[2,2-difluoro-2-(4-fluorophenyl)ethyl]amino)propoxy]-2-fluoro-6-methanesulfonylphenyl}methanol,
[4-(3-{[2,2-difluoro-2-(4-fluorophenyl)ethyl]({[2-fluoro-3-(trifluoromethyl)phenyl]methyl})amino}propoxy)-2-fluoro-6-methanesulfonylphenyl]methanol,
[4-(3-{[2,2-difluoro-2-(4-fluorophenyl)ethyl]({[3-(trifluoromethyl)phenyl]methyl})amino}propoxy)-2-fluoro-6-methanesulfonylphenyl]methanol,
{4-[3-({[2-chloro-3-(trifluoromethyl)phenyl]methyl}[(4-fluorophenyl)methyl]amino)propoxy]-2-fluoro-6-methanesulfonylphenyl}methanol,
{4-[3-({[2-chloro-3-(trifluoromethyl)phenyl]methyl}[2-(4-fluorophenyl)-2-methylpropyl]amino)propoxy]-2-fluoro-6-methanesulfonylphenyl}methanol,
{4-[3-({[2-chloro-3-(trifluoromethyl)phenyl]methyl}[2-(4-fluorophenyl)ethyl]amino)propoxy]-2-fluoro-6-methanesulfonylphenyl}methanol,
{4-[3-({[2-chloro-3-(trifluoromethyl)phenyl]methyl}[2-(4-fluorophenyl)propyl]amino)propoxy]-2-fluoro-6-methanesulfonylphenyl}methanol,
{2-fluoro-4-[3-({[2-fluoro-3-(trifluoromethyl)phenyl]methyl}(2-methyl-2-phenylpropyl)amino)propoxy]-6-methanesulfonylphenyl}methanol,
{2-fluoro-4-[3-({[2-fluoro-3-(trifluoromethyl)phenyl]methyl}(2-phenylethyl)amino)propoxy]-6-methanesulfonylphenyl}methanol,
{2-fluoro-4-[3-({[2-fluoro-3-(trifluoromethyl)phenyl]methyl}(2-phenylpropyl)amino)propoxy]-6-methanesulfonylphenyl}methanol,
{2-fluoro-4-[3-({[2-fluoro-3-(trifluoromethyl)phenyl]methyl}[(4-fluorophenyl)methyl]amino)propoxy]-6-methanesulfonylphenyl}methanol,
{2-fluoro-4-[3-({[2-fluoro-3-(trifluoromethyl)phenyl]methyl}[2-(4-fluorophenyl)-2-methylpropyl]amino)propoxy]-6-methanesulfonylphenyl}methanol,
{2-fluoro-4-[3-({[2-fluoro-3-(trifluoromethyl)phenyl]methyl}[2-(4-fluorophenyl)ethyl]amino)propoxy]-6-methanesulfonylphenyl}methanol,
{2-fluoro-4-[3-({[2-fluoro-3-(trifluoromethyl)phenyl]methyl}[2-(4-fluorophenyl)propyl]amino)propoxy]-6-methanesulfonylphenyl}methanol,
(2-methanesulfonyl-4-{3-[(2-methyl-2-phenylpropyl)({[3-(trifluoromethyl)phenyl]methyl})amino]propoxy}phenyl) methanol,
(2-methanesulfonyl-4-{3-[(2-phenylethyl)({[3-(trifluoromethyl)phenyl]methyl})amino]propoxy}phenyl) methanol,
(2-methanesulfonyl-4-{3-[(2-phenylpropyl)({[3-(trifluoromethyl)phenyl]methyl})amino]propoxy}phenyl) methanol, {4-[3-({[2-chloro-3-(trifluoromethyl)phenyl]methyl}(2,2-diphenylethyl)amino)propoxy]-2-methanesulfonylphenyl}methanol,
(4-{3-[(2,2-diphenylethyl)({[2-fluoro-3-(trifluoromethyl)phenyl]methyl})amino]propoxy}-2-methanesulfonylphenyl) methanol,
(4-{3-[(2,2-diphenylethyl)({[3-(trifluoromethyl)phenyl]methyl})amino]propoxy}-2-methanesulfonylphenyl) methanol,
(4-{3-[benzyl({[2-chloro-3-(trifluoromethyl)phenyl]methyl})amino]propoxy}-2-methanesulfonylphenyl) methanol,
(4-{3-[benzyl({[2-fluoro-3-(trifluoromethyl)phenyl]methyl})amino]propoxy}-2-methanesulfonylphenyl) methanol,
(4-{3-[benzyl({[3-(trifluoromethyl)phenyl]methyl})amino]propoxy}-2-methanesulfonylphenyl) methanol,
[4-(3-{[(4-fluorophenyl)methyl]({[3-(trifluoromethyl)phenyl]methyl})amino}propoxy)-2-methanesulfonylphenyl]methanol,
[4-(3-{[2-(4-fluorophenyl)-2-methylpropyl]({[3-(trifluoromethyl)phenyl]methyl})amino}propoxy)-2-methanesulfonylphenyl]methanol,
[4-(3-{[2-(4-fluorophenyl)ethyl]({[3-(trifluoromethyl)phenyl]methyl})amino}propoxy)-2-methanesulfonylphenyl]methanol,
[4-(3-{[2-(4-fluorophenyl)propyl]({[3-(trifluoromethyl)phenyl]methyl})amino}propoxy)-2-methanesulfonylphenyl]methanol,
{4-[3-({[2-chloro-3-(trifluoromethyl)phenyl]methyl}[2,2-difluoro-2-(4-fluorophenyl)ethyl]amino)propoxy]-2-methanesulfonylphenyl}methanol,
[4-(3-{[2,2-difluoro-2-(4-fluorophenyl)ethyl]({[2-fluoro-3-(trifluoromethyl)phenyl]methyl})amino}propoxy)-2-methanesulfonylphenyl]methanol,
[4-(3-{[2,2-difluoro-2-(4-fluorophenyl)ethyl]({[3-(trifluoromethyl)phenyl]methyl})amino}propoxy)-2-methanesulfonylphenyl]methanol,
{4-[3-({[2-chloro-3-(trifluoromethyl)phenyl]methyl}(2-methyl-2-phenylpropyl)amino)propoxy]-2-methanesulfonylphenyl}methanol,
{4-[3-({[2-chloro-3-(trifluoromethyl)phenyl]methyl}(2-phenylethyl)amino)propoxy]-2-methanesulfonylphenyl}methanol,
{4-[3-({[2-chloro-3-(trifluoromethyl)phenyl]methyl}(2-phenylpropyl)amino)propoxy]-2-methanesulfonylphenyl}methanol,
{4-[3-({[2-chloro-3-(trifluoromethyl)phenyl]methyl}[(4-fluorophenyl)methyl]amino)propoxy]-2-methanesulfonylphenyl}methanol,
{4-[3-({[2-chloro-3-(trifluoromethyl)phenyl]methyl}[2-(4-fluorophenyl)-2-methylpropyl]amino)propoxy]-2-methanesulfonylphenyl}methanol,
{4-[3-({[2-chloro-3-(trifluoromethyl)phenyl]methyl}[2-(4-fluorophenyl)ethyl]amino)propoxy]-2-methanesulfonylphenyl}methanol,
{4-[3-({[2-chloro-3-(trifluoromethyl)phenyl]methyl}[2-(4-fluorophenyl)propyl]amino)propoxy]-2-methanesulfonylphenyl}methanol,
{4-[3-({[2-fluoro-3-(trifluoromethyl)phenyl]methyl}(2-methyl-2-phenylpropyl)amino)propoxy]-2-methanesulfonylphenyl}methanol,
{4-[3-({[2-fluoro-3-(trifluoromethyl)phenyl]methyl}(2-phenylethyl)amino)propoxy]-2-methanesulfonylphenyl}methanol,
{4-[3-({[2-fluoro-3-(trifluoromethyl)phenyl]methyl}(2-phenylpropyl)amino)propoxy]-2-methanesulfonylphenyl}methanol,
{4-[3-({[2-fluoro-3-(trifluoromethyl)phenyl]methyl}[(4-fluorophenyl)methyl]amino)propoxy]-2-methanesulfonylphenyl}methanol,
{4-[3-({[2-fluoro-3-(trifluoromethyl)phenyl]methyl}[2-(4-fluorophenyl)-2-methylpropyl]amino)propoxy]-2-methanesulfonylphenyl}methanol,
{4-[3-({[2-fluoro-3-(trifluoromethyl)phenyl]methyl}[2-(4-fluorophenyl)ethyl]amino)propoxy]-2-methanesulfonylphenyl}methanol,
{4-[3-({[2-fluoro-3-(trifluoromethyl)phenyl]methyl}[2-(4-fluorophenyl) propyl]amino)propoxy]-2-methanesulfonylphenyl}methanol,
[3-(3-methanesulfonylphenoxy)propyl](2-methyl-2-phenylpropyl){[3-(trifluoromethyl)phenyl]methyl}amine,
[3-(3-methanesulfonylphenoxy)propyl](2-phenylethyl){[3-(trifluoromethyl)phenyl]methyl}amine,
[3-(3-methanesulfonylphenoxy)propyl](2-phenylpropyl){[3-(trifluoromethyl)phenyl]methyl}amine,
(2,2-diphenylethyl)({[2-fluoro-3-(trifluoromethyl)phenyl]methyl})[3-(3-methanesulfonylphenoxy)propyl]amine,
(2,2-diphenylethyl)[3-(3-methanesulfonylphenoxy)propyl]{[3-(trifluoromethyl)phenyl]methyl}amine,
benzyl({[2-chloro-3-(trifluoromethyl)phenyl]methyl})[3-(3-methanesulfonylphenoxy)propyl]amine,
benzyl({[2-fluoro-3-(trifluoromethyl)phenyl]methyl})[3-(3-methanesulfonylphenoxy)propyl]amine,
benzyl[3-(3-methanesulfonylphenoxy)propyl]{[3-(trifluoromethyl)phenyl]methyl}amine,
[(4-fluorophenyl)methyl][3-(3-methanesulfonylphenoxy)propyl]{[3-(trifluoromethyl)phenyl]methyl}amine,
[2-(4-fluorophenyl)-2-methylpropyl][3-(3-methanesulfonylphenoxy)propyl]{[3-(trifluoromethyl)phenyl]methyl}amine,
[2-(4-fluorophenyl)ethyl][3-(3-methanesulfonylphenoxy)propyl]{[3-(trifluoromethyl)phenyl]methyl}amine,
[2-(4-fluorophenyl) propyl][3-(3-methanesulfonylphenoxy)propyl]{[3-(trifluoromethyl)phenyl]methyl}amine,
{[2-chloro-3-(trifluoromethyl)phenyl]methyl}[2,2-difluoro-2-(4-fluorophenyl)ethyl][3-(3-methanesulfonylphenoxy)propyl]amine,
[2,2-difluoro-2-(4-fluorophenyl) ethyl]({[2-fluoro-3-(trifluoromethyl)phenyl]methyl})[3-(3-methanesulfonylphenoxy)propyl]amine,
[2,2-difluoro-2-(4-fluorophenyl) ethyl][3-(3-methanesulfonylphenoxy)propyl]{[3-(trifluoromethyl)phenyl]methyl}amine,
{[2-chloro-3-(trifluoromethyl)phenyl]methyl}[3-(3-methanesulfonylphenoxy)propyl](2-methyl-2-phenylpropyl)amine,
{[2-chloro-3-(trifluoromethyl)phenyl]methyl}[3-(3-methanesulfonylphenoxy)propyl](2-phenylethyl)amine,
{[2-chloro-3-(trifluoromethyl)phenyl]methyl}[3-(3-methanesulfonylphenoxy)propyl](2-phenylpropyl)amine,
{[2-chloro-3-(trifluoromethyl)phenyl]methyl}[(4-fluorophenyl)methyl][3-(3-methanesulfonylphenoxy)propyl]amine,
{[2-chloro-3-(trifluoromethyl)phenyl]methyl}[2-(4-fluorophenyl)-2-methylpropyl][3-(3-methanesulfonylphenoxy)propyl]amine, {[2-chloro-3-(trifluoromethyl)phenyl]methyl}[2-(4-fluorophenyl)ethyl][3-(3-methanesulfonylphenoxy)propyl]amine,
{[2-chloro-3-(trifluoromethyl)phenyl]methyl}[2-(4-fluorophenyl) propyl][3-(3-methanesulfonylphenoxy)propyl]amine,
{[2-fluoro-3-(trifluoromethyl)phenyl]methyl}[3-(3-methanesulfonylphenoxy)propyl](2-methyl-2-phenylpropyl)amine,
{[2-fluoro-3-(trifluoromethyl)phenyl]methyl}[3-(3-methanesulfonylphenoxy)propyl](2-phenylethyl)amine,
{[2-fluoro-3-(trifluoromethyl)phenyl]methyl}[3-(3-methanesulfonylphenoxy)propyl](2-phenylpropyl)amine,
{[2-fluoro-3-(trifluoromethyl)phenyl]methyl}[(4-fluorophenyl)methyl][3-(3-methanesulfonylphenoxy)propyl]amine,
{[2-fluoro-3-(trifluoromethyl)phenyl]methyl}[2-(4-fluorophenyl)-2-methylpropyl][3-(3-methanesulfonylphenoxy)propyl]amine,
{[2-fluoro-3-(trifluoromethyl)phenyl]methyl}[2-(4-fluorophenyl)ethyl][3-(3-methanesulfonylphenoxy)propyl]amine,
{[2-fluoro-3-(trifluoromethyl)phenyl]methyl}[2-(4-fluorophenyl)propyl][3-(3-methanesulfonylphenoxy)propyl]amine,
1-(2-fluoro-6-methanesulfonyl-4-{3-[(2-phenylethyl)({[3-(trifluoromethyl)phenyl]methyl})amino]propoxy}phenyl)ethan-1-ol,
1-(2-fluoro-6-methanesulfonyl-4-{3-[(2-methyl-2-phenylpropyl)({[3-(trifluoromethyl)phenyl]methyl})amino]propoxy}phenyl)ethan-1-ol,
1-(2-fluoro-6-methanesulfonyl-4-{3-[(2-phenylpropyl)({[3-(trifluoromethyl)phenyl]methyl})amino]propoxy}phenyl)ethan-1-ol,
1-(4-{3-[(2,2-diphenylethyl)({[2-fluoro-3-(trifluoromethyl)phenyl]methyl})amino]propoxy}-2-fluoro-6-methanesulfonylphenyl)ethan-1-ol,
1-(4-{3-[(2,2-diphenylethyl)({[3-(trifluoromethyl)phenyl]methyl})amino]propoxy}-2-fluoro-6-methanesulfonylphenyl)ethan-1-ol,
1-(4-{3-[benzyl({[2-chloro-3-(trifluoromethyl)phenyl]methyl})amino]propoxy}-2-fluoro-6-methanesulfonylphenyl)ethan-1-ol,
1-(4-{3-[benzyl({[2-fluoro-3-(trifluoromethyl)phenyl]methyl})amino]propoxy}-2-fluoro-6-methanesulfonylphenyl)ethan-1-ol,
1-(4-{3-[benzyl({[3-(trifluoromethyl)phenyl]methyl})amino]propoxy}-2-fluoro-6-methanesulfonylphenyl)ethan-1-ol,
1-[2-fluoro-4-(3-{[(4-fluorophenyl)methyl]({[3-(trifluoromethyl)phenyl]methyl})amino}propoxy)-6-methanesulfonylphenyl]ethan-1-ol,
1-[2-fluoro-4-(3-{[2-(4-fluorophenyl)-2-methylpropyl]({[3-(trifluoromethyl)phenyl]methyl})amino}propoxy)-6-methanesulfonylphenyl]ethan-1-ol,
1-[2-fluoro-4-(3-{[2-(4-fluorophenyl)ethyl]({[3-(trifluoromethyl)phenyl]methyl})amino}propoxy)-6-methanesulfonylphenyl]ethan-1-ol,
1-[2-fluoro-4-(3-{[2-(4-fluorophenyl)propyl]({[3-(trifluoromethyl)phenyl]methyl})amino}propoxy)-6-methanesulfonylphenyl]ethan-1-ol,
1-{4-[3-({[2-chloro-3-(trifluoromethyl)phenyl]methyl}[2,2-difluoro-2-(4-fluorophenyl)ethyl]amino)propoxy]-2-fluoro-6-methanesulfonylphenyl}ethan-1-ol,
1-[4-(3-{[2,2-difluoro-2-(4-fluorophenyl)ethyl]({[2-fluoro-3-(trifluoromethyl)phenyl]methyl})amino}propoxy)-2-fluoro-6-methanesulfonylphenyl]ethan-1-ol,
1-[4-(3-{[2,2-difluoro-2-(4-fluorophenyl)ethyl]({[3-(trifluoromethyl)phenyl]methyl})amino}propoxy)-2-fluoro-6-methanesulfonylphenyl]ethan-1-ol,
1-{4-[3-({[2-chloro-3-(trifluoromethyl)phenyl]methyl}(2-methyl-2-phenylpropyl)amino)propoxy]-2-fluoro-6-methanesulfonylphenyl}ethan-1-ol,
1-{4-[3-({[2-chloro-3-(trifluoromethyl)phenyl]methyl}(2-phenylpropyl)amino)propoxy]-2-fluoro-6-methanesulfonylphenyl}ethan-1-ol,
1-{4-[3-({[2-chloro-3-(trifluoromethyl)phenyl]methyl}[2-(4-fluorophenyl)-2-methylpropyl]amino)propoxy]-2-fluoro-6-methanesulfonylphenyl}ethan-1-ol,
1-{4-[3-({[2-chloro-3-(trifluoromethyl)phenyl]methyl}[(4-fluorophenyl)methyl]amino)propoxy]-2-fluoro-6-methanesulfonylphenyl}ethan-1-ol,
1-{4-[3-({[2-chloro-3-(trifluoromethyl)phenyl]methyl}[2-(4-fluorophenyl)ethyl]amino)propoxy]-2-fluoro-6-methanesulfonylphenyl}ethan-1-ol,
1-{2-fluoro-4-[3-({[2-fluoro-3-(trifluoromethyl)phenyl]methyl}(2-methyl-2-phenylpropyl)amino)propoxy]-6-methanesulfonylphenyl}ethan-1-ol,
1-{4-[3-({[2-chloro-3-(trifluoromethyl)phenyl]methyl}[2-(4-fluorophenyl)propyl]amino)propoxy]-2-fluoro-6-methanesulfonylphenyl}ethan-1-ol,
1-{2-fluoro-4-[3-({[2-fluoro-3-(trifluoromethyl)phenyl]methyl}(2-phenylethyl)amino)propoxy]-6-methanesulfonylphenyl}ethan-1-ol,
1-{2-fluoro-4-[3-({[2-fluoro-3-(trifluoromethyl)phenyl]methyl}(2-phenylpropyl)amino)propoxy]-6-methanesulfonylphenyl}ethan-1-ol,
1-{2-fluoro-4-[3-({[2-fluoro-3-(trifluoromethyl)phenyl]methyl}[(4-fluorophenyl)methyl]amino)propoxy]-6-methanesulfonylphenyl}ethan-1-ol,
1-{4-[3-({[2-chloro-3-(trifluoromethyl)phenyl]methyl}(2-phenylethyl)amino)propoxy]-2-fluoro-6-methanesulfonylphenyl}ethan-1-ol,
1-{2-fluoro-4-[3-({[2-fluoro-3-(trifluoromethyl)phenyl]methyl}[2-(4-fluorophenyl)-2-methylpropyl]amino)propoxy]-6-methanesulfonylphenyl}ethan-1-ol,
1-{2-fluoro-4-[3-({[2-fluoro-3-(trifluoromethyl)phenyl]methyl}[2-(4-fluorophenyl)ethyl]amino)propoxy]-6-methanesulfonylphenyl}ethan-1-ol,
1-{2-fluoro-4-[3-({[2-fluoro-3-(trifluoromethyl)phenyl]methyl}[2-(4-fluorophenyl)propyl]amino)propoxy]-6-methanesulfonylphenyl}ethan-1-ol,
1-(2-methanesulfonyl-4-{3-[(2-methyl-2-phenylpropyl)({[3-(trifluoromethyl)phenyl]methyl})amino]propoxy}phenyl)ethan-1-ol,
1-(2-methanesulfonyl-4-{3-[(2-phenylethyl)({[3-(trifluoromethyl)phenyl]methyl})amino]propoxy}phenyl)ethan-1-ol,
1-(2-methanesulfonyl-4-{3-[(2-phenylpropyl)({[3-(trifluoromethyl)phenyl]methyl})amino]propoxy}phenyl)ethan-1-ol,
1-(4-{3-[(2,2-diphenylethyl)({[2-fluoro-3-(trifluoromethyl)phenyl]methyl})amino]propoxy}-2-methanesulfonylphenyl)ethan-1-ol,
1-(4-{3-[(2,2-diphenylethyl)({[3-(trifluoromethyl)phenyl]methyl})amino]propoxy}-2-methanesulfonylphenyl)ethan-1-ol,
1-(4-{3-[benzyl({[2-chloro-3-(trifluoromethyl)phenyl]methyl})amino]propoxy}-2-methanesulfonylphenyl)ethan-1-ol, 1-(4-{3-[benzyl({[2-fluoro-3-(trifluoromethyl)phenyl]
methyl})amino]propoxy}-2-methanesulfonylphenyl)
ethan-1-ol, 1-(4-{3-[benzyl({[3-(trifluoromethyl)phenyl]methyl})
amino]propoxy}-2-methanesulfonylphenyl)ethan-1-ol, 1-[4-(3-{[(4-fluorophenyl)methyl]({[3-(trifluoromethyl)
phenyl]methyl})amino}propoxy)-2-methanesulfonyl-
phenyl]ethan-1-ol, 1-[4-(3-{[2-(4-fluorophenyl)-2-methylpropyl]({[3-(trif-
luoromethyl)phenyl]methyl})amino}propoxy)-2-
methanesulfonylphenyl]ethan-1-ol, 1-[4-(3-{[2-(4-fluorophenyl)ethyl]({[3-(trifluoromethyl)
phenyl]methyl})amino}propoxy)-2-methanesulfonyl-
phenyl]ethan-1-ol, 1-[4-(3-{[2-(4-fluorophenyl)propyl]({[3-(trifluorom-
ethyl)phenyl]methyl})amino}propoxy)-2-methanesul-
fonylphenyl]ethan-1-ol, 1-{4-[3-({[2-chloro-3-(trifluoromethyl)phenyl]methyl}
[2,2-difluoro-2-(4-fluorophenyl)ethyl]amino)
propoxy]-2-methanesulfonylphenyl}ethan-1-ol, 1-[4-(3-{[2,2-difluoro-2-(4-fluorophenyl)ethyl]({[2-
fluoro-3-(trifluoromethyl)phenyl]methyl})
amino}propoxy)-2-methanesulfonylphenyl]ethan-1-ol, 1-[4-(3-{[2,2-difluoro-2-(4-fluorophenyl)ethyl]({[3-(trif-
luoromethyl)phenyl]methyl})amino}propoxy)-2-
methanesulfonylphenyl]ethan-1-ol, 1-{4-[3-({[2-chloro-3-(trifluoromethyl)phenyl]methyl}
(2-methyl-2-phenylpropyl)amino)propoxy]-2-
methanesulfonylphenyl}ethan-1-ol, 1-{4-[3-({[2-chloro-3-(trifluoromethyl)phenyl]methyl}
(2-phenylethyl)amino)propoxy]-2-
methanesulfonylphenyl}ethan-1-ol, 1-{4-[3-({[2-chloro-3-(trifluoromethyl)phenyl]methyl}
(2-phenylpropyl)amino)propoxy]-2-
methanesulfonylphenyl}ethan-1-ol, 1-{4-[3-({[2-chloro-3-(trifluoromethyl)phenyl]methyl}
[(4-fluorophenyl)methyl]amino)propoxy]-2-
methanesulfonylphenyl}ethan-1-ol, 1-{4-[3-({[2-chloro-3-(trifluoromethyl)phenyl]methyl}
[2-(4-fluorophenyl)-2-methylpropyl]amino)propoxy]-
2-methanesulfonylphenyl}ethan-1-ol, 1-{4-[3-({[2-chloro-3-(trifluoromethyl)phenyl]methyl}
[2-(4-fluorophenyl)ethyl]amino)propoxy]-2-
methanesulfonylphenyl}ethan-1-ol, 1-{4-[3-({[2-chloro-3-(trifluoromethyl)phenyl]methyl}
[2-(4-fluorophenyl)propyl]amino)propoxy]-2-
methanesulfonylphenyl}ethan-1-ol, 1-{4-[3-({[2-fluoro-3-(trifluoromethyl)phenyl]methyl}
(2-methyl-2-phenylpropyl)amino)propoxy]-2-
methanesulfonylphenyl}ethan-1-ol, 1-{4-[3-({[2-fluoro-3-(trifluoromethyl)phenyl]methyl}
(2-phenylethyl)amino)propoxy]-2-
methanesulfonylphenyl}ethan-1-ol, 1-{4-[3-({[2-fluoro-3-(trifluoromethyl)phenyl]methyl}
(2-phenylpropyl)amino)propoxy]-2-
methanesulfonylphenyl}ethan-1-ol, 1-{4-[3-({[2-fluoro-3-(trifluoromethyl)phenyl]methyl}
[(4-fluorophenyl)methyl]amino)propoxy]-2-
methanesulfonylphenyl}ethan-1-ol, 1-{4-[3-({[2-fluoro-3-(trifluoromethyl)phenyl]methyl}
[2-(4-fluorophenyl)-2-methylpropyl]amino)propoxy]-
2-methanesulfonylphenyl}ethan-1-ol, 1-{4-[3-({[2-fluoro-3-(trifluoromethyl)phenyl]methyl}
[2-(4-fluorophenyl)ethyl]amino)propoxy]-2-
methanesulfonylphenyl}ethan-1-ol, 1-{4-[3-({[2-fluoro-3-(trifluoromethyl)phenyl]methyl}
[2-(4-fluorophenyl)propyl]amino)propoxy]-2-
methanesulfonylphenyl}ethan-1-ol, 1-{4-[3-({[2-chloro-3-(trifluoromethyl)phenyl]methyl}
(2,2-diphenylethyl)amino)propoxy]-2-
methanesulfonylphenyl}ethan-1-ol, 2-fluoro-6-methanesulfonyl-4-{3-[(2-phenylethyl)({[3-
(trifluoromethyl)phenyl]methyl})amino]
propoxy}benzaldehyde, 4-{3-[(2,2-diphenylethyl)({[2-fluoro-3-(trifluoromethyl)
phenyl]methyl})amino]propoxy}-2-fluoro-6-methane-
sulfonylbenzaldehyde, 2-fluoro-6-methanesulfonyl-4-{3-[(2-methyl-2-phenyl-
propyl)({[3-(trifluoromethyl)phenyl]methyl})amino]
propoxy}benzaldehyde, 4-{3-[(2,2-diphenylethyl)({[3-(trifluoromethyl)phenyl]
methyl})amino]propoxy}-2-fluoro-6-methanesulfo-
nylbenzaldehyde, 4-{3-[benzyl({[2-chloro-3-(trifluoromethyl)phenyl]
methyl})amino]propoxy}-2-fluoro-6-methanesulfo-
nylbenzaldehyde, 4-{3-[benzyl({[2-fluoro-3-(trifluoromethyl)phenyl]
methyl})amino]propoxy}-2-fluoro-6-methanesulfo-
nylbenzaldehyde, 4-{3-[benzyl({[3-(trifluoromethyl)phenyl]methyl})
amino]propoxy}-2-fluoro-6-methanesulfonylbenzalde-
hyde, 2-fluoro-4-(3-{[(4-fluorophenyl)methyl]({[3-(trifluorom-
ethyl)phenyl]methyl})amino}propoxy)-6-methanesul-
fonylbenzaldehyde, 2-fluoro-4-(3-{[2-(4-fluorophenyl)-2-methylpropyl]({[3-
(trifluoromethyl)phenyl]methyl})amino}propoxy)-6-
methanesulfonylbenzaldehyde, 2-fluoro-4-(3-{[2-(4-fluorophenyl)ethyl]({[3-(trifluorom-
ethyl)phenyl]methyl})amino}propoxy)-6-methanesul-
fonylbenzaldehyde, 2-fluoro-4-(3-{[2-(4-fluorophenyl)propyl]({[3-(trifluo-
romethyl)phenyl]methyl})amino}propoxy)-6-meth-
anesulfonylbenzaldehyde, 4-(3-{[2,2-difluoro-2-(4-fluorophenyl)ethyl]({[2-fluoro-
3-(trifluoromethyl)phenyl]methyl})amino}propoxy)-
2-fluoro-6-methanesulfonylbenzaldehyde, 4-[3-({[2-chloro-3-(trifluoromethyl)phenyl]methyl}[2,2-
difluoro-2-(4-fluorophenyl)ethyl]amino)propoxy]-2-
fluoro-6-methanesulfonylbenzaldehyde, 4-(3-{[2,2-difluoro-2-(4-fluorophenyl)ethyl]({[3-(trifluo-
romethyl)phenyl]methyl})amino}propoxy)-2-fluoro-
6-methanesulfonylbenzaldehyde, 4-[3-({[2-chloro-3-(trifluoromethyl)phenyl]methyl}(2-
methyl-2-phenylpropyl)amino)propoxy]-2-fluoro-6-
methanesulfonylbenzaldehyde, 4-[3-({[2-chloro-3-(trifluoromethyl)phenyl]methyl}(2-
phenylethyl)amino)propoxy]-2-fluoro-6-methanesul-
fonylbenzaldehyde, 4-[3-({[2-chloro-3-(trifluoromethyl)phenyl]methyl}(2-
phenylpropyl)amino)propoxy]-2-fluoro-6-methanesul-
fonylbenzaldehyde, 4-[3-({[2-chloro-3-(trifluoromethyl)phenyl]methyl}[(4-
fluorophenyl)methyl]amino)propoxy]-2-fluoro-6-
methanesulfonylbenzaldehyde, 4-[3-({[2-chloro-3-(trifluoromethyl)phenyl]methyl}[2-
(4-fluorophenyl)-2-methylpropyl]amino)propoxy]-2-
fluoro-6-methanesulfonylbenzaldehyde, 2-fluoro-4-[3-({[2-fluoro-3-(trifluoromethyl)phenyl]
methyl}(2-methyl-2-phenylpropyl)amino)propoxy]-6-
methanesulfonylbenzaldehyde, 4-[3-({[2-chloro-3-(trifluoromethyl)phenyl]methyl}[2-(4-fluorophenyl)propyl]amino)propoxy]-2-fluoro-6-methanesulfonylbenzaldehyde,
2-fluoro-4-[3-({[2-fluoro-3-(trifluoromethyl)phenyl]methyl}(2-phenylethyl)amino)propoxy]-6-methanesulfonylbenzaldehyde,
2-fluoro-4-[3-({[2-fluoro-3-(trifluoromethyl)phenyl]methyl}(2-phenylpropyl)amino)propoxy]-6-methanesulfonylbenzaldehyde,
2-fluoro-4-[3-({[2-fluoro-3-(trifluoromethyl)phenyl]methyl}[(4-fluorophenyl)methyl]amino)propoxy]-6-methanesulfonylbenzaldehyde,
2-fluoro-4-[3-({[2-fluoro-3-(trifluoromethyl)phenyl]methyl}[2-(4-fluorophenyl)-2-methylpropyl]amino)propoxy]-6-methanesulfonylbenzaldehyde,
2-fluoro-6-methanesulfonyl-4-{3-[(2-phenylpropyl)({[3-(trifluoromethyl)phenyl]methyl})amino]propoxy}benzaldehyde,
2-fluoro-4-[3-({[2-fluoro-3-(trifluoromethyl)phenyl]methyl}[2-(4-fluorophenyl)ethyl]amino)propoxy]-6-methanesulfonylbenzaldehyde,
2-fluoro-4-[3-({[2-fluoro-3-(trifluoromethyl)phenyl]methyl}[2-(4-fluorophenyl)propyl]amino)propoxy]-6-methanesulfonylbenzaldehyde,
4-[3-({[2-chloro-3-(trifluoromethyl)phenyl]methyl}[2-(4-fluorophenyl)ethyl]amino)propoxy]-2-fluoro-6-methanesulfonylbenzaldehyde,
2-methanesulfonyl-4-{3-[(2-methyl-2-phenylpropyl)({[3-(trifluoromethyl)phenyl]methyl})amino]propoxy}benzaldehyde,
2-methanesulfonyl-4-{3-[(2-phenylethyl)({[3-(trifluoromethyl)phenyl]methyl})amino]propoxy}benzaldehyde,
2-methanesulfonyl-4-{3-[(2-phenylpropyl)({[3-(trifluoromethyl)phenyl]methyl})amino]propoxy}benzaldehyde,
4-{3-[(2,2-diphenylethyl)({[2-fluoro-3-(trifluoromethyl)phenyl]methyl})amino]propoxy}-2-methanesulfonylbenzaldehyde,
4-{3-[(2,2-diphenylethyl)({[3-(trifluoromethyl)phenyl]methyl})amino]propoxy}-2-methanesulfonylbenzaldehyde,
4-{3-[benzyl({[2-chloro-3-(trifluoromethyl)phenyl]methyl})amino]propoxy}-2-methanesulfonylbenzaldehyde,
4-{3-[benzyl({[2-fluoro-3-(trifluoromethyl)phenyl]methyl})amino]propoxy}-2-methanesulfonylbenzaldehyde,
4-{3-[benzyl({[3-(trifluoromethyl)phenyl]methyl})amino]propoxy}-2-methanesulfonylbenzaldehyde,
4-(3-{[(4-fluorophenyl)methyl]({[3-(trifluoromethyl)phenyl]methyl})amino}propoxy)-2-methanesulfonylbenzaldehyde,
4-(3-{[2-(4-fluorophenyl)-2-methylpropyl]({[3-(trifluoromethyl)phenyl]methyl})amino}propoxy)-2-methanesulfonylbenzaldehyde,
4-(3-{[2-(4-fluorophenyl)ethyl]({[3-(trifluoromethyl)phenyl]methyl})amino}propoxy)-2-methanesulfonylbenzaldehyde,
4-(3-{[2-(4-fluorophenyl)propyl]({[3-(trifluoromethyl)phenyl]methyl})amino}propoxy)-2-methanesulfonylbenzaldehyde,
4-[3-({[2-chloro-3-(trifluoromethyl)phenyl]methyl}[2,2-difluoro-2-(4-fluorophenyl)ethyl]amino)propoxy]-2-methanesulfonylbenzaldehyde,
4-(3-{[2,2-difluoro-2-(4-fluorophenyl)ethyl]({[2-fluoro-3-(trifluoromethyl)phenyl]methyl})amino}propoxy)-2-methanesulfonylbenzaldehyde,
4-(3-{[2,2-difluoro-2-(4-fluorophenyl)ethyl]({[3-(trifluoromethyl)phenyl]methyl})amino}propoxy)-2-methanesulfonylbenzaldehyde,
4-[3-({[2-chloro-3-(trifluoromethyl)phenyl]methyl}(2-methyl-2-phenylpropyl)amino)propoxy]-2-methanesulfonylbenzaldehyde,
4-[3-({[2-chloro-3-(trifluoromethyl)phenyl]methyl}(2-phenylethyl)amino)propoxy]-2-methanesulfonylbenzaldehyde,
4-[3-({[2-chloro-3-(trifluoromethyl)phenyl]methyl}(2-phenylpropyl)amino)propoxy]-2-methanesulfonylbenzaldehyde,
4-[3-({[2-chloro-3-(trifluoromethyl)phenyl]methyl}(2,2-diphenylethyl)amino)propoxy]-2-methanesulfonylbenzaldehyde,
4-[3-({[2-chloro-3-(trifluoromethyl)phenyl]methyl}[(4-fluorophenyl)methyl]amino)propoxy]-2-methanesulfonylbenzaldehyde,
4-[3-({[2-chloro-3-(trifluoromethyl)phenyl]methyl}[2-(4-fluorophenyl)-2-methylpropyl]amino)propoxy]-2-methanesulfonylbenzaldehyde,
4-[3-({[2-chloro-3-(trifluoromethyl)phenyl]methyl}[2-(4-fluorophenyl)ethyl]amino)propoxy]-2-methanesulfonylbenzaldehyde,
4-[3-({[2-chloro-3-(trifluoromethyl)phenyl]methyl}[2-(4-fluorophenyl)propyl]amino)propoxy]-2-methanesulfonylbenzaldehyde,
4-[3-({[2-fluoro-3-(trifluoromethyl)phenyl]methyl}(2-methyl-2-phenylpropyl)amino)propoxy]-2-methanesulfonylbenzaldehyde,
4-[3-({[2-fluoro-3-(trifluoromethyl)phenyl]methyl}(2-phenylethyl)amino)propoxy]-2-methanesulfonylbenzaldehyde,
4-[3-({[2-fluoro-3-(trifluoromethyl)phenyl]methyl}(2-phenylpropyl)amino)propoxy]-2-methanesulfonylbenzaldehyde,
4-[3-({[2-fluoro-3-(trifluoromethyl)phenyl]methyl}[(4-fluorophenyl)methyl]amino)propoxy]-2-methanesulfonylbenzaldehyde,
4-[3-({[2-fluoro-3-(trifluoromethyl)phenyl]methyl}[2-(4-fluorophenyl)-2-methylpropyl]amino)propoxy]-2-methanesulfonylbenzaldehyde,
4-[3-({[2-fluoro-3-(trifluoromethyl)phenyl]methyl}[2-(4-fluorophenyl)ethyl]amino)propoxy]-2-methanesulfonylbenzaldehyde,
4-[3-({[2-fluoro-3-(trifluoromethyl)phenyl]methyl}[2-(4-fluorophenyl)propyl]amino)propoxy]-2-methanesulfonylbenzaldehyde,
methyl 2-fluoro-6-methanesulfonyl-4-{3-[(2-methyl-2-phenylpropyl)({[3-(trifluoromethyl)phenyl]methyl})amino]propoxy}benzoate,
methyl 2-fluoro-6-methanesulfonyl-4-{3-[(2-phenylpropyl)({[3-(trifluoromethyl)phenyl]methyl})amino]propoxy}benzoate,
methyl 4-{3-[(2,2-diphenylethyl)({[3-(trifluoromethyl)phenyl]methyl})amino]propoxy}-2-fluoro-6-methanesulfonylbenzoate,
methyl 2-fluoro-6-methanesulfonyl-4-{3-[(2-phenylethyl)({[3-(trifluoromethyl)phenyl]methyl})amino]propoxy}benzoate,
methyl 4-{3-[(2,2-diphenylethyl)({[2-fluoro-3-(trifluoromethyl)phenyl]methyl})amino]propoxy}-2-fluoro-6-methanesulfonylbenzoate, methyl 4-{3-[benzyl({[2-chloro-3-(trifluoromethyl)phenyl]methyl})amino]propoxy}-2-fluoro-6-methanesulfonylbenzoate,
methyl 4-{3-[benzyl({[2-fluoro-3-(trifluoromethyl)phenyl]methyl})amino]propoxy}-2-fluoro-6-methanesulfonylbenzoate,
methyl 4-{3-[benzyl({[3-(trifluoromethyl)phenyl]methyl})amino]propoxy}-2-fluoro-6-methanesulfonylbenzoate,
methyl 2-fluoro-4-(3-{[(4-fluorophenyl)methyl]({[3-(trifluoromethyl)phenyl]methyl})amino}propoxy)-6-methanesulfonylbenzoate,
methyl 2-fluoro-4-(3-{[2-(4-fluorophenyl)-2-methylpropyl]({[3-(trifluoromethyl)phenyl]methyl})amino}propoxy)-6-methanesulfonylbenzoate,
methyl 2-fluoro-4-(3-{[2-(4-fluorophenyl)ethyl]({[3-(trifluoromethyl)phenyl]methyl})amino}propoxy)-6-methanesulfonylbenzoate,
methyl 2-fluoro-4-(3-{[2-(4-fluorophenyl)propyl]({[3-(trifluoromethyl)phenyl]methyl})amino}propoxy)-6-methanesulfonylbenzoate,
methyl 4-[3-({[2-chloro-3-(trifluoromethyl)phenyl]methyl}[2,2-difluoro-2-(4-fluorophenyl)ethyl]amino)propoxy]-2-fluoro-6-methanesulfonylbenzoate,
methyl 4-(3-{[2,2-difluoro-2-(4-fluorophenyl)ethyl]({[2-fluoro-3-(trifluoromethyl)phenyl]methyl})amino}propoxy)-2-fluoro-6-methanesulfonylbenzoate,
methyl 4-(3-{[2,2-difluoro-2-(4-fluorophenyl)ethyl]({[3-(trifluoromethyl)phenyl]methyl})amino}propoxy)-2-fluoro-6-methanesulfonylbenzoate,
methyl 4-[3-({[2-chloro-3-(trifluoromethyl)phenyl]methyl}(2-methyl-2-phenylpropyl)amino)propoxy]-2-fluoro-6-methanesulfonylbenzoate,
methyl 4-[3-({[2-chloro-3-(trifluoromethyl)phenyl]methyl}(2-phenylethyl)amino)propoxy]-2-fluoro-6-methanesulfonylbenzoate,
methyl 4-[3-({[2-chloro-3-(trifluoromethyl)phenyl]methyl}[2-(4-fluorophenyl)-2-methylpropyl]amino)propoxy]-2-fluoro-6-methanesulfonylbenzoate,
methyl 4-[3-({[2-chloro-3-(trifluoromethyl)phenyl]methyl}[(4-fluorophenyl)methyl]amino)propoxy]-2-fluoro-6-methanesulfonylbenzoate,
methyl 4-[3-({[2-chloro-3-(trifluoromethyl)phenyl]methyl}(2-phenylpropyl)amino)propoxy]-2-fluoro-6-methanesulfonylbenzoate,
methyl 4-[3-({[2-chloro-3-(trifluoromethyl)phenyl]methyl}[2-(4-fluorophenyl)propyl]amino)propoxy]-2-fluoro-6-methanesulfonylbenzoate,
methyl 4-[3-({[2-chloro-3-(trifluoromethyl)phenyl]methyl}[2-(4-fluorophenyl)ethyl]amino)propoxy]-2-fluoro-6-methanesulfonylbenzoate,
methyl 2-fluoro-4-[3-({[2-fluoro-3-(trifluoromethyl)phenyl]methyl}(2-methyl-2-phenylpropyl)amino)propoxy]-6-methanesulfonylbenzoate,
methyl 2-fluoro-4-[3-({[2-fluoro-3-(trifluoromethyl)phenyl]methyl}(2-phenylethyl)amino)propoxy]-6-methanesulfonylbenzoate,
methyl 2-fluoro-4-[3-({[2-fluoro-3-(trifluoromethyl)phenyl]methyl}(2-phenylpropyl)amino)propoxy]-6-methanesulfonylbenzoate,
methyl 2-fluoro-4-[3-({[2-fluoro-3-(trifluoromethyl)phenyl]methyl}[(4-fluorophenyl)methyl]amino)propoxy]-6-methanesulfonylbenzoate,
methyl 2-fluoro-4-[3-({[2-fluoro-3-(trifluoromethyl)phenyl]methyl}[2-(4-fluorophenyl)-2-methylpropyl]amino)propoxy]-6-methanesulfonylbenzoate,
methyl 2-fluoro-4-[3-({[2-fluoro-3-(trifluoromethyl)phenyl]methyl}[2-(4-fluorophenyl)ethyl]amino)propoxy]-6-methanesulfonylbenzoate,
methyl 2-fluoro-4-[3-({[2-fluoro-3-(trifluoromethyl)phenyl]methyl}[2-(4-fluorophenyl)propyl]amino)propoxy]-6-methanesulfonylbenzoate,
methyl 2-methanesulfonyl-4-{3-[(2-methyl-2-phenylpropyl)({[3-(trifluoromethyl)phenyl]methyl})amino]propoxy}benzoate,
methyl 2-methanesulfonyl-4-{3-[(2-phenylethyl)({[3-(trifluoromethyl)phenyl]methyl})amino]propoxy}benzoate,
methyl 2-methanesulfonyl-4-{3-[(2-phenylpropyl)({[3-(trifluoromethyl)phenyl]methyl})amino]propoxy}benzoate,
methyl 4-{3-[(2,2-diphenylethyl)({[2-fluoro-3-(trifluoromethyl)phenyl]methyl})amino]propoxy}-2-methanesulfonylbenzoate,
methyl 4-{3-[(2,2-diphenylethyl)({[3-(trifluoromethyl)phenyl]methyl})amino]propoxy}-2-methanesulfonylbenzoate,
methyl 4-{3-[benzyl({[2-chloro-3-(trifluoromethyl)phenyl]methyl})amino]propoxy}-2-methanesulfonylbenzoate,
methyl 4-{3-[benzyl({[2-fluoro-3-(trifluoromethyl)phenyl]methyl})amino]propoxy}-2-methanesulfonylbenzoate,
methyl 4-{3-[benzyl({[3-(trifluoromethyl)phenyl]methyl})amino]propoxy}-2-methanesulfonylbenzoate,
methyl 4-(3-{[(4-fluorophenyl)methyl]({[3-(trifluoromethyl)phenyl]methyl})amino}propoxy)-2-methanesulfonylbenzoate,
methyl 4-(3-{[2-(4-fluorophenyl)-2-methylpropyl]({[3-(trifluoromethyl)phenyl]methyl})amino}propoxy)-2-methanesulfonylbenzoate,
methyl 4-(3-{[2-(4-fluorophenyl)ethyl]({[3-(trifluoromethyl)phenyl]methyl})amino}propoxy)-2-methanesulfonylbenzoate,
methyl 4-(3-{[2-(4-fluorophenyl) propyl]({[3-(trifluoromethyl)phenyl]methyl})amino}propoxy)-2-methanesulfonylbenzoate,
methyl 4-[3-({[2-chloro-3-(trifluoromethyl)phenyl]methyl}[2,2-difluoro-2-(4-fluorophenyl)ethyl]amino)propoxy]-2-methanesulfonylbenzoate,
methyl 4-(3-{[2,2-difluoro-2-(4-fluorophenyl)ethyl]({[2-fluoro-3-(trifluoromethyl)phenyl]methyl})amino}propoxy)-2-methanesulfonylbenzoate,
methyl 4-(3-{[2,2-difluoro-2-(4-fluorophenyl)ethyl]({[3-(trifluoromethyl)phenyl]methyl})amino}propoxy)-2-methanesulfonylbenzoate,
methyl 4-[3-({[2-chloro-3-(trifluoromethyl)phenyl]methyl}(2-methyl-2-phenylpropyl)amino)propoxy]-2-methanesulfonylbenzoate,
methyl 4-[3-({[2-chloro-3-(trifluoromethyl)phenyl]methyl}(2-phenylethyl)amino)propoxy]-2-methanesulfonylbenzoate,
methyl 4-[3-({[2-chloro-3-(trifluoromethyl)phenyl]methyl}(2-phenylpropyl)amino)propoxy]-2-methanesulfonylbenzoate,
methyl 4-[3-({[2-chloro-3-(trifluoromethyl)phenyl]methyl}(2,2-diphenylethyl)amino)propoxy]-2-methanesulfonylbenzoate,
methyl 4-[3-({[2-chloro-3-(trifluoromethyl)phenyl]methyl}[(4-fluorophenyl)methyl]amino)propoxy]-2-methanesulfonylbenzoate, methyl 4-[3-({[2-chloro-3-(trifluoromethyl)phenyl]methyl}[2-(4-fluorophenyl)-2-methylpropyl]amino)propoxy]-2-methanesulfonylbenzoate,
methyl 4-[3-({[2-chloro-3-(trifluoromethyl)phenyl]methyl}[2-(4-fluorophenyl)ethyl]amino)propoxy]-2-methanesulfonylbenzoate,
methyl 4-[3-({[2-chloro-3-(trifluoromethyl)phenyl]methyl}[2-(4-fluorophenyl)propyl]amino)propoxy]-2-methanesulfonylbenzoate,
methyl 4-[3-({[2-fluoro-3-(trifluoromethyl)phenyl]methyl}(2-methyl-2-phenylpropyl)amino)propoxy]-2-methanesulfonylbenzoate,
methyl 4-[3-({[2-fluoro-3-(trifluoromethyl)phenyl]methyl}(2-phenylethyl)amino)propoxy]-2-methanesulfonylbenzoate,
methyl 4-[3-({[2-fluoro-3-(trifluoromethyl)phenyl]methyl}(2-phenylpropyl)amino)propoxy]-2-methanesulfonylbenzoate,
methyl 4-[3-({[2-fluoro-3-(trifluoromethyl)phenyl]methyl}[(4-fluorophenyl)methyl]amino)propoxy]-2-methanesulfonylbenzoate,
methyl 4-[3-({[2-fluoro-3-(trifluoromethyl)phenyl]methyl}[2-(4-fluorophenyl)-2-methylpropyl]amino)propoxy]-2-methanesulfonylbenzoate,
methyl 4-[3-({[2-fluoro-3-(trifluoromethyl)phenyl]methyl}[2-(4-fluorophenyl)ethyl]amino)propoxy]-2-methanesulfonylbenzoate,
methyl 4-[3-({[2-fluoro-3-(trifluoromethyl)phenyl]methyl}[2-(4-fluorophenyl)propyl]amino)propoxy]-2-methanesulfonylbenzoate,
2-(2-fluoro-6-methanesulfonyl-4-{3-[(2-phenylpropyl)({[3-(trifluoromethyl)phenyl]methyl})amino]propoxy}phenyl)ethan-1-ol,
2-(2-fluoro-6-methanesulfonyl-4-{3-[(2-phenylethyl)({[3-(trifluoromethyl)phenyl]methyl})amino]propoxy}phenyl)ethan-1-ol,
2-(2-fluoro-6-methanesulfonyl-4-{3-[(2-methyl-2-phenylpropyl)({[3-(trifluoromethyl)phenyl]methyl})amino]propoxy}phenyl)ethan-1-ol,
2-(4-{3-[(2,2-diphenylethyl)({[2-fluoro-3-(trifluoromethyl)phenyl]methyl})amino]propoxy}-2-fluoro-6-methanesulfonylphenyl)ethan-1-ol,
2-(4-{3-[benzyl({[2-chloro-3-(trifluoromethyl)phenyl]methyl})amino]propoxy}-2-fluoro-6-methanesulfonylphenyl)ethan-1-ol,
2-(4-{3-[benzyl({[3-(trifluoromethyl)phenyl]methyl})amino]propoxy}-2-fluoro-6-methanesulfonylphenyl)ethan-1-ol,
2-(4-{3-[benzyl({[2-fluoro-3-(trifluoromethyl)phenyl]methyl})amino]propoxy}-2-fluoro-6-methanesulfonylphenyl)ethan-1-ol,
2-[2-fluoro-4-(3-{[2-(4-fluorophenyl)ethyl]({[3-(trifluoromethyl)phenyl]methyl})amino}propoxy)-6-methanesulfonylphenyl]ethan-1-ol,
2-[2-fluoro-4-(3-{[2-(4-fluorophenyl)-2-methylpropyl]({[3-(trifluoromethyl)phenyl]methyl})amino}propoxy)-6-methanesulfonylphenyl]ethan-1-ol,
2-[2-fluoro-4-(3-{[2-(4-fluorophenyl)propyl]({[3-(trifluoromethyl)phenyl]methyl})amino}propoxy)-6-methanesulfonylphenyl]ethan-1-ol,
2-{4-[3-({[2-chloro-3-(trifluoromethyl)phenyl]methyl}[2,2-difluoro-2-(4-fluorophenyl)ethyl]amino)propoxy]-2-fluoro-6-methanesulfonylphenyl}ethan-1-ol,
2-[2-fluoro-4-(3-{[(4-fluorophenyl)methyl]({[3-(trifluoromethyl)phenyl]methyl})amino}propoxy)-6-methanesulfonylphenyl]ethan-1-ol,
2-[4-(3-{[2,2-difluoro-2-(4-fluorophenyl)ethyl]({[3-(trifluoromethyl)phenyl]methyl})amino}propoxy)-2-fluoro-6-methanesulfonylphenyl]ethan-1-ol,
2-{4-[3-({[2-chloro-3-(trifluoromethyl)phenyl]methyl}(2-methyl-2-phenylpropyl)amino)propoxy]-2-fluoro-6-methanesulfonylphenyl}ethan-1-ol,
2-(4-{3-[(2,2-diphenylethyl)({[3-(trifluoromethyl)phenyl]methyl})amino]propoxy}-2-fluoro-6-methanesulfonylphenyl)ethan-1-ol,
2-{4-[3-({[2-chloro-3-(trifluoromethyl)phenyl]methyl}(2-phenylethyl)amino)propoxy]-2-fluoro-6-methanesulfonylphenyl}ethan-1-ol,
2-{4-[3-({[2-chloro-3-(trifluoromethyl)phenyl]methyl}(2-phenylpropyl)amino)propoxy]-2-fluoro-6-methanesulfonylphenyl}ethan-1-ol,
2-{4-[3-({[2-chloro-3-(trifluoromethyl)phenyl]methyl}[2-(4-fluorophenyl)-2-methylpropyl]amino)propoxy]-2-fluoro-6-methanesulfonylphenyl}ethan-1-ol,
2-{4-[3-({[2-chloro-3-(trifluoromethyl)phenyl]methyl}[(4-fluorophenyl)methyl]amino)propoxy]-2-fluoro-6-methanesulfonylphenyl}ethan-1-ol,
2-{4-[3-({[2-chloro-3-(trifluoromethyl)phenyl]methyl}[2-(4-fluorophenyl)ethyl]amino)propoxy]-2-fluoro-6-methanesulfonylphenyl}ethan-1-ol,
2-{4-[3-({[2-chloro-3-(trifluoromethyl)phenyl]methyl}[2-(4-fluorophenyl)propyl]amino)propoxy]-2-fluoro-6-methanesulfonylphenyl}ethan-1-ol,
2-{2-fluoro-4-[3-({[2-fluoro-3-(trifluoromethyl)phenyl]methyl}(2-methyl-2-phenylpropyl)amino)propoxy]-6-methanesulfonylphenyl}ethan-1-ol,
2-[4-(3-{[2,2-difluoro-2-(4-fluorophenyl)ethyl]({[2-fluoro-3-(trifluoromethyl)phenyl]methyl})amino}propoxy)-2-fluoro-6-methanesulfonylphenyl]ethan-1-ol,
2-{2-fluoro-4-[3-({[2-fluoro-3-(trifluoromethyl)phenyl]methyl}(2-phenylpropyl)amino)propoxy]-6-methanesulfonylphenyl}ethan-1-ol,
2-{2-fluoro-4-[3-({[2-fluoro-3-(trifluoromethyl)phenyl]methyl}[(4-fluorophenyl)methyl]amino)propoxy]-6-methanesulfonylphenyl}ethan-1-ol,
2-{2-fluoro-4-[3-({[2-fluoro-3-(trifluoromethyl)phenyl]methyl}(2-phenylethyl)amino)propoxy]-6-methanesulfonylphenyl}ethan-1-ol,
2-{2-fluoro-4-[3-({[2-fluoro-3-(trifluoromethyl)phenyl]methyl}[2-(4-fluorophenyl)-2-methylpropyl]amino)propoxy]-6-methanesulfonylphenyl}ethan-1-ol,
2-{2-fluoro-4-[3-({[2-fluoro-3-(trifluoromethyl)phenyl]methyl}[2-(4-fluorophenyl)ethyl]amino)propoxy]-6-methanesulfonylphenyl}ethan-1-ol,
2-{2-fluoro-4-[3-({[2-fluoro-3-(trifluoromethyl)phenyl]methyl}[2-(4-fluorophenyl)propyl]amino)propoxy]-6-methanesulfonylphenyl}ethan-1-ol,
2-(2-methanesulfonyl-4-{3-[(2-methyl-2-phenylpropyl)({[3-(trifluoromethyl)phenyl]methyl})amino]propoxy}phenyl)ethan-1-ol,
2-(2-methanesulfonyl-4-{3-[(2-phenylethyl)({[3-(trifluoromethyl)phenyl]methyl})amino]propoxy}phenyl)ethan-1-ol,
2-(2-methanesulfonyl-4-{3-[(2-phenylpropyl)({[3-(trifluoromethyl)phenyl]methyl})amino]propoxy}phenyl)ethan-1-ol,
2-(4-{3-[(2,2-diphenylethyl)({[2-fluoro-3-(trifluoromethyl)phenyl]methyl})amino]propoxy}-2-methanesulfonylphenyl)ethan-1-ol,
2-(4-{3-[(2,2-diphenylethyl)({[3-(trifluoromethyl)phenyl]methyl})amino]propoxy}-2-methanesulfonylphenyl)ethan-1-ol, 2-(4-{3-[benzyl({[2-chloro-3-(trifluoromethyl)phenyl]methyl})amino]propoxy}-2-methanesulfonylphenyl)ethan-1-ol, 2-(4-{3-[benzyl({[2-fluoro-3-(trifluoromethyl)phenyl]methyl})amino]propoxy}-2-methanesulfonylphenyl)ethan-1-ol, 2-(4-{3-[benzyl({[3-(trifluoromethyl)phenyl]methyl})amino]propoxy}-2-methanesulfonylphenyl)ethan-1-ol, 2-[4-(3-{[(4-fluorophenyl)methyl]({[3-(trifluoromethyl)phenyl]methyl})amino}propoxy)-2-methanesulfonylphenyl]ethan-1-ol, 2-[4-(3-{[2-(4-fluorophenyl)-2-methylpropyl]({[3-(trifluoromethyl)phenyl]methyl})amino}propoxy)-2-methanesulfonylphenyl]ethan-1-ol, 2-[4-(3-{[2-(4-fluorophenyl)ethyl]({[3-(trifluoromethyl)phenyl]methyl})amino}propoxy)-2-methanesulfonylphenyl]ethan-1-ol, 2-[4-(3-{[2-(4-fluorophenyl)propyl]({[3-(trifluoromethyl)phenyl]methyl})amino}propoxy)-2-methanesulfonylphenyl]ethan-1-ol, 2-{4-[3-({[2-chloro-3-(trifluoromethyl)phenyl]methyl}[2,2-difluoro-2-(4-fluorophenyl)ethyl]amino)propoxy]-2-methanesulfonylphenyl}ethan-1-ol, 2-[4-(3-{[2,2-difluoro-2-(4-fluorophenyl)ethyl]({[2-fluoro-3-(trifluoromethyl)phenyl]methyl})amino}propoxy)-2-methanesulfonylphenyl]ethan-1-ol, 2-[4-(3-{[2,2-difluoro-2-(4-fluorophenyl)ethyl]({[3-(trifluoromethyl)phenyl]methyl})amino}propoxy)-2-methanesulfonylphenyl]ethan-1-ol, 2-{4-[3-({[2-chloro-3-(trifluoromethyl)phenyl]methyl}(2-methyl-2-phenylpropyl)amino)propoxy]-2-methanesulfonylphenyl}ethan-1-ol, 2-{4-[3-({[2-chloro-3-(trifluoromethyl)phenyl]methyl}(2-phenylethyl)amino)propoxy]-2-methanesulfonylphenyl}ethan-1-ol, 2-{4-[3-({[2-chloro-3-(trifluoromethyl)phenyl]methyl}(2-phenylpropyl)amino)propoxy]-2-methanesulfonylphenyl}ethan-1-ol, 2-{4-[3-({[2-chloro-3-(trifluoromethyl)phenyl]methyl}(2,2-diphenylethyl)amino)propoxy]-2-methanesulfonylphenyl}ethan-1-ol, 2-{4-[3-({[2-chloro-3-(trifluoromethyl)phenyl]methyl}[(4-fluorophenyl)methyl]amino)propoxy]-2-methanesulfonylphenyl}ethan-1-ol, 2-{4-[3-({[2-chloro-3-(trifluoromethyl)phenyl]methyl}[2-(4-fluorophenyl)-2-methylpropyl]amino)propoxy]-2-methanesulfonylphenyl}ethan-1-ol, 2-{4-[3-({[2-chloro-3-(trifluoromethyl)phenyl]methyl}[2-(4-fluorophenyl)ethyl]amino)propoxy]-2-methanesulfonylphenyl}ethan-1-ol, 2-{4-[3-({[2-chloro-3-(trifluoromethyl)phenyl]methyl}[2-(4-fluorophenyl)propyl]amino)propoxy]-2-methanesulfonylphenyl}ethan-1-ol, 2-{4-[3-({[2-fluoro-3-(trifluoromethyl)phenyl]methyl}(2-methyl-2-phenylpropyl)amino)propoxy]-2-methanesulfonylphenyl}ethan-1-ol, 2-{4-[3-({[2-fluoro-3-(trifluoromethyl)phenyl]methyl}(2-phenylethyl)amino)propoxy]-2-methanesulfonylphenyl}ethan-1-ol, 2-{4-[3-({[2-fluoro-3-(trifluoromethyl)phenyl]methyl}(2-phenylpropyl)amino)propoxy]-2-methanesulfonylphenyl}ethan-1-ol, 2-{4-[3-({[2-fluoro-3-(trifluoromethyl)phenyl]methyl}[(4-fluorophenyl)methyl]amino)propoxy]-2-methanesulfonylphenyl}ethan-1-ol, 2-{4-[3-({[2-fluoro-3-(trifluoromethyl)phenyl]methyl}[2-(4-fluorophenyl)-2-methylpropyl]amino)propoxy]-2-methanesulfonylphenyl}ethan-1-ol, 2-{4-[3-({[2-fluoro-3-(trifluoromethyl)phenyl]methyl}[2-(4-fluorophenyl)ethyl]amino)propoxy]-2-methanesulfonylphenyl}ethan-1-ol, 2-{4-[3-({[2-fluoro-3-(trifluoromethyl)phenyl]methyl}[2-(4-fluorophenyl)propyl]amino)propoxy]-2-methanesulfonylphenyl}ethan-1-ol, 2-(2-fluoro-6-methanesulfonyl-4-{3-[(2-phenylethyl)({[3-(trifluoromethyl)phenyl]methyl})amino]propoxy}phenyl)acetic acid, 2-(2-fluoro-6-methanesulfonyl-4-{3-[(2-phenylpropyl)({[3-(trifluoromethyl)phenyl]methyl})amino]propoxy}phenyl)acetic acid, 2-(4-{3-[(2,2-diphenylethyl)({[2-fluoro-3-(trifluoromethyl)phenyl]methyl})amino]propoxy}-2-fluoro-6-methanesulfonylphenyl)acetic acid, 2-(4-{3-[benzyl({[2-chloro-3-(trifluoromethyl)phenyl]methyl})amino]propoxy}-2-fluoro-6-methanesulfonylphenyl)acetic acid, 2-(4-{3-[benzyl({[2-fluoro-3-(trifluoromethyl)phenyl]methyl})amino]propoxy}-2-fluoro-6-methanesulfonylphenyl)acetic acid, 2-(4-{3-[benzyl({[3-(trifluoromethyl)phenyl]methyl})amino]propoxy}-2-fluoro-6-methanesulfonylphenyl)acetic acid, 2-[2-fluoro-4-(3-{[(4-fluorophenyl)methyl]({[3-(trifluoromethyl)phenyl]methyl})amino}propoxy)-6-methanesulfonylphenyl]acetic acid, 2-[2-fluoro-4-(3-{[2-(4-fluorophenyl)-2-methylpropyl]({[3-(trifluoromethyl)phenyl]methyl})amino}propoxy)-6-methanesulfonylphenyl]acetic acid, 2-[2-fluoro-4-(3-{[2-(4-fluorophenyl)ethyl]({[3-(trifluoromethyl)phenyl]methyl})amino}propoxy)-6-methanesulfonylphenyl]acetic acid, 2-[2-fluoro-4-(3-{[2-(4-fluorophenyl)propyl]({[3-(trifluoromethyl)phenyl]methyl})amino}propoxy)-6-methanesulfonylphenyl]acetic acid, 2-{4-[3-({[2-chloro-3-(trifluoromethyl)phenyl]methyl}[2,2-difluoro-2-(4-fluorophenyl)ethyl]amino)propoxy]-2-fluoro-6-methanesulfonylphenyl}acetic acid, 2-[4-(3-{[2,2-difluoro-2-(4-fluorophenyl)ethyl]({[2-fluoro-3-(trifluoromethyl)phenyl]methyl})amino}propoxy)-2-fluoro-6-methanesulfonylphenyl]acetic acid, 2-[4-(3-{[2,2-difluoro-2-(4-fluorophenyl)ethyl]({[3-(trifluoromethyl)phenyl]methyl})amino}propoxy)-2-fluoro-6-methanesulfonylphenyl]acetic acid, 2-{4-[3-({[2-chloro-3-(trifluoromethyl)phenyl]methyl}(2-methyl-2-phenylpropyl)amino)propoxy]-2-fluoro-6-methanesulfonylphenyl}acetic acid, 2-{4-[3-({[2-chloro-3-(trifluoromethyl)phenyl]methyl}(2-phenylethyl)amino)propoxy]-2-fluoro-6-methanesulfonylphenyl}acetic acid, 2-{4-[3-({[2-chloro-3-(trifluoromethyl)phenyl]methyl}(2-phenylpropyl)amino)propoxy]-2-fluoro-6-methanesulfonylphenyl}acetic acid, 2-{4-[3-({[2-chloro-3-(trifluoromethyl)phenyl]methyl}(2,2-diphenylethyl)amino)propoxy]-2-fluoro-6-methanesulfonylphenyl}acetic acid, 2-{4-[3-({[2-chloro-3-(trifluoromethyl)phenyl]methyl}[(4-fluorophenyl)methyl]amino)propoxy]-2-fluoro-6-methanesulfonylphenyl}acetic acid, 2-{4-[3-({[2-chloro-3-(trifluoromethyl)phenyl]methyl}[2-(4-fluorophenyl)-2-methylpropyl]amino)propoxy]-2-fluoro-6-methanesulfonylphenyl}acetic acid, 2-{4-[3-({[2-chloro-3-(trifluoromethyl)phenyl]methyl}[2-(4-fluorophenyl)ethyl]amino)propoxy]-2-fluoro-6-methanesulfonylphenyl}acetic acid, 2-{4-[3-({[2-chloro-3-(trifluoromethyl)phenyl]methyl}[2-(4-fluorophenyl)propyl]amino)propoxy]-2-fluoro-6-methanesulfonylphenyl}acetic acid, 2-(4-{3-[(2,2-diphenylethyl)({[3-(trifluoromethyl)phenyl]methyl})amino]propoxy}-2-fluoro-6-methanesulfonylphenyl)acetic acid, 2-{2-fluoro-4-[3-({[2-fluoro-3-(trifluoromethyl)phenyl]methyl}(2-methyl-2-phenylpropyl)amino)propoxy]-6-methanesulfonylphenyl}acetic acid, 2-(2-fluoro-6-methanesulfonyl-4-{3-[(2-methyl-2-phenylpropyl)({[3-(trifluoromethyl)phenyl]methyl})amino]propoxy}phenyl)acetic acid, 2-{2-fluoro-4-[3-({[2-fluoro-3-(trifluoromethyl)phenyl]methyl}(2-phenylpropyl)amino)propoxy]-6-methanesulfonylphenyl}acetic acid, 2-{2-fluoro-4-[3-({[2-fluoro-3-(trifluoromethyl)phenyl]methyl}[(4-fluorophenyl)methyl]amino)propoxy]-6-methanesulfonylphenyl}acetic acid, 2-{2-fluoro-4-[3-({[2-fluoro-3-(trifluoromethyl)phenyl]methyl}[2-(4-fluorophenyl)-2-methylpropyl]amino)propoxy]-6-methanesulfonylphenyl}acetic acid, 2-{2-fluoro-4-[3-({[2-fluoro-3-(trifluoromethyl)phenyl]methyl}[2-(4-fluorophenyl)ethyl]amino)propoxy]-6-methanesulfonylphenyl}acetic acid, 2-{2-fluoro-4-[3-({[2-fluoro-3-(trifluoromethyl)phenyl]methyl}(2-phenylethyl)amino)propoxy]-6-methanesulfonylphenyl}acetic acid, 2-{2-fluoro-4-[3-({[2-fluoro-3-(trifluoromethyl)phenyl]methyl}[2-(4-fluorophenyl)propyl]amino)propoxy]-6-methanesulfonylphenyl}acetic acid, 2-(2-methanesulfonyl-4-{3-[(2-methyl-2-phenylpropyl)({[3-(trifluoromethyl)phenyl]methyl})amino]propoxy}phenyl)acetic acid, 2-(2-methanesulfonyl-4-{3-[(2-phenylethyl)({[3-(trifluoromethyl)phenyl]methyl})amino]propoxy}phenyl)acetic acid, 2-(2-methanesulfonyl-4-{3-[(2-phenylpropyl)({[3-(trifluoromethyl)phenyl]methyl})amino]propoxy}phenyl)acetic acid, 2-(4-{3-[(2,2-diphenylethyl)({[2-fluoro-3-(trifluoromethyl)phenyl]methyl})amino]propoxy}-2-methanesulfonylphenyl)acetic acid, 2-(4-{3-[(2,2-diphenylethyl)({[3-(trifluoromethyl)phenyl]methyl})amino]propoxy}-2-methanesulfonylphenyl)acetic acid, 2-(4-{3-[benzyl({[2-chloro-3-(trifluoromethyl)phenyl]methyl})amino]propoxy}-2-methanesulfonylphenyl)acetic acid, 2-(4-{3-[benzyl({[2-fluoro-3-(trifluoromethyl)phenyl]methyl})amino]propoxy}-2-methanesulfonylphenyl)acetic acid, 2-(4-{3-[benzyl({[3-(trifluoromethyl)phenyl]methyl})amino]propoxy}-2-methanesulfonylphenyl)acetic acid, 2-[4-(3-{[(4-fluorophenyl)methyl]({[3-(trifluoromethyl)phenyl]methyl})amino}propoxy)-2-methanesulfonylphenyl]acetic acid, 2-[4-(3-{[2-(4-fluorophenyl)-2-methylpropyl]({[3-(trifluoromethyl)phenyl]methyl})amino}propoxy)-2-methanesulfonylphenyl]acetic acid, 2-[4-(3-{[2-(4-fluorophenyl)ethyl]({[3-(trifluoromethyl)phenyl]methyl})amino}propoxy)-2-methanesulfonylphenyl]acetic acid, 2-[4-(3-{[2-(4-fluorophenyl)propyl]({[3-(trifluoromethyl)phenyl]methyl})amino}propoxy)-2-methanesulfonylphenyl]acetic acid, 2-[4-(3-{[2-chloro-3-(trifluoromethyl)phenyl]methyl}[2,2-difluoro-2-(4-fluorophenyl)ethyl]amino)propoxy]-2-methanesulfonylphenyl}acetic acid, 2-[4-(3-{[2,2-difluoro-2-(4-fluorophenyl)ethyl]({[2-fluoro-3-(trifluoromethyl)phenyl]methyl})amino}propoxy)-2-methanesulfonylphenyl]acetic acid, 2-[4-(3-{[2,2-difluoro-2-(4-fluorophenyl)ethyl]({[3-(trifluoromethyl)phenyl]methyl})amino}propoxy)-2-methanesulfonylphenyl]acetic acid, 2-{4-[3-({[2-chloro-3-(trifluoromethyl)phenyl]methyl}(2-methyl-2-phenylpropyl)amino)propoxy]-2-methanesulfonylphenyl}acetic acid, 2-{4-[3-({[2-chloro-3-(trifluoromethyl)phenyl]methyl}(2-phenylethyl)amino)propoxy]-2-methanesulfonylphenyl}acetic acid, 2-{4-[3-({[2-chloro-3-(trifluoromethyl)phenyl]methyl}(2-phenylpropyl)amino)propoxy]-2-methanesulfonylphenyl}acetic acid, 2-{4-[3-({[2-chloro-3-(trifluoromethyl)phenyl]methyl}(2,2-diphenylethyl)amino)propoxy]-2-methanesulfonylphenyl}acetic acid, 2-{4-[3-({[2-chloro-3-(trifluoromethyl)phenyl]methyl}[(4-fluorophenyl)methyl]amino)propoxy]-2-methanesulfonylphenyl}acetic acid, 2-{4-[3-({[2-chloro-3-(trifluoromethyl)phenyl]methyl}[2-(4-fluorophenyl)-2-methylpropyl]amino)propoxy]-2-methanesulfonylphenyl}acetic acid, 2-{4-[3-({[2-chloro-3-(trifluoromethyl)phenyl]methyl}[2-(4-fluorophenyl)ethyl]amino)propoxy]-2-methanesulfonylphenyl}acetic acid, 2-{4-[3-({[2-chloro-3-(trifluoromethyl)phenyl]methyl}[2-(4-fluorophenyl)propyl]amino)propoxy]-2-methanesulfonylphenyl}acetic acid, 2-{4-[3-({[2-fluoro-3-(trifluoromethyl)phenyl]methyl}(2-methyl-2-phenylpropyl)amino)propoxy]-2-methanesulfonylphenyl}acetic acid, 2-{4-[3-({[2-fluoro-3-(trifluoromethyl)phenyl]methyl}(2-phenylethyl)amino)propoxy]-2-methanesulfonylphenyl}acetic acid, 2-{4-[3-({[2-fluoro-3-(trifluoromethyl)phenyl]methyl}(2-phenylpropyl)amino)propoxy]-2-methanesulfonylphenyl}acetic acid, 2-{4-[3-({[2-fluoro-3-(trifluoromethyl)phenyl]methyl}[(4-fluorophenyl)methyl]amino)propoxy]-2-methanesulfonylphenyl}acetic acid, 2-{4-[3-({[2-fluoro-3-(trifluoromethyl)phenyl]methyl}[2-(4-fluorophenyl)-2-methylpropyl]amino)propoxy]-2-methanesulfonylphenyl}acetic acid, 2-{4-[3-({[2-fluoro-3-(trifluoromethyl)phenyl]methyl}[2-(4-fluorophenyl)ethyl]amino)propoxy]-2-methanesulfonylphenyl}acetic acid, 2-{4-[3-({[2-fluoro-3-(trifluoromethyl)phenyl]methyl}[2-(4-fluorophenyl)propyl]amino)propoxy]-2-methanesulfonylphenyl}acetic acid, N-[(2-fluoro-6-methanesulfonyl-4-{3-[(2-phenylethyl)({[3-(trifluoromethyl)phenyl]methyl})amino]propoxy}phenyl)methyl]acetamide, N-[(4-{3-[(2,2-diphenylethyl)({[2-fluoro-3-(trifluoromethyl)phenyl]methyl})amino]propoxy}-2-fluoro-6-methanesulfonylphenyl)methyl]acetamide, N-[(2-fluoro-6-methanesulfonyl-4-{3-[(2-phenylpropyl)({[3-(trifluoromethyl)phenyl]methyl})amino]propoxy}phenyl)methyl]acetamide, N-[(2-fluoro-6-methanesulfonyl-4-{3-[(2-methyl-2-phenylpropyl)({[3-(trifluoromethyl)phenyl]methyl})amino]propoxy}phenyl) methyl]acetamide, N-[(4-{3-[(2,2-diphenylethyl)({[3-(trifluoromethyl)phenyl]methyl})amino]propoxy}-2-fluoro-6-methanesulfonylphenyl)methyl]acetamide, N-[(4-{3-[benzyl({[2-chloro-3-(trifluoromethyl)phenyl]methyl})amino]propoxy}-2-fluoro-6-methanesulfonylphenyl)methyl]acetamide, N-[(4-{3-[benzyl({[3-(trifluoromethyl)phenyl]methyl})amino]propoxy}-2-fluoro-6-methanesulfonylphenyl)methyl]acetamide, N-{[2-fluoro-4-(3-{[(4-fluorophenyl)methyl]({[3-(trifluoromethyl)phenyl]methyl})amino}propoxy)-6-methanesulfonylphenyl]methyl}acetamide, N-{[2-fluoro-4-(3-{[2-(4-fluorophenyl)-2-methylpropyl]({[3-(trifluoromethyl)phenyl]methyl})amino}propoxy)-6-methanesulfonylphenyl]methyl}acetamide, N-{[2-fluoro-4-(3-{[2-(4-fluorophenyl)propyl]({[3-(trifluoromethyl)phenyl]methyl})amino}propoxy)-6-methanesulfonylphenyl]methyl}acetamide, N-{[4-(3-{[2,2-difluoro-2-(4-fluorophenyl)ethyl]({[2-fluoro-3-(trifluoromethyl)phenyl]methyl})amino}propoxy)-2-fluoro-6-methanesulfonylphenyl]methyl}acetamide, N-({4-[3-({[2-chloro-3-(trifluoromethyl)phenyl]methyl}[2,2-difluoro-2-(4-fluorophenyl)ethyl]amino)propoxy]-2-fluoro-6-methanesulfonylphenyl}methyl)acetamide, N-{[4-(3-{[2,2-difluoro-2-(4-fluorophenyl)ethyl]({[3-(trifluoromethyl)phenyl]methyl})amino}propoxy)-2-fluoro-6-methanesulfonylphenyl]methyl}acetamide, N-({4-[3-({[2-chloro-3-(trifluoromethyl)phenyl]methyl}(2-methyl-2-phenylpropyl)amino)propoxy]-2-fluoro-6-methanesulfonylphenyl}methyl)acetamide, N-({4-[3-({[2-chloro-3-(trifluoromethyl)phenyl]methyl}(2-phenylethyl)amino)propoxy]-2-fluoro-6-methanesulfonylphenyl}methyl)acetamide, N-({4-[3-({[2-chloro-3-(trifluoromethyl)phenyl]methyl}(2-phenylpropyl)amino)propoxy]-2-fluoro-6-methanesulfonylphenyl}methyl)acetamide, N-({4-[3-({[2-chloro-3-(trifluoromethyl)phenyl]methyl}[(4-fluorophenyl)methyl]amino)propoxy]-2-fluoro-6-methanesulfonylphenyl}methyl)acetamide, N-({4-[3-({[2-chloro-3-(trifluoromethyl)phenyl]methyl}[2-(4-fluorophenyl)-2-methylpropyl]amino)propoxy]-2-fluoro-6-methanesulfonylphenyl}methyl)acetamide, N-({4-[3-({[2-chloro-3-(trifluoromethyl)phenyl]methyl}[2-(4-fluorophenyl)ethyl]amino)propoxy]-2-fluoro-6-methanesulfonylphenyl}methyl)acetamide, N-({4-[3-({[2-chloro-3-(trifluoromethyl)phenyl]methyl}[2-(4-fluorophenyl)propyl]amino)propoxy]-2-fluoro-6-methanesulfonylphenyl}methyl)acetamide, N-({2-fluoro-4-[3-({[2-fluoro-3-(trifluoromethyl)phenyl]methyl}(2-methyl-2-phenylpropyl)amino)propoxy]-6-methanesulfonylphenyl}methyl)acetamide, N-({2-fluoro-4-[3-({[2-fluoro-3-(trifluoromethyl)phenyl]methyl}(2-phenylethyl)amino)propoxy]-6-methanesulfonylphenyl}methyl)acetamide, N-({2-fluoro-4-[3-({[2-fluoro-3-(trifluoromethyl)phenyl]methyl}(2-phenylpropyl)amino)propoxy]-6-methanesulfonylphenyl}methyl)acetamide, N-{[2-fluoro-4-(3-{[2-(4-fluorophenyl)ethyl]({[3-(trifluoromethyl)phenyl]methyl})amino}propoxy)-6-methanesulfonylphenyl]methyl}acetamide, N-[(4-{3-[benzyl({[2-fluoro-3-(trifluoromethyl)phenyl]methyl})amino]propoxy}-2-fluoro-6-methanesulfonylphenyl)methyl]acetamide, N-({2-fluoro-4-[3-({[2-fluoro-3-(trifluoromethyl)phenyl]methyl}[(4-fluorophenyl)methyl]amino)propoxy]-6-methanesulfonylphenyl}methyl)acetamide, N-({2-fluoro-4-[3-({[2-fluoro-3-(trifluoromethyl)phenyl]methyl}[2-(4-fluorophenyl)-2-methylpropyl]amino)propoxy]-6-methanesulfonylphenyl}methyl)acetamide, N-({2-fluoro-4-[3-({[2-fluoro-3-(trifluoromethyl)phenyl]methyl}[2-(4-fluorophenyl)ethyl]amino)propoxy]-6-methanesulfonylphenyl}methyl)acetamide, N-({2-fluoro-4-[3-({[2-fluoro-3-(trifluoromethyl)phenyl]methyl}[2-(4-fluorophenyl)propyl]amino)propoxy]-6-methanesulfonylphenyl}methyl)acetamide, N-[(2-methanesulfonyl-4-{3-[(2-methyl-2-phenylpropyl)({[3-(trifluoromethyl)phenyl]methyl})amino]propoxy}phenyl)methyl]acetamide, N-[(2-methanesulfonyl-4-{3-[(2-phenylethyl)({[3-(trifluoromethyl)phenyl]methyl})amino]propoxy}phenyl)methyl]acetamide, N-[(2-methanesulfonyl-4-{3-[(2-phenylpropyl)({[3-(trifluoromethyl)phenyl]methyl})amino]propoxy}phenyl)methyl]acetamide, N-[(4-{3-[(2,2-diphenylethyl)({[2-fluoro-3-(trifluoromethyl)phenyl]methyl})amino]propoxy}-2-methanesulfonylphenyl)methyl]acetamide, N-[(4-{3-[(2,2-diphenylethyl)({[3-(trifluoromethyl)phenyl]methyl})amino]propoxy}-2-methanesulfonylphenyl)methyl]acetamide, N-[(4-{3-[benzyl({[2-chloro-3-(trifluoromethyl)phenyl]methyl})amino]propoxy}-2-methanesulfonylphenyl)methyl]acetamide, N-[(4-{3-[benzyl({[2-fluoro-3-(trifluoromethyl)phenyl]methyl})amino]propoxy}-2-methanesulfonylphenyl)methyl]acetamide, N-[(4-{3-[benzyl({[3-(trifluoromethyl)phenyl]methyl})amino]propoxy}-2-methanesulfonylphenyl)methyl]acetamide, N-{[4-(3-{[(4-fluorophenyl)methyl]({[3-(trifluoromethyl)phenyl]methyl})amino}propoxy)-2-methanesulfonylphenyl]methyl}acetamide, N-{[4-(3-{[2-(4-fluorophenyl)-2-methylpropyl]({[3-(trifluoromethyl)phenyl]methyl})amino}propoxy)-2-methanesulfonylphenyl]methyl}acetamide, N-{[4-(3-{[2-(4-fluorophenyl)ethyl]({[3-(trifluoromethyl)phenyl]methyl})amino}propoxy)-2-methanesulfonylphenyl]methyl}acetamide, N-{[4-(3-{[2-(4-fluorophenyl)propyl]({[3-(trifluoromethyl)phenyl]methyl})amino}propoxy)-2-methanesulfonylphenyl]methyl}acetamide, N-({4-[3-({[2-chloro-3-(trifluoromethyl)phenyl]methyl}[2,2-difluoro-2-(4-fluorophenyl)ethyl]amino)propoxy]-2-methanesulfonylphenyl}methyl)acetamide, N-{[4-(3-{[2,2-difluoro-2-(4-fluorophenyl)ethyl]({[2-fluoro-3-(trifluoromethyl)phenyl]methyl})amino}propoxy)-2-methanesulfonylphenyl]methyl}acetamide, N-{[4-(3-{[2,2-difluoro-2-(4-fluorophenyl)ethyl]({[3-(trifluoromethyl)phenyl]methyl})amino}propoxy)-2-methanesulfonylphenyl]methyl}acetamide, N-({4-[3-({[2-chloro-3-(trifluoromethyl)phenyl]methyl}(2-methyl-2-phenylpropyl)amino)propoxy]-2-methanesulfonylphenyl}methyl)acetamide,
N-({4-[3-({[2-chloro-3-(trifluoromethyl)phenyl]methyl}(2-phenylethyl)amino)propoxy]-2-methanesulfonylphenyl}methyl)acetamide,
N-({4-[3-({[2-chloro-3-(trifluoromethyl)phenyl]methyl}(2-phenylpropyl)amino)propoxy]-2-methanesulfonylphenyl}methyl)acetamide,
N-({4-[3-({[2-chloro-3-(trifluoromethyl)phenyl]methyl}(2,2-diphenylethyl)amino)propoxy]-2-methanesulfonylphenyl}methyl)acetamide,
N-({4-[3-({[2-chloro-3-(trifluoromethyl)phenyl]methyl}[(4-fluorophenyl)methyl]amino)propoxy]-2-methanesulfonylphenyl}methyl)acetamide,
N-({4-[3-({[2-chloro-3-(trifluoromethyl)phenyl]methyl}[2-(4-fluorophenyl)-2-methylpropyl]amino)propoxy]-2-methanesulfonylphenyl}methyl)acetamide,
N-({4-[3-({[2-chloro-3-(trifluoromethyl)phenyl]methyl}[2-(4-fluorophenyl)ethyl]amino)propoxy]-2-methanesulfonylphenyl}methyl)acetamide,
N-({4-[3-({[2-chloro-3-(trifluoromethyl)phenyl]methyl}[2-(4-fluorophenyl)propyl]amino)propoxy]-2-methanesulfonylphenyl}methyl)acetamide,
N-({4-[3-({[2-fluoro-3-(trifluoromethyl)phenyl]methyl}(2-methyl-2-phenylpropyl)amino)propoxy]-2-methanesulfonylphenyl}methyl)acetamide,
N-({4-[3-({[2-fluoro-3-(trifluoromethyl)phenyl]methyl}(2-phenylethyl)amino)propoxy]-2-methanesulfonylphenyl}methyl)acetamide,
N-({4-[3-({[2-fluoro-3-(trifluoromethyl)phenyl]methyl}(2-phenylpropyl)amino)propoxy]-2-methanesulfonylphenyl}methyl)acetamide,
N-({4-[3-({[2-fluoro-3-(trifluoromethyl)phenyl]methyl}[(4-fluorophenyl)methyl]amino)propoxy]-2-methanesulfonylphenyl}methyl)acetamide,
N-({4-[3-({[2-fluoro-3-(trifluoromethyl)phenyl]methyl}[2-(4-fluorophenyl)-2-methylpropyl]amino)propoxy]-2-methanesulfonylphenyl}methyl)acetamide,
N-({4-[3-({[2-fluoro-3-(trifluoromethyl)phenyl]methyl}[2-(4-fluorophenyl)ethyl]amino)propoxy]-2-methanesulfonylphenyl}methyl)acetamide,
N-({4-[3-({[2-fluoro-3-(trifluoromethyl)phenyl]methyl}[2-(4-fluorophenyl)propyl]amino)propoxy]-2-methanesulfonylphenyl}methyl)acetamide,
2-(2-fluoro-6-methanesulfonyl-4-{3-[(2-methyl-2-phenylpropyl)({[3-(trifluoromethyl)phenyl]methyl})amino]propoxy}phenyl)propan-2-ol,
2-(2-fluoro-6-methanesulfonyl-4-{3-[(2-phenylethyl)({[3-(trifluoromethyl)phenyl]methyl})amino]propoxy}phenyl)propan-2-ol,
2-(2-fluoro-6-methanesulfonyl-4-{3-[(2-phenylpropyl)({[3-(trifluoromethyl)phenyl]methyl})amino]propoxy}phenyl)propan-2-ol,
2-(4-{3-[(2,2-diphenylethyl)({[3-(trifluoromethyl)phenyl]methyl})amino]propoxy}-2-fluoro-6-methanesulfonylphenyl) propan-2-ol,
2-(4-{3-[benzyl({[2-chloro-3-(trifluoromethyl)phenyl]methyl})amino]propoxy}-2-fluoro-6-methanesulfonylphenyl)propan-2-ol,
2-(4-{3-[benzyl({[2-fluoro-3-(trifluoromethyl)phenyl]methyl})amino]propoxy}-2-fluoro-6-methanesulfonylphenyl)propan-2-ol,
2-(4-{3-[benzyl({[3-(trifluoromethyl)phenyl]methyl})amino]propoxy}-2-fluoro-6-methanesulfonylphenyl)propan-2-ol,
2-(4-{3-[(2,2-diphenylethyl)({[2-fluoro-3-(trifluoromethyl)phenyl]methyl})amino]propoxy}-2-fluoro-6-methanesulfonylphenyl)propan-2-ol,
2-[2-fluoro-4-(3-{[(4-fluorophenyl)methyl]({[3-(trifluoromethyl)phenyl]methyl})amino}propoxy)-6-methanesulfonylphenyl]propan-2-ol,
2-[2-fluoro-4-(3-{[2-(4-fluorophenyl)ethyl]({[3-(trifluoromethyl)phenyl]methyl})amino}propoxy)-6-methanesulfonylphenyl]propan-2-ol,
2-[2-fluoro-4-(3-{[2-(4-fluorophenyl)-2-methylpropyl]({[3-(trifluoromethyl)phenyl]methyl})amino}propoxy)-6-methanesulfonylphenyl]propan-2-ol,
2-[2-fluoro-4-(3-{[2-(4-fluorophenyl)propyl]({[3-(trifluoromethyl)phenyl]methyl})amino}propoxy)-6-methanesulfonylphenyl]propan-2-ol,
2-{4-[3-({[2-chloro-3-(trifluoromethyl)phenyl]methyl}[2,2-difluoro-2-(4-fluorophenyl)ethyl]amino)propoxy]-2-fluoro-6-methanesulfonylphenyl}propan-2-ol,
2-[4-(3-{[2,2-difluoro-2-(4-fluorophenyl)ethyl]({[3-(trifluoromethyl)phenyl]methyl})amino}propoxy)-2-fluoro-6-methanesulfonylphenyl]propan-2-ol,
2-[4-(3-{[2,2-difluoro-2-(4-fluorophenyl)ethyl]({[2-fluoro-3-(trifluoromethyl)phenyl]methyl})amino}propoxy)-2-fluoro-6-methanesulfonylphenyl]propan-2-ol,
2-{4-[3-({[2-chloro-3-(trifluoromethyl)phenyl]methyl}(2-methyl-2-phenylpropyl)amino)propoxy]-2-fluoro-6-methanesulfonylphenyl}propan-2-ol,
2-{4-[3-({[2-chloro-3-(trifluoromethyl)phenyl]methyl}(2-phenylethyl)amino)propoxy]-2-fluoro-6-methanesulfonylphenyl}propan-2-ol,
2-{4-[3-({[2-chloro-3-(trifluoromethyl)phenyl]methyl}[(4-fluorophenyl)methyl]amino)propoxy]-2-fluoro-6-methanesulfonylphenyl}propan-2-ol,
2-{4-[3-({[2-chloro-3-(trifluoromethyl)phenyl]methyl}(2-phenylpropyl)amino)propoxy]-2-fluoro-6-methanesulfonylphenyl}propan-2-ol,
2-{4-[3-({[2-chloro-3-(trifluoromethyl)phenyl]methyl}[2-(4-fluorophenyl)-2-methylpropyl]amino)propoxy]-2-fluoro-6-methanesulfonylphenyl}propan-2-ol,
2-{4-[3-({[2-chloro-3-(trifluoromethyl)phenyl]methyl}[2-(4-fluorophenyl)ethyl]amino)propoxy]-2-fluoro-6-methanesulfonylphenyl}propan-2-ol,
2-{2-fluoro-4-[3-({[2-fluoro-3-(trifluoromethyl)phenyl]methyl}(2-methyl-2-phenylpropyl)amino)propoxy]-6-methanesulfonylphenyl}propan-2-ol,
2-{4-[3-({[2-chloro-3-(trifluoromethyl)phenyl]methyl}[2-(4-fluorophenyl)propyl]amino)propoxy]-2-fluoro-6-methanesulfonylphenyl}propan-2-ol,
2-{2-fluoro-4-[3-({[2-fluoro-3-(trifluoromethyl)phenyl]methyl}(2-phenylethyl)amino)propoxy]-6-methanesulfonylphenyl}propan-2-ol,
2-{2-fluoro-4-[3-({[2-fluoro-3-(trifluoromethyl)phenyl]methyl}(2-phenylpropyl)amino)propoxy]-6-methanesulfonylphenyl}propan-2-ol,
2-{2-fluoro-4-[3-({[2-fluoro-3-(trifluoromethyl)phenyl]methyl}[(4-fluorophenyl)methyl]amino)propoxy]-6-methanesulfonylphenyl}propan-2-ol,
2-{2-fluoro-4-[3-({[2-fluoro-3-(trifluoromethyl)phenyl]methyl}[2-(4-fluorophenyl)-2-methylpropyl]amino)propoxy]-6-methanesulfonylphenyl}propan-2-ol,
2-{2-fluoro-4-[3-({[2-fluoro-3-(trifluoromethyl)phenyl]methyl}[2-(4-fluorophenyl)ethyl]amino)propoxy]-6-methanesulfonylphenyl}propan-2-ol, 2-{2-fluoro-4-[3-({[2-fluoro-3-(trifluoromethyl)phenyl]methyl}[2-(4-fluorophenyl)propyl]amino)propoxy]-6-methanesulfonylphenyl}propan-2-ol,
2-(2-methanesulfonyl-4-{3-[(2-methyl-2-phenylpropyl)({[3-(trifluoromethyl)phenyl]methyl})amino]propoxy}phenyl)propan-2-ol,
2-(2-methanesulfonyl-4-{3-[(2-phenylethyl)({[3-(trifluoromethyl)phenyl]methyl})amino]propoxy}phenyl)propan-2-ol,
2-(2-methanesulfonyl-4-{3-[(2-phenylpropyl)({[3-(trifluoromethyl)phenyl]methyl})amino]propoxy}phenyl)propan-2-ol,
2-(4-{3-[(2,2-diphenylethyl)({[2-fluoro-3-(trifluoromethyl)phenyl]methyl})amino]propoxy}-2-methanesulfonylphenyl)propan-2-ol,
2-(4-{3-[(2,2-diphenylethyl)({[3-(trifluoromethyl)phenyl]methyl})amino]propoxy}-2-methanesulfonylphenyl)propan-2-ol,
2-(4-{3-[benzyl({[2-chloro-3-(trifluoromethyl)phenyl]methyl})amino]propoxy}-2-methanesulfonylphenyl)propan-2-ol,
2-(4-{3-[benzyl({[2-fluoro-3-(trifluoromethyl)phenyl]methyl})amino]propoxy}-2-methanesulfonylphenyl)propan-2-ol,
2-(4-{3-[benzyl({[3-(trifluoromethyl)phenyl]methyl})amino]propoxy}-2-methanesulfonylphenyl)propan-2-ol,
2-[4-(3-{[(4-fluorophenyl)methyl]({[3-(trifluoromethyl)phenyl]methyl})amino}propoxy)-2-methanesulfonylphenyl]propan-2-ol,
2-[4-(3-{[2-(4-fluorophenyl)-2-methylpropyl]({[3-(trifluoromethyl)phenyl]methyl})amino}propoxy)-2-methanesulfonylphenyl]propan-2-ol,
2-[4-(3-{[2-(4-fluorophenyl)ethyl]({[3-(trifluoromethyl)phenyl]methyl})amino}propoxy)-2-methanesulfonylphenyl]propan-2-ol,
2-[4-(3-{[2-(4-fluorophenyl)propyl]({[3-(trifluoromethyl)phenyl]methyl})amino}propoxy)-2-methanesulfonylphenyl]propan-2-ol,
2-{4-[3-({[2-chloro-3-(trifluoromethyl)phenyl]methyl}[2,2-difluoro-2-(4-fluorophenyl)ethyl]amino)propoxy]-2-methanesulfonylphenyl}propan-2-ol,
2-[4-(3-{[2,2-difluoro-2-(4-fluorophenyl)ethyl]({[2-fluoro-3-(trifluoromethyl)phenyl]methyl})amino}propoxy)-2-methanesulfonylphenyl]propan-2-ol,
2-[4-(3-{[2,2-difluoro-2-(4-fluorophenyl)ethyl]({[3-(trifluoromethyl)phenyl]methyl})amino}propoxy)-2-methanesulfonylphenyl]propan-2-ol,
2-{4-[3-({[2-chloro-3-(trifluoromethyl)phenyl]methyl}(2-methyl-2-phenylpropyl)amino)propoxy]-2-methanesulfonylphenyl}propan-2-ol,
2-{4-[3-({[2-chloro-3-(trifluoromethyl)phenyl]methyl}(2-phenylethyl)amino)propoxy]-2-methanesulfonylphenyl}propan-2-ol,
2-{4-[3-({[2-chloro-3-(trifluoromethyl)phenyl]methyl}(2-phenylpropyl)amino)propoxy]-2-methanesulfonylphenyl}propan-2-ol,
2-{4-[3-({[2-chloro-3-(trifluoromethyl)phenyl]methyl}[(4-fluorophenyl)methyl]amino)propoxy]-2-methanesulfonylphenyl}propan-2-ol,
2-{4-[3-({[2-chloro-3-(trifluoromethyl)phenyl]methyl}[2-(4-fluorophenyl)-2-methylpropyl]amino)propoxy]-2-methanesulfonylphenyl}propan-2-ol,
2-{4-[3-({[2-chloro-3-(trifluoromethyl)phenyl]methyl}[2-(4-fluorophenyl)ethyl]amino)propoxy]-2-methanesulfonylphenyl}propan-2-ol,
2-{4-[3-({[2-chloro-3-(trifluoromethyl)phenyl]methyl}[2-(4-fluorophenyl)propyl]amino)propoxy]-2-methanesulfonylphenyl}propan-2-ol,
2-{4-[3-({[2-fluoro-3-(trifluoromethyl)phenyl]methyl}(2-methyl-2-phenylpropyl)amino)propoxy]-2-methanesulfonylphenyl}propan-2-ol,
2-{4-[3-({[2-fluoro-3-(trifluoromethyl)phenyl]methyl}(2-phenylethyl)amino)propoxy]-2-methanesulfonylphenyl}propan-2-ol,
2-{4-[3-({[2-fluoro-3-(trifluoromethyl)phenyl]methyl}(2-phenylpropyl)amino)propoxy]-2-methanesulfonylphenyl}propan-2-ol,
2-{4-[3-({[2-fluoro-3-(trifluoromethyl)phenyl]methyl}[(4-fluorophenyl)methyl]amino)propoxy]-2-methanesulfonylphenyl}propan-2-ol,
2-{4-[3-({[2-fluoro-3-(trifluoromethyl)phenyl]methyl}[2-(4-fluorophenyl)-2-methylpropyl]amino)propoxy]-2-methanesulfonylphenyl}propan-2-ol,
2-{4-[3-({[2-fluoro-3-(trifluoromethyl)phenyl]methyl}[2-(4-fluorophenyl)ethyl]amino)propoxy]-2-methanesulfonylphenyl}propan-2-ol,
2-{4-[3-({[2-fluoro-3-(trifluoromethyl)phenyl]methyl}[2-(4-fluorophenyl)propyl]amino)propoxy]-2-methanesulfonylphenyl}propan-2-ol, and
2-{4-[3-({[2-chloro-3-(trifluoromethyl)phenyl]methyl}(2,2-diphenylethyl)amino)propoxy]-2-methanesulfonylphenyl}propan-2-ol.

14. The compound of claim 1, wherein at least one of $R^A$ or $R^B$ is optionally substituted $C_1$-$C_6$ heteroalkyl, wherein the optionally substituted $C_1$-$C_6$ heteroalkyl is —$OR^V$, wherein $R^V$ is:

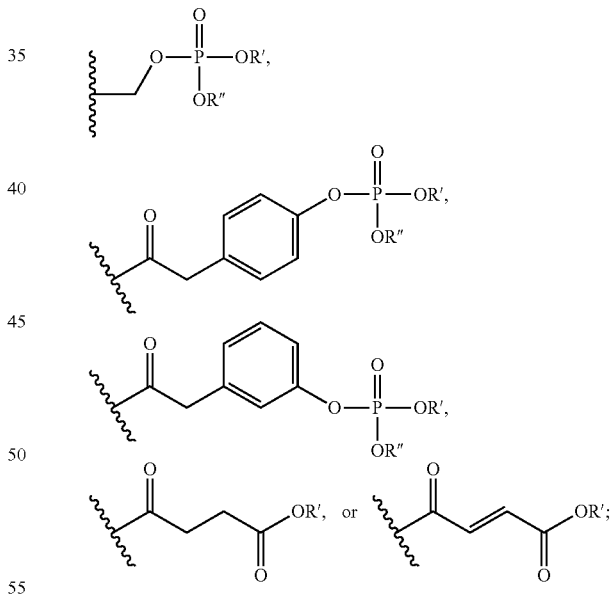

wherein each R' and R" is independently hydrogen, optionally substituted $C_1$-$C_6$ alkyl, or optionally substituted $C_6$-$C_{10}$ aryl $C_1$-$C_6$ alkyl.

15. A method of ameliorating one or more symptoms of cancer comprising administering an effective amount of a compound of claim 1, or pharmaceutically acceptable salts thereof to a subject in need thereof.

16. A method of ameliorating one or more symptoms of cancer comprising contacting a cell with an effective amount of a compound of claim 1, or pharmaceutically acceptable salts thereof.

17. The method of claim 15, wherein said cancer is breast cancer, colon cancer, renal cell cancer, non-small cell lung cancer, hepatocellular carcinoma, gastric cancer, ovarian cancer, pancreatic cancer, esophageal cancer, prostate cancer, sarcoma, glioblastoma, diffuse large B-cell lymphoma, acute myeloid leukemia, multiple myeloma, or melanoma.

18. The method of claim 15, wherein said method further comprises administration of an additional anticancer therapy.

19. The method of ameliorating one or more symptoms of a neurological disorder comprising administering an effective amount of a compound of claim 1, or pharmaceutically acceptable salts thereof to a subject in nee thereof, wherein said neurological disorder is Alzheimer's disease.

\* \* \* \* \*

SEQUENCE LISTING

<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Synthetic construct

<400> SEQUENCE: 1
tgggtcgctt ttgggattac                                           20

<210> SEQ ID NO 2
<211> LENGTH: 21
<212> TYPE: DNA
<213> ORGANISM: Artificial Sequence
<220> FEATURE:
<223> OTHER INFORMATION: Synthetic construct

<400> SEQUENCE: 2
ttcaactcct tcatggtctc g                                         21

<210> SEQ ID NO 3
<211> LENGTH: 19
<212> TYPE: DNA
<213> ORGANISM: Artificial Sequence
<220> FEATURE:
<223> OTHER INFORMATION: Synthetic construct

<400> SEQUENCE: 3
agccacatcg ctcagacac                                            19

<210> SEQ ID NO 4
<211> LENGTH: 19
<212> TYPE: DNA
<213> ORGANISM: Artificial Sequence
<220> FEATURE:
<223> OTHER INFORMATION: Synthetic construct

<400> SEQUENCE: 4
gcccaatacg accaaatcc                                            19

<210> SEQ ID NO 5
<211> LENGTH: 22
<212> TYPE: DNA
<213> ORGANISM: Artificial Sequence
<220> FEATURE:
<223> OTHER INFORMATION: Synthetic construct

<400> SEQUENCE: 5
gccactttcg tgggcccagt ga                                        22

<210> SEQ ID NO 6
<211> LENGTH: 22
<212> TYPE: DNA
<213> ORGANISM: Artificial Sequence
<220> FEATURE:
<223> OTHER INFORMATION: Synthetic construct

<400> SEQUENCE: 6
tctcatcacc agctgtgttg ca                                        22

<210> SEQ ID NO 7
<211> LENGTH: 21
<212> TYPE: DNA
<213> ORGANISM: Artificial Sequence

```
<220> FEATURE:
<223> OTHER INFORMATION: Synthetic construct

<400> SEQUENCE: 7
tgctgcatag tcttgggact c                                              21

<210> SEQ ID NO 8
<211> LENGTH: 20
<212> TYPE: DNA
<213> ORGANISM: Artificial Sequence
<220> FEATURE:
<223> OTHER INFORMATION: Synthetic construct

<400> SEQUENCE: 8
acctcctgtc gcatgtcact                                                20

<210> SEQ ID NO 9
<211> LENGTH: 20
<212> TYPE: DNA
<213> ORGANISM: Artificial Sequence
<220> FEATURE:
<223> OTHER INFORMATION: Synthetic construct

<400> SEQUENCE: 9
gaccctggag gctaaggact                                                20

<210> SEQ ID NO 10
<211> LENGTH: 20
<212> TYPE: DNA
<213> ORGANISM: Artificial Sequence
<220> FEATURE:
<223> OTHER INFORMATION: Synthetic construct

<400> SEQUENCE: 10
agagccttca tcttcgcaat                                                20

<210> SEQ ID NO 11
<211> LENGTH: 20
<212> TYPE: DNA
<213> ORGANISM: Artificial Sequence
<220> FEATURE:
<223> OTHER INFORMATION: Synthetic construct

<400> SEQUENCE: 11
gcacagtcaa ggccgagaat                                                20

<210> SEQ ID NO 12
<211> LENGTH: 20
<212> TYPE: DNA
<213> ORGANISM: Artificial Sequence
<220> FEATURE:
<223> OTHER INFORMATION: Synthetic construct

<400> SEQUENCE: 12
gccttctcca tggtggtgaa                                                20

<210> SEQ ID NO 13
<211> LENGTH: 19
<212> TYPE: DNA
<213> ORGANISM: Artificial Sequence
<220> FEATURE:
<223> OTHER INFORMATION: Synthetic construct

<400> SEQUENCE: 13
atggagcagg gaagaccac                                                 19
```

```
<210> SEQ ID NO 14
<211> LENGTH: 19
<212> TYPE: DNA
<213> ORGANISM: Artificial Sequence
<220> FEATURE:
<223> OTHER INFORMATION: Synthetic construct

<400> SEQUENCE: 14
gtaggccgtg ccagaagtt                                              19

<210> SEQ ID NO 15
<211> LENGTH: 20
<212> TYPE: DNA
<213> ORGANISM: Artificial Sequence
<220> FEATURE:
<223> OTHER INFORMATION: Synthetic construct

<400> SEQUENCE: 15
tttcccagag atccctttca                                             20

<210> SEQ ID NO 16
<211> LENGTH: 21
<212> TYPE: DNA
<213> ORGANISM: Artificial Sequence
<220> FEATURE:
<223> OTHER INFORMATION: Synthetic construct

<400> SEQUENCE: 16
atcgaattca aggacctttc c                                           21
```